US012655226B2

(12) United States Patent
Johnson et al.

(10) Patent No.: US 12,655,226 B2
(45) Date of Patent: Jun. 16, 2026

(54) CELL SECRETED MINIBODIES AND USES THEREOF

(71) Applicants: Novartis AG, Basel (CH); The Trustees of the University of Pennsylvania, Philadelphia, PA (US)

(72) Inventors: Laura Alexandra Johnson, Media, PA (US); Danielle Cook, Boston, MA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 380 days.

(21) Appl. No.: 18/064,070

(22) Filed: Dec. 9, 2022

(65) Prior Publication Data

US 2023/0357717 A1 Nov. 9, 2023

Related U.S. Application Data

(62) Division of application No. 16/087,047, filed as application No. PCT/US2017/023869 on Mar. 23, 2017, now Pat. No. 11,549,099.

(60) Provisional application No. 62/312,278, filed on Mar. 23, 2016.

(51) Int. Cl.

| | |
|---|---|
| ***A61K 40/31*** | (2025.01) |
| ***A61K 40/11*** | (2025.01) |
| ***A61K 40/33*** | (2025.01) |
| ***A61K 40/36*** | (2025.01) |
| ***A61K 40/42*** | (2025.01) |
| ***A61P 35/00*** | (2006.01) |
| ***A61P 37/00*** | (2006.01) |
| ***C07K 14/705*** | (2006.01) |
| ***C07K 16/28*** | (2006.01) |
| ***C07K 16/30*** | (2006.01) |
| ***C12N 5/0783*** | (2010.01) |

(52) U.S. Cl.

CPC .............. *C07K 16/30* (2013.01); *A61K 40/11* (2025.01); *A61K 40/31* (2025.01); *A61K 40/36* (2025.01); *A61K 40/4204* (2025.01); *A61K 40/4211* (2025.01); *C07K 14/7051* (2013.01); *C07K 16/2818* (2013.01); *C07K 16/2827* (2013.01); *C12N 5/0636* (2013.01); *A61K 2239/31* (2023.05); *A61K 2239/38* (2023.05); *C07K 2317/24* (2013.01); *C07K 2317/31* (2013.01); *C07K 2317/53* (2013.01); *C07K 2319/02* (2013.01); *C07K 2319/03* (2013.01); *C07K 2319/33* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,712,149 | A | 1/1998 | Roberts |
| 5,874,240 | A | 2/1999 | Ni et al. |
| 5,906,936 | A | 5/1999 | Eshhar et al. |
| 6,103,521 | A | 8/2000 | Capon et al. |
| 6,319,494 | B1 | 11/2001 | Capon et al. |
| 6,355,779 | B1 | 3/2002 | Goodwin et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,994,298 | B2 | 8/2011 | Zhang et al. |
| 8,211,422 | B2 | 7/2012 | Eshhar et al. |
| 8,252,914 | B2 | 8/2012 | Zhang et al. |

(Continued)

FOREIGN PATENT DOCUMENTS

| | | |
|---|---|---|
| EP | 0574512 A1 | 12/1993 |
| EP | 0871495 A1 | 10/1998 |

(Continued)

OTHER PUBLICATIONS

Shahied et al (Journal of Biological Chemistry, 2004, 279:53907-53914).*
Beckman et al (Cancer, 2007, 109:170-9).*
Olafsen et al (Chapter 6, pp. 69-84 in Antibody Engineering, Roland Kontermann and Stefan Dubel, Second Edition, Springer-Verlag, Berlin, Heidelberg, Germany, 2010).*
Gonzalez-Cao et al (Lung Cancer: Targets and Therapy, 2015, 6:55-70).*

(Continued)

*Primary Examiner* — Laura B Goddard
(74) *Attorney, Agent, or Firm* — K&L Gates LLP

(57) ABSTRACT

The present invention relates to compositions and methods for using a minibody. Minibodies described herein comprise a secretion signal, a variable heavy chain fragment, a variable light chain fragment, a constant chain fragment, and a hinge domain between the variable light chain fragment and the constant chain fragment. One aspect includes a nucleic acid encoding a minibody. Other aspects include compositions comprising a minibody and a modified T cell comprising a nucleic acid encoding a minibody. Also included are methods and pharmaceutical compositions comprising the modified T cells for adoptive therapy and treating a condition, such as cancer.

24 Claims, 23 Drawing Sheets

Specification includes a Sequence Listing.

(56) References Cited

U.S. PATENT DOCUMENTS 8,389,282 B2 3/2013 Sadelain et al.
8,399,645 B2 3/2013 Campana et al.
8,465,743 B2 6/2013 Rosenberg et al.
8,637,307 B2 1/2014 June et al.
8,722,400 B2 5/2014 Riley et al.
8,906,682 B2 12/2014 June et al.
8,911,993 B2 12/2014 June et al.
8,916,381 B1 12/2014 June et al.
8,975,071 B1 3/2015 June et al.
9,101,584 B2 8/2015 June et al.
9,102,760 B2 8/2015 June et al.
9,102,761 B2 8/2015 June et al.
9,394,368 B2 7/2016 Brogdon et al.
9,573,988 B2 2/2017 Brogdon et al.
9,745,368 B2 8/2017 Milone et al.
9,765,156 B2 9/2017 June et al.
9,777,061 B2 10/2017 Ebersbach et al.
9,815,901 B2 11/2017 Brogdon et al.
10,696,749 B2 6/2020 June et al.
10,954,301 B2 * 3/2021 Johnson ............... C07K 16/468
11,549,099 B2 1/2023 Johnson et al.
2003/0060444 A1 3/2003 Finney et al.
2003/0077249 A1 4/2003 Bebbington et al.
2003/0147869 A1 8/2003 Riley et al.
2003/0148982 A1 8/2003 Brenner et al.
2003/0224520 A1 12/2003 June et al.
2004/0038886 A1 2/2004 Finney et al.
2004/0043401 A1 3/2004 Sadelain et al.
2004/0101519 A1 5/2004 June et al.
2004/0110290 A1 6/2004 June et al.
2005/0113564 A1 5/2005 Campana et al.
2005/0129671 A1 6/2005 Cooper et al.
2006/0034810 A1 2/2006 Riley et al.
2007/0036773 A1 2/2007 Cooper et al.
2008/0131415 A1 6/2008 Riddell et al.
2009/0257994 A1 10/2009 Jensen
2010/0261269 A1 10/2010 June et al.
2011/0052554 A1 3/2011 Zakrzewski et al.
2011/0262467 A1 10/2011 Riley et al.
2012/0148552 A1 6/2012 Jensen
2012/0321667 A1 12/2012 Sentman
2013/0071409 A1 3/2013 Riley et al.
2013/0071414 A1 3/2013 Dotti et al.
2013/0149337 A1 6/2013 Cooper et al.
2013/0155909 A1 6/2013 Jackson et al.
2013/0287748 A1 10/2013 June et al.
2013/0288368 A1 10/2013 June et al.
2013/0309258 A1 11/2013 June et al.
2014/0050708 A1 2/2014 Powell et al.
2014/0099309 A1 4/2014 Powell, Jr. et al.
2014/0099340 A1 4/2014 June et al.
2014/0106449 A1 4/2014 June et al.
2014/0186947 A1 7/2014 June et al.
2014/0212446 A1 7/2014 Riley et al.
2014/0219975 A1 8/2014 June et al.
2014/0227237 A1 8/2014 June et al.
2014/0271635 A1 9/2014 Brogdon et al.
2014/0302064 A1 10/2014 Moore
2014/0322169 A1 10/2014 Harper et al.
2014/0322183 A1 10/2014 Milone et al.
2014/0322212 A1 10/2014 Brogdon et al.
2014/0322275 A1 10/2014 Brogdon et al.
2014/0370017 A1 12/2014 June et al.
2014/0370045 A1 12/2014 June et al.
2015/0017141 A1 1/2015 June et al.
2015/0024482 A1 1/2015 Frigault et al.
2015/0050729 A1 2/2015 June et al.
2015/0093822 A1 4/2015 June et al.
2015/0099299 A1 4/2015 June et al.
2015/0118202 A1 4/2015 June et al.
2015/0140019 A1 5/2015 June et al.
2015/0190428 A1 7/2015 June et al.
2015/0202286 A1 7/2015 June et al.
2015/0203579 A1 7/2015 Papadopoulos et al.
2015/0203580 A1 7/2015 Papadopoulos et al.
2015/0283178 A1 10/2015 June et al.
2015/0290244 A1 10/2015 June et al.
2015/0342994 A1 12/2015 Riley et al.
2016/0046724 A1 2/2016 Brogdon et al.
2016/0051651 A1 2/2016 Brogdon et al.
2016/0068601 A1 3/2016 Brogdon et al.
2016/0096892 A1 4/2016 Brogdon et al.
2016/0185861 A1 6/2016 Bedoya et al.
2016/0311907 A1 10/2016 Brogdon et al.
2016/0311917 A1 10/2016 Beatty et al.
2016/0340406 A1 11/2016 Zhao et al.
2016/0362472 A1 12/2016 Bitter et al.
2017/0008963 A1 1/2017 Brogdon et al.
2017/0051044 A1 * 2/2017 Chan .................. C07K 16/2809
2017/0081411 A1 3/2017 Engels et al.
2017/0137783 A1 5/2017 Bedoya et al.
2017/0183415 A1 6/2017 Brogdon et al.
2017/0209492 A1 7/2017 June et al.
2017/0211055 A1 7/2017 Brogdon et al.
2017/0226495 A1 8/2017 Guimaraes
2017/0239294 A1 8/2017 Thomas-Tikhonenko et al.
2017/0260268 A1 9/2017 Beatty et al.
2017/0274014 A1 9/2017 Brogdon et al.
2017/0306416 A1 10/2017 Bedoya et al.
2017/0335281 A1 11/2017 Loew et al.
2017/0349668 A1 12/2017 Rattel et al.
2017/0362297 A1 * 12/2017 Marasco .............. C07K 14/705
2018/0022795 A1 1/2018 Milone et al.
2018/0044423 A1 2/2018 Ebersbach et al.
2018/0044424 A1 2/2018 June et al.
2018/0118834 A1 5/2018 Brogdon et al.
2018/0125892 A1 5/2018 Brannetti et al.
2018/0133296 A1 5/2018 Barrett et al.
2018/0140602 A1 5/2018 Angst et al.
2018/0230193 A1 8/2018 Loew et al.
2018/0252727 A1 9/2018 Garfall et al.
2018/0258149 A1 9/2018 Motz et al.
2018/0298068 A1 10/2018 Albelda
2018/0312595 A1 11/2018 Brogdon et al.
2019/0000880 A1 1/2019 Motz et al.
2019/0000944 A1 1/2019 Brogdon et al.
2019/0135940 A1 5/2019 Brogdon et al.
2019/0151365 A1 5/2019 Anak et al.
2019/0153061 A1 5/2019 Brogdon et al.
2019/0161542 A1 5/2019 Gill et al.
2019/0263914 A1 8/2019 Brogdon et al.
2019/0269727 A1 9/2019 Fachin et al.
2019/0292238 A1 9/2019 Bitter et al.
2019/0292257 A1 9/2019 Bedoya et al.
2019/0298715 A1 10/2019 Motz et al.
2019/0330356 A1 10/2019 Brogdon et al.
2019/0336504 A1 11/2019 Gill et al.
2019/0375815 A1 12/2019 Engels et al.
2019/0382500 A1 12/2019 Abujoub et al.
2019/0388471 A1 12/2019 June et al.
2019/0389928 A1 12/2019 Posey et al.
2020/0048359 A1 2/2020 Albelda et al.
2020/0055948 A1 2/2020 Daley et al.
2020/0061113 A1 2/2020 Kassim et al.
2020/0085869 A1 3/2020 Schuster et al.
2020/0087376 A1 3/2020 Fraietta et al.
2020/0113941 A1 4/2020 Brannetti et al.
2020/0179511 A1 6/2020 Daley et al.
2020/0215171 A1 7/2020 Brogdon et al.
2020/0281973 A1 9/2020 Dranoff
2020/0283729 A1 9/2020 Loew et al.
2020/0291354 A1 9/2020 Johnson et al.
2020/0339704 A1 10/2020 Bradner et al.
2020/0360431 A1 11/2020 Garfall et al.
2020/0368268 A1 11/2020 Johnson et al.
2020/0370012 A1 11/2020 Fraietta et al.
2020/0371091 A1 11/2020 Pruteanu-Malinici et al.
2020/0399383 A1 12/2020 Scholler et al.
2021/0002377 A1 1/2021 Brogdon et al.
2021/0047405 A1 2/2021 Nobles et al.
2021/0079073 A1 3/2021 Milone et al.
2021/0087279 A1 3/2021 Engels et al.
2021/0139595 A1 5/2021 Ebersbach et al.
2021/0171909 A1 6/2021 Golovina

(56) References Cited

U.S. PATENT DOCUMENTS

| | | | |
|---|---|---|---|
| 2021/0172020 | A1 | 6/2021 | Bedoya et al. |
| 2021/0177896 | A1 | 6/2021 | Porter et al. |
| 2021/0177900 | A1 | 6/2021 | Engels et al. |
| 2021/0213063 | A1 | 7/2021 | Isaacs et al. |
| 2021/0214459 | A1 | 7/2021 | Brock et al. |
| 2021/0220404 | A1 | 7/2021 | Abujoub et al. |
| 2021/0246423 | A1 | 8/2021 | Bedoya et al. |
| 2021/0284752 | A1 | 9/2021 | Brogdon et al. |
| 2021/0317183 | A1 | 10/2021 | Zhao et al. |
| 2021/0347851 | A1 | 11/2021 | Isaacs et al. |
| 2021/0396739 | A1 | 12/2021 | Pruteanu-Malinici et al. |
| 2022/0047633 | A1 | 2/2022 | Grupp |
| 2022/0064316 | A1 | 3/2022 | Brogdon et al. |
| 2022/0089750 | A1 | 3/2022 | June et al. |
| 2022/0152150 | A1 | 5/2022 | Koshy et al. |
| 2022/0168389 | A1 | 6/2022 | Ghassemi et al. |
| 2022/0195010 | A1 | 6/2022 | Bitter et al. |
| 2022/0251152 | A1 | 8/2022 | Carbonneau et al. |
| 2022/0364055 | A1 | 11/2022 | Treanor et al. |
| 2022/0387486 | A1 | 12/2022 | Brannetti et al. |
| 2023/0026049 | A1 | 1/2023 | Brogdon et al. |
| 2023/0071283 | A1 | 3/2023 | Golosov et al. |
| 2023/0074800 | A1 | 3/2023 | Berger et al. |
| 2023/0111593 | A1 | 4/2023 | Schuster et al. |
| 2023/0139800 | A1 | 5/2023 | Motz et al. |
| 2023/0174933 | A1 | 6/2023 | Brogdon et al. |
| 2023/0183368 | A1 | 6/2023 | Abujoub et al. |
| 2023/0220090 | A1 | 7/2023 | Brogdon et al. |
| 2023/0250179 | A1 | 8/2023 | Abujoub et al. |
| 2023/0256017 | A1 | 8/2023 | Brogdon et al. |
| 2023/0295296 | A1 | 9/2023 | Bedoya et al. |
| 2023/0302155 | A1 | 9/2023 | Koshy et al. |
| 2023/0312677 | A1 | 10/2023 | Posey et al. |
| 2023/0332104 | A1 | 10/2023 | Estevez Silva et al. |
| 2023/0357717 | A1 | 11/2023 | Johnson et al. |
| 2023/0374105 | A1 | 11/2023 | Bitter et al. |
| 2023/0416390 | A1 | 12/2023 | Abujoub et al. |
| 2024/0024360 | A1 | 1/2024 | Fachin et al. |
| 2024/0033358 | A1 | 2/2024 | Chadbourne et al. |
| 2024/0083968 | A1 | 3/2024 | Loew et al. |
| 2024/0139244 | A1 | 5/2024 | Dranoff |
| 2024/0238396 | A1 | 7/2024 | Brogdon et al. |
| 2024/0252538 | A1 | 8/2024 | Brannetti et al. |
| 2024/0288444 | A1 | 8/2024 | Garfall et al. |
| 2024/0343783 | A1 | 10/2024 | Milone et al. |
| 2024/0384007 | A1 | 11/2024 | Bradner et al. |
| 2024/0390492 | A1 | 11/2024 | Engels et al. |
| 2024/0398913 | A1 | 12/2024 | Barrett et al. |
| 2025/0163123 | A1 | 5/2025 | Porter et al. |
| 2025/0215096 | A1 | 7/2025 | Scholler et al. |
| 2025/0243285 | A1 | 7/2025 | June et al. |
| 2025/0382621 | A1 | 12/2025 | Motz et al. |
| 2026/0021178 | A1 | 1/2026 | Daley et al. |

FOREIGN PATENT DOCUMENTS

| | | | | |
|---|---|---|---|---|
| EP | 1226244 | A2 | 7/2002 | |
| EP | 2 742 953 | A1 | 6/2014 | |
| NO | 2012138858 | A1 | 10/2012 | |
| NO | 2014011988 | A2 | 1/2014 | |
| WO | 1992015322 | A1 | 9/1992 | |
| WO | 199530014 | A1 | 11/1995 | |
| WO | 9623814 | A1 | 8/1996 | |
| WO | 9624671 | A1 | 8/1996 | |
| WO | 1997015669 | A1 | 5/1997 | |
| WO | 9723613 | A2 | 7/1997 | |
| WO | 9818809 | A1 | 5/1998 | |
| WO | 9900494 | A2 | 1/1999 | |
| WO | 9957268 | A1 | 11/1999 | |
| WO | 0014257 | A1 | 3/2000 | |
| WO | 2002033101 | A1 | 4/2002 | |
| WO | 02077029 | A2 | 10/2002 | |
| WO | 02088334 | A1 | 11/2002 | |
| WO | 2003057171 | A2 | 7/2003 | |
| WO | 2005019429 | A2 | 3/2005 | |
| WO | 2005044996 | A2 | 5/2005 | |
| WO | 2005118788 | A2 | 12/2005 | |
| WO | 2006060878 | A1 | 6/2006 | |
| WO | 2008045437 | A2 | 4/2008 | |
| WO | 2010085660 | A2 | 7/2010 | |
| WO | 2011059836 | A2 | 5/2011 | |
| WO | 2011097477 | A1 | 8/2011 | |
| WO | 2012058460 | A2 | 5/2012 | |
| WO | 2012079000 | A1 | 6/2012 | |
| WO | 2012082841 | A2 | 6/2012 | |
| WO | 2012099973 | A2 | 7/2012 | |
| WO | 2012127464 | A2 | 9/2012 | |
| WO | 2012129514 | A1 | 9/2012 | |
| WO | 2012135854 | A2 | 10/2012 | |
| WO | 2013019615 | A2 | 2/2013 | |
| WO | 2013033626 | A2 | 3/2013 | |
| WO | 2013040371 | A2 | 3/2013 | |
| WO | 2013059593 | A1 | 4/2013 | |
| WO | 2013126712 | A1 | 8/2013 | |
| WO | 2013126729 | A1 | 8/2013 | |
| WO | 2013126733 | A1 | 8/2013 | |
| WO | 2014011984 | A1 | 1/2014 | |
| WO | 2014011987 | A1 | 1/2014 | |
| WO | 2014011993 | A2 | 1/2014 | |
| WO | 2014011996 | A1 | 1/2014 | |
| WO | 2014012001 | A2 | 1/2014 | |
| WO | 2014022758 | A1 | 2/2014 | |
| WO | 2014031687 | A1 | 2/2014 | |
| WO | 2014039513 | A2 | 3/2014 | |
| WO | 2014055442 | A2 | 4/2014 | |
| WO | 2014055657 | A1 | 4/2014 | |
| WO | 2014130635 | A1 | 8/2014 | |
| WO | 2014145252 | A2 | 9/2014 | |
| WO | 2015090229 | A1 | 6/2015 | |
| WO | 2015090230 | A1 | 6/2015 | |
| WO | 2015112534 | A2 | 7/2015 | |
| WO | 2015112626 | A1 | 7/2015 | |
| WO | 2015142661 | A1 | 9/2015 | |
| WO | 2015142675 | A2 | 9/2015 | |
| WO | 2015157252 | A1 | 10/2015 | |
| WO | 2016014501 | A1 | 1/2016 | |
| WO | 2016014530 | A1 | 1/2016 | |
| WO | 2016014535 | A1 | 1/2016 | |
| WO | 2016014553 | A1 | 1/2016 | |
| WO | 2016014565 | A2 | 1/2016 | |
| WO | 2016014576 | A1 | 1/2016 | |
| WO | 2016019300 | A1 | 2/2016 | |
| WO | 2016025880 | A1 | 2/2016 | |
| WO | 2016028896 | A1 | 2/2016 | |
| WO | 2016044605 | A1 | 3/2016 | |
| WO | 2016100985 | A2 | 6/2016 | |
| WO | 2016113203 | A1 | 7/2016 | |
| WO | 2016126608 | A1 | 8/2016 | |
| WO | 2016210129 | A1 | 12/2016 | |
| WO | WO-2017123978 | A1 * | 7/2017 | ........... A61K 39/395 |
| WO | 2017165683 | A1 | 9/2017 | |

OTHER PUBLICATIONS

Kochenderfer et al., "Eradication of B-lineage cells and regression of lymphoma in a patient treated with autologous T cells genetically-engineered to recognize CD19," Blood 116: 4099-4102 (2010).

Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.

Kwon et al., "cDNA sequences of two inducible T-cell genes". Proc. Natl. Acad. Sci. U.S.A. 86(6): 1963-1967 (1989).

Lamanna et al., "Pentostatin, Cyclophosphamide, and Rutuximab is an Active, Well-Tolerated Regimen for Patients With Previously Treated Chronic Lymphocytic Leukemia" Journal of Clinical Oncology (2008) vol. 24 No. 10 pp. 1575-1581.

Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).

Laport et al., "Adoptive transfer of costimulated T cells induces lymphocytosis in patients with relapsed/refractory non-Hodgkin

(56) References Cited

OTHER PUBLICATIONS lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
MaCallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).
Milone et al., "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Olafsen et al. "Characterization of engineered anti-p185 HER-2 (scFv-CH3)2 antibody fragments (minibodies)for tumoe targeting" Protein Engineering, Design & Selection (2004) vol. 17, No. 4, pp. 315-323.
Olafsen et al., "Generation of Single-Chain Fv Fragments and Multivalent Derivatives scFv-Fc and scFv-CH3 (Minibodies)," Chapter 6 in Antibody Engineering vol. 2, Kontermann et al. ed., pp. 69-85, (2010) Springer-Verlag Berlin.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al., "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Tanque et al. "Armed Oncolytic Adenovirus-Expressing PD-LI Mini-Body Enhances Antitumor Effects of Chimeric Antigen Receptor T Cells in Solid Tumors" Cancer Research (2017) vol. 77, No. 8, pp. 1-12.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay and Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Yin et al., "Checkpoint Blockage Reverses Anergy in IL-13Ralpha2 Humanized scFV-Based Car T Cells to Treat Murine and Canine Gliomas," Molecular Therapy: Oncolytics (2018) vol. 11, pp. 20-38 and supplementary materials.
Zhao et al., "A Herceptin-Based Chimeric Antigen Receptor with Modified Signaling Domains Leads to Enhanced Survival of Transduced T Lymphocytes and Antitumor Activity," J Immunol (2009) vol. 183, No. 9, pp. 5563-5574.
Zufferey et al., "Multiply attenuated lentiviral vector achieves efficient gene delivery in vivo" Nature Biotechnology (1997) vol. 15 pp. 871-876.
Baeksgaard and Sorensen, "Acute tumor lysis syndrome in solid tumors—a case report and review of the literature" Cancer Chemotherapy Pharmacology (2003) vol. 51 pp. 187-192.

(56) References Cited

OTHER PUBLICATIONS

Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone are Insufficient to Prime Resting T Lymphocytes" J. Exp. Med. (1995) vol. 181 pp. 1653-1659.
Call and Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Eshhar et al. "Specific activation and targeting of cytotoxic lymphocytes through chimeric single chains consisting of antibody binding domains and the gamma or zeta subunits of the immunoglobulin and T-cell receptors" PNAS (1993) vol. 90, pp. 720-724.
Finney et al. "Activation of Resting Human Primary T Cells with Chimeric Receptors: Costimulation from CD28, Inducible Costimulator, CD134, and CD137 in Series with Signals from the TCRzeta Chain" The Journal of Immunology (2004) vol. 172, pp. 104-113.
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger and Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
González-Cao et al., "Targeting PD-1/PD-L1 in lung cancer: current perspectives," Lung Cancer: Targets and Therapy (2015) vol. 6, pp. 55-70.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors By Adoptive Transfer of Cytotoxic T Lymphocytes Reprogrammed by CD44V6-Specific SCFV:zeta-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International Application No. PCT/US2017/023869 dated Jul. 7, 2017.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets hormal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.

(56) References Cited

OTHER PUBLICATIONS

Kalos et al. "T Cells with Chimeric Antigen Receptors Have Potent Antitumor Effects and can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al., "A Phase I Clinical Trial of Treatment of B-Cell Malignancies with Autologous Anti-Cd19-CAR-Transduced T Cells" Blood (2010) vol. 116 No. 21 pp. 1179-1180, 52nd Annual Meeting of the American-Society-of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.

* cited by examiner

Figure 4
secretion signal
PD1Vh
linker
PD1Vl

CELL SECRETED MINIBODIES AND USES THEREOF

CLAIM OF PRIORITY

This application is a divisional of U.S. patent application Ser. No. 16/087,047, filed Sep. 20, 2018, now U.S. Pat. No. 11,549,099, which is a U.S. National Stage Application under 35 U.S.C. § 371 of International Application No. PCT/US2017/023869, filed Mar. 23, 2017, which claims priority to provisional U.S. Patent Application No. 62/312,278, filed on Mar. 23, 2016. The entire contents of the aforesaid applications are hereby incorporated herein by reference.

STATEMENT REGARDING FEDERALLY SPONSORED RESEARCH OR DEVELOPMENT

This invention was made with government support under CA174502-02 awarded by the National Institute of Health. The government has certain rights in the invention.

SEQUENCE LISTING

The instant application contains a Sequence Listing which has been submitted electronically in XML format and is hereby incorporated by reference in its entirety. Said XML copy, created on Dec. 7, 2022, is named N2067-712740_SL.xml and is 451,710 bytes in size.

BACKGROUND OF THE INVENTION

Monoclonal antibodies are used as therapeutics for the treatment of several major diseases, including autoimmune, cardiovascular and infectious diseases, cancer and inflammation. Clinical trials and research using antibodies have generated a wealth of useful information regarding clinical responses. While antibodies are highly specific and have the ability to bind a wide variety of molecules, some functional limitations of therapeutic antibodies have come to light, such as inadequate pharmacokinetics, failure to engage the cellular immune system, lack of retention or tissue penetration in target tissues, and off-site tissue toxicity.

Therefore a need exists for developing a tissue specific and optimized antibody therapeutic.

SUMMARY OF THE INVENTION

The present invention pertains, at least in part, to compositions and uses that improve an activity (e.g., one or more of function, persistence, cancer killing effect, or tumor infiltration) of an immune effector cell, e.g., a population of immune effector cells (e.g., T cells, NK cells). In some embodiments, the immune effector cell expresses a Chimeric Antigen Receptor molecule (e.g., a CAR polypeptide) that binds to a tumor antigen. In some embodiments, the immune effector cell comprises a nucleic acid encoding a minibody, wherein the minibody comprises a single chain antibody comprising a secretion signal, a variable heavy chain fragment, a variable light chain fragment, a constant chain fragment and a hinge domain between the variable light chain fragment and the constant chain fragment, wherein the modified T cell expresses and secretes the minibody. In some embodiments, the minibody binds to one or more immune checkpoint molecules described herein. In one embodiment, the minibody binds to Programmed Death 1 (PD-1). In another embodiment, the minibody is a bispecific minibody. In some embodiments, the bispecific minibody binds to PD-1 and PD-L1. Without wishing to be bound by theory, minibody binding to immune checkpoint molecules present on the surface of target (e.g., cancer or immune-suppressive) cells and/or the surface of immune effector cells (e.g., T cells, NK cells) is thought to prevent immune suppressive signaling by the immune checkpoint molecule, thereby decreasing immune checkpoint inhibition and enhancing one or more activities of the immune effector cell (e.g., increased killing of a tumor cell). Accordingly, disclosed herein are, inter alia: modified T cells comprising nucleic acid encoding a minibody with or without a CAR molecule, T cell receptor (TCR), or a bispecific minibody; nucleic acid encoding a minibody with or without further encoding a CAR molecule, T cell receptor (TCR), or a bispecific minibody; minibodies; compositions and pharmaceutical compositions comprising the same; methods of treatment comprising use of the same; and methods for generating modified T cells comprising nucleic acids capable of expressing and secreting a minibody.

Accordingly, in one aspect, the invention pertains to a modified T cell comprising a nucleic acid encoding a minibody, wherein the minibody comprises a single chain antibody comprising a secretion signal, a variable heavy chain fragment, a variable light chain fragment, a constant chain fragment and a minibody hinge domain between the variable light chain fragment and the constant chain fragment, wherein the modified T cell expresses and secretes the minibody.

In some embodiments, the modified T cell further comprises a nucleic acid encoding a chimeric antigen receptor (CAR), a T cell receptor (TCR), or a bispecific minibody.

In some embodiments, the CAR, TCR, or bispecific minibody is capable of binding to a tumor antigen, and the variable heavy chain fragment and the variable light chain fragment of the minibody bind the same tumor antigen.

In some embodiments, the CAR comprises an antigen binding domain, a transmembrane domain, and an intracellular signalling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12.

In some embodiments, the costimulatory domain comprises a functional domain of one or more proteins selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NY-ESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-1, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, β2-Microglobulin, Fc Receptor-like 5 (FcRL5), or molecules expressed by HIV, HCV, HBV, or other pathogens.

In some embodiments, the tumor antigen is a solid tumor antigen, e.g., mesothelin.

In some embodiments, the tumor antigen is expressed in a solid tumor that also expresses an immune checkpoint inhibitor, e.g., PD-L1.

In some embodiments, the antigen binding domain comprises an antibody, an antibody fragment, an scFv, a Fv, a Fab, a (Fab')2, a single domain antibody (SDAB), a VH or VL domain, or a camelid VHH domain.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain is connected to the transmembrane domain by a CAR hinge region.

In some embodiments, the nucleic acid encoding the CAR further encodes a leader sequence.

In some embodiments, the minibody binds to an immune checkpoint molecule.

In some embodiments, the immune checkpoint molecule is selected from the group consisting of Programmed Death 1 (PD-1), PD-1, PD-L1, PD-L2, Cytotoxic T-Lymphocyte Antigen 4 (CTLA-4), TIM-3, CEACAM (e.g., CEACAM-1, CEACAM-3 and/or CEACAM-5), LAG-3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GALS, adenosine, and TGFR (e.g., TGFR beta).

In some embodiments, the immune checkpoint molecule is Programmed Death 1 (PD-1).

In some embodiments, the minibody is a bispecific minibody.

In some embodiments, the bispecific minibody binds to two immune checkpoint molecules selected from the group consisting of Programmed Death 1 (PD-1), PD-1, PD-L1, PD-L2, Cytotoxic T-Lymphocyte Antigen 4 (CTLA-4), TIM-3, CEACAM (e.g., CEACAM-1, CEACAM-3 and/or CEACAM-5), LAG-3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GALS, adenosine, and TGFR (e.g., TGFR beta).

In some embodiments, the bispecific minibody binds to Programmed Death 1 (PD-1) and PD-L1.

In another aspect, the invention pertains to a nucleic acid encoding a minibody, wherein the minibody comprises a single chain antibody comprising a secretion signal, a variable heavy chain fragment, a variable light chain fragment, a constant chain fragment and a minibody hinge domain between the variable light chain fragment and the constant chain fragment.

In some embodiments, the nucleic acid encoding a minibody further comprises a nucleic acid sequence encoding a linker between the variable heavy chain fragment and the variable light chain fragment.

In some embodiments, the secretion signal comprises amino acid sequence SEQ ID NO:2.

In some embodiments, the nucleic acid encoding a minibody further comprises a nucleic acid sequence encoding a chimeric antigen receptor, a T cell receptor, or a bispecific minibody.

In another aspect, the invention pertains to a minibody comprising a single chain antibody comprising a secretion signal, a variable heavy chain fragment, a variable light chain fragment, a constant chain fragment and a minibody hinge domain between the variable light chain fragment and the constant chain fragment.

In some embodiments, the minibody further comprises a linker between the variable heavy chain fragment and the variable light chain fragment.

In some embodiments, the linker comprises amino acid sequence SEQ ID NO:3.

In some embodiments, the variable heavy chain fragment and the variable light chain fragment bind to an antigen on a tumor cell.

In some embodiments, the variable heavy chain fragment and the variable light chain fragment are independently selected from a fragment from the group consisting of a synthetic antibody, a human antibody, a humanized antibody, and any combination thereof.

In some embodiments, the variable heavy chain fragment comprises amino acid sequence SEQ ID NO:6.

In some embodiments, the variable light chain fragment comprises amino acid sequence SEQ ID NO:7.

In some embodiments, the constant chain fragment is a fragment from an antibody selected from the group consisting of IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 and IgG19.

In some embodiments, the constant chain fragment is a fragment from a heavy chain.

In some embodiments, the constant chain fragment comprises amino acid sequence SEQ ID NO:5.

In some embodiments, the minibody hinge domain comprises a hinge domain selected from the group consisting of alpha, beta or zeta chain of the T-cell receptor; CD28; CD3 epsilon; CD45; CD4; CD5; CD8; CD9; CD16; CD22; CD33; CD37; CD64; CD80; CD86; CD134; CD137; CD154; IgG1; IgG2; IgG3; IgG4; IgG5; IgG6; IgG7; IgG8; IgG9; IgG10; IgG11; IgG12; IgG13; IgG14; IgG15; IgG16; IgG17; IgG18 and IgG19.

In some embodiments, the minibody hinge domain comprises amino acid sequence SEQ ID NO:4.

In some embodiments, the secretion signal comprises amino acid sequence SEQ ID NO:2.

In some embodiments, the minibody comprises amino acid sequence SEQ ID NO:1.

In another aspect, the invention pertains to a composition comprising a modified T cell comprising a nucleic acid encoding a minibody, wherein the minibody comprises a single chain antibody comprising a secretion signal, a variable heavy chain fragment, a variable light chain fragment, a constant chain fragment and a minibody hinge domain between the variable light chain fragment and the constant chain fragment, wherein the modified T cell expresses and secretes the minibody.

In some embodiments, the composition comprises a modified T cell which further comprises a chimeric antigen receptor (CAR), a T cell receptor (TCR), or a bispecific minibody.

In some embodiments, the CAR, TCR, or bispecific minibody is capable of binding to an antigen and the variable heavy chain fragment and the variable light chain fragment of the minibody bind the same antigen.

In another aspect, the invention pertains to a method for generating a modified T cell comprising:

introducing a nucleic acid encoding a minibody into the T cell, wherein the T cell is capable of expressing and secreting the minibody, and the minibody comprises a single chain antibody comprising a secretion signal, a variable heavy chain fragment, a variable light chain fragment, a constant chain fragment and a minibody hinge domain between the variable light chain fragment and the constant chain fragment.

In some embodiments, the population of T cells is comprised within cells selected from the group consisting of peripheral blood mononuclear cells, cord blood cells, a purified population of T cells, and a T cell line.

In some embodiments, peripheral blood mononuclear cells comprises the population of T cells.

In some embodiments, purified T cells comprises the population of T cells.

In some embodiments, introducing the nucleic acid into the T cell comprises electroporating the T cell, transducing the T cell or transfecting the T cell.

In some embodiments, the method for generating a modified T cell further comprises cryopreserving the modified T cell.

In some embodiments, the method for generating a modified T cell further comprises introducing a nucleic acid encoding a chimeric antigen receptor (CAR), a T cell receptor (TCR), or a bispecific minibody into the T cell.

In some embodiments, the CAR, TCR, or bispecific minibody is capable of binding to a tumor antigen and the variable heavy chain fragment and the variable light chain fragment of the minibody bind the same tumor antigen.

In another aspect, the invention pertains to a pharmaceutical composition comprising a modified T cell and a pharmaceutically acceptable carrier, wherein the modified T cell is generated by introducing a nucleic acid encoding a minibody into the T cell, wherein the T cell is capable of expressing and secreting the minibody, and the minibody comprises a single chain antibody comprising a secretion signal, a variable heavy chain fragment, a variable light chain fragment, a constant chain fragment and a minibody hinge domain between the variable light chain fragment and the constant chain fragment.

In another aspect, the invention pertains to a method of treating a disease or condition in a subject comprising administering a population of modified T cells to a subject in need thereof, wherein the modified T cells express a nucleic acid encoding a minibody comprising a secretion signal, a variable heavy chain fragment, a variable light chain fragment and a constant chain fragment, and the modified T cells secrete the minibody.

In another aspect, the invention pertains to a method of treating a condition in a subject, comprising administering to the subject a therapeutically effective amount of a pharmaceutical composition comprising a minibody comprising a single chain antibody comprising a secretion signal, a variable heavy chain fragment, a variable light chain fragment, a constant chain fragment and a minibody hinge domain between the variable light chain fragment and the constant chain fragment.

In another aspect, the invention pertains to a use of a minibody in the manufacture of a medicament for the treatment of an immune response in a subject in need thereof, wherein the minibody comprises a single chain antibody comprising a secretion signal, a variable heavy chain fragment, a variable light chain fragment, a constant chain fragment and a minibody hinge domain between the variable light chain fragment and the constant chain fragment.

In another aspect, the invention pertains to a nucleic acid composition comprising a nucleic acid encoding a minibody and a nucleic acid encoding a chimeric antigen receptor (CAR), a T cell receptor (TCR), or a bispecific minibody, wherein the minibody comprises a single chain antibody comprising a secretion signal, a variable heavy chain fragment, a variable light chain fragment, a constant chain fragment and a minibody hinge domain between the variable light chain fragment and the constant chain fragment.

In some embodiments, the CAR comprises an antigen binding domain, a transmembrane domain, and an intracellular signalling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCER1G), FcR beta (Fc Epsilon Rib), CD79a, CD79b, Fcgamma RIIa, DAP10, and DAP12.

In some embodiments, the costimulatory domain comprises a functional domain of one or more proteins selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R $\alpha$, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain is connected to the transmembrane domain by a CAR hinge region.

In some embodiments, the nucleic acid encoding the CAR further encodes a leader sequence.

In some embodiments, the minibody binds to an immune checkpoint molecule.

In some embodiments, the immune checkpoint molecule is selected from the group consisting of Programmed Death 1 (PD-1), PD-1, PD-L1, PD-L2, Cytotoxic T-Lymphocyte Antigen 4 (CTLA-4), TIM-3, CEACAM (e.g., CEACAM-1, CEACAM-3 and/or CEACAM-5), LAG-3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GALS, adenosine, and TGFR (e.g., TGFR beta).

In some embodiments, the nucleic acid encoding a minibody is disposed on the same nucleic acid molecule as the nucleic acid encoding a chimeric antigen receptor (CAR), a T cell receptor (TCR), or a bispecific minibody.

In some embodiments, the nucleic acid encoding a minibody is disposed on a first nucleic acid molecule and the nucleic acid encoding a chimeric antigen receptor (CAR), a T cell receptor (TCR), or a bispecific minibody is disposed on a second different nucleic acid molecule.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Definitions

Figure 1:
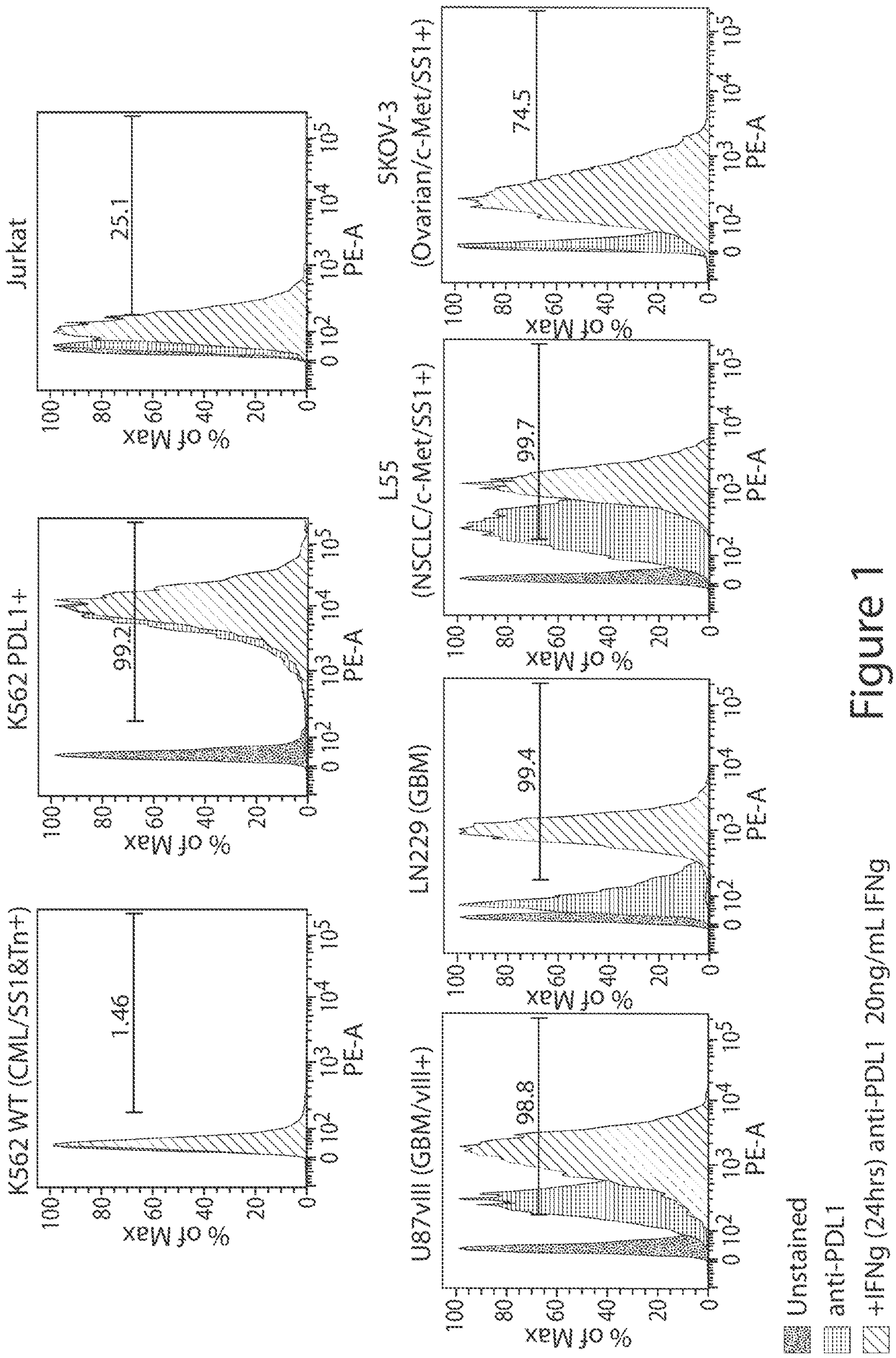
FIG. 1 is a panel of graphs showing that PDL1 expression is constitutively expressed in many tumor cell lines and/or can be upregulated in response to IFNg. Various cell lines were stained for PDL1 expression using anti-PDL1-PE both at normal culture conditions and then at 24 hours post-treatment with 20 ng/mL of IFNg.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

The terms "antibody minibody" and "minibody" are used interchangeably herein and refer to a single chain polypeptide that comprises a secretion signal, a variable heavy chain fragment, a variable light chain fragment and a constant chain fragment. After expression in a cell, the minibody is secreted from the cell by virtue of the secretion signal.

A "bispecific minibody," as used herein, refers to a minibody having binding specificities for at least two different antigenic epitopes. In one embodiment, the epitopes are from the same antigen. In another embodiment, the epitopes are from two different antigens. Methods for making bispecific minibodies are known in the art. For example, bispecific minibodies can be produced recombinantly using the co-expression of two immunoglobulin heavy chain/light chain pairs. See, e.g., Milstein et al. (1983) Nature 305: 537-39. Alternatively, bispecific minibodies can be prepared using chemical linkage. See, e.g., Brennan et al. (1985) Science 229:81. Bispecific minibodies include bispecific antibody fragments. See, e.g., Holliger et al. (1993) Proc. Natl. Acad. Sci. U.S.A. 90:6444-48, Gruber et al. (1994) J. Immunol. 152:5368.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a reduction in the rate of tumor growth, decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system. Auto-antigens comprise, but are not limited to, cellular proteins, phosphoproteins, cellular surface proteins, cellular lipids, nucleic acids, glycoproteins, including cell surface receptors.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Bispecificity," as used herein, refers to a molecule having binding specificities for at least two different binding epitopes. In one embodiment, the epitopes are from the same binding partner. In another embodiment, the epitopes are from two different binding partners. The molecule with bispecificity to different epitopes may include a bispecific minibody.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to CD3-zeta transmembrane and intracellular domain. The specificity of CAR designs may be derived from ligands of receptors (e.g., peptides). In some embodiments, a CAR can target cancers by redirecting the specificity of a T cell expressing the CAR specific for tumor associated antigens.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MEW class I molecule, BTLA a Toll ligand receptor, and any molecule that binds to those listed above.

A "co-stimulatory signal", as used herein, refers to a signal, which in combination with a primary signal, such as TCR/CD3 ligation, leads to T cell proliferation and/or upregulation or downregulation of key molecules.

The term "derived from" refers to being generated, synthesized, or originating from a particular source, such that the derived matter is related to the source. The derived matter does not need to be identical to the particular source. In one embodiment, an antigen is derived from a protein. In another embodiment, a single-chain variable fragment is derived from a monoclonal antibody.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or a RNA like mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

The phrases "an immunologically effective amount", "an anti-immune response effective amount", "an immune response-inhibiting effective amount", or "therapeutic amount" refer to the amount of the composition of the present invention to be administered to a subject which amount is determined by a physician, optionally in consultation with a scientist, in consideration of individual differences in age, weight, immune response, type of disease/condition, and the health of the subject (patient) so that the desired result is obtained in the subject.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human FSHR.

"Similarity" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are similar at that position. The similarity between two sequences is a direct function of the number of matching or similar positions; e.g., if half (e.g., five positions in a polymer ten subunits in length) of the positions in two sequences are similar, the two sequences are 50% similar; if 90% of the positions (e.g., 9 of 10), are matched or similar, the two sequences are 90% similar.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes methods and compositions comprising a minibody. Unlike a full length antibody, the minibody of the present invention comprises a single chain antibody with a secretion signal, a variable heavy chain fragment, a variable light chain fragment, a constant chain fragment and a hinge domain between the variable light chain fragment and the constant chain fragment.

The minibodies described herein include those that are genetically engineered and expressed in primary lymphocytes, and capable of inducing intracellular production and secretion in vivo by the lymphocyte. Using tumor or disease-targeted lymphocytes, the present invention can provide the advantage of a continuous supply of antibody/minibody/bispecific minibody at a desired anatomic site. This offers the potential to achieve high localized levels of continuous antibody/minibody, while also reducing systemic levels of drug otherwise required to reach efficacious levels while also reducing off-site toxicity. Since they are a 'living drug', this treatment could be a single administration with the potential to continue indefinitely over the lifetime of the patient.

Minibody

The minibody of the present invention comprises a single chain antibody having a secretion signal, a variable heavy chain fragment, a variable light chain fragment, and a constant chain fragment. The minibody of the present invention is novel since the variable light chain fragment and the constant chain fragment are connected to one another through a hinge domain. Some aspects of the invention encompass a nucleic acid encoding a minibody, a composition comprising a minibody, and a modified T cell comprising a minibody. In an exemplary embodiment, the minibody binds and blocks an inhibitory receptor on a T cell.

Variable Chain Fragment

In one embodiment, the minibody is capable of binding to an antigen, such as a tumor antigen or a stimulating or inhibitory molecule on an immune effector or regulatory cell, such as a T or B lymphocyte, macrophage, dendritic cell or myeloid-derived suppressor cell, or other CD45 positive bone-marrow derived progenitor. The minibody binds the antigen through the variable heavy chain fragment and/or the variable light chain fragment. The variable heavy chain fragment and/or variable light chain fragment may comprise a fragment from a synthetic antibody, human antibody, a humanized antibody, and any combination thereof.

The minibody can bind an antigen from a diseased cell, such as a tumor specific antigen. The antigen may include, but is not limited to, CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the minibody binds to one or more immune checkpoint molecule(s) or immunomodulator(s). Immune checkpoint molecules useful in the methods and compositions of the present invention include, but are not limited to, Programmed Death 1 (PD-1), PD-1, PD-L1, PD-L2, Cytotoxic T-Lymphocyte Antigen 4 (CTLA-4), TIM-3, CEACAM (e.g., CEACAM-1, CEACAM-3 and/or CEACAM-5), LAG-3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GALS, adenosine, TGFR (e.g., TGFR beta). In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5) or CTLA-4, or any combination thereof).

In one embodiment, the variable heavy chain fragment comprises a fragment of an anti-PD1 antibody. In another embodiment, the variable heavy chain fragment comprises amino acid sequence QVQLQESGPGVVKPSGTLSLTCAISGGSIGSGGSIRSTRWWSWVRQSPGKGLEWIGEIYH SGSTNYNPSLKSRVTISLDKSRNHFSLRLNSVTAADTAVYYCARQDYGDSGDWYFDLW GKGTMVTVSS (SEQ ID NO:6). In yet another embodiment, the variable light chain fragment comprises a fragment of an anti-PD1 antibody. In still another embodiment, the variable light chain fragment comprises amino acid sequence

```
                                        (SEQ ID NO: 7)
NFMLTQPHSVSESPGKTVTISCTRSSGSIASNSVQWYQQRPGS

SPTTVIYEDNQRPSGVPDRFSGSIDSSSNSASLTVSGLKTEDE

ADYYCQSSDSSAVVFGSGTKLTVL.
```

In one embodiment, the nucleic acid encoding the minibody comprises a nucleic acid encoding a variable heavy chain fragment of an anti-PD1 heavy chain. In another embodiment, the nucleic acid encoding a variable heavy chain fragment comprises the nucleic acid sequence encoding SEQ ID NO:6. In yet another embodiment, the nucleic acid encoding the minibody comprises nucleic acid encoding a variable light chain fragment of an anti-PD1 light chain. In still another embodiment, the nucleic acid encoding a variable light chain fragment comprises the nucleic acid sequence encoding SEQ ID NO:7.

Constant Domain

The minibody further comprises a constant domain. The constant domain can be a fragment from an antibody such as, but not limited to, IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19. The constant domain can be a fragment from any heavy or light chain of an antibody. A heavy-chain constant domain that corresponds to the different classes of antibodies are denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

In one embodiment, the constant chain fragment comprises an IgG constant domain and comprises the amino acid sequence

```
                                        (SEQ ID NO: 5)
GQPREPQVYTLPPSRDELTKNQVSLTCLVKGFYPSDIAVEWES

NGQPENNYKTTPPVLDSDGSFFLYSKLTVDKSRWQQGNVFSCS

VMHEALHNHYTQKSLSLSPGK.
```

In another embodiment, the nucleic acid encoding the minibody comprises a nucleic acid encoding a constant chain fragment, wherein the constant chain fragment comprises the nucleic acid sequence encoding SEQ ID NO:5.

Hinge Domain

The minibody also includes a hinge domain between the variable light chain fragment and the constant chain fragment. Minibody hinge, minibody hinge domain, and hinge domain are used interchangeably herein. The hinge domain can be derived from either a natural or a synthetic source. When the source is natural, the hinge domain may be derived from any membrane-bound or transmembrane protein. Hinges of particular use in this invention may be derived from (i.e. comprise at least the hinge domain(s) of) a receptor or cell surface molecule, including but not limited to, the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, and CD154. In some instances, a variety of human hinges can be employed as well including the human Ig (immunoglobulin) hinge, such as but not limited to, a hinge domain from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19.

In one embodiment, the hinge domain may comprise up to 300 amino acids, for example, from 10 to 100 amino acids, or from 20 to 50 amino acids.

In one embodiment, the hinge domain comprises a hinge from IgG. In another embodiment, the hinge domain comprises the amino acid sequence EPKSCDKTHTCPPCGGGSSGGGSG (SEQ ID NO:4). In yet another embodiment, the nucleic acid encoding the minibody comprises a nucleic acid encoding a hinge domain from IgG. In still another embodiment, the hinge domain nucleic acid comprises the nucleic acid sequence encoding SEQ ID NO:4.

Secretion Signal Domain

The minibody also includes a secretion signal. In one embodiment, the secretion signal comprises the amino acid sequence METDTLLLWVLLLWVPGSTG (SEQ ID NO:2). In another embodiment, the nucleic acid encoding the minibody comprises a nucleic acid encoding the secretion signal, wherein the secretion signal comprises the nucleic acid sequence encoding SEQ ID NO:2.

Other Domains

The minibody may include a linker or spacer domain. In one embodiment, the minibody comprises a linker between the variable heavy chain fragment and the variable light chain fragment. As used herein, the term "linker" or "spacer domain" generally means any oligo- or polypeptide that functions to link one domain to another in the polypeptide chain. In one embodiment, the linker or spacer domain may comprise up to 300 amino acids, for example, from 5 to 75 amino acids, or from 10 to 50 amino acids. In another embodiment, a short oligo- or polypeptide linker, for example, from 4 and 20 amino acids in length may form the linkage between the variable heavy chain fragment and the variable light chain fragment. An example of a linker includes a glycine-serine polypeptide. In one embodiment, the linker comprises the amino acid sequence GGGSGGGSGGGSGGGSN (SEQ ID NO:3). In another embodiment, the nucleic acid encoding the minibody comprises a nucleic acid encoding a linker, wherein the linker comprises the nucleic acid sequence encoding SEQ ID NO:3.

The minibody may also include a protein tag or label. In one embodiment, the protein tag or label is attached to the N' terminus of the minibody. In another embodiment, the protein tag or label is at the C' terminus of the minibody. In yet another embodiment, the protein tag or label is between a variable domain and a constant domain of the minibody. Some nonlimiting examples of protein tags or labels may include myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, green fluorescent protein, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

Combination Compositions

The present invention also includes a composition comprising a minibody in combination with a TCR, a CAR or a bispecific minibody, or unmodified lymphocytes. Thus, the present invention encompasses a nucleic acid encoding a minibody and a nucleic acid encoding a TCR, CAR or bispecific minibody, and a modified T cell capable of expressing a minibody and a TCR, CAR or bispecific minibody.

One or more domains or a fragment of a domain of the TCR, CAR or bispecific minibody may be human. In one embodiment, the present invention includes a fully human TCR, CAR or bispecific minibody. The nucleic acid sequences encoding the desired domains can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as a cloned molecule.

T Cell Receptor

The present invention also includes a composition comprising a minibody and a TCR. The TCR generally comprises six different membrane bound chains that form the TCR heterodimer responsible for ligand recognition. TCRs exist in alpha/beta and gamma/delta forms, which are structurally similar but have distinct anatomical locations and functions.

Each chain is composed of two extracellular domains, a variable and constant domain. In one embodiment, the TCR comprises at least one murine constant region. The constant domain is proximal to the cell membrane, followed by a transmembrane domain and a short cytoplasmic tail. In one embodiment, the modified TCR comprises a cytoplasmic domain including a co-stimulatory signaling domain, such as a 4-1BB co-stimulatory signaling domain. The variable domain contributes to the determination of the particular antigen and MHC molecule to which the TCR has binding specificity. In turn, the specificity of a T cell for a unique antigen-MHC complex resides in the particular TCR expressed by the T cell.

Each of the constant and variable domains may include an intra-chain disulfide bond. In one embodiment, the TCR comprises at least one disulfide bond. The variable domains include the highly polymorphic loops analogous to the complementarity determining regions (CDRs) of antibodies. The diversity of TCR sequences is generated via somatic rearrangement of linked variable (V), diversity (D), joining (J), and constant genes.

Functional alpha and gamma chain polypeptides are formed by rearranged V-J-C regions, whereas beta and delta chains consist of V-D-J-C regions. The extracellular constant domain includes a membrane proximal region and an immunoglobulin region.

In one embodiment, the TCR includes a wildtype TCR, a high affinity TCR, and a chimeric TCR. When the TCR is modified, it may have higher affinity for the target cell surface antigen than a wildtype TCR. In embodiments where the TCR is a chimeric TCR, the TCR may be engineered to comprise specificity to a target cell antigen. The target cell surface antigen may include any type of ligand that defines the surface of a target cell, such as a tumor cell antigen. Thus examples of cell surface markers that may act as ligands for the TCR include antigens associated with viral, bacterial and parasitic infections, autoimmune disease and cancer cells. In one embodiment, the target cell surface antigen includes any tumor associated antigen (TAA) and viral antigen, disease cell associated antigen, or any fragment thereof.

In one embodiment, the TCR binds to a tumor antigen, such as an antigen that is specific for a tumor or cancer of interest. In another embodiment, the TCR is capable of binding to an antigen and the variable heavy chain fragment and the variable light chain fragment of the minibody bind the same antigen.

Techniques for engineering and expressing T cell receptors include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

CAR Molecules

The present invention also includes a composition comprising a minibody and a CAR. The CAR comprises an antigen binding domain, a transmembrane domain and an intracellular domain of a co-stimulatory molecule.

Example of CARs are described in U.S. Pat. Nos. 8,911,993, 8,906,682, 8,975,071, 8,916,381, 9,102,760, 9,101,584, and 9,102,761, all of which are incorporated herein by reference in their entireties.

In one embodiment, the CAR comprises an antigen binding domain that binds to an antigen on a target cell. Examples of cell surface markers that may act as an antigen that binds to the antigen binding domain of the CAR include those associated with viral, bacterial and parasitic infections, autoimmune disease, and cancer cells.

The choice of antigen binding domain depends upon the type and number of antigens that are present on the surface of a target cell. For example, the antigen binding domain may be chosen to recognize an antigen that acts as a cell surface marker on a target cell associated with a particular disease state.

In one embodiment, the antigen binding domain binds to a tumor antigen, such as an antigen that is specific for a tumor or cancer of interest. In another embodiment, the antigen binding domain of the CAR is capable of binding to an antigen and the variable heavy chain fragment and the variable light chain fragment of the minibody bind the same antigen.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof.

In one aspect, the antigen binding domain of a CAR described herein is a scFv antibody fragment. In one aspect, such antibody fragments are functional in that they retain the equivalent binding affinity, e.g., they bind the same antigen with comparable affinity, as the IgG antibody from which it is derived. In other embodiments, the antibody fragment has a lower binding affinity, e.g., it binds the same antigen with a lower binding affinity than the antibody from which it is derived, but is functional in that it provides a biological response described herein. In one embodiment, the CAR molecule comprises an antibody fragment that has a binding affinity KD of $10^{-4}$ M to $10^{-8}$M, e.g., $10^{-5}$M to $10^{-7}$ M, e.g., $10^{-6}$ M or $10^{-7}$ M, for the target antigen. In one embodiment, the antibody fragment has a binding affinity that is at least five-fold, 10-fold, 20-fold, 30-fold, 50-fold, 100-fold or 1,000-fold less than a reference antibody, e.g., an antibody described herein.

In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In one aspect, the antigen binding domain of the CAR is a scFv antibody fragment that is humanized compared to the murine sequence of the scFv from which it is derived.

In one aspect, the antigen binding domain of a CAR of the invention (e.g., a scFv) is encoded by a nucleic acid molecule whose sequence has been codon optimized for expression in a mammalian cell. In one aspect, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the CARs of the invention combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the antigen binding domain binds to a tumor antigen as described herein.

Furthermore, the present invention provides CARs and CAR-expressing cells and their use in medicaments or methods for treating, among other diseases, cancer or any malignancy or autoimmune diseases involving cells or tissues which express a tumor antigen as described herein.

In one aspect, the CAR of the invention can be used to eradicate a normal cell that express a tumor antigen as described herein, thereby applicable for use as a cellular conditioning therapy prior to cell transplantation. In one aspect, the normal cell that expresses a tumor antigen as described herein is a normal stem cell and the cell transplantation is a stem cell transplantation.

In one aspect, the invention provides an immune effector cell (e.g., T cell, NK cell) engineered to express a chimeric antigen receptor (CAR), wherein the engineered immune effector cell exhibits an antitumor property. A preferred antigen is a cancer associated antigen (i.e., tumor antigen) described herein. In one aspect, the antigen binding domain of the CAR comprises a partially humanized antibody fragment. In one aspect, the antigen binding domain of the CAR comprises a partially humanized scFv. Accordingly, the invention provides CARs that comprises a humanized antigen binding domain and is engineered into a cell, e.g., a T cell or a NK cell, and methods of their use for adoptive therapy.

In one aspect, the CARs of the invention comprise at least one intracellular domain selected from the group of a CD137 (4-1BB) signaling domain, a CD28 signaling domain, a CD27 signal domain, a CD3zeta signal domain, and any combination thereof. In one aspect, the CARs of the invention comprise at least one intracellular signaling domain is from one or more costimulatory molecule(s) other than a CD137 (4-1BB) or CD28.

Sequences of some examples of various components of CARs of the instant invention is listed in Table 1, where aa stands for amino acids, and na stands for nucleic acids that encode the corresponding peptide.

TABLE 1

Sequences of various components of CAR (aa—amino acids, na—nucleic acids that encodes the corresponding protein)

| SEQ ID NO | Descrip-tion | Sequence | Corresp. To huCD19 |
|---|---|---|---|
| 400 | EF-1 promoter | CGTGAGGCTCCGGTGCCCGTCAGTG<br>GGCAGAGCGCACATCGCCCACAGTC<br>CCCGAGAAGTTGGGGGGAGGGGTCG<br>GCAATTGAACCGGTGCCTAGAGAAG<br>GTGGCGCGGGGTAAACTGGGAAAGT<br>GATGTCGTGTACTGGCTCCGCCTTT<br>TTCCCGAGGGTGGGGGAGAACCGTA<br>TATAAGTGCAGTAGTCGCCGTGAAC<br>GTTCTTTTTCGCAACGGGTTTGCCG<br>CCAGAACACAGGTAAGTGCCGTGTG<br>TGGTTCCCGCGGGCCTGGCCTCTTT<br>ACGGGTTATGGCCCTTGCGTGCCTT<br>GAATTACTTCCACCTGGCTGCAGTA<br>CGTGATTCTTGATCCCGAGCTTCGG<br>GTTGGAAGTGGGTGGGAGAGTTCGA<br>GGCCTTGCGCTTAAGGAGCCCCTTC<br>GCCTCGTGCTTGAGTTGAGGCCTGG<br>CCTGGGCGCTGGGGCCGCCGCGTGC<br>GAATCTGGTGGCACCTTCGCGCCTG<br>TCTCGCTGCTTTCGATAAGTCTCTA<br>GCCATTTAAAATTTTTGATGACCTG<br>CTGCGACGCTTTTTTTCTGGCAAGA<br>TAGTCTTGTAAATGCGGGCCAAGAT<br>CTGCACACTGGTATTTCGGTTTTTG<br>GGGCCGCGGGCGGCGACGGGGCCCG<br>TGCGTCCCAGCGCACATGTTCGGCG<br>AGGCGGGGCCTGCGAGCGCGGCCAC<br>CGAGAATCGGACGGGGGTAGTCTCA<br>AGCTGGCCGGCCTGCTCTGGTGCCT<br>GGCCTCGCGCCGCCGTGTATCGCCC<br>CGCCCTGGGCGGCAAGGCTGGCCCG<br>GTCGGCACCAGTTGCGTGAGCGGAA<br>AGATGGCCGCTTCCCGGCCCTGCTG<br>CAGGGAGCTCAAAATGGAGGACGCG<br>GCGCTCGGGAGAGCGGGCGGGTGAG<br>TCACCCACACAAAGGAAAAGGGCCT<br>TTCCGTCCTCAGCCGTCGCTTCATG<br>TGACTCCACGGAGTACCGGGCGCCG<br>TCCAGGCACCTCGATTAGTTCTCGA<br>GCTTTTGGAGTACGTCGTCTTTAGG<br>TTGGGGGGAGGGGTTTTATGCGATG<br>GAGTTTCCCCACACTGAGTGGGTGG<br>AGACTGAAGTTAGGCCAGCTTGGCA<br>CTTGATGTAATTCTCCTTGGAATTT<br>GCCCTTTTTGAGTTTGGATCTTGGT<br>TCATTCTCAAGCCTCAGACAGTGGT<br>TCAAAGTTTTTTTCTTCCATTTCAG<br>GTGTCGTGA | 100 |
| 401 | Leader (aa) | MALPVTALLLPLALLLHAARP | 13 |
| 402 | Leader (na) | ATGGCCCTGCCTGTGACAGCCCTGC<br>TGCTGCCTCTGGCTCTGCTGCTGCA<br>TGCCGCTAGACCC | 54 |
| 518 | Leader (na) | ATGGCCCTCCCTGTCACCGCCCTGC<br>TGCTTCCGCTGGCTCTTCTGCTCCA<br>CGCCGCTCGGCCC | |
| 519 | Leader (na) | ATGGCCTTACCAGTGACCGCCTTGC<br>TCCTGCCGCTGGCCTTGCTGCTCCA | |

TABLE 1-continued

Sequences of various components of CAR (aa—amino acids, na—nucleic acids that encodes the corresponding protein)

| SEQ ID NO | Descrip-tion | Sequence | Corresp. To huCD19 |
|---|---|---|---|
| | | CGCCGCCAGGCCG | |
| 403 | CD8 hinge (aa) | TTTPAPRPPTPAPTIASQPLSLRPE<br>ACRPAAGGAVHTRGLDFACD | 14 |
| 404 | CD8 hinge (na) | ACCACGACGCCAGCGCCGCGACCAC<br>CAACACCGGCGCCCACCATCGCGTC<br>GCAGCCCCTGTCCCTGCGCCCAGAG<br>GCGTGCCGGCCAGCGGCGGGGGGCG<br>CAGTGCACACGAGGGGGCTGGACTT<br>CGCCTGTGAT | 55 |
| 405 | Ig4 hinge (aa) | ESKYGPPCPPCPAPEFLGGPSVFLF<br>PPKPKDTLMISRTPEVTCVVVDVSQ<br>EDPEVQFNWYVDGVEVHNAKTKPRE<br>EQFNSTYRVVSVLTVLHQDWLNGKE<br>YKCKVSNKGLPSSIEKTISKAKGQP<br>REPQVYTLPPSQEEMTKNQVSLTCL<br>VKGFYPSDIAVEWESNGQPENNYKT<br>TPPVLDSDGSFFLYSRLTVDKSRWQ<br>EGNVFSCSVMHEALHNHYTQKSLSL<br>SLGKM | 102 |
| 406 | Ig4 hinge (na) | GAGAGCAAGTACGGCCCTCCCTGCC<br>CCCCTTGCCCTGCCCCCGAGTTCCT<br>GGGCGGACCCAGCGTGTTCCTGTTC<br>CCCCCCAAGCCCAAGGACACCCTGA<br>TGATCAGCCGGACCCCCGAGGTGAC<br>CTGTGTGGTGGTGGACGTGTCCCAG<br>GAGGACCCCGAGGTCCAGTTCAACT<br>GGTACGTGGACGGCGTGGAGGTGCA<br>CAACGCCAAGACCAAGCCCCGGGAG<br>GAGCAGTTCAATAGCACCTACCGGG<br>TGGTGTCCGTGCTGACCGTGCTGCA<br>CCAGGACTGGCTGAACGGCAAGGAA<br>TACAAGTGTAAGGTGTCCAACAAGG<br>GCCTGCCCAGCAGCATCGAGAAAAC<br>CATCAGCAAGGCCAAGGGCCAGCCT<br>CGGGAGCCCCAGGTGTACACCCTGC<br>CCCCTAGCCAAGAGGAGATGACCAA<br>GAACCAGGTGTCCCTGACCTGCCTG<br>GTGAAGGGCTTCTACCCCAGCGACA<br>TCGCCGTGGAGTGGGAGAGCAACGG<br>CCAGCCCGAGAACAACTACAAGACC<br>ACCCCCCCTGTGCTGGACAGCGACG<br>GCAGCTTCTTCCTGTACAGCCGGCT<br>GACCGTGGACAAGAGCCGGTGGCAG<br>GAGGGCAACGTCTTTAGCTGCTCCG<br>TGATGCACGAGGCCCTGCACAACCA<br>CTACACCCAGAAGAGCCTGAGCCTG<br>TCCCTGGGCAAGATG | 103 |
| 407 | IgD hinge (aa) | RWPESPKAQASSVPTAQPQAEGSLA<br>KATTAPATTRNTGRGGEEKKKEKEK<br>EEQEERETKTPECPSHTQPLGVYLL<br>TPAVQDLWLRDKATFTCFVVGSDLK<br>DAHLTWEVAGKVPTGGVEEGLLERH<br>SNGSQSQHSRLTLPRSLWNAGTSVT<br>CTLNHPSLPPQRLMALREPAAQAPV<br>KLSLNLLASSDPPEAASWLLCEVSG<br>FSPPNILLMWLEDQREVNTSGFAPA<br>RPPPQPGSTTFWAWSVLRVPAPPSP<br>QPATYTCVVSHEDSRTLLNASRSLE<br>VSYVTDH | 47 |
| 408 | IgD hinge (na) | AGGTGGCCCGAAAGTCCCAAGGCCC<br>AGGCATCTAGTGTTCCTACTGCACA<br>GCCCCAGGCAGAAGGCAGCCTAGCC<br>AAAGCTACTACTGCACCTGCCACTA<br>CGCGCAATACTGGCCGTGGCGGGGA<br>GGAGAAGAAAAAGGAGAAAGAGAAA<br>GAAGAACAGGAAGAGAGGGAGACCA | 48 |

TABLE 1-continued

Sequences of various components of CAR (aa—amino acids, na—nucleic acids that encodes the corresponding protein)

| SEQ ID NO | Description | Sequence | Corresp. To huCD19 |
|---|---|---|---|
| | | AGACCCCTGAATGTCCATCCCATACCCAGCCGCTGGGCGTCTATCTCTTGACTCCCGCAGTACAGGACTTGTGGCTTAGAGATAAGGCCACCTTTACATGTTTCGTCGTGGGCTCTGACCTGAAGGATGCCCATTTGACTTGGGAGGTTGCCGGAAAGGTACCCACAGGGGGGGTTGAGGAAGGGTTGCTGGAGCGCCATTCCAATGGCTCTCAGAGCCAGCACTCAAGACTCACCCTTCCGAGATCCCTGTGGAACGCCGGGACCTCTGTCACATGTACTCTAAATCATCCTAGCCTGCCCCCACAGCGTCTGATGGCCCTTAGAGAGCCAGCCGCCCAGGCACCAGTTAAGCTTAGCCTGAATCTGCTCGCCAGTAGTGATCCCCCAGAGGCCGCCAGCTGGCTCTTATGCGAAGTGTCCGGCTTTAGCCCGCCCAACATCTTGCTCATGTGGCTGGAGGACCAGCGAGAAGTGAACACCAGCGGCTTCGCTCCAGCCCGGCCCCCACCCCAGCCGGGTTCTACCACATTCTGGGCCTGGAGTGTCTTAAGGGTCCCAGCACCACCTAGCCCCCAGCCAGCCACATACACCTGTGTTGTGTCCCATGAAGATAGCAGGACCCTGCTAAATGCTTCTAGGAGTCTGGAGGTTTCCTACGTGACTGACCATT | |
| 510 | GS hinge/linker (aa) | GGGGSGGGGS | 49 |
| 511 | GS hinge/linker (na) | GGTGGCGGAGGTTCTGGAGGTGGAGGTTCC | 50 |
| 12 | CD8TM (aa) | IYIWAPLAGTCGVLLLSLVITLYC | 15 |
| 13 | CD8 TM (na) | ATCTACATCTGGGCGCCCTTGGCCGGGACTTGTGGGGTCCTTCTCCTGTCACTGGTTATCACCCTTTACTGC | 56 |
| 520 | CD8 TM (na) | ATCTACATTTGGGCCCCTCTGGCTGGTACTTGCGGGGTCCTGCTGCTTTCACTCGTGATCACTCTTTACTGT | |
| 14 | 4-1BB intracellular domain (aa) | KRGRKKLLYIFKQPFMRPVQTTQEEDGCSCRFPEEEEGGCEL | 16 |
| 15 | 4-1BB intracellular domain (na) | AAACGGGGCAGAAAGAAACTCCTGTATATATTCAAACAACCATTTATGAGACCAGTACAAACTACTCAAGAGGAAGATGGCTGTAGCTGCCGATTTCCAGAAGAAGAAGAAGGAGGATGTGAACTG | 60 |
| 521 | 4-1BB intracellular domain (na) | AAGCGCGGTCGGAAGAAGCTGCTGTACATCTTTAAGCAACCCTTCATGAGGCCTGTGCAGACTACTCAAGAGGAGGACGGCTGTTCATGCCGGTTCCCAGAGGAGGAGGAAGGCGGCTGCGAACTG | |
| 16 | CD27 (aa) | QRRKYRSNKGESPVEPAEPCRYSCPREEEGSTIPIQEDYRKPEPACSP | 51 |
| 17 | CD27 (na) | AGGAGTAAGAGGAGCAGGCTCCTGCACAGTGACTACATGAACATGACTCCCCGCCGCCCCGGGCCCACCCGCAAGCATTACCAGCCCTATGCCCCACCACGCGACTTCGCAGCCTATCGCTCC | 52 |
| 18 | CD3-zeta (aa) | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 17 |
| 19 | CD3-zeta (na) | AGAGTGAAGTTCAGCAGGAGCGCAGACGCCCCCGCGTACAAGCAGGGCCAGAACCAGCTCTATAACGAGCTCAATCTAGGACGAAGAGAGGAGTACGATGTTTTGGACAAGAGACGTGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGTCTCAGTACAGCCACCAAGGACACCTACGACGCCCTTCACATGCAGGCCCTGCCCCCTCGC | 101 |
| 20 | CD3-zeta (aa) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 43 |
| 21 | CD3-zeta (na) | AGAGTGAAGTTCAGCAGGAGCGCAGACGCCCCCGCGTACCAGCAGGGCCAGAACCAGCTCTATAACGAGCTCAATCTAGGACGAAGAGAGGAGTACGATGTTTTGGACAAGAGACGTGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGTCTCAGTACAGCCACCAAGGACACCTACGACGCCCTTCACATGCAGGCCCTGCCCCCTCGC | 44 |
| 522 | CD3-zeta (na) | CGCGTGAAATTCAGCCGCAGCGCAGATGCTCCAGCCTACAAGCAGGGGCAGAACCAGCTCTACAACGAACTCAATCTTGGTCGGAGAGAGGAGTACGACGTGCTGGACAAGCGGAGAGGACGGGACCCAGAAATGGGCGGGAAGCCGCGCAGAAAGAATCCCCAAGAGGGCCTGTACAACGAGCTCCAAAAGGATAAGATGGCAGAAGCCTATAGCGAGATTGGTATGAAAGGGGAACGCAGAAGAGGCAAAGGCCACGACGGACTGTACCAGGGACTCAGCACCGCCACCAAGGACACCTATGACGCTCTTCACATGCAGGCCCTGCCGCCTCGG | |
| 22 | linker | GGGGS | 18 |
| 23 | linker | GGTGGCGGAGGTTCTGGAGGTGGAGGTTCC | 50 |
| 24 | PD-1 extracellular domain (aa) | Pgwfldspdrpwnpptfspallvvtegdnatftcsfsntsesfvlnwyrmspsnqtdklaafpedrsqpgqdcrfrvtqlpngrdfhmsvvrarrndsgtylcgaislapkaqikeslraelrvterraevptahpspsprpagqfqtlv | |

TABLE 1-continued

Sequences of various components of CAR (aa—amino acids, na—nucleic acids that encodes the corresponding protein)

| SEQ ID NO | Description | Sequence | Corresp. To huCD19 |
| --- | --- | --- | --- |
| 25 | PD-1 extracellular domain (na) | Cccggatggtttctggactctccgg<br>atcgcccgtggaatcccccaacctt<br>ctcaccggcac<br>tcttggttgtgactgagggcgataa<br>tgcgaccttcacgtgctcgttctcc<br>aacacctccgaatcattcgtgctga<br>actggtaccgcatgagcccgtcaaa<br>ccagaccgacaagctcgccgcgttt<br>ccggaagatcggtcgcaaccgggac<br>aggattgtcggttccgcgtgactca<br>actgccgaatggcagagacttccac<br>atgagcgtggtccgcgctaggcgaa<br>acgactccgggacctacctgtgcgg<br>agccatctcgctggcgcctaaggcc<br>caaatcaaagagagcttgagggccg<br>aactgagagtgaccgagcgcagagc<br>tgaggtgccaactgcacatccatcc<br>ccatcgcctcggcctgcggggcagt<br>ttcagaccctggtc | |
| 26 | PD-1 CAR (aa) with 1 signal PD-1 CAR (na) | Malpvtalllplalllhaarppgwf<br>ldspdrpwnpptfspallvvtegdn<br>atftcsfsntsesfvlnwyrmspsn<br>qtdklaafpedrsqpgqdcrfrvtq<br>lpngrdfhmsvvrarrndsgttias<br>qplslrpeacrpaaggavhtrgldf<br>acdiyiwaplagtcgvlllslvitl<br>yckrgrkkllyifkqpfmrpvqttq<br>eedgcscrfpeeeeggcelrvkfsr<br>sadapaykqgqnqlynelnlgrree<br>ydvldkrrgrdpemggkprrknpqe<br>glynelqkdkmaeayseigmkgerr<br>rgkghdglyqglstatkdtydalhm<br>qalppr | |
| 27 | | Atggccctccctgtcactgccctgc<br>ttctcccctcgcactcctgctcca<br>cgccgctagaccacccggatggttt<br>ctggactctccggatcgcccgtgga<br>atcccccaaccttctcaccggcact<br>cttggttgtgactgagggcgataat<br>gcgaccttcacgtgctcgttctcca<br>acacctccgaatcattcgtgctgaa<br>ctggtaccgcatgagcccgtcaaac<br>cagaccgacaagctcgccgcgtttc<br>cggaagatcggtcgcaaccgggaca<br>ggattgtcggttccgcgtgactcaa<br>ctgccgaatggcagagacttccaca<br>tgagcgtggtccgcgctaggcgaaa<br>cgactccgggacctacctgtgcgga<br>gccatctcgctggcgcctaaggccc<br>aaatcaaagagagcttgagggccga<br>actgagagtgaccgagcgcagagct<br>gaggtgccaactgcacatccatccc<br>catcgcctcggcctgcggggcagtt<br>tcagaccctggtcacgaccactccg<br>gcgccgcgcccaccgactccggccc<br>caactatcgcgagccagcccctgtc<br>gctgaggccggaagcatgccgccct<br>gccgccggaggtgctgtgcataccc<br>ggggattggacttcgcatgcgacat<br>ctacatttgggctcctctcgccgga<br>acttgtggcgtgctccttctgtccc<br>tggtcatcaccctgtactgcaagcg<br>gggtoggaaaaagcttctgtacatt<br>ttcaagcagcccttcatgaggcccg<br>tgcaaaccacccaggaggaggacgg<br>ttgctcctgccggttccccgaagag<br>gaagaaggaggttgcgagctgcgcg<br>tgaagttctcccggagcgccgacgc<br>cccgcctataagcagggccagaac<br>cagctgtacaacgaactgaacctgg<br>gacggcgggaagagtacgatgtgct<br>ggacaagcggcgcggccgggacccc<br>gaaatgggggggaagcctagaagaaa<br>gaaccctcaggaaggcctgtataac<br>gagctgcagaaggacaagatggccg<br>aggcctactccgaaattgggatgaa<br>gggagagcggcggaggggaaagggg<br>cacgacggcctgtaccaaggactgt<br>ccaccgccaccaaggacacatacga<br>tgccctgcacatgcaggcccttccc<br>cctcgc | |
| 28 | linker | (Gly-Gly-Gly-Ser)$_n$,<br>where n = 1-10 | 105 |
| 29 | linker | (Gly4 Ser)4 | 106 |
| 30 | linker | (Gly4 Ser)3 | 107 |
| 31 | linker | (Gly3Ser) | 108 |
| 32 | polyA | (aaaaaaaaaa)$_n$,<br>where n = 200 | 118 |
| 33 | polyA | (aaaaaaaaaa)$_n$,<br>where n = 15 | 104 |
| 34 | polyA | (aaaaaaaaaa)$_n$,<br>where n = 500 | 109 |
| 35 | polyA | (tttttttttt)$_n$,<br>where n = 10 | 110 |
| 36 | polyA | (tttttttttt)$_n$,<br>where n = 500 | 111 |
| 37 | polyA | (aaaaaaaaaa)$_n$,<br>where n = 500 | 112 |
| 38 | polyA | (aaaaaaaaaa)$_n$,<br>where n = 40 | 113 |
| 39 | PD1 CAR (aa) | Pgwfldspdrpwnpptfspallvvt<br>egdnatftcsfsntsesfvlnwyrm<br>spsnqtdklaafpedrsqpgqdcrf<br>rvtqlpngrdfhmsvvrarrndsgt<br>ylcgaislapkaqikeslraelrvt<br>erraevptahpspsprpagqfqtlv<br>tttpaprpptpaptiasqplslrpe<br>acrpaaggavhtrgldfacdiyiwa<br>plagtcgvlllslvitlyckrgrkk<br>llyifkqpfmrpvqttqeedgcscr<br>fpeeeeggcelrvkfsrsadapayk<br>qgqnqlynelnlgrreeydvldkrr<br>grdpemggkprrknpqeglynelqk<br>dkmaeayseigmkgerrrgkghdgl<br>yqglstatkdtydalhmqalppr | |
| 505 | CD28 costimulatory domain (aa) | RSKRSRLLHSDYMNMTPRRPGPTRK<br>HYQPYAPPRDFAAYRS | |
| 600 | CD28 costimulatory domain (na) | aggagtaagaggagcaggctcctgc<br>acagtgactacatgaacatgactcc<br>ccgccgccccgggcccacccgcaag<br>cattaccagccctatgccccaccac<br>gcgacttcgcagcctatcgctcc | |

Cancer Associated Antigens

In certain aspects, the present invention provides immune effector cells (e.g., T cells, NK cells) that are engineered to contain one or more CARs that direct the immune effector cells to cancer. This is achieved through an antigen binding domain on the CAR that is specific for a cancer associated antigen. There are two classes of cancer associated antigens (tumor antigens) that can be targeted by the CARs of the instant invention: (1) cancer associated antigens that are expressed on the surface of cancer cells; and (2) cancer associated antigens that itself is intracelluar, however, a fragment of such antigen (peptide) is presented on the surface of the cancer cells by MHC (major histocompatibility complex).

Accordingly, the present invention provides CARs that target the following cancer associated antigens (tumor antigens): CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

Tumor-Supporting Antigens

A CAR described herein can comprise an antigen binding domain (e.g., antibody or antibody fragment, TCR or TCR fragment) that binds to a tumor-supporting antigen (e.g., a tumor-supporting antigen as described herein). In some embodiments, the tumor-supporting antigen is an antigen present on a stromal cell or a myeloid-derived suppressor cell (MDSC). Stromal cells can secrete growth factors to promote cell division in the microenvironment. MDSC cells can inhibit T cell proliferation and activation. Without wishing to be bound by theory, in some embodiments, the CAR-expressing cells destroy the tumor-supporting cells, thereby indirectly inhibiting tumor growth or survival.

In embodiments, the stromal cell antigen is chosen from one or more of: bone marrow stromal cell antigen 2 (BST2), fibroblast activation protein (FAP) and tenascin. In an embodiment, the FAP-specific antibody is, competes for binding with, or has the same CDRs as, sibrotuzumab. In embodiments, the MDSC antigen is chosen from one or more of: CD33, CD11b, C14, CD15, and CD66b. Accordingly, in some embodiments, the tumor-supporting antigen is chosen from one or more of: bone marrow stromal cell antigen 2 (BST2), fibroblast activation protein (FAP) or tenascin, CD33, CD11b, C14, CD15, and CD66b.

Features of Chimeric Antigen Receptor (CAR)

The present invention encompasses a recombinant DNA construct comprising sequences encoding a CAR, wherein the CAR comprises an antigen binding domain (e.g., antibody or antibody fragment, TCR or TCR fragment) that binds specifically to a cancer associated antigen described herein, wherein the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

In specific aspects, a CAR construct of the invention comprises a scFv domain, wherein the scFv may be preceded by an optional leader sequence such as provided in SEQ ID NO: 401, and followed by an optional hinge sequence such as provided in SEQ ID NO: 22, 28-31, 403, 510, 514, or 516, a transmembrane region such as provided in SEQ ID NO:12, an intracellular signalling domain that includes SEQ ID NO: 505, and a CD3 zeta sequence that includes SEQ ID NO:18 or SEQ ID NO:20, e.g., wherein the domains are contiguous with and in the same reading frame to form a single fusion protein.

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein). As used herein, CAR hinge, CAR hinge region, and hinge region are used interchangeably.

An exemplary leader sequence is provided as SEQ ID NO: 401. An exemplary hinge/spacer sequence is provided as SEQ ID NOs: 22, 28-31, 510, 514, or 516. An exemplary transmembrane domain sequence is provided as SEQ ID NO:12. An exemplary sequence of the intracellular signaling domain of CD28 is provided as SEQ ID NO: 505. An exemplary CD3zeta domain sequence is provided as SEQ ID NO: 18 or SEQ ID NO:20.

In one aspect, the present invention encompasses a recombinant nucleic acid construct comprising a nucleic acid molecule encoding a CAR, wherein the nucleic acid molecule comprises the nucleic acid sequence encoding an antigen binding domain, e.g., described herein, that is contiguous with and in the same reading frame as a nucleic acid sequence encoding an intracellular signaling domain.

In one aspect, the present invention encompasses a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, CD27, 4-1BB, and the like. In some instances, the CAR can comprise any combination of CD3-zeta, CD28, 4-1BB, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR") (e.g., a 3' and/or 5' UTR described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length (SEQ ID NO:32). RNA so produced can efficiently transfect different kinds of cells. In one embodiment, the template includes sequences for the CAR. In an embodiment, an RNA CAR vector is transduced into a cell, e.g., a T cell or a NK cell, by electroporation.

Antigen Binding Domain

In one aspect, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets a tumor antigen, e.g., a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD).

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014).

In one embodiment, an antigen binding domain against GD2 is an antigen binding portion, e.g., CDRs, of an antibody described in, e.g., Mujoo et al., Cancer Res. 47(4):1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody described in, e.g., WO2012163805, WO200112812, and WO2003062401.

In one embodiment, an antigen binding domain against Tn antigen is an antigen binding portion, e.g., CDRs, of an antibody described in, e.g., U.S. Pat. No. 8,440,798, Brooks et al., PNAS 107(22):10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat #ab55262) or Novus Biologicals (cat #EPR5446). In another embodiment, an antigen binding domain again IL-11Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore)

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or US19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., 0520100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501,415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D:MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013).

In one embodiment, an antigen binding domain against PLAC1 is an antigen binding portion, e.g., CDRs, of an antibody described in, e.g., Ghods et al., Biotechnol Appl Biochem 2013 doi:10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748—Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of $56^{th}$ ASH Annual Meeting and Exposition, San Francisco, CA Dec. 6-9, 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma. 1995 June; 18(1-2):119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCARAntibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2], available from BioLegend, or Rat Anti-CMRF35-like molecule 1 antibody, Monoclonal [234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1×CD3 BiTE Antibody" $53^{rd}$ ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal[696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033] available from Lifespan Biosciences, or Mouse Anti-CD312 antibody, Monoclonal [494025] available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al. Generation of a humanized anti-glypican 3 antibody by CDR grafting and stability optimization. Anticancer Drugs. 2010 November; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32.

In one embodiment, an antigen binding domain against IGLL1 is an antigen binding portion, e.g., CDRs, of the antibody Mouse Anti-Immunoglobulin lambda-like polypeptide 1 antibody, Monoclonal[AT1G4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp): 5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., from the amino acid at the corresponding murine sequence.

In some aspects, the portion of a CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human a cancer associated antigen as described herein. In some embodiments, a humanized antibody or antibody fragment may have improved affinity and/or specificity of binding to human a cancer associated antigen as described herein.

In one aspect, the antigen binding domain of the invention is characterized by particular functional features or properties of an antibody or antibody fragment. For example, in one aspect, the portion of a CAR composition of the invention that comprises an antigen binding domain specifically binds a tumor antigen as described herein.

In one aspect, the anti-cancer associated antigen as described herein binding domain is a fragment, e.g., a single chain variable fragment (scFv). In one aspect, the anti-cancer associated antigen as described herein binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a cancer associated antigen as described herein protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO:22). In one embodiment, the linker can be $(Gly_4Ser)_4$ (SEQ ID NO:29) or $(Gly_4Ser)_3$ (SEQ ID NO:30). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracelluar, however, a fragment of such antigen (peptide) is presented on the surface of the cancer cells by MHC.

In one embodiment, an antigen binding domain against EGFRvIII is an antigen binding portion, e.g., CDRs, of a CAR, antibody or antigen-binding fragment thereof described in, e.g., PCT publication WO2014/130657 or US2014/0322275A1. In one embodiment, the CAR molecule comprises an EGFRvIII CAR, or an antigen binding domain according to Table 2 or SEQ ID NO:11 of WO 2014/130657, incorporated herein by reference, or a sequence substantially identical thereto (e.g., at least 85%, 90%, 95% or more identical thereto). The amino acid and nucleotide sequences encoding the EGFRvIII CAR molecules and antigen binding domains (e.g., including one, two, three VH CDRs; and one, two, three VL CDRs according to Kabat or Chothia), are specified in WO 2014/130657.

In one embodiment, an antigen binding domain against mesothelin is an antigen binding portion, e.g., CDRs, of an antibody, antigen-binding fragment or CAR described in, e.g., PCT publication WO2015/090230. In one embodiment, an antigen binding domain against mesothelin is an antigen binding portion, e.g., CDRs, of an antibody, antigen-binding fragment, or CAR described in, e.g., PCT publication WO1997/025068, WO1999/028471, WO2005/014652, WO2006/099141, WO2009/045957, WO2009/068204, WO2013/142034, WO2013/040557, or WO2013/063419.

In an embodiment, the CAR molecule comprises a mesothelin CAR described herein, e.g., a mesothelin CAR described in WO 2015/090230, incorporated herein by reference. In embodiments, the mesothelin CAR comprises an amino acid, or has a nucleotide sequence shown in Tables 2 or 3, or a sequence substantially identical to any of the aforesaid sequences (e.g., at least 85%, 90%, 95% or more identical to any of the aforesaid mesothelin CAR sequences). In one embodiment, the CAR molecule comprises a mesothelin CAR, or an antigen binding domain according to Tables 2-3 of WO 2015/090230, incorporated herein by reference and included in adapted form below, or a sequence substantially identical thereto (e.g., at least 85%, 90%, 95% or more identical thereto). The amino acid and nucleotide sequences encoding the mesothelin CAR molecules and antigen binding domains (e.g., including one, two, three VH CDRs; and one, two, three VL CDRs according to Kabat or Chothia), are specified in WO 2015/090230.

In one embodiment, an antigen binding domain against CD123 is an antigen binding portion, e.g., CDRs, of an antibody, antigen-binding fragment or CAR described in, e.g., PCT publication WO2016/028896. In one embodiment, an antigen binding domain against CD123 is an antigen binding portion, e.g., CDRs, of an antibody, antigen-binding fragment or CAR described in, e.g., PCT publication WO2014/130635. In one embodiment, an antigen binding domain against CD123 is an antigen binding portion, e.g., CDRs, of an antibody, antigen-binding fragment, or CAR described in, e.g., PCT publication WO2014/138805, WO2014/138819, WO2013/173820, WO2014/144622, WO2001/66139, WO2010/126066, WO2014/144622, or US2009/0252742.

In one embodiment, an antigen binding domain against CD123 is an antigen binding portion, e.g., CDRs, of an antibody, antigen-binding fragment or CAR described in, e.g., US2014/0322212A1 or US2016/0068601A1, both incorporated herein by reference. In embodiments, the CD123 CAR comprises an amino acid, or has a nucleotide sequence shown in US2014/0322212A1 or US2016/0068601A1, both incorporated herein by reference, or a sequence substantially identical to any of the aforesaid sequences (e.g., at least 85%, 90%, 95% or more identical to any of the aforesaid CD123 CAR sequences). In one embodiment, the CAR molecule comprises a CD123 CAR (e.g., any of the CAR1-CAR8), or an antigen binding domain according to Tables 1-2 of WO 2014/130635, incorporated herein by reference, or a sequence substantially identical thereto (e.g., at least 85%, 90%, 95% or more identical to any of the aforesaid CD123 CAR sequences). The amino acid and nucleotide sequences encoding the CD123 CAR molecules and antigen binding domains (e.g., including one, two, three VH CDRs; and one, two, three VL CDRs according to Kabat or Chothia), are specified in WO 2014/130635.

In other embodiments, the CAR molecule comprises a CD123 CAR comprises a CAR molecule (e.g., any of the CAR123-1 to CAR123-4 and hzCAR123-1 to hzCAR123-

32), or an antigen binding domain according to Tables 2, 6, and 9 of WO2016/028896, incorporated herein by reference, or a sequence substantially identical thereto (e.g., at least 85%, 90%, 95% or more identical to any of the aforesaid CD123 CAR sequences). The amino acid and nucleotide sequences encoding the CD123 CAR molecules and antigen binding domains (e.g., including one, two, three VH CDRs; and one, two, three VL CDRs according to Kabat or Chothia), are specified in WO2016/028896.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD).

In other embodiments, the CLL1 CAR includes a CAR molecule, or an antigen binding domain according to Table 2 of WO2016/014535, incorporated herein by reference. The amino acid and nucleotide sequences encoding the CLL-1 CAR molecules and antigen binding domains (e.g., including one, two, three VH CDRs; and one, two, three VL CDRs according to Kabat or Chothia), are specified in WO2016/014535.

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014).

In one embodiment, an antigen binding domain against CD33 is an antigen binding portion, e.g., CDRs, of an antibody described in, US2016/0096892A1, incorporated herein by reference. In embodiments, the CD33 CAR comprises an amino acid, or has a nucleotide sequence shown in US2016/0096892A1, incorporated herein by reference, or a sequence substantially identical to any of the aforesaid sequences (e.g., at least 85%, 90%, 95% or more identical to any of the aforesaid CD33 CAR sequences). In other embodiments, the CD33 CAR CAR or antigen binding domain thereof can include a CAR molecule (e.g., any of CAR33-1 to CAR-33-9), or an antigen binding domain according to Table 2 or 9 of WO2016/014576, incorporated herein by reference, or a sequence substantially identical to any of the aforesaid sequences (e.g., at least 85%, 90%, 95% or more identical to any of the aforesaid CD33 CAR sequences). The amino acid and nucleotide sequences encoding the CD33 CAR molecules and antigen binding domains (e.g., including one, two, three VH CDRs; and one, two, three VL CDRs according to Kabat or Chothia), are specified in WO2016/014576.

In one embodiment, an antigen binding domain against GD2 is an antigen binding portion, e.g., CDRs, of an antibody described in, e.g., Mujoo et al., Cancer Res. 47(4):1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody, antigen-binding fragment or CAR described in, e.g., PCT publication WO2016/014565, e.g., the antigen binding portion of CAR BCMA-10 as described in WO2016/014565. In one embodiment, an antigen binding domain against BCMA is an antigen binding portion, e.g., CDRs, of an antibody, antigen-binding fragment or CAR described in, e.g., PCT publication WO2016/014789. In one embodiment, an antigen binding domain against BCMA is an antigen binding portion, e.g., CDRs, of an antibody described in, e.g., WO2012/163805, WO2001/12812, and WO2003/062401.

In other embodiment, the CAR molecule comprises a BCMA CAR molecule, or an antigen binding domain against BCMA described herein, e.g., a BCMA CAR described in US-2016-0046724-A1 or WO2016/014565. In embodiments, the BCMA CAR comprises an amino acid, or has a nucleotide sequence of a CAR molecule, or an antigen binding domain according to US-2016-0046724-A1, or Table 1 or 16, SEQ ID NO: 271 or SEQ ID NO: 273 of WO2016/014565, incorporated herein by reference, or a sequence substantially identical to any of the aforesaid sequences (e.g., at least 85%, 90%, 95% or more identical to any of the aforesaid BCMA CAR sequences). The amino acid and nucleotide sequences encoding the BCMA CAR molecules and antigen binding domains (e.g., including one, two, three VH CDRs; and one, two, three VL CDRs according to Kabat or Chothia), are specified in WO2016/014565.

In one embodiment, an antigen binding domain against GFR ALPHA-4 CAR antigen is an antigen binding portion, e.g., CDRs, of an antibody described in, e.g., WO2016/025880, incorporated herein by reference. In one embodiment, the CAR molecule comprises an a GFR ALPHA-4 CAR, e.g., a CAR molecule, or an antigen binding domain according to Table 2 of WO2016/025880, incorporated herein by reference, or a sequence substantially identical to any of the aforesaid sequences (e.g., at least 85%, 90%, 95% or more identical to any of the aforesaid GFR ALPHA-4 sequences). The amino acid and nucleotide sequences encoding the GFR ALPHA-4 CAR molecules and antigen binding domains (e.g., including one, two, three VH CDRs; and one, two, three VL CDRs according to Kabat or Chothia), are specified in WO2016/025880.

In one embodiment, an antigen binding domain against Tn antigen is an antigen binding portion, e.g., CDRs, of an antibody described in, e.g., U.S. Pat. No. 8,440,798; Brooks et al., PNAS 107(22):10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat #ab55262) or Novus Biologicals (cat #EPR5446). In another embodiment, an antigen binding domain again IL-11Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore).

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1;

WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or US19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., 0520100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501,415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D: MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013).

In one embodiment, an antigen binding domain against PLAC1 is an antigen binding portion, e.g., CDRs, of an antibody described in, e.g., Ghods et al., Biotechnol Appl Biochem 2013 doi:10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6):2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748—Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of $56^{th}$ ASH Annual Meeting and Exposition, San Francisco, CA Dec. 6-9, 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma. 1995 June; 18(1-2):119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCARAntibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2], available from BioLegend, or Rat Anti-CMRF35-like molecule 1 antibody, Monoclonal [234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1×CD3 BiTE Antibody" $53^{rd}$ ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal[696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033] available from Lifespan Biosciences, or Mouse Anti-CD312 antibody, Monoclonal [494025] available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al. Generation of a humanized anti-glypican 3 antibody by CDR grafting and stability optimization. Anticancer Drugs. 2010 November; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32.

In one embodiment, an antigen binding domain against IGLL1 is an antigen binding portion, e.g., CDRs, of the antibody Mouse Anti-Immunoglobulin lambda-like polypeptide 1 antibody, Monoclonal[AT1G4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

The antigen binding domain may bind one or more antigens, such as but not limited to CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some instances, the antigen binding domain is derived from the same species in which the CAR will ultimately be used. For example, for use in humans, it may be beneficial for the antigen binding domain of the CAR to comprise a human antibody, humanized antibody as described elsewhere herein, or a fragment thereof.

The antigen binding domain may be operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with cross-linkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 78). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

Stability and Mutations

The stability of an antigen binding domain to a cancer associated antigen as described herein, e.g., scFv molecules (e.g., soluble scFv), can be evaluated in reference to the biophysical properties (e.g., thermal stability) of a conventional control scFv molecule or a full length antibody. In one embodiment, the humanized scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the antigen binding domain to a cancer associated antigen described herein, e.g., scFv is subsequently conferred to the entire CAR construct, leading to improved therapeutic properties of the CAR construct. The thermal stability of the antigen binding domain of a cancer associated antigen described herein, e.g., scFv, can be improved by at least about 2° C. or 3° C. as compared to a conventional antibody. In one embodiment, the antigen binding domain of a cancer associated antigen described herein, e.g., scFv, has a 1° C. improved thermal stability as compared to a conventional antibody. In another embodiment, the antigen binding domain of a cancer associated antigen described herein, e.g., scFv, has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

Mutations in scFv (arising through humanization or direct mutagenesis of the soluble scFv) can alter the stability of the scFv and improve the overall stability of the scFv and the CAR construct. Stability of the humanized scFv is compared against the murine scFv using measurements such as Tm, temperature denaturation and temperature aggregation.

The binding capacity of the mutant scFvs can be determined using assays know in the art and described herein.

In one embodiment, the antigen binding domain of a cancer associated antigen described herein, e.g., scFv, comprises at least one mutation arising from the humanization process such that the mutated scFv confers improved stability to the CAR construct. In another embodiment, the antigen binding domain of a cancer associated antigen described herein, e.g., scFv, comprises at least 1, 2, 3, 4, 5, 6, 7, 8, 9, 10 mutations arising from the humanization process such that the mutated scFv confers improved stability to the CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:403. In one aspect, the transmembrane domain comprises (e.g., consists of) a transmembrane domain of SEQ ID NO: 12.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTIS KAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKM (SEQ ID NO:512). In some embodiments, the hinge or spacer comprises a hinge encoded by a nucleotide sequence of (SEQ ID NO: 513)
```
GAGAGCAAGTACGGCCCTCCCTGCCCCCCTTGCCCTGCCC
CCGAGTTCCTGGGCGGACCCAGCGTGTTCCTGTTCCCCCC
CAAGCCCAAGGACACCCTGATGATCAGCCGGACCCCCGAG
GTGACCTGTGTGGTGGTGGACGTGTCCCAGGAGGACCCCG
AGGTCCAGTTCAACTGGTACGTGGACGGCGTGGAGGTGCA
CAACGCCAAGACCAAGCCCCGGGAGGAGCAGTTCAATAGC
ACCTACCGGGTGGTGTCCGTGCTGACCGTGCTGCACCAGG
ACTGGCTGAACGGCAAGGAATACAAGTGTAAGGTGTCCAA
CAAGGGCCTGCCCAGCAGCATCGAGAAAACCATCAGCAAG
GCCAAGGGCCAGCCTCGGGAGCCCCAGGTGTACACCCTGC
CCCCTAGCCAAGAGGAGATGACCAAGAACCAGGTGTCCCT
GACCTGCCTGGTGAAGGGCTTCTACCCCAGCGACATCGCC
GTGGAGTGGGAGAGCAACGGCCAGCCCGAGAACAACTACA
AGACCACCCCCCCTGTGCTGGACAGCGACGGCAGCTTCTT
CCTGTACAGCCGGCTGACCGTGGACAAGAGCCGGTGGCAG
GAGGGCAACGTCTTTAGCTGCTCCGTGATGCACGAGGCCC
TGCACAACCACTACACCCAGAAGAGCCTGAGCCTGTCCCT
GGGCAAGATG.
```

In one aspect, the hinge or spacer comprises an IgD hinge. For example, in one embodiment, the hinge or spacer comprises a hinge of the amino acid sequence (SEQ ID NO: 514)
```
RWPESPKAQASSVPTAQPQAEGSLAKATTAPATTRNTGRG
GEEKKKEKEKEEQEERETKTPECPSHTQPLGVYLLTPAVQ
DLWLRDKATFTCFVVGSDLKDAHLTWEVAGKVPTGGVEEG
LLERHSNGSQSQHSRLTLPRSLWNAGTSVTCTLNHPSLPP
QRLMALREPAAQAPVKLSLNLLASSDPPEAASWLLCEVSG
FSPPNILLMWLEDQREVNTSGFAPARPPPQPGSTTFWAWS
VLRVPAPPSPQPATYTCVVSHEDSRTLLNASRSLEVSYVT
DH.
```

In some embodiments, the hinge or spacer comprises a hinge encoded by a nucleotide sequence of (SEQ ID NO: 515)
```
AGGTGGCCCGAAAGTCCCAAGGCCCAGGCATCTAGTGTTC
CTACTGCACAGCCCCAGGCAGAAGGCAGCCTAGCCAAAGC
TACTACTGCACCTGCCACTACGCGCAATACTGGCCGTGGC
GGGGAGGAGAAGAAAAAGGAGAAAGAGAAAGAAGAACAGG
AAGAGAGGGAGACCAAGACCCCTGAATGTCCATCCCATAC
CCAGCCGCTGGGCGTCTATCTCTTGACTCCCGCAGTACAG
GACTTGTGGCTTAGAGATAAGGCCACCTTTACATGTTTCG
TCGTGGGCTCTGACCTGAAGGATGCCCATTTGACTTGGGA
GGTTGCCGGAAAGGTACCCACAGGGGGGGTTGAGGAAGGG
TTGCTGGAGCGCCATTCCAATGGCTCTCAGAGCCAGCACT
CAAGACTCACCCTTCCGAGATCCCTGTGGAACGCCGGGAC
CTCTGTCACATGTACTCTAAATCATCCTAGCCTGCCCCCA
CAGCGTCTGATGGCCCTTAGAGAGCCAGCCGCCCAGGCAC
CAGTTAAGCTTAGCCTGAATCTGCTCGCCAGTAGTGATCC
CCCAGAGGCCGCCAGCTGGCTCTTATGCGAAGTGTCCGGC
TTTAGCCCGCCCAACATCTTGCTCATGTGGCTGGAGGACC
AGCGAGAAGTGAACACCAGCGGCTTCGCTCCAGCCCGGCC
CCCACCCCAGCCGGGTTCTACCACATTCTGGGCCTGGAGT
GTCTTAAGGGTCCCAGCACCACCTAGCCCCCAGCCAGCCA
CATACACCTGTGTTGTGTCCCATGAAGATAGCAGGACCCT
GCTAAATGCTTCTAGGAGTCTGGAGGTTTCCTACGTGACT
GACCATT.
```

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:516). In some embodiments, the linker is encoded by a nucleotide sequence of (SEQ ID NO: 517)
```
GGTGGCGGAGGTTCTGGAGGTGGAGGTTCC.
```

In one aspect, the hinge or spacer comprises a KIR2DS2 hinge.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signalling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta, the signalling domain of CD28, and the signaling domain of 4-1BB. In one aspect, the signaling domain of 4-1BB is a signaling domain of SEQ ID NO: 14. In one aspect, the signaling domain of CD3-zeta is a signaling domain of SEQ ID NO: 18. In one aspect, the signaling domain of CD28 is selected from SEQ ID NO: 505.

In one aspect, the intracellular signaling domain is designed to comprise the signaling domain of CD3-zeta, the signaling domain of CD28, and the signaling domain of CD27. In one aspect, the signaling domain of CD27 comprises an amino acid sequence of QRRKYRSNKGESPVEPAEPCRYSCPREEEGSTIPIQEDYRKPEPACSP (SEQ ID NO:16). In one aspect, the signalling domain of CD27 is encoded by a nucleic acid sequence of

```
                                    (SEQ ID NO: 17)
AGGAGTAAGAGGAGCAGGCTCCTGCACAGTGACTACATGA

ACATGACTCCCCGCCGCCCCGGGCCCACCCGCAAGCATTA

CCAGCCCTATGCCCCACCACGCGACTTCGCAGCCTATCGC
```

-continued

TCC.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, for example, 10 to 100 amino acids, or 25 to 50 amino acids. In another embodiment, a short oligo- or polypeptide linker, from 2 and 10 amino acids in length may form the linkage between the transmembrane domain and the intracellular domain of the CAR. An example of a linker includes a glycine-serine doublet.

Exemplary CAR Molecules

The CAR molecules disclosed herein can comprise a binding domain that binds to a target, e.g., a target as described herein; a transmembrane domain, e.g., a transmembrane domain as described herein; and an intracellular signaling domain, e.g., an intracellular domain as described herein. In embodiments, the binding domain comprises a heavy chain complementary determining region 1 (HC CDR1), a heavy chain complementary determining region 2 (HC CDR2), and a heavy chain complementary determining region 3 (HC CDR3) of a heavy chain binding domain described herein, and/or a light chain complementary determining region 1 (LC CDR1), a light chain complementary determining region 2 (LC CDR2), and a light chain complementary determining region 3 (LC CDR3) of a light chain binding domain described herein.

In other embodiments, the CAR molecule comprises a CD19 CAR molecule described herein, e.g., a CD19 CAR molecule described in US-2015-0283178-A1, e.g., CTL019. In embodiments, the CD19 CAR comprises an amino acid, or has a nucleotide sequence shown in US-2015-0283178-A1, incorporated herein by reference, or a sequence substantially identical thereto (e.g., at least 85%, 90%, 95% or more identical thereto).

In one embodiment, the CAR T cell that specifically binds to CD19 has the USAN designation TISAGENLECLEU-CEL-T. CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CD19 CAR includes a CAR molecule, or an antigen binding domain (e.g., a humanized antigen binding domain) according to Table 3 of WO2014/153270, incorporated herein by reference. The amino acid and nucleotide sequences encoding the CD19 CAR molecules and antigen binding domains (e.g., including one, two, three VH CDRs; and one, two, three VL CDRs according to Kabat or Chothia), are specified in WO2014/153270. In embodiments, the CD19 CAR comprises an amino acid, or has a nucleotide sequence shown in WO2014/153270 incorporated herein by reference, or a sequence substantially identical to any of the aforesaid sequences (e.g., at least 85%, 90%, 95% or more identical to any of the aforesaid CD19 CAR sequences).

In one embodiment, the parental murine scFv sequence is the CAR19 construct provided in PCT publication WO2012/079000 (incorporated herein by reference) and provided herein in Table 2.

In one embodiment, the anti-CD19 binding domain is a scFv described in WO2012/079000 and provided herein in Table 2.

In one embodiment, the CD19 CAR comprises an amino acid sequence provided as SEQ ID NO: 12 in PCT publication WO2012/079000. In embodiment, the amino acid sequence is: MALPVTALLLPLALLLHAARPdiqmtqttssl-saslgdrvtiscrasqdiskylnwyqqkpdgtvklliyhtsrlhsgvps rfsgs gsgtdysltisnleqediatyfcqqgntlpytfgggtkleitgg ggsggg gsggggsevklqesgpglvapsqslsvtctvsgvslp dygvswirqpprk-glewlgviwgsettyynsalksrltiikdnsksqvflkmnslqtddtaiyy-cakhyyyggsyamdywgqgtsvt vsstttpaprpptpaptiasqplslr peacrpaaggavhtrgldfacdiyiwaplagtcgvlllslvitlyckrgrkklly-ifkqpfmrpvqtt qeedgcscrfpeeeeggcelrvkfsrsadapaykqgqn qlynelnlgrreeydvldkrrgrdpemggkprrknpqeglynelqkdk maeayseigmkgerrrgkghdglyqglstatkdtydalhmqalppr (SEQ ID NO: 891), or a sequence substantially identical thereto (e.g., at least 85%, 90% or 95% or higher identical thereto), with or without the signal peptide sequence indicated in capital letters.

In embodiment, the amino acid sequence is: diqmtqttssl-saslgdrvtiscrasqdiskylnwyqqkpdgtvklliyhtsrlhsgvpsr fsgsgsgtdysltisnleqediatyfcqqgntl pytfgggtklei tggggsgg ggsggggsevklqesgpglvapsqslsvtctvsgvslpdygvswirqpprk-glewlgviwgsettyyn salksrltiikdnsksqvflkmnslqtddtaiyy-cakhyyyggsyamdywgqgtsvtvsstttpaprpptpaptiasqplslrp eacrpa aggavhtrgldfacdiyiwaplagtcgvlllslvitlyckrgrkklly-ifkqpfmrpvqttqeedgcscrfpeeeeggcelrvkfsrsadap aykq gqnqlynelnlgrreeydvldkrrgrdpemggkprrknpqeglynelqkdk-maeayseigmkgerrrgkghdglyqglstat kdtydalhmqalppr (SEQ ID NO: 892), or a sequence substantially homologous thereto (e.g., at least 85%, 90% or 95% or higher identical thereto).

In embodiments, the CAR molecule is a CD19 CAR molecule described herein, e.g., a humanized CAR molecule described herein, e.g., a humanized CD19 CAR molecule of Table 2. In embodiments, the CAR molecule is a CD19 CAR molecule described herein, e.g., a murine CAR molecule described herein, e.g., a murine CD19 CAR molecule of Table 2.

In one embodiment, the antigen binding domain comprises one, two three (e.g., all three) heavy chain CDRs, HC CDR1, HC CDR2 and HC CDR3, from an antibody listed herein, and/or one, two, three (e.g., all three) light chain CDRs, LC CDR1, LC CDR2 and LC CDR3, from an antibody listed herein. In one embodiment, the antigen binding domain comprises a heavy chain variable region and/or a variable light chain region of an antibody listed or described herein.

Exemplary CD19 CARs include any of the CD19 CARs or anti-CD19 binding domains described herein, e.g., in one or more tables (e.g., Table 2) described herein (e.g., or an anti-CD19 CAR described in Xu et al. Blood 123.24 (2014): 3750-9; Kochenderfer et al. Blood 122.25 (2013):4129-39, Cruz et al. Blood 122.17 (2013):2965-73, NCT00586391, NCT01087294, NCT02456350, NCT00840853, NCT02659943, NCT02650999, NCT02640209, NCT01747486, NCT02546739, NCT02656147, NCT02772198, NCT00709033, NCT02081937, NCT00924326, NCT02735083, NCT02794246, NCT02746952, NCT01593696, NCT02134262, NCT01853631, NCT02443831, NCT02277522, NCT02348216, NCT02614066, NCT02030834, NCT02624258, NCT02625480, NCT02030847, NCT02644655, NCT02349698, NCT02813837, NCT02050347, NCT01683279, NCT02529813, NCT02537977, NCT02799550, NCT02672501, NCT02819583, NCT02028455, NCT01840566, NCT01318317, NCT01864889, NCT02706405, NCT01475058, NCT01430390, NCT02146924, NCT02051257, NCT02431988, NCT01815749, NCT02153580, NCT01865617, NCT02208362, NCT02685670, NCT02535364, NCT02631044, NCT02728882, NCT02735291, NCT01860937, NCT02822326, NCT02737085, NCT02465983, NCT02132624, NCT02782351, NCT01493453, NCT02652910, NCT02247609, NCT01029366, NCT01626495, NCT02721407, NCT01044069, NCT00422383, NCT01680991, NCT02794961, or NCT02456207, each of which is incorporated herein by reference in its entirety.

Exemplary CD19 CAR and antigen binding domain constructs that can be used in the methods described herein are shown in Table 2. The light and heavy chain CDR sequences according to Kabat are shown by the bold and underlined text, and are also summarized in Table 2. The location of the signal sequence and histidine tag are also underlined. In embodiments, the CD19 CAR sequences and antigen binding fragments thereof do not include the signal sequence and/or histidine tag sequences.

In embodiments, the CD19 CAR comprises an anti-CD19 binding domain (e.g., murine or humanized anti-CD19 binding domain), a transmembrane domain, and an intracellular signaling domain, and wherein said anti-CD19 binding domain comprises a heavy chain complementary determining region 1 (HC CDR1), a heavy chain complementary determining region 2 (HC CDR2), and a heavy chain complementary determining region 3 (HC CDR3) of any anti-CD19 heavy chain binding domain amino acid sequences listed in Table 2, or a sequence at least 85%, 90%, 95% or more identical thereto (e.g., having less than 5, 4, 3, 2 or 1 amino acid substitutions, e.g., conservative substitutions).

In one embodiment, the anti-CD19 binding domain comprises a light chain variable region described herein (e.g., in Table 2) and/or a heavy chain variable region described herein (e.g., in Table 2), or a sequence at least 85%, 90%, 95% or more identical thereto.

In one embodiment, the encoded anti-CD19 binding domain is a scFv comprising a light chain and a heavy chain of an amino acid sequence of Table 2, or a sequence at least 85%, 90%, 95% or more identical thereto.

In an embodiment, the human or humanized anti-CD19 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 2, or a sequence at least 85%, 90%, 95% or more identical thereto; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 2, or a sequence at least 85%, 90%, 95% or more identical thereto.

TABLE 2

CD19 CAR Constructs

| Name | SEQ ID NO: | Sequence |
| --- | --- | --- |
| | | CAR 1 |
| CAR1 scFv domain | 893 | EIVMTQSPATLSLSPGERATLSCRASQDISKYLNWYQQKPGQ<br>APRLLIYHTSRLHSGIPARFSGSGSGTDYTLTISSLQPEDFAVY<br>FCQQGNTLPYTFGQGTKLEIKGGGGSGGGGSGGGGSQVQLQ<br>ESGPGLVKPSETLSLTCTVSGVSLPDYGVSWIRQPPGKGLEWI<br>GVIWGSETTYYSSSLKSRVTISKDNSKNQVSLKLSSVTAADT<br>AVYYCAKHYYYGGSYAMDYWGQGTLVTVSS |
| 103101 CAR1 Soluble scFv-nt | 894 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagccaggtccaactccaagaaagcg<br>gaccgggtcttgtgaagccatcagaaactctttcactgacttgtactgtgagcggagtgtctctccc<br>cgattacggggtgtcttggatcagacagccaccggggaagggtctggaatggattggagtgattt<br>ggggctctgagactacttactactcttcatccctcaagtcacgcgtcaccatctcaaaggacaact<br>ctaagaatcaggtgtcactgaaactgtcatctgtgaccgcagccgacaccgccgtgtactattgc<br>gctaagcattactattatggcgggagctacgcaatggattactggggacagggtactctggtcac<br>cgtgtccagccaccaccatcatcaccatcaccat |
| 103101 CAR1 Soluble scFv-aa | 895 | **MALPVTALLLPLALLLHAARP**eivmtqspatlslspgeratlscrasqdisk<br>ylnwyqqkpgqaprlliyhtsrlhsgiparfsgsgsgtdytltisslqpedfavyfcqqgntlpy<br>tfgqgtkleikggggsggggsggggsqvqlqesgpglvkpsetlsltctvsgvslpdygvswi<br>rqppgkglewigviwgsettyyssslksrvtiskdnsknqvslklssvtaadtavyycakhyy<br>yggsyamdywgqgtlvtvss**hhhhhhhh** |
| 104875 CAR 1- Full-nt | 896 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc |

TABLE 2-continued

| CD19 CAR Constructs | | |
|---|---|---|
| Name | SEQ ID NO: | Sequence |
| | | gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagccaggtccaactccaagaaagcg<br>gaccgggtcttgtgaagccatcagaaactctttcactgacttgtactgtgagcggagtgtctctccc<br>cgattacggggtgtcttggatcagacagccaccggggaagggtctggaatggattggagtgattt<br>ggggctctgagactacttactactcttcatccctcaagtcacgcgtcaccatctcaaaggacaact<br>ctaagaatcaggtgtcactgaaactgtcatctgtgaccgcagccgacaccgccgtgtactattgc<br>gctaagcattactattatggcgggagctacgcaatggattactggggacagggtactctggtcac<br>cgtgtccagcaccactaccccagcaccgaggccacccaccccggctcctaccatcgcctccca<br>gcctctgtccctgcgtccggaggcatgtagacccgcagctggtggggccgtgcatacccgggg<br>tcttgacttcgcctgcgatatctacatttgggcccctctggctggtacttgcggggtcctgctgcttt<br>cactcgtgatcactctttactgtaagcgcggtcggaagaagctgctgtacatctttaagcaaccctt<br>catgaggcctgtgcagactactcaagaggaggacggctgttcatgccggttcccagaggagga<br>ggaaggcggctgcgaactgcgcgtgaaattcagccgcagcgcagatgctccagcctacaagc<br>aggggcagaaccagctctacaacgaactcaatcttggtcggagagaggagtacgacgtgctgg<br>acaagcggagaggacgggacccagaaatgggcgggaagccgcgcagaaagaatccccaag<br>agggcctgtacaacgagctccaaaaggataagatggcagaagcctatagcgagattggtatga<br>aaggggaacgcagaagaggcaaaggccacgacggactgtaccagggactcagcaccgcca<br>ccaaggacacctatgacgctcttcacatgcaggccctgccgcctcgg |
| 104875<br>Full-aa<br>CAR 1- | 897 | MALPVTALLLPLALLLHAARPeivmtqspatlslspgeratlscra**sqdiskyl**<br>**n**wyqqkpgqaprlliy**htsrlhs**giparfsgsgsgtdytltisslqpedfavyfc**qqgntlpyt**<br>fgqgtkleikggggggggsggggsqvqlqesgpglvkpsetlsltctvsgvslp**dygvs**wir<br>qppgkglewig**viwgsettyyssslks**rvtiskdnsknqvslklssvtaadtavyycak**hyy**<br>**yggsyamdy**wgqgtlvtvsstttpaprpptpaptiasqplslrpeacrpaaggavhtrgldfa<br>cdiyiwaplagtcgvlllslvitlyckrgrkkllyifkqpfmrpvqttqeedgcscrfpeeeegg<br>celrvkfsrsadapaykqgqnqlynelnlgrreeydvldkrrgrdpemggkprrknpqegly<br>nelqkdkmaeayseigmkgerrrgkghdglyqglstatkdtydalhmqalppr |
| CAR 2 | | |
| CAR2<br>scFv<br>domain | 898 | eivmtqspatlslspgeratlscrasqdiskylnwyqqkpgqaprlliyhtsrlhsgiparfsgs<br>gsgtdytltisslqpedfavyfcqqgntlpytfgqgtkleikggggsggggsggggsqvqlqes<br>gpglvkpsetlsltctvsgvslpdygvswirqppgkglewigviwgsettyyqsslksrvtisk<br>dnsknqvslklssvtaadtavyycakhyyyggsyamdywgqgtlvtvss |
| 103102<br>CAR2-<br>Soluble<br>scFv-nt | 899 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagccaggtccaactccaagaaagcg<br>gaccgggtcttgtgaagccatcagaaactctttcactgacttgtactgtgagcggagtgtctctccc<br>cgattacggggtgtcttggatcagacagccaccggggaagggtctggaatggattggagtgattt<br>ggggctctgagactacttactaccaatcatccctcaagtcacgcgtcaccatctcaaaggacaact<br>ctaagaatcaggtgtcactgaaactgtcatctgtgaccgcagccgacaccgccgtgtactattgc<br>gctaagcattactattatggcgggagctacgcaatggattactggggacagggtactctggtcac<br>cgtgtccagccaccaccatcatcaccatcaccat |
| 103102<br>Soluble<br>scFv-aa<br>CAR2- | 900 | **MALPVTALLLPLALLLHAARP**eivmtqspatlslspgeratlscrasqdisk<br>ylnwyqqkpgqaprlliyhtsrlhsgiparfsgsgsgtdytltisslqpedfavyfcqqgntlpy<br>tfgqgtkleikggggggggsggggsqvqlqesgpglvkpsetlsltctvsgvslpdygvswi<br>rqppgkglewigviwgsettyyqsslksrvtiskdnsknqvslklssvtaadtavyycakhyy<br>yggsyamdywgqgtlvtvss**hhhhhhhh** |
| 104876<br>CAR 2-<br>Full-nt | 901 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagccaggtccaactccaagaaagcg<br>gaccgggtcttgtgaagccatcagaaactctttcactgacttgtactgtgagcggagtgtctctccc<br>cgattacggggtgtcttggatcagacagccaccggggaagggtctggaatggattggagtgattt<br>ggggctctgagactacttactaccaatcatccctcaagtcacgcgtcaccatctcaaaggacaact<br>ctaagaatcaggtgtcactgaaactgtcatctgtgaccgcagccgacaccgccgtgtactattgc<br>gctaagcattactattatggcgggagctacgcaatggattactggggacagggtactctggtcac<br>cgtgtccagcaccactaccccagcaccgaggccacccaccccggctcctaccatcgcctccca<br>gcctctgtccctgcgtccggaggcatgtagacccgcagctggtggggccgtgcatacccgggg<br>tcttgacttcgcctgcgatatctacatttgggcccctctggctggtacttgcggggtcctgctgcttt<br>cactcgtgatcactctttactgtaagcgcggtcggaagaagctgctgtacatctttaagcaaccctt<br>catgaggcctgtgcagactactcaagaggaggacggctgttcatgccggttcccagaggagga<br>ggaaggcggctgcgaactgcgcgtgaaattcagccgcagcgcagatgctccagcctacaagc |

TABLE 2-continued

| CD19 CAR Constructs | | |
|---|---|---|
| Name | SEQ ID NO: | Sequence |
| | | aggggcagaaccagctctacaacgaactcaatcttggtcggagagaggagtacgacgtgctgg<br>acaagcggagaggacgggacccagaaatgggcgggaagccgcgcagaaagaatccccaag<br>agggcctgtacaacgagctccaaaaggataagatggcagaagcctatagcgagattggtatga<br>aaggggaacgcagaagaggcaaaggccacgacggactgtaccagggactcagcaccgcca<br>ccaaggacacctatgacgctcttcacatgcaggccctgccgcctcgg |
| 104876<br>CAR 2-<br>Full-aa | 902 | MALPVTALLLPLALLLHAARPeivmtqspatlslspgeratlscra**sqdiskyl**<br>**n**wyqqkpgqaprlliy**htsrlhs**giparfsgsgsgtdytltisslqpedfavyfc**qqgntlpyt**<br>fgqgtkleikggggggggsggggsqvqlqesgpglvkpsetlsltctvsgvslp**dygvs**wir<br>qppgkglewig**viwgsettyyqsslks**rvtiskdnsknqvslklssvtaadtavyycak**hyy**<br>**yggsyamdy**wgqgtlvtvsstttpaprpptpaptiasqplslrpeacrpaaggavhtrgldfa<br>cdiyiwaplagtcgvlllslvitlyckrgrkkllyifkqpfmrpvqttqeedgcscrfpeeeegg<br>celrvkfsrsadapaykqgqnqlynelnlgrreeydvldkrrgrdpemggkprrknpqegly<br>nelqkdkmaeayseigmkgerrrgkghdglyqglstatkdtydalhmqalppr |
| CAR 3 | | |
| CAR3<br>scFv<br>domain | 903 | qvqlqesgpglvkpsetlsltctvsgvslpdygvswirqppgkglewigviwgsettyysssl<br>ksrvtiskdnsknqvslklssvtaadtavyycakhyyyggsyamdywgqgtlvtvssgggg<br>sggggsggggseivmtqspatlslspgeratlscrasqdiskylnwyqqkpgqaprlliyhtsr<br>lhsgiparfsgsgsgtdytltisslqpedfavyfcqqgntlpytfgqgtkleik |
| 103104<br>CAR 3-<br>Soluble<br>scFv-nt | 904 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactattcatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccgaaatcgtgatgacccagagccctgcaaccctgtccctttctcccgggg<br>aacgggctaccctttcttgtcgggcatcacaagatatctcaaaatacctcaattggtatcaacagaa<br>gccgggacaggcccctaggcttcttatctaccacacctctcgcctgcatagcgggattcccgcac<br>gctttagcgggtctggaagcgggaccgactacactctgaccatctcatctctccagcccgagga<br>cttcgccgtctacttctgccagcagggtaacaccctgccgtacaccttcggccagggcaccaag<br>cttgagatcaaacatcaccaccatcatcaccatcac |
| 103104<br>CAR 3-<br>Soluble<br>scFv-aa | 905 | **MALPVTALLLPLALLLHAARP**qvqlqesgpglvkpsetlsltctvsgvslp<br>dygvswirqppgkglewigviwgsettyysssslksrvtiskdnsknqvslklssvtaadtavy<br>ycakhyyyggsyamdywgqgtlvtvssggggsggggsggggseivmtqspatlslspger<br>atlscrasqdiskylnwyqqkpgqaprlliyhtsrlhsgiparfsgsgsgtdytltisslqpedfa<br>vyfcqqgntlpytfgqgtkleik**hhhhhhhh** |
| 104877<br>CAR 3-<br>Full-nt | 906 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactattcatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccgaaatcgtgatgacccagagccctgcaaccctgtccctttctcccgggg<br>aacgggctaccctttcttgtcgggcatcacaagatatctcaaaatacctcaattggtatcaacagaa<br>gccgggacaggcccctaggcttcttatctaccacacctctcgcctgcatagcgggattcccgcac<br>gctttagcgggtctggaagcgggaccgactacactctgaccatctcatctctccagcccgagga<br>cttcgccgtctacttctgccagcagggtaacaccctgccgtacaccttcggccagggcaccaag<br>cttgagatcaaaaccactactcccgctccaaggccacccacccctgccccgaccatcgcctctc<br>agccgctttccctgcgtccggaggcatgtagacccgcagctggtggggccgtgcatacccggg<br>gtcttgacttcgcctgcgatatctacatttgggcccctctggctggtacttgcggggtcctgctgctt<br>tcactcgtgatcactctttactgtaagcgcggtcggaagaagctgctgtacatctttaagcaaccct<br>tcatgaggcctgtgcagactactcaagaggaggacggctgttcatgccggttcccagaggagg<br>aggaaggcggctgcgaactgcgcgtgaaattcagccgcagcgcagatgctccagcctacaag<br>caggggcagaaccagctctacaacgaactcaatcttggtcggagagaggagtacgacgtgctg<br>gacaagcggagaggacgggacccagaaatgggcgggaagccgcgcagaaagaatccccaa<br>gagggcctgtacaacgagctccaaaaggataagatggcagaagcctatagcgagattggtatg<br>aaaggggaacgcagaagaggcaaaggccacgacggactgtaccagggactcagcaccgcc<br>accaaggacacctatgacgctcttcacatgcaggccctgccgcctcgg |
| 104877<br>CAR 3-<br>Full-aa | 907 | MALPVTALLLPLALLLHAARPqvqlqesgpglvkpsetlsltctvsgvslp**dy**<br>**gvs**wirqppgkglewig**viwgsettyyssslks**rvtiskdnsknqvslklssvtaadtavyyc<br>ak**hyyyggsyamdy**wgqgtlvtvssggggsggggsggggseivmtqspatlslspgerat<br>lsc**rasqdiskyln**wyqqkpgqaprlliy**htsrlhs**giparfsgsgsgtdytltisslqpedfa<br>vyfc**qqgntlpyt**fgqgtkleiktttpaprpptpaptiasqplslrpeacrpaaggavhtrgldf<br>acdiyiwaplagtcgvlllslvitlyckrgrkkllyifkqpfmrpvqttqeedgcscrfpeeeeg<br>gcelrvkfsrsadapaykqgqnqlynelnlgrreeydvldkrrgrdpemggkprrknpqegl<br>ynelqkdkmaeayseigmkgerrrgkghdglyqglstatkdtydalhmqalppr |

TABLE 2-continued

CD19 CAR Constructs

| Name | SEQ ID NO: | Sequence |
|---|---|---|
| | | CAR 4 |
| CAR4 scFv domain | 908 | qvqlqesgpglvkpsetlsltctvsgvslpdygvswirqppgkglewigviwgsettyyqssl<br>ksrvtiskdnsknqvslklssvtaadtavyycakhyyyggsyamdywgqgtlvtvssgggg<br>sggggsggggseivmtqspatlslspgeratlscrasqdiskylnwyqqkpgqaprlliyhtsr<br>lhsgiparfsgsgsgtdytltisslqpedfavyfcqqgntlpytfgqgtkleik |
| 103106 CAR4-Soluble scFv-nt | 909 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactatcaatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccgaaatcgtgatgacccagagccctgcaaccctgtccctttctcccgggg<br>aacgggctaccctttcttgtcgggcatcacaagatatctcaaaatacctcaattggtatcaacagaa<br>gccgggacaggcccctaggcttcttatctaccacacctctcgcctgcatagcgggattcccgcac<br>gctttagcgggtctggaagcgggaccgactacactctgaccatctcatctctccagcccgagga<br>cttcgccgtctacttctgccagcagggtaacaccctgccgtacaccttcggccagggcaccaag<br>cttgagatcaaacatcaccaccatcatcaccatcac |
| 103106 Soluble scFv-aa CAR4- | 910 | **MALPVTALLLPLALLLHAARP**qvqlqesgpglvkpsetlsltctvsgvslp<br>dygvswirqppgkglewigviwgsettyyqsslksrvtiskdnsknqvslklssvtaadtavy<br>ycakhyyyggsyamdywgqgtlvtvssggggsggggsggggseivmtqspatlslspger<br>atlscrasqdiskylnwyqqkpgqaprlliyhtsrlhsgiparfsgsgsgtdytltisslqpedfa<br>vyfcqqgntlpytfgqgtkleik**hhhhhhhh** |
| 104878 CAR 4-Full-nt | 911 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactatcaatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccgaaatcgtgatgacccagagccctgcaaccctgtccctttctcccgggg<br>aacgggctaccctttcttgtcgggcatcacaagatatctcaaaatacctcaattggtatcaacagaa<br>gccgggacaggcccctaggcttcttatctaccacacctctcgcctgcatagcgggattcccgcac<br>gctttagcgggtctggaagcgggaccgactacactctgaccatctcatctctccagcccgagga<br>cttcgccgtctacttctgccagcagggtaacaccctgccgtacaccttcggccagggcaccaag<br>cttgagatcaaaaccactactcccgctccaaggccacccacccctgccccgaccatcgcctctc<br>agccgctttccctgcgtccggaggcatgtagacccgcagctggtggggccgtgcatacccggg<br>gtcttgacttcgcctgcgatatctacatttgggcccctctggctggtacttgcggggtcctgctgctt<br>tcactcgtgatcactctttactgtaagcgcggtcggaagaagctgctgtacatctttaagcaaccct<br>tcatgaggcctgtgcagactactcaagaggaggacggctgttcatgccggttcccagaggagg<br>aggaaggcggctgcgaactgcgcgtgaaattcagccgcagcgcagatgctccagcctacaag<br>caggggcagaaccagctctacaacgaactcaatcttggtcggagagaggagtacgacgtgctg<br>gacaagcggagaggacgggacccagaaatgggcgggaagccgcgcagaaagaatccccaa<br>gagggcctgtacaacgagctccaaaaggataagatggcagaagcctatagcgagattggtatg<br>aaaggggaacgcagaagaggcaaaggccacgacggactgtaccagggactcagcaccgcc<br>accaaggacacctatgacgctcttcacatgcaggccctgccgcctcgg |
| 104878 Full-aa CAR 4- | 912 | MALPVTALLLPLALLLHAARPqvqlqesgpglvkpsetlsltctvsgvslp**dy**<br>**gvs**wirqppgkglewig**viwgsettyyqsslks**rvtiskdnsknqvslklssvtaadtavyy<br>cak**hyyyggsyamdy**wgqgtlvtvssggggsggggsggggseivmtqspatlslspger<br>atlsc**rasqdiskyln**wyqqkpgqaprlliy**htsrlhs**giparfsgsgsgtdytltisslqpedf<br>avyfc**qqgntlpyt**fgqgtkleikttpaprpptpaptiasqplslrpeacrpaaggavhtrgld<br>facdiyiwaplagtcgvlllslvitlyckrgrkkllyifkqpfmrpvqttqeedgcscrfpeeee<br>ggcelrvkfsrsadapaykqgqnqlynelnlgrreeydvldkrrgrdpemggkprrknpqe<br>glynelqkdkmaeayseigmkgerrrgkghdglyqglstatkdtydalhmqalppr |
| | | CAR 5 |
| CAR5 scFv domain | 913 | eivmtqspatlslspgeratlscrasqdiskylnwyqqkpgqaprlliyhtsrlhsgiparfsgs<br>gsgtdytltisslqpedfavyfcqqgntlpytfgqgtkleikggggsggggsggggsggggsq<br>vqlqesgpglvkpsetlsltctvsgvslpdygvswirqppgkglewigviwgsettyysssslk<br>srvtiskdnsknqvslklssvtaadtavyycakhyyyggsyamdywgqgtlvtvss |
| 99789 CAR5-Soluble scFv-nt | 914 | atggccctcccagtgaccgctctgctgctgcctctcgcacttcttctccatgccgctcggcctgag<br>atcgtcatgacccaaagccccgctaccctgtccctgtcacccggcgagagggcaaccctttcat<br>gcagggccagccaggacatttctaagtacctcaactggtatcagcagaagccagggcaggctc<br>ctcgcctgctgatctaccacaccagccgcctccacagcggtatccccgccagatttccgggag<br>cgggtctggaaccgactacaccctcaccatctcttctctgcagcccgaggatttcgccgtctatttc<br>tgccagcaggggaatactctgccgtacaccttcggtcaaggtaccaagctggaaatcaaggga<br>ggcggaggatcaggcggtggcggaagcggaggaggtggctccggaggaggaggttcccaa<br>gtgcagcttcaagaatcaggacccggacttgtgaagccatcagaaaccctctccctgacttgtac |

TABLE 2-continued

| CD19 CAR Constructs | | |
|---|---|---|
| Name | SEQ ID NO: | Sequence |
| | | cgtgtccggtgtgagcctccccgactacggagtctcttggattcgccagcctccggggaagggt<br>cttgaatggattggggtgatttggggatcagagactacttactactcttcatcacttaagtcacgggt<br>caccatcagcaaagataatagcaagaaccaagtgtcacttaagctgtcatctgtgaccgccgctg<br>acaccgccgtgtactattgtgccaaacattactattacggagggtcttatgctatggactactgggg<br>acaggggaccctggtgactgtctctagccatcaccatcaccaccatcatcac |
| 99789<br>CAR5-<br>Soluble<br>scFv-aa | 915 | **MALPVTALLLPLALLLHAARP**eivmtqspatlslspgeratlscrasqdisk<br>ylnwyqqkpgqaprlliyhtsrlhsgiparfsgsgsgtdytltisslqpedfavyfcqqgntlpy<br>tfgqgtkleikggggggggsggggsggggsqvqlqesgpglvkpsetlsltctvsgvslpdy<br>gvswirqppgkglewigviwgsettyyssslksrvtiskdnsknqvslklssvtaadtavyyc<br>akhyyyggsyamdywgqgtlvtvss**hhhhhhhh** |
| 104879<br>CAR 5-<br>Full-nt | 916 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagcggcggaggcgggagccaggtc<br>caactccaagaaagcggaccgggtcttgtgaagccatcagaaactctttcactgacttgtactgtg<br>agcggagtgtctctccccgattacggggtgtcttggatcagacagccaccggggaagggtctgg<br>aatggattggagtgatttggggctctgagactacttactactcttcatccctcaagtcacgcgtcac<br>catctcaaaggacaactctaagaatcaggtgtcactgaaactgtcatctgtgaccgcagccgaca<br>ccgccgtgtactattgcgctaagcattactattatggcgggagctacgcaatggattactggggac<br>agggtactctggtcaccgtgtccagcaccactaccccagcaccgaggccacccaccccggctc<br>ctaccatcgcctcccagcctctgtccctgcgtccggaggcatgtagacccgcagctggtggggc<br>cgtgcatacccggggtcttgacttcgcctgcgatatctacatttgggcccctctggctggtacttgc<br>ggggtcctgctgctttcactcgtgatcactctttactgtaagcgcggtcggaagaagctgctgtac<br>atctttaagcaacccttcatgaggcctgtgcagactactcaagaggaggacggctgttcatgccg<br>gttcccagaggaggaggaaggcggctgcgaactgcgcgtgaaattcagccgcagcgcagatg<br>ctccagcctacaagcaggggcagaaccagctctacaacgaactcaatcttggtcggagagagg<br>agtacgacgtgctggacaagcggagaggacgggacccagaaatgggcgggaagccgcgca<br>gaaagaatccccaagagggcctgtacaacgagctccaaaaggataagatggcagaagcctata<br>gcgagattggtatgaaaggggaacgcagaagaggcaaaggccacgacggactgtaccaggg<br>actcagcaccgccaccaaggacacctatgacgctcttcacatgcaggccctgccgcctcgg |
| 104879<br>CAR 5-<br>Full-aa | 917 | MALPVTALLLPLALLLHAARPeivmtqspatlslspgeratlsc**rasqdiskyl**<br>**n**wyqqkpgqaprlliy**htsrlhs**giparfsgsgsgtdytltisslqpedfavyfc**qqgntlpyt**<br>fgqgtkleikggggggggsggggggggsqvqlqesgpglvkpsetlsltctvsgvslp**dy**<br>**gvs**wirqppgkglewig**viwgsettyyssslks**rvtiskdnsknqvslklssvtaadtavyyc<br>ak**hyyyggsyamdy**wgqgtlvtvsstttpaprpptpaptiasqplslrpeacrpaaggavht<br>rgldfacdiyiwaplagtcgvlllslvitlyckrgrkkllyifkqpfmrpvqttqeedgcscrfpe<br>eeeggcelrvkfsrsadapaykqgqnqlynelnlgrreeydvldkrrgrdpemggkprrkn<br>pqeglynelqkdkmaeayseigmkgerrrgkghdglyqglstatkdtydalhmqalppr |
| | | CAR 6 |
| CAR6<br>scFv<br>domain | 918 | eivmtqspatlslspgeratlscrasqdiskylnwyqqkpgqaprlliyhtsrlhsgiparfsgs<br>gsgtdytltisslqpedfavyfcqqgntlpytfgqgtkleikggggsggggsggggsggggsq<br>vqlqesgpglvkpsetlsltctvsgvslpdygvswirqppgkglewigviwgsettyyqsslk<br>srvtiskdnsknqvslklssvtaadtavyycakhyyyggsyamdywgqgtlvtvss |
| 99790<br>CAR6-<br>Soluble<br>scFv-nt | 919 | atggccctcccagtgaccgctctgctgctgcctctcgcacttcttctccatgccgctcggcctgag<br>atcgtcatgacccaaagccccgctaccctgtccctgtcacccggcgagagggcaaccctttcat<br>gcagggccagccaggacatttctaagtacctcaactggtatcagcagaagccagggcaggctc<br>ctcgcctgctgatctaccacaccagccgcctccacagcggtatccccgccagattttccgggag<br>cgggtctggaaccgactacaccctcaccatctcttctctgcagcccgaggatttcgccgtctatttc<br>tgccagcaggggaatactctgccgtacaccttcggtcaaggtaccaagctggaaatcaaggga<br>ggcggaggatcaggcggtggcggaagcggaggaggtggctccggaggaggaggttcccaa<br>gtgcagcttcaagaatcaggacccggacttgtgaagccatcagaaaccctctccctgacttgtac<br>cgtgtccggtgtgagcctccccgactacggagtctcttggattcgccagcctccggggaagggt<br>cttgaatggattggggtgatttggggatcagagactacttactaccagtcatcacttaagtcacgg<br>gtcaccatcagcaaagataatagcaagaaccaagtgtcacttaagctgtcatctgtgaccgccgc<br>tgacaccgccgtgtactattgtgccaaacattactattacggagggtcttatgctatggactactgg<br>ggacaggggaccctggtgactgtctctagccatcaccatcaccaccatcatcac |
| 99790<br>CAR6-<br>Soluble<br>scFv-aa | 920 | **MALPVTALLLPLALLLHAARP**eivmtqspatlslspgeratlscrasqdisk<br>ylnwyqqkpgqaprlliyhtsrlhsgiparfsgsgsgtdytltisslqpedfavyfcqqgntlpy<br>tfgqgtkleikggggggggsggggsggggsqvqlqesgpglvkpsetlsltctvsgvslpdy<br>gvswirqppgkglewigviwgsettyyqsslksrvtiskdnsknqvslklssvtaadtavyyc<br>akhyyyggsyamdywgqgtlvtvss**hhhhhhhh** |
| 104880<br>CAR6-<br>Full-nt | 921 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc |

TABLE 2-continued

| CD19 CAR Constructs | | |
|---|---|---|
| Name | SEQ ID NO: | Sequence |
| | | gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagcggaggcggagggagccaggtc<br>caactccaagaaagcggaccgggtcttgtgaagccatcagaaactctttcactgacttgtactgtg<br>agcggagtgtctctccccgattacggggtgtcttggatcagacagccaccggggaagggtctgg<br>aatggattggagtgatttggggctctgagactacttactaccaatcatccctcaagtcacgcgtcac<br>catctcaaaggacaactctaagaatcaggtgtcactgaaactgtcatctgtgaccgcagccgaca<br>ccgccgtgtactattgcgctaagcattactattatggcgggagctacgcaatggattactggggac<br>agggtactctggtcaccgtgtccagcaccactaccccagcaccgaggccacccaccccggctc<br>ctaccatcgcctcccagcctctgtccctgcgtccggaggcatgtagacccgcagctggtggggc<br>cgtgcatacccggggtcttgacttcgcctgcgatatctacatttgggcccctctggctggtacttgc<br>ggggtcctgctgctttcactcgtgatcactctttactgtaagcgcggtcggaagaagctgctgtac<br>atctttaagcaacccttcatgaggcctgtgcagactactcaagaggaggacggctgttcatgccg<br>gttcccagaggaggaggaaggcggctgcgaactgcgcgtgaaattcagccgcagcgcagatg<br>ctccagcctacaagcaggggcagaaccagctctacaacgaactcaatcttggtcggagagagg<br>agtacgacgtgctggacaagcggagaggacgggacccagaaatgggcgggaagccgcgca<br>gaaagaatccccaagagggcctgtacaacgagctccaaaaggataagatggcagaagcctata<br>gcgagattggtatgaaaggggaacgcagaagaggcaaaggccacgacggactgtaccaggg<br>actcagcaccgccaccaaggacacctatgacgctcttcacatgcaggccctgccgcctcgg |
| 104880<br>CAR6-<br>Full-aa | 922 | MALPVTALLLPLALLLHAARPeivmtqspatlslspgeratlsc**rasqdiskyl**<br>**n**wyqqkpgqaprlliy**htsrlhs**giparfsgsgsgtdytltisslqpedfavyfc**qqgntlpyt**<br>fgqgtkleikggggggggsggggggggsqvqlqesgpglvkpsetlsltctvsgvslp**dy**<br>**gvs**wirqppgkglewig**viwgsettyyqsslks**rvtiskdnsknqvslklssvtaadtavyy<br>cak**hyyyggsyamdy**wgqgtlvtvssttttpaprpptpaptiasqplslrpeacrpaaggavh<br>trgldfacdiyiwaplagtcgvlllslvitlyckrgrkkllyifkqpfmrpvqttqeedgcscrfp<br>eeeeggcelrvkfsrsadapaykqgqnqlynelnlgrreeydvldkrrgrdpemggkprrkn<br>pqeglynelqkdkmaeayseigmkgerrrgkghdglyqglstatkdtydalhmqalppr |
| CAR 7 | | |
| CAR7<br>scFv<br>domain | 923 | qvqlqesgpglvkpsetlsltctvsgvslpdygvswirqppgkglewigviwgsettyysssl<br>ksrvtiskdnsknqvslklssvtaadtavyycakhyyyggsyamdywgqgtlvtvssgggg<br>sggggsgggggggseivmtqspatlslspgeratlscrasqdiskylnwyqqkpgqaprll<br>iyhtsrlhsgiparfsgsgsgtdytltisslqpedfavyfcqqgntlpytfgqgtkleik |
| 100796<br>CAR7-<br>Soluble<br>scFv-nt | 924 | atggcactgcctgtcactgccctcctgctgcctctggccctccttctgcatgccgccaggccccaa<br>gtccagctgcaagagtcaggacccggactggtgaagccgtctgagactctctcactgacttgtac<br>cgtcagcggcgtgtccctccccgactacggagtgtcatggatccgccaacctcccgggaaagg<br>gcttgaatggattggtgtcatctggggttctgaaaccacctactactcatcttccctgaagtccagg<br>gtgaccatcagcaaggataattccaagaaccaggtcagccttaagctgtcatctgtgaccgctgc<br>tgacaccgccgtgtattactgcgccaagcactactattacggaggaagctacgctatggactattg<br>gggacagggcactctcgtgactgtgagcagcggcggtggagggtctggaggtggaggatccg<br>gtggtggtgggtcaggcggaggagggagcgagattgtgatgactcagtcaccagccaccctttt<br>ctctttcacccggcgagagagcaaccctgagctgtagagccagccaggacatttctaagtacctc<br>aactggtatcagcaaaaaccggggcaggcccctcgcctcctgatctaccatacctcacgccttca<br>ctctggtatccccgctcggtttagcggatcaggatctggtaccgactacactctgaccatttccagc<br>ctgcagccagaagatttcgcagtgtatttctgccagcagggcaataccctttccttacaccttcggtc<br>agggaaccaagctcgaaatcaagcaccatcaccatcatcaccaccat |
| 100796<br>scFv-aa<br>CAR7- | 925 | **MALPVTALLLPLALLLHAARP**qvqlqesgpglvkpsetlsltctvsgvslp<br>dygvswirqppgkglewigviwgsettyysssslksrvtiskdnsknqvslklssvtaadtavy<br>ycakhyyyggsyamdywgqgtlvtvssggggsggggsggggsggggseivmtqspatls<br>lspgeratlscrasqdiskylnwyqqkpgqaprlliyhtsrlhsgiparfsgsgsgtdytltisslq<br>pedfavyfcqqgntlpytfgqgtkleik**hhhhhhhh** |
| 104881<br>Soluble<br>CAR 7<br>Full-nt | 926 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactattcatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccggaggtggcggaagcgaaatcgtgatgacccagagccctgcaaccct<br>gtccctttctcccggggaacgggctaccctttcttgtcgggcatcacaagatatctcaaaatacctc<br>aattggtatcaacagaagccgggacaggcccctaggcttcttatctaccacacctctcgcctgcat<br>agcgggattcccgcacgctttagcgggtctggaagcgggaccgactacactctgaccatctcat<br>ctctccagcccgaggacttcgccgtctacttctgccagcagggtaacaccctgccgtacaccttc<br>ggccagggcaccaagcttgagatcaaaaccactactcccgctccaaggccacccacccctgcc<br>ccgaccatcgcctctcagccgctttccctgcgtccggaggcatgtagacccgcagctggtgggg<br>ccgtgcatacccggggtcttgacttcgcctgcgatatctacatttgggcccctctggctggtacttg<br>cggggtcctgctgctttcactcgtgatcactctttactgtaagcgcggtcggaagaagctgctgta<br>catctttaagcaacccttcatgaggcctgtgcagactactcaagaggaggacggctgttcatgcc<br>ggttcccagaggaggaggaaggcggctgcgaactgcgcgtgaaattcagccgcagcgcagat |

TABLE 2-continued

CD19 CAR Constructs

| Name | SEQ ID NO: | Sequence |
|---|---|---|
| | | gctccagcctacaagcaggggcagaaccagctctacaacgaactcaatcttggtcggagagag<br>gagtacgacgtgctggacaagcggagaggacgggacccagaaatgggcgggaagccgcgc<br>agaaagaatccccaagagggcctgtacaacgagctccaaaaggataagatggcagaagcctat<br>agcgagattggtatgaaaggggaacgcagaagaggcaaaggccacgacggactgtaccagg<br>gactcagcaccgccaccaaggacacctatgacgctcttcacatgcaggccctgccgcctcgg |
| 104881<br>CAR 7<br>Full-aa | 927 | MALPVTALLLPLALLLHAARPqvqlqesgpglvkpsetlsltctvsgvslp**dy**<br>**gvs**wirqppgkglewig**viwgsettyyssslks**rvtiskdnsknqvslklssvtaadtavyyc<br>ak**hyyyggsyamdy**wgqgtlvtvssggggsggggsggggsggggseivmtqspatlsls<br>pgeratlscrasqdiskylnwyqqkpgqaprlliy**htsrlhs**giparfsgsgsgtdytltisslq<br>pedfavyfc**qqgntlpyt**fgqgtkleikttpaprpptpaptiasqplslrpeacrpaaggavht<br>rgldfacdiyiwaplagtcgvlllslvitlyckrgrkkllyifkqpfmrpvqttqeedgcscrfpe<br>eeeggcelrvkfsrsadapaykqgqnqlynelnlgrreeydvldkrrgrdpemggkprrkn<br>pqeglynelqkdkmaeayseigmkgerrrgkghdglyqglstatkdtydalhmqalppr |
| | | CAR8 |
| CAR8<br>scFv<br>domain | 928 | qvqlqesgpglvkpsetlsltctvsgvslpdygvswirqppgkglewigviwgsettyyqssl<br>ksrvtiskdnsknqvslklssvtaadtavyycakhyyyggsyamdywgqgtlvtvssgggg<br>sggggsggggsggggseivmtqspatlslspgeratlscrasqdiskylnwyqqkpgqaprll<br>iyhtsrlhsgiparfsgsgsgtdytltisslqpedfavyfcqqgntlpytfgqgtkleik |
| 100798<br>Soluble<br>scFv-nt<br>CAR8- | 929 | atggcactgcctgtcactgccctcctgctgcctctggccctccttctgcatgccgccaggccccaa<br>gtccagctgcaagagtcaggacccggactggtgaagccgtctgagactctctcactgacttgtac<br>cgtcagcggcgtgtccctccccgactacggagtgtcatggatccgccaacctcccgggaaagg<br>gcttgaatggattggtgtcatctggggttctgaaaccacctactaccagtcttccctgaagtccagg<br>gtgaccatcagcaaggataattccaagaaccaggtcagccttaagctgtcatctgtgaccgctgc<br>tgacaccgccgtgtattactgcgccaagcactactattacggaggaagctacgctatggactattg<br>gggacagggcactctcgtgactgtgagcagcggcggtggagggtctggaggtggaggatccg<br>gtggtggtgggtcaggcggaggagggagcgagattgtgatgactcagtcaccagccaccctttt<br>ctctttcacccggcgagagagcaaccctgagctgtagagccagccaggacatttctaagtacctc<br>aactggtatcagcaaaaaccggggcaggcccctcgcctcctgatctaccatacctcacgccttca<br>ctctggtatccccgctcggtttagcggatcaggatctggtaccgactacactctgaccatttccagc<br>ctgcagccagaagatttcgcagtgtatttctgccagcagggcaatacccttccttacaccttcggtc<br>agggaaccaagctcgaaatcaagcaccatcaccatcatcatcaccac |
| 100798<br>Soluble<br>scFv-aa<br>CAR8- | 930 | **MALPVTALLLPLALLLHAARP**qvqlqesgpglvkpsetlsltctvsgvslp<br>dygvswirqppgkglewigviwgsettyyqsslksrvtiskdnsknqvslklssvtaadtavy<br>ycakhyyyggsyamdywgqgtlvtvssggggsggggsggggsggggseivmtqspatls<br>lspgeratlscrasqdiskylnwyqqkpgqaprlliyhtsrlhsgiparfsgsgsgtdytltisslq<br>pedfavyfcqqgntlpytfgqgtkleik**hhhhhhhh** |
| 104882<br>CAR 8-<br>Full-nt | 931 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactatcaatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccggaggcggtgggtcagaaatcgtgatgacccagagccctgcaaccct<br>gtccctttctcccggggaacggctaccctttcttgtcgggcatcacaagatatctcaaaatacctc<br>aattggtatcaacagaagccgggacaggcccctaggcttcttatctaccacacctctcgcctgcat<br>agcgggattcccgcacgctttagcgggtctggaagcgggaccgactacactctgaccatctcat<br>ctctccagcccgaggacttcgccgtctacttctgccagcagggtaacaccctgccgtacaccttc<br>ggccagggcaccaagcttgagatcaaaaccactactcccgctccaaggccacccacccctgcc<br>ccgaccatcgcctctcagccgctttccctgcgtccggaggcatgtagacccgcagctggtgggg<br>ccgtgcatacccggggtcttgacttcgcctgcgatatctacatttgggcccctctggctggtacttg<br>cggggtcctgctgctttcactcgtgatcactctttactgtaagcgcggtcggaagaagctgctgta<br>catctttaagcaacccttcatgaggcctgtgcagactactcaagaggaggacggctgttcatgcc<br>ggttcccagaggaggaggaaggcggctgcgaactgcgcgtgaaattcagccgcagcgcagat<br>gctccagcctacaagcaggggcagaaccagctctacaacgaactcaatcttggtcggagagag<br>gagtacgacgtgctggacaagcggagaggacgggacccagaaatgggcgggaagccgcgc<br>agaaagaatccccaagagggcctgtacaacgagctccaaaaggataagatggcagaagcctat<br>agcgagattggtatgaaaggggaacgcagaagaggcaaaggccacgacggactgtaccagg<br>gactcagcaccgccaccaaggacacctatgacgctcttcacatgcaggccctgccgcctcgg |
| 104882<br>Full-aa<br>CAR 8- | 932 | MALPVTALLLPLALLLHAARPqvqlqesgpglvkpsetlsltctvsgvslp**dy**<br>**gvs**wirqppgkglewig**viwgsettyyqsslks**rvtiskdnsknqvslklssvtaadtavyy<br>cak**hyyyggsyamdy**wgqgtlvtvssggggsggggsggggsggggseivmtqspatlsl<br>spgeratlscrasqdiskylnwyqqkpgqaprlliy**htsrlhs**giparfsgsgsgtdytltissl<br>qpedfavyfc**qqgntlpyt**fgqgtkleikttpaprpptpaptiasqplslrpeacrpaaggav<br>htrgldfacdiyiwaplagtcgvlllslvitlyckrgrkkllyifkqpfmrpvqttqeedgcscrf<br>peeeeggcelrvkfsrsadapaykqgqnqlynelnlgrreeydvldkrrgrdpemggkprrk<br>npqeglynelqkdkmaeayseigmkgerrrgkghdglyqglstatkdtydalhmqalppr |

TABLE 2-continued

CD19 CAR Constructs

| Name | SEQ ID NO: | Sequence |
|---|---|---|
| | | CAR 9 |
| CAR9<br>scFv<br>domain | 933 | eivmtqspatlslspgeratlscrasqdiskylnwyqqkpgqaprlliyhtsrlhsgiparfsgs<br>gsgtdytltisslqpedfavyfcqqgntlpytfgqgtkleikggggsggggsggggsggggsq<br>vqlqesgpglvkpsetlsltctvsgvslpdygvswirqppgkglewigviwgsettyynsslk<br>srvtiskdnsknqvslklssvtaadtavyycakhyyyggsyamdywgqgtlvtvss |
| 99789<br>CAR9-<br>Soluble<br>scFv-nt | 934 | atggccctcccagtgaccgctctgctgctgcctctcgcacttcttctccatgccgctcggcctgag<br>atcgtcatgacccaaagccccgctaccctgtccctgtcacccggcgagagggcaaccctttcat<br>gcagggccagccaggacatttctaagtacctcaactggtatcagcagaagccagggcaggctc<br>ctcgcctgctgatctaccacaccagccgcctccacagcggtatccccgccagattttccgggag<br>cgggtctggaaccgactacaccctcaccatctcttctctgcagcccgaggatttcgccgtctatttc<br>tgccagcaggggaatactctgccgtacaccttcggtcaaggtaccaagctggaaatcaaggga<br>ggcggaggatcaggcggtggcggaagcggaggaggtggctccggaggaggaggttcccaa<br>gtgcagcttcaagaatcaggacccggacttgtgaagccatcagaaaccctctccctgacttgtac<br>cgtgtccggtgtgagcctccccgactacggagtctcttggattcgccagcctccggggaagggt<br>cttgaatggattggggtgatttggggatcagagactacttactacaattcatcacttaagtcacggg<br>tcaccatcagcaaagataatagcaagaaccaagtgtcacttaagctgtcatctgtgaccgccgct<br>gacaccgccgtgtactattgtgccaaacattactattacggagggtcttatgctatggactactggg<br>gacaggggaccctggtgactgtctctagccatcaccatcaccaccatcatcac |
| 99789<br>Soluble<br>scFv-aa<br>CAR9- | 935 | **MALPVTALLLPLALLLHAARP**eivmtqspatlslspgeratlscrasqdisk<br>ylnwyqqkpgqaprlliyhtsrlhsgiparfsgsgsgtdytltisslqpedfavyfcqqgntlpy<br>tfgqgtkleikggggsggggsggggsggggsqvqlqesgpglvkpsetlsltctvsgvslpdy<br>gvswirqppgkglewigviwgsettyynsslksrvtiskdnsknqvslklssvtaadtavyyc<br>akhyyyggsyamdywgqgtlvtvss**hhhhhhhh** |
| 105974<br>CAR 9-<br>Full-nt | 936 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagcggaggcggtgggagccaggtcc<br>aactccaagaaagcggaccgggtcttgtgaagccatcagaaactctttcactgacttgtactgtga<br>gcggagtgtctctccccgattacggggtgtcttggatcagacagccaccggggaagggtctgga<br>atggattggagtgatttggggctctgagactacttactacaactcatccctcaagtcacgcgtcacc<br>atctcaaaggacaactctaagaatcaggtgtcactgaaactgtcatctgtgaccgcagccgacac<br>cgccgtgtactattgcgctaagcattactattatggcgggagctacgcaatggattactggggaca<br>gggtactctggtcaccgtgtccagcaccactaccccagcaccgaggccacccaccccggctcc<br>taccatcgcctcccagcctctgtccctgcgtccggaggcatgtagacccgcagctggtggggcc<br>gtgcatacccggggtcttgacttcgcctgcgatatctacatttgggcccctctggctggtacttgcg<br>gggtcctgctgctttcactcgtgatcactctttactgtaagcgcggtcggaagaagctgctgtacat<br>ctttaagcaacccttcatgaggcctgtgcagactactcaagaggaggacggctgttcatgccggt<br>tcccagaggaggaggaaggcggctgcgaactgcgcgtgaaattcagccgcagcgcagatgct<br>ccagcctacaagcaggggcagaaccagctctacaacgaactcaatcttggtcggagagagga<br>gtacgacgtgctggacaagcggagaggacgggacccagaaatgggcgggaagccgcgcag<br>aaagaatccccaagagggcctgtacaacgagctccaaaaggataagatggcagaagcctatag<br>cgagattggtatgaaaggggaacgcagaagaggcaaaggccacgacggactgtaccaggga<br>ctcagcaccgccaccaaggacacctatgacgctcttcacatgcaggccctgccgcctcgg |
| 105974<br>CAR 9-<br>Full-aa | 937 | MALPVTALLLPLALLLHAARPeivmtqspatlslspgeratlsc**rasqdiskyl**<br>**n**wyqqkpgqaprlliy**htsrlhs**giparfsgsgsgtdytltisslqpedfavyfc**qqgntlpyt**<br>fgqgtkleikggggggggsggggggggsqvqlqesgpglvkpsetlsltctvsgvslp**dy**<br>**gvs**wirqppgkglewig**viwgsettyynsslks**rvtiskdnsknqvslklssvtaadtavyy<br>cak**hyyyggsyamdy**wgqgtlvtvsstttpaprpptpaptiasqplslrpeacrpaaggavh<br>trgldfacdiyiwaplagtcgvlllslvitlyckrgrkkllyifkqpfmrpvqttqeedgcscrfp<br>eeeeggcelrvkfsrsadapaykqgqnqlynelnlgrreeydvldkrrgrdpemggkprrkn<br>pqeglynelqkdkmaeayseigmkgerrrgkghdglyqglstatkdtydalhmqalppr |
| | | CAR10 |
| CAR10<br>scFv<br>domain | 938 | qvqlqesgpglvkpsetlsltctvsgvslpdygvswirqppgkglewigviwgsettyynssl<br>ksrvtiskdnsknqvslklssvtaadtavyycakhyyyggsyamdywgqgtlvtvssgggg<br>sggggsggggggggseivmtqspatlslspgeratlscrasqdiskylnwyqqkpgqaprll<br>iyhtsrlhsgiparfsgsgsgtdytltisslqpedfavyfcqqgntlpytfgqgtkleik |
| 100796<br>CAR10<br>Soluble<br>scFv-nt | 939 | atggcactgcctgtcactgccctcctgctgcctctggccctccttctgcatgccgccaggccccaa<br>gtccagctgcaagagtcaggacccggactggtgaagccgtctgagactctctcactgacttgtac<br>cgtcagcggcgtgtccctccccgactacggagtgtcatggatccgccaacctcccgggaaagg<br>gcttgaatggattggtgtcatctggggttctgaaaccacctactacaactcttccctgaagtccagg<br>gtgaccatcagcaaggataattccaagaaccaggtcagccttaagctgtcatctgtgaccgctgc<br>tgacaccgccgtgtattactgcgccaagcactactattacggaggaagctacgctatggactattg<br>gggacagggcactctcgtgactgtgagcagcggcggtggagggtctggaggtggaggatccg<br>gtggtggtgggtcaggcggaggagggagcgagattgtgatgactcagtcaccagccacccttt |

TABLE 2-continued

| CD19 CAR Constructs | | |
|---|---|---|
| Name | SEQ ID NO: | Sequence |
| | | ctctttcacccggcgagagagcaaccctgagctgtagagccagccaggacatttctaagtacctc<br>aactggtatcagcaaaaaccggggcaggcccctcgcctcctgatctaccatacctcacgccttca<br>ctctggtatccccgctcggtttagcggatcaggatctggtaccgactacactctgaccatttccagc<br>ctgcagccagaagatttcgcagtgtatttctgccagcagggcaatacccttccttacaccttcggtc<br>agggaaccaagctcgaaatcaagcaccatcaccatcatcaccaccat |
| 100796<br>Soluble<br>CAR10 | 940 | **MALPVTALLLPLALLLHAARP**qvqlqesgpglvkpsetlsltctvsgvslp<br>dygvswirqppgkglewigviwgsettyynsslksrvtiskdnsknqvslklssvtaadtavy<br>ycakhyyyggsyamdywgqgtlvtvssggggsggggsggggsggggseivmtqspatls<br>lspgeratlscrasqdiskylnwyqqkpgqaprlliyhtsrlhsgiparfsgsgsgtdytltisslq<br>pedfavyfcqqgntlpytfgqgtkleik**hhhhhhhh** |
| 105975<br>CAR 10<br>Full-nt | 941 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagcggaggcggtgggagccaggtcc<br>aactccaagaaagcggaccgggtcttgtgaagccatcagaaactctttcactgacttgtactgtga<br>gcggagtgtctctccccgattacggggtgtcttggatcagacagccaccggggaagggtctgga<br>atggattggagtgatttggggctctgagactacttactacaactcatccctcaagtcacgcgtcacc<br>atctcaaaggacaactctaagaatcaggtgtcactgaaactgtcatctgtgaccgcagccgacac<br>cgccgtgtactattgcgctaagcattactattatggcgggagctacgcaatggattactggggaca<br>gggtactctggtcaccgtgtccagcaccactaccccagcaccgaggccacccaccccggctcc<br>taccatcgcctcccagcctctgtccctgcgtccggaggcatgtagacccgcagctggtggggcc<br>gtgcatacccggggtcttgacttcgcctgcgatatctacatttgggcccctctggctggtacttgcg<br>gggtcctgctgctttcactcgtgatcactctttactgtaagcgcggtcggaagaagctgctgtacat<br>ctttaagcaacccttcatgaggcctgtgcagactactcaagaggaggacggctgttcatgccggt<br>tcccagaggaggaggaaggcggctgcgaactgcgcgtgaaattcagccgcagcgcagatgct<br>ccagcctacaagcaggggcagaaccagctctacaacgaactcaatcttggtcggagagagga<br>gtacgacgtgctggacaagcggagaggacgggacccagaaatgggcgggaagccgcgcag<br>aaagaatccccaagagggcctgtacaacgagctccaaaaggataagatggcagaagcctatag<br>cgagattggtatgaaaggggaacgcagaagaggcaaaggccacgacggactgtaccaggga<br>ctcagcaccgccaccaaggacacctatgacgctcttcacatgcaggccctgccgcctcgg |
| 105975<br>scFv-aa<br>CAR 10<br>Full-aa | 942 | MALPVTALLLPLALLLHAARPEIVMTQSPATLSLSPGERATLS<br>C**RASQDISKYLN**WYQQKPGQAPRLLIY**HTSRLHS**GIPARFS<br>GSGSGTDYTLTISSLQPEDFAVYFC**QQGNTLPYT**FGQGTKLE<br>IKGGGGSGGGGSGGGGSGGGGSQVQLQESGPGLVKPSETLS<br>LTCTVSGVSLPDYGVSWIRQPPGKGLEWIG**VIWGSETTYYN**<br>**SSLKS**RVTISKDNSKNQVSLKLSSVTAADTAVYYCAK**HYYY**<br>**GGSYAMDY**WGQGTLVTVSSTTTPAPRPPTPAPTIASQPLSLR<br>PEACRPAAGGAVHTRGLDFACDIYIWAPLAGTCGVLLLSLVI<br>TLYCKRGRKKLLYIFKQPFMRPVQTTQEEDGCSCRFPEEEEG<br>GCELRVKFSRSADAPAYKQGQNQLYNELNLGRREEYDVLD<br>KRRGRDPEMGGKPRRKNPQEGLYNELQKDKMAEAYSEIGM<br>KGERRRGKGHDGLYQGLSTATKDTYDALHMQALPPR |
| CAR11 | | |
| CAR11<br>scFv<br>domain | 943 | eivmtqspatlslspgeratlscrasqdiskylnwyqqkpgqaprlliyhtsrlhsgiparfsgs<br>gsgtdytltisslqpedfavyfcqqgntlpytfgqgtkleikggggsggggsggggsqvqlqes<br>gpglvkpsetlsltctvsgvslpdygvswirqppgkglewigviwgsettyynsslksrvtisk<br>dnsknqvslklssvtaadtavyycakhyyyggsyamdywgqgtlvtvss |
| 103101<br>CAR11-<br>Soluble<br>scFv-nt | 944 | Atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagccaggtccaactccaagaaagcg<br>gaccgggtcttgtgaagccatcagaaactctttcactgacttgtactgtgagcggagtgtctctccc<br>cgattacggggtgtcttggatcagacagccaccggggaagggtctggaatggattggagtgattt<br>ggggctctgagactacttactacaattcatccctcaagtcacgcgtcaccatctcaaaggacaact<br>ctaagaatcaggtgtcactgaaactgtcatctgtgaccgcagccgacaccgccgtgtactattgc<br>gctaagcattactattatggcgggagctacgcaatggattactggggacagggtactctggtcac<br>cgtgtccagccaccaccatcatcaccatcaccat |
| 103101<br>CAR11-<br>Soluble<br>scFv-aa | 945 | **MALPVTALLLPLALLLHAARP**eivmtqspatlslspgeratlscrasqdisk<br>ylnwyqqkpgqaprlliyhtsrlhsgiparfsgsgsgtdytltisslqpedfavyfcqqgntlpy<br>tfgqgtkleikggggggggsggggsqvqlqesgpglvkpsetlsltctvsgvslpdygvswi<br>rqppgkglewigviwgsettyynsslksrvtiskdnsknqvslklssvtaadtavyycakhyy<br>yggsyamdywgqgtlvtvss**hhhhhhhh** |

TABLE 2-continued

| CD19 CAR Constructs | | |
|---|---|---|
| Name | SEQ ID NO: | Sequence |
| 105976<br>CAR 11<br>Full-nt | 946 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactataactcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccggaggtggcggaagcgaaatcgtgatgacccagagccctgcaaccct<br>gtccctttctcccggggaacgggctaccctttcttgtcgggcatcacaagatatctcaaaatacctc<br>aattggtatcaacagaagccgggacaggcccctaggcttcttatctaccacacctctcgcctgcat<br>agcgggattcccgcacgctttagcgggtctggaagcgggaccgactacactctgaccatctcat<br>ctctccagcccgaggacttcgccgtctacttctgccagcagggtaacaccctgccgtacaccttc<br>ggccagggcaccaagcttgagatcaaaaccactactcccgctccaaggccacccacccctgcc<br>ccgaccatcgcctctcagccgctttccctgcgtccggaggcatgtagacccgcagctggtgggg<br>ccgtgcatacccggggtcttgacttcgcctgcgatatctacatttgggcccctctggctggtacttg<br>cggggtcctgctgctttcactcgtgatcactctttactgtaagcgcggtcggaagaagctgctgta<br>catctttaagcaacccttcatgaggcctgtgcagactactcaagaggaggacggctgttcatgcc<br>ggttcccagaggaggaggaaggcggctgcgaactgcgcgtgaaattcagccgcagcgcagat<br>gctccagcctacaagcaggggcagaaccagctctacaacgaactcaatcttggtcggagagag<br>gagtacgacgtgctggacaagcggagaggacgggacccagaaatgggcgggaagccgcgc<br>agaaagaatccccaagagggcctgtacaacgagctccaaaaggataagatggcagaagcctat<br>agcgagattggtatgaaaggggaacgcagaagaggcaaaggccacgacggactgtaccagg<br>gactcagcaccgccaccaaggacacctatgacgctcttcacatgcaggccctgccgcctcgg |
| 105976<br>Full-aa<br>CAR 11 | 947 | MALPVTALLLPLALLLHAARPQVQLQESGPGLVKPSETLSLT<br>CTVSGVSLP**DYGVS**WIRQPPGKGLEWIG**VIWGSETTYYNSS<br>LKS**RVTISKDNSKNQVSLKLSSVTAADTAVYYCAK**HYYYG<br>GSYAMDY**WGQGTLVTVSSGGGGSGGGGSGGGGSGGGGSEI<br>VMTQSPATLSLSPGERATLSC**RASQDISKYLN**WYQQKPGQA<br>PRLLIY**HTSRLHS**GIPARFSGSGSGTDYTLTISSLQPEDFAVYF<br>C**QQGNTLPYT**FGQGTKLEIKTTTPAPRPPTPAPTIASQPLSLR<br>PEACRPAAGGAVHTRGLDFACDIYIWAPLAGTCGVLLLSLVI<br>TLYCKRGRKKLLYIFKQPFMRPVQTTQEEDGCSCRFPEEEEG<br>GCELRVKFSRSADAPAYKQGQNQLYNELNLGRREEYDVLD<br>KRRGRDPEMGGKPRRKNPQEGLYNELQKDKMAEAYSEIGM<br>KGERRRGKGHDGLYQGLSTATKDTYDALHMQALPPR |
| CAR12 | | |
| CAR12<br>scFv<br>domain | 948 | qvqlqesgpglvkpsetlsltctvsgvslpdygvswirqppgkglewigviwgsettyynssl<br>ksrvtiskdnsknqvslklssvtaadtavyycakhyyyggsyamdywgqgtlvtvssgggg<br>sggggsggggseivmtqspatlslspgeratlscrasqdiskylnwyqqkpgqaprlliyhtsr<br>lhsgiparfsgsgsgtdytltisslqpedfavyfcqqgntlpytfgqgtkleik |
| 103104<br>CAR12-<br>Soluble<br>scFv-nt | 949 | atggctctgcccgtgaccgcactcctcctgccactggctctgctgcttcacgccgctcgcccaca<br>agtccagcttcaagaatcagggcctggtctggtgaagccatctgagactctgtccctcacttgcac<br>cgtgagcggagtgtccctcccagactacggagtgagctggattagacagcctcccggaaaggg<br>actggagtggatcggagtgatttggggtagcgaaaccacttactataactcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactact<br>ggggccagggaactctggtcactgtgtcatctggtggaggaggtagcggaggaggcgggagc<br>ggtggaggtggctccgaaatcgtgatgacccagagccctgcaaccctgtccctttctcccgggg<br>aacgggctaccctttcttgtcgggcatcacaagatatctcaaaatacctcaattggtatcaacagaa<br>gccgggacaggcccctaggcttcttatctaccacacctctcgcctgcatagcgggattcccgcac<br>gctttagcgggtctggaagcgggaccgactacactctgaccatctcatctctccagcccgagga<br>cttcgccgtctacttctgccagcagggtaacaccctgccgtacaccttcggccagggcaccaag<br>cttgagatcaaacatcaccaccatcatcaccatcac |
| 103104<br>CAR12-<br>Soluble<br>scFv-aa | 950 | **MALPVTALLLPLALLLHAARP**qvqlqesgpglvkpsetlsltctvsgvslp<br>dygvswirqppgkglewigviwgsettyynsslksrvtiskdnsknqvslklssvtaadtavy<br>ycakhyyyggsyamdywgqgtlvtvssggggsggggsggggseivmtqspatlslspger<br>atlscrasqdiskylnwyqqkpgqaprlliyhtsrlhsgiparfsgsgsgtdytltisslqpedfa<br>vyfcqqgntlpytfgqgtkleik**hhhhhhhh** |
| 105977<br>CAR 12-<br>Full-nt | 951 | atggccctccctgtcaccgccctgctgcttccgctggctcttctgctccacgccgctcggcccga<br>aattgtgatgacccagtcacccgccactcttagcctttcacccggtgagcgcgcaaccctgtcttg<br>cagagcctcccaagacatctcaaaataccttaattggtatcaacagaagcccggacaggctcctc<br>gccttctgatctaccacaccagccggctccattctggaatccctgccaggttcagcggtagcgga<br>tctgggaccgactacaccctcactatcagctcactgcagccagaggacttcgctgtctatttctgtc<br>agcaagggaacaccctgccctacacctttggacagggcaccaagctcgagattaaaggtggag<br>gtggcagcggaggaggtgggtccggcggtggaggaagccaggtccaactccaagaaagcg<br>gaccgggtcttgtgaagccatcagaaactctttcactgacttgtactgtgagcggagtgtctctccc<br>cgattacggggtgtcttggatcagacagccaccggggaagggtctggaatggattggagtgattt<br>ggggctctgagactacttactacaactcatccctcaagtcacgcgtcaccatctcaaaggacaact |

TABLE 2-continued

| CD19 CAR Constructs | | |
|---|---|---|
| Name | SEQ ID NO: | Sequence |
| | | ctaagaatcaggtgtcactgaaactgtcatctgtgaccgcagccgacaccgccgtgtactattgc<br>gctaagcattactattatggcgggagctacgcaatggattactggggacagggtactctggtcac<br>cgtgtccagcaccactaccccagcaccgaggccacccaccccggctcctaccatcgcctccca<br>gcctctgtccctgcgtccggaggcatgtagacccgcagctggtggggccgtgcatacccgggg<br>tcttgacttcgcctgcgatatctacatttgggcccctctggctggtacttgcggggtcctgctgcttt<br>cactcgtgatcactctttactgtaagcgcggtcggaagaagctgctgtacatctttaagcaaccctt<br>catgaggcctgtgcagactactcaagaggaggacggctgttcatgccggttcccagaggagga<br>ggaaggcggctgcgaactgcgcgtgaaattcagccgcagcgcagatgctccagcctacaagc<br>aggggcagaaccagctctacaacgaactcaatcttggtcggagagaggagtacgacgtgctgg<br>acaagcggagaggacgggacccagaaatgggcgggaagccgcgcagaaagaatccccaag<br>agggcctgtacaacgagctccaaaaggataagatggcagaagcctatagcgagattggtatga<br>aaggggaacgcagaagaggcaaaggccacgacggactgtaccagggactcagcaccgcca<br>ccaaggacacctatgacgctcttcacatgcaggccctgccgcctcgg |
| 105977<br>CAR 12-<br>Full-aa | 952 | MALPVTALLLPLALLLHAARPEIVMTQSPATLSLSPGERATLS<br>C**RASQDISKYLN**WYQQKPGQAPRLLIY**HTSRLHS**GIPARFS<br>GSGSGTDYTLTISSLQPEDFAVYFC**QQGNTLPY**TFGQGTKLE<br>IKGGGGSGGGGSGGGGSQVQLQESGPGLVKPSETLSLTCTVS<br>GVSLP**DYGVS**WIRQPPGKGLEWIG**VIWGSETTYYNSSLKS**R<br>VTISKDNSKNQVSLKLSSVTAADTAVYYCAK**HYYYGGSYA**<br>**MDY**WGQGTLVTVSSTTTPAPRPPTPAPTIASQPLSLRPEACRP<br>AAGGAVHTRGLDFACDIYIWAPLAGTCGVLLLSLVITLYCKR<br>GRKKLLYIFKQPFMRPVQTTQEEDGCSCRFPEEEEGGCELRV<br>KFSRSADAPAYKQGQNQLYNELNLGRREEYDVLDKRRGRD<br>PEMGGKPRRKNPQEGLYNELQKDKMAEAYSEIGMKGERRR<br>GKGHDGLYQGLSTATKDTYDALHMQALPPR |
| CTL019 | | |
| CTL019-<br>Soluble<br>scFv-<br>Histag-nt | 953 | atggccctgcccgtcaccgctctgctgctgccccttgctctgcttcttcatgcagcaaggccggac<br>atccagatgacccaaaccacctcatccctctctgcctctcttggagacagggtgaccatttcttgtc<br>gcgccagccaggacatcagcaagtatctgaactggtatcagcagaagccggacggaaccgtg<br>aagctcctgatctaccatacctctcgcctgcatagcggcgtgccctcacgcttctctggaagcgg<br>atcaggaaccgattattctctcactatttcaaatcttgagcaggaagatattgccacctatttctgcca<br>gcagggtaataccctgccctacaccttcggaggagggaccaagctcgaaatcaccggtggagg<br>aggcagcggcggtggagggtctggtggaggtggttctgaggtgaagctgcaagaatcaggcc<br>ctggacttgtggccccttcacagtccctgagcgtgacttgcaccgtgtccggagtctccctgccc<br>gactacggagtgtcatggatcagacaacctccacggaaaggactggaatggctcggtgtcatct<br>ggggtagcgaaactacttactacaattcagccctcaaaagcaggctgactattatcaaggacaac<br>agcaagtcccaagtctttcttaagatgaactcactccagactgacgacaccgcaatctactattgtg<br>ctaagcactactactacggaggatcctacgctatggattactggggacaaggtacttccgtcactg<br>tctcttcacaccatcatcaccatcaccatcac |
| CTL019-<br>Soluble<br>scFv-<br>Histag-aa | 954 | **MALPVTALLLPLALLLHAARP**diqmtqttsslsaslgdrvtiscrasqdisk<br>ylnwyqqkpdgtvklliyhtsrlhsgvpsrfsgsgsgtdysltisnleqediatyfcqqgntlpy<br>tfgggtkleitggggsggggsggggsevklqesgpglvapsqslsvtctvsgvslpdygvswi<br>rqpprkglewlgviwgsettyynsalksrltiikdnsksqvflkmnslqtddtaiyycakhyy<br>yggsyamdywgqgtsvtvss**hhhhhhhh** |
| CTL019<br>Full-nt | 955 | atggccttaccagtgaccgccttgctcctgccgctggccttgctgctccacgccgccaggccgg<br>acatccagatgacacagactacatcctccctgtctgcctctctgggagacagagtcaccatcagtt<br>gcagggcaagtcaggacattagtaaatatttaaattggtatcagcagaaaccagatggaactgtta<br>aactcctgatctaccatacatcaagattacactcaggagtcccatcaaggttcagtggcagtgggt<br>ctggaacagattattctctcaccattagcaacctggagcaagaagatattgccacttacttttgcca<br>acagggtaatacgcttccgtacacgttcggaggggggaccaagctggagatcacaggtggcg<br>gtggctcgggcggtggtgggtcgggtggcggcggatctgaggtgaaactgcaggagtcagga<br>cctggcctggtggcgccctcacagagcctgtccgtcacatgcactgtctcaggggtctcattacc<br>cgactatggtgtaagctggattcgccagcctccacgaaagggtctggagtggctgggagtaatat<br>ggggtagtgaaaccacatactataattcagctctcaaatccagactgaccatcatcaaggacaact<br>ccaagagccaagttttcttaaaaatgaacagtctgcaaactgatgacacagccatttactactgtgc<br>caaacattattactacggtggtagctatgctatggactactggggccaaggaacctcagtcaccgt<br>ctcctcaaccacgacgccagcgccgcgaccaccaacaccggcgcccaccatcgcgtcgcagc<br>ccctgtccctgcgcccagaggcgtgccggccagcggcggggggcgcagtgcacacgaggg<br>ggctggacttcgcctgtgatatctacatctgggcgcccttggccgggacttgtggggtccttctcct<br>gtcactggttatcaccctttactgcaaacggggcagaaagaaactcctgtatatattcaaacaacc<br>atttatgagaccagtacaaactactcaagaggaagatggctgtagctgccgatttccagaagaag<br>aagaaggaggatgtgaactgagagtgaagttcagcaggagcgcagacgcccccgcgtacaag<br>cagggccagaaccagctctataacgagctcaatctaggacgaagagaggagtacgatgttttgg<br>acaagagacgtggccgggaccctgagatggggggaaagccgagaaggaagaaccctcagg<br>aaggcctgtacaatgaactgcagaaagataagatggcggaggcctacagtgagattgggatga<br>aaggcgagcgccggaggggcaaggggcacgatggcctttaccagggtctcagtacagccac<br>caaggacacctacgacgcccttcacatgcaggccctgccccctcgc |

TABLE 2-continued

| CD19 CAR Constructs | | |
|---|---|---|
| Name | SEQ ID NO: | Sequence |
| CTL019<br>Full-aa | 956 | MALPVTALLLPLALLLHAARPdiqmtqttsslsaslgdrvtiscrasqdiskyln<br>wyqqkpdgtvklliyhtsrlhsgvpsrfsgsgsgtdysltisnleqediatyfcqqgntlpytfg<br>ggtkleitggggsggggsggggsevklqesgpglvapsqslsvtctvsgvslpdygvswirq<br>pprkglewlgviwgsettyynsalksrltiikdnsksqvflkmnslqtddtaiyycakhyyyg<br>gsyamdywgqgtsvtvsstttpaprpptpaptiasqplslrpeacrpaaggavhtrgldfacdi<br>yiwaplagtcgvlllslvitlyckrgrkkllyifkqpfmrpvqttqeedgcscrfpeeeeggcel<br>rvkfsrsadapaykqgqnqlynelnlgrreeydvldkrrgrdpemggkprrknpqeglynel<br>qkdkmaeayseigmkgerrrgkghdglyqglstatkdtydalhmqalppr |
| CTL019<br>scFv<br>domain | 957 | diqmtqttsslsaslgdrvtiscrasqdiskylnwyqqkpdgtvklliyhtsrlhsgvpsrfsgs<br>gsgtdysltisnleqediatyfcqqgntlpytfgggtkleitggggsggggsggggsevklqes<br>gpglvapsqslsvtctvsgvslpdygvswirqpprkglewlgviwgsettyynsalksrltiik<br>dnsksqvflkmnslqtddtaiyycakhyyyggsyamdywgqgtsvtvss |
| mCAR1<br>scFv | | QVQLLESGAELVRPGSSVKISCKASGYAFSSYWMNWVKQRP<br>GQGLEWIGQIYPGDGDTNYNGKFKGQATLTADKSSSTAYM<br>QLSGLTSEDSAVYSCARKTISSVVDFYFDYWGQGTTVTGGG<br>SGGGSGGGSGGGSELVLTQSPKFMSTSVGDRVSVTCKASQN<br>VGTNVAWYQQKPGQSPKPLIYSATYRNSGVPDRFTGSGSGT<br>DFTLTITNVQSKDLADYFCQYNRYPYTSFFFTKLEIKRRS |
| mCAR1<br>Full-aa | | QVQLLESGAELVRPGSSVKISCKASGYAFSSYWMNWVKQRP<br>GQGLEWIGQIYPGDGDTNYNGKFKGQATLTADKSSSTAYM<br>QLSGLTSEDSAVYSCARKTISSVVDFYFDYWGQGTTVTGGG<br>SGGGSGGGSGGGSELVLTQSPKFMSTSVGDRVSVTCKASQN<br>VGTNVAWYQQKPGQSPKPLIYSATYRNSGVPDRFTGSGSGT<br>DFTLTITNVQSKDLADYFCQYNRYPYTSFFFTKLEIKRRSKIE<br>VMYPPPYLDNEKSNGTIIHVKGKHLCPSPLFPGPSKPFWVLV<br>VVGGVLACYSLLVTVAFIIFWVRSKRSRLLHSDYMNMTPRR<br>PGPTRKHYQPYAPPRDFAAYRSRVKFSRSADAPAYQQGQNQ<br>LYNELNLGRREEYDVLDKRRGRDPEMGGKPRRKNPQEGLY<br>NELQKDKMAEAYSEIGMKGERRRGKGHDGLYQGLSTATKD<br>TYDALHMQALPPR |
| mCAR2<br>scFv | | DIQMTQTTSSLSASLGDRVTISCRASQDISKYLNWYQQKPDG<br>TVKLLIYHTSRLHSGVPSRFSGSGSGTDYSLTISNLEQEDIATY<br>FCQQGNTLPYTFGGGTKLEITGSTSGSGKPGSGEGSTKGEVK<br>LQESGPGLVAPSQSLSVTCTVSGVSLPDYGVSWIRQPPRKGL<br>EWLGVIWGSETTYYNSALKSRLTIIKDNSKSQVFLKMNSLQT<br>DDTAIYYCAKHYYYGGSYAMDYWGQGTSVTVSSE |
| mCAR2<br>CAR-aa | | DIQMTQTTSSLSASLGDRVTISCRASQDISKYLNWYQQKPDG<br>TVKLLIYHTSRLHSGVPSRFSGSGSGTDYSLTISNLEQEDIATY<br>FCQQGNTLPYTFGGGTKLEITGSTSGSGKPGSGEGSTKGEVK<br>LQESGPGLVAPSQSLSVTCTVSGVSLPDYGVSWIRQPPRKGL<br>EWLGVIWGSETTYYNSALKSRLTIIKDNSKSQVFLKMNSLQT<br>DDTAIY<br>YCAKHYYYGGSYAMDYWGQGTSVTVSSESKYGPPCPPCPM<br>FWVLVVVGGVLACYSLLVTVAFIIFWVKRGRKKLLYIFKQPF<br>MRPVQTTQEEDGCSCRFEEEEGGCELRVKFSRSADAPAYQQ<br>GQNQLYNELNLGRREEYDVLDKRRGRDPEMGGKPRRKNPQ<br>EGLYNELQKDKMAEAYSEIGMKGERRRGKGHDGLYQGLST<br>ATKDTYDALHMQALPPRL |
| mCAR2<br>Full-aa | | DIQMTOTT SSLSASLGDR VTISCRASQD ISKYLNWYQQ<br>KPDGTVKLLI YHTSRLHSGV PSRFSGSGSG TDYSLTISNL<br>EQEDIATYFC QOGNTLPYTF GGGTKLEITG STSGSGKPGS<br>GEGSTKGEVK LQESGPGLVA PSQSLSVTCT VSGVSLPDYG<br>VSWIRQPPRK GLEWLGVIWG SETTYYNSAL KSRLTIIKDN<br>SKSQVFLKMN SLQTDDTAIY YCAKHYYYGG<br>SYAMDYWGQG TSVTVSSESK YGPPCPPCPM<br>FWVLVVVGGV LACYSLLVTV<br>AFIIFWVKRG RKKLLYIFKQ PFMRPVQTTQ EEDGCSCRFE<br>EEEGGCELRV KFSRSADAPA YQQGQNQLYN ELNLGRREEY<br>DVLDKRRGRD PEMGGKPRRK NPQEGLYNEL<br>QKDKMAEAYS EIGMKGERRR GKGHDGLYQG<br>LSTATKDTYD ALHMQALPPR LEGGGEGRGS LLTCGDVEEN<br>PGPRMLLLVT SLLLCELPHP AFLLIPRKVC NGIGIGEFKD<br>SLSINATNIK HFKNCTSISG DLHILPVAFR GDSFTHTPPL<br>DPQELDILKT VKEITGFLLI QAWPENRTDL HAFENLEIIR<br>GRTKQHGQFS LAVVSLNITS LGLRSLKEIS DGDVIISGNK<br>NLCYANTINW KKLFGTSGQK TKIISNRGEN SCKATGQVCH<br>ALCSPEGCWG PEPRDCVSCR NVSRGRECVD KCNLLEGEPR<br>EFVENSECIQ CHPECLPQAM NITCTGRGPD NCIQCAHYID<br>GPHCVKTCPA GVMGENNTLV WKYADAGHVC |

TABLE 2-continued

| CD19 CAR Constructs | | |
|---|---|---|
| Name | SEQ ID NO: | Sequence |
| | | HLCHPNCTYG CTGPGLEGCP TNGPKIPSIA TGMVGALLLL LVVALGIGLF M |
| mCAR3 scFv | | DIQMTQTTSSLSASLGDRVTISCRASQDISKYLNWYQQKPDG TVKLLIYHTSRLHSGVPSRFSGSGSGTDYSLTISNLEQEDIATY FCQQGNTLPYTFGGGTKLEITGSTSGSGKPGSGEGSTKGEVK LQESGPGLVAPSQSLSVTCTVSGVSLPDYGVSWIRQPPRKGL EWLGVIWGSETTYYNSALKSRLTIIKDNSKSQVFLKMNSLQT DDTAIYYCAKHYYYGGSYAMDYWGQGTSVTVSS |
| mCAR3 Full-aa | | DIQMTQTTSSLSASLGDRVTISCRASQDISKYLNWYQQKPDG TVKLLIYHTSRLHSGVPSRFSGSGSGTDYSLTISNLEQEDIATY FCQQGNTLPYTFGGGTKLEITGSTSGSGKPGSGEGSTKGEVK LQESGPGLVAPSQSLSVTCTVSGVSLPDYGVSWIRQPPRKGL EWLGVIWGSETTYYNSALKSRLTIIKDNSKSQVFLKMNSLQT DDTAIYYCAKHYYYGGSYAMDYWGQGTSVTVSSAAAIEVM YPPPYLDNEKSNGTIIHVKGKHLCPSPLFPGPSKPFWVLVVV GGVLACYSLLVTVAFIIFWVRSKRSRLLHSDYMNMTPRRPGP TRKHYQPYAPPRDFAAYRSRVKFSRSADAPAYQQGQNQLY NELNLGRREEYDVLDKRRGRDPEMGGKPRRKNPQEGLYNE LQKDKMAEAYSEIGMKGERRRGKGHDGLYQGLSTATKDTY DALHMQALPPR |
| SSJ25-C1 VH sequence | | QVQLLESGAELVRPGSSVKISCKASGYAFSSYWMNWVKQRP GQGLEWIGQIYPGDGDTNYNGKFKGQATLTADKSSSTAYM QLSGLTSEDSAVYSCARKTISSVVDFYFDYWGQGTTVT |
| SSJ25-C1 VL sequence | | ELVLTQSPKFMSTSVGDRVSVTCKASQNVGTNVAWYQQKP GQSPKPLIYSATYRNSGVPDRFTGSGSGTDFTLTITNVQSKDL ADYFYFCQYNRYPYTSGGGTKLEIKRRS |

In some embodiments, the CD19 CAR or binding domain includes the amino acid sequence of CTL019, or is encoded by the nucleotide sequence of CTL019 according to Table 2 with or without the leader sequence or the his tag, or a sequence substantially identical thereto (e.g., at least 85%, 90%, 95% or higher identity).

In some embodiments, the CDRs are defined according to the Kabat numbering scheme, the Chothia numbering scheme, or a combination thereof Bispecific Minibodies The present invention also includes a composition comprising a minibody and a bispecific minibody. A bispecific minibody comprises two different binding specificities and thus binds to two different antigens. In one embodiment, the bispecific minibody comprises a first antigen binding domain that binds to a first antigen and a second antigen binding domain that binds to a second antigen. In another embodiment, the bispecific minibody comprises an antigen binding domain comprising a first and a second single chain variable fragment (scFv) molecules. In yet another embodiment, the bispecific minibody comprises a first and second single chain variable fragment (scFv) molecules and a constant domain.

The constant domain can be a fragment from an antibody such as, but not limited to, IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19. The constant domain can be a fragment from any heavy or light chain of an antibody. A heavy-chain constant domain that corresponds to the different classes of antibodies are denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains. The bispecific minibody may also be expressed as a membrane protein with specificity for at least one target cell associated antigen. Examples of target cell associated antigens are described elsewhere herein, all of which may be targeted by the bispecific minibody of the present invention. In one embodiment, the bispecific minibody comprises a bispecific antigen binding domain. In this embodiment, the bispecific antigen binding domain includes a synthetic antibody, human antibody, a humanized antibody, single chain variable fragment, single domain antibody, an antigen binding fragment thereof, and any combination thereof.

In one embodiment, the bispecific minibody comprises specificity for a target cell antigen. The target cell antigen may include the same target cell antigen that the T cell receptor binds or may include a different target cell antigen. The target cell antigen may include any type of ligand that defines any target cell. For example, the target cell antigen may be chosen to recognize a ligand that acts as a cell marker on target cells associated with a particular disease state. Thus examples of cell markers that may act as ligands for the antigen moiety domain in a bispecific minibody, including those associated with viral, bacterial and parasitic infections, autoimmune disease and cancer cells.

In one embodiment, the bispecific minibody binds to a tumor antigen, such as an antigen that is specific for a tumor or cancer of interest. In another embodiment, the bispecific minibody is capable of binding to an antigen and the variable heavy chain fragment and the variable light chain fragment of the minibody bind the same antigen.

In an exemplary embodiment, the present invention comprises a minibody that binds and blocks an inhibitory receptor on a T cell and a bispecific minibody that binds and blocks an inhibitory receptor on the T cell with one arm and binds a target on a tumor cell with the other arm to bring the tumor cell in close proximity to the T cell.

Techniques for engineering and expressing bispecific minibodies include, but are not limited to, recombinant co-expression of two immunoglobulin heavy chain-light chain pairs having different specificities (see Milstein and Cuello, Nature 305: 537 (1983), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science 229:81 (1985)); using leucine zippers to produce bispecific antibodies (see, e.g., Kostelny et al., J. Immunol. 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991). Engineered antibodies with three or more functional antigen binding sites, including "Octopus antibodies," are also included herein (see, e.g. US 2006/0025576A1). Bispecific minibodies can be constructed by linking two different antibodies, or portions thereof. For example, a bispecific minibody can comprise Fab, F(ab')2, Fab', scFv, and sdAb from two different antibodies.

Human Minibodies

For in vivo use of minibodies described herein in humans, it may be preferable to use human antibody fragments. Completely human minibodies are particularly desirable for therapeutic treatment of human subjects. Human minibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human minibody can also be an antibody wherein the heavy and light chains are encoded by a nucleotide sequence derived from one or more sources of human DNA.

Human minibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Minibodies can be engineered from antibodies directed against the target of choice obtained from immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human minibodies can also be made from antibodies derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human minibodies may also be generated from antibodies obtained from in vitro activated B cells (see, U.S. Pat. Nos. 5,567,610 and 5,229,275, each of which is incorporated herein by reference in its entirety). Human minibodies can also be generated from antibodies made from in vitro hybridoma techniques such as, but not limited to, that described by Roder et al. (Methods Enzymol., 121:140-167 (1986)).

Humanized Minibodies

Alternatively, in some embodiments, a non-human minibody is humanized, where specific sequences or regions of the antibody fragments are modified to increase similarity to an antibody naturally produced in a human. In one embodiment, the variable chains are humanized.

A "humanized" minibody retains a similar antigenic specificity as the original antibody fragments. However, using certain methods of humanization, the affinity and/or specificity of binding of the minibody for a human antigen may be increased using methods of "directed evolution," as described by Wu et al., J. Mol. Biol., 294:151 (1999), the contents of which are incorporated herein by reference herein in their entirety.

A humanized minibody has one or more amino acid residues introduced into it from a source which is nonhuman. These nonhuman amino acid residues are often referred to as "import" residues, which are typically taken from an "import" variable domain. Thus, humanized minibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. Humanized minibodies include human antibody fragments in which some CDR residues and possibly some FR residues are substituted by residues from analogous sites in rodent antibodies. Humanization of minibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized minibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized minibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains to be used in the minibody. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Minibodies can be humanized with retention of high affinity for the target antigen and other favorable biological properties. According to one aspect of the invention, humanized minibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired minibody characteristic, such as increased affinity for the target antigen, is achieved. In general, the CDR residues are directly and most substantially involved in influencing antigen binding.

Exemplary Minibody Sequences

Figure 3:
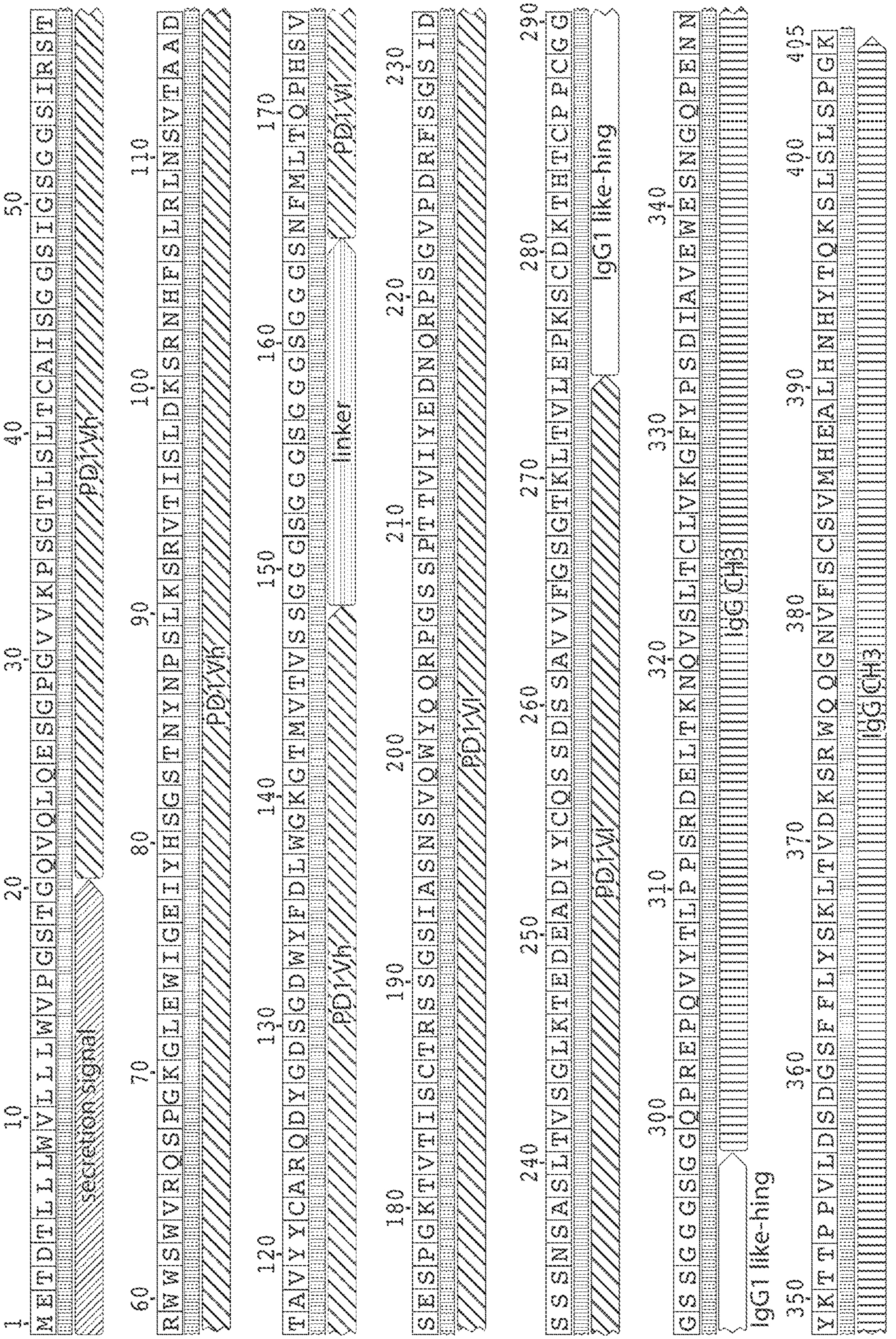
FIG. 3 is an image showing the PD1 minibody amino acid sequence (SEQ ID NO:1). The corresponding nucleic acid sequence is SEQ ID NO:10. The secretion signal comprises an amino acid sequence corresponding to SEQ ID NO:2. The linker comprises an amino acid sequence corresponding to SEQ ID NO:3. The hinge comprises an amino acid sequence corresponding to SEQ ID NO:4. The constant chain fragment from IgG comprises an amino acid sequence corresponding to SEQ ID NO:5. The variable heavy chain fragment comprises an amino acid sequence corresponding to SEQ ID NO:6. The variable light chain fragment comprises an amino acid sequence corresponding to SEQ ID NO:7.
Figure 4:
FIG. 4 is an image showing the PD1-PDL1 bispecific minibody amino acid sequence (SEQ ID NO:8). The corresponding nucleotide sequence is SEQ ID NO:11.

FIGS. 3 and 4 show exemplary minibody and bispecific minibody amino acid sequences.

FIG. 3 is an image showing the PD1 minibody amino acid sequence METDTLLLWVLLLWVPGSTGQVQLQE SGPGVVKPSGTLSLTCAISGGSIGSGGSIRSTRW WSWVRQSPGKGLEWIGEIYHSGSTNYNPSLKSRVTI- SLDKSRNHFSLRLNSVTAADTAV YYCARQDYGDS GDWYFDLWGKGTMVTVSSGGGSGGGSGGGSGGG- SNFMLTQPHSVS ESPGKTVTISCTRSSGSIASNSVQ WYQQRPGSSPTTVIYEDNQRPSGVPDRFSG SIDSS SNS ASLTVSGLKTEDEADYYCQSSDSSAVVFGSGTK LTVLEPKSCDKTHTCPPCGGGSSGGG SGGQPREP QVYTLPPSRDELTKNQVSLTCLVKGFYPSDIA- VEWESNGQPENNYKTTPPV LDSDGSFFLYSKLTVD KSRWQQGNVFSCSVMHEALHNHYTQKSLSLSPGK (SEQ ID NO:1). The corresponding nucleic acid sequence is ATGGAAACCGACACCCTGCTGCTGTGGGTG CTG CTGCTGTGGGTGCCAGGCTCTACA GGACAGG TGCAGCTGCAGGAATCTGGCCCTGGCGTCGTGA AGCCTAGCGGCACACT GAGCCTGACCTGTGC- CATCAGCGGCGGCTCTATTGGCTCCGGCGGCAG- CATCAGATC CACCAGATGGTGGTCTTGGGTG CGCCAGTCTCCTGGCAAGGGCCTGGAATGGATCG GCGAGATCTACCACAGCGGCTCCACCAACTA- CAACCCCAGCCTGAAGTCCAGAGTG ACCAT CAGCCTGGACAAGAGCCGGAACCACTTCAGCCT- GAGACTGAACAGCGTGAC AGCCGCCGACAC CG CCGTGTACTACTGCGCCAGACAGGACTACGGCG ACAGCGGCG ACTGGTACTTCGACCTGTGGGGC AAGGGCACAATGGTCACCGTGTCTAGCGGCGGA GGAAGCGGAGGCGGATCTGGGGGAGGAAG TG GCGGAGGCAGCAACTTCATGCTGA CCCAGCCTCA CAGCGTGTCCGAGAGCCCTGGCAAGACCGTGAC- CATCTCCTGCACCA GAAGCTCCGGCTCTAT CGCC AGCAACAGCGTGCAGTGGTATCAGCAGAGGCCCG GC AGCAGCCCTACCACCGTGATCTACGAGG ACAACCAGAGGCCCAGCGGCGTGCCCGA TAGAT- TCTCTGGCAGCATCGACAGCAGCTCCAACAGC GCCAGCCTGACCGTGTCCGG CCTGAAAACAG AGGACGAGGCCGACTACTACTGCCAGAGCAGCGA- TAGCAGCGCCG TGGTGTTTGGCAGCGGCACCAA GCTGACCGTGCTGGAACCCAAGAGCTGCGACAAG ACCCACACCTGTCCCCCTTGTGGCGGCGGATCT TC TGGCGGAGGATCTGGCGGACAG CCCAGAGAA CCCCAGGTGTACACACTGCCCCCCAGCAGAGAT-GAGCTGACCAAGAA CCAGGTGTCCCTGACCT GCCTCGTGAAGGGCTTCTACCCCTCCGATATCG CCGTGGA ATGGGAGAGCAATGGCCAGCCC GAGAACAACTACAAGACCACTCCCCCTGTGCTGG ACAGCGACGGCTCATTCTTCCTGTACAGCAAGC TGACAGTGGACAAGTCCCGGTGG CAGCAGG GCA ACGTGTTCAGCTGCAGCGTGATGCACGAGGC- CC TGCACAACCACTA CACCCAGAAGTCCCTGTCCCT-GAGCCCCGGCAAA (SEQ ID NO:10). The secretion signal comprises amino acid sequence METDTLLLWVLLLWVPGSTG (SEQ ID NO:2). The linker comprises amino acid sequence GGGSGGGSGGGSGGGSN (SEQ ID NO:3). The hinge comprises amino acid sequence EPKSCDKTHTCPPCGGGSSGGGSG (SEQ ID NO:4). The constant chain fragment from IgG comprises amino acid sequence (SEQ ID NO: 5)
GQPREPQVYTLPPSRDELTKNQVSLTCLVKGFYPSDIAVE

WESNGQPENNYKTTPPVLDSDGSFFLYSKLTVDKSRWQQG

NVFSCSVMHEALHNHYTQKSLSLSPGK.

The variable heavy chain fragment comprises amino acid sequence QVQLQESGPGVVKPSGTLSLTCAISGGSI GSGGSIRSTRWWSWVRQSPGKGLEWIGEIYH SGS TNYNPSLKSRVTISLDKSRNHFSLRLNSVTAADTA-VYYCARQDYGDSGDWYFDLW GKGTMVTVSS (SEQ ID NO:6). The variable light chain fragment comprises amino acid sequence (SEQ ID NO: 7)
NFMLTQPHSVSESPGKTVTISCTRSSGSIASNSVQWYQQR

PGSSPTTVIYEDNQRPSGVPDRFSGSIDSSSNSASLTVSG

LKTEDEADYYCQSSDSSAVVFGSGTKLTVL.

FIG. 4 is an image showing the PD1-PDL1 bispecific minibody amino acid sequence METDTLLLWVLLL-WVPGSTGQVQLQESGPGVVKPSGTLSLTCAISGG SIGSGGSIRSTRW WSWVRQSPGKGLEWIGEIYHSG-STNYNPSLKSRVTISLDKSRNHFSLRLNSVTAADTAV YYCARQDYGDSGDWYFDLWGKGTMVTVSSGG-GSGGGSGGGSGGGSNFMLTQPHSVS ESPGKTVTISC-TRSSGSIASNSVQWYQQRPGSSPTTVIYEDNQR-PSGVPDRFSGSIDSSSNS ASLTVSGLKTEDEADYYC-QSSDSSAVVFGSGTKLTVLGGGSGGGSGG- GSG GGSQVQLV QSGAEVKKPGSSVKVSCKTSGDTF-STYAISWVRQAPGQGLEWMGGIIPIFGKAHYAQKF QGRVTITADESTSTAYMELSSLRSEDTAVYFCA RKFHFVSGSPFGMDVWGQGTTVTVSS GGGSGG GSGGGSGGGSEIVLTQSPATLSLSPGERATLSCR ASQSVSSYLAWYQQKPGQA PRLLIYDASNRATGI-PARFSGSGSGTDFTLTISSLEPEDFAVYYCQQ RSNWPTFGQGTKVE IK (SEQ ID NO:8). The corresponding nucleotide sequence is (SEQ ID NO: 11)
ATGGAAACCGACACCCTGCTGCTGTGGGTGCTGCTGCTGT

GGGTGCCAGGCTCTACAGGACAGGTGCAGCTGCAGGAATC

-continued

TGGCCCTGGCGTCGTGAAGCCTAGCGGCACACTGAGCCTG

ACCTGTGCCATCAGCGGCGGCTCTATTGGCTCCGGCGGCA

GCATCAGATCCACCAGATGGTGGTCTTGGGTGCGCCAGTC

TCCTGGCAAGGGCCTGGAATGGATCGGCGAGATCTACCAC

AGCGGCTCCACCAACTACAACCCCAGCCTGAAGTCCAGAG

TGACCATCAGCCTGGACAAGAGCCGGAACCACTTCAGCCT

GAGACTGAACAGCGTGACAGCCGCCGACACCGCCGTGTAC

TACTGCGCCAGACAGGACTACGGCGACAGCGGCGACTGGT

ACTTCGACCTGTGGGGCAAGGGCACAATGGTCACCGTGTC

TAGCGGCGGAGAAGCGGAGGCGGATCTGGGGGAGGAAGTG

GCGGAGGCAGCAACTTCATGCTGACCCAGCCTCACAGCGT

GTCCGAGAGCCCTGGCAAGACCGTGACCATCTCCTGCACC

AGAAGCTCCGGCTCTATCGCCAGCAACAGCGTGCAGTGGT

ATCAGCAGAGGCCCGGCAGCAGCCCTACCACCGTGATCTA

CGAGGACAACCAGAGGCCCAGCGGCGTGCCCGATAGATTC

TCTGGCAGCATCGACAGCAGCTCCAACAGCGCCAGCCTGA

CCGTGTCCGGCCTGAAAACAGAGGACGAGGCCGACTACTA

CTGCCAGAGCAGCGATAGCAGCGCCGTGGTGTTTGGCAGC

GGCACCAAGCTGACAGTGCTGGGAGGCGGCTCAGGCGGAG

GATCTGGCGGCGGATCCGGCGGAGGCTCTCAGGTGCAGCT

GGTGCAGTCTGGCGCCGAAGTGAAGAAACCCGGCAGCTCC

GTGAAGGTGTCCTGCAAGACAAGCGGCGACACCTTCTCCA

CCTACGCCATCAGTTGGGTGCGGCAGGCACCTGGACAGGG

ACTGGAATGGATGGGAGGCATCATCCCCATCTTCGGCAAG

GCCCACTACGCCCAGAAATTCCAGGGCCGCGTGACAATCA

CCGCCGACGAGAGCACAAGCACCGCCTACATGGAACTGAG

CAGCCTGCGGAGCGAGGATACCGCTGTGTACTTCTGTGCC

CGGAAGTTCCACTTTGTGTCCGGCAGCCCCTTCGGCATGG

ATGTGTGGGGACAGGGCACCACAGTGACTGTGTCCTCCGG

GGGAGGCAGCGGAGGGGGAAGTGGCGGCGGAAGTGGGGGA

GGATCTGAGATCGTGCTGACACAGAGCCCCGCCACCCTGT

CACTGTCTCCAGGCGAAAGAGCCACCCTGAGCTGCAGAGC

CAGCCAGTCTGTGTCCAGCTACCTGGCCTGGTATCAGCAG

AAACCCGGCCAGGCCCCCAGACTGCTGATCTATGACGCCA

GCAATCGGGCCACCGGCATCCCTGCCAGATTTTCCGGAAG

CGGCTCCGGCACCGACTTCACCCTGACAATCAGCAGCCTG

GAACCCGAGGACTTCGCCGTGTATTATTGCCAGCAGCGGA

GCAACTGGCCCACCTTTGGCCAGGGCACTAAGGTGGAAAT

CAAG.

The strep-tagII has an amino acid sequence of: WSHPQFEK, SEQ ID NO:9.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA

In one embodiment, RNA is introduced into target cells. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA encoding bispecific minibodies is electroporated into the cells. In one embodiment, the RNA encoding bispecific minibodies is in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

The methods described herein also include obtaining T cells from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Therapy

The modified T cells comprising minibodies described herein may be included in a composition for therapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering a population of modified T cells capable of expressing and secreting a minibody to a subject in need thereof to prevent or treat an immune reaction adverse to the subject. In another embodiment, the modified T cells further express a TCR, a CAR or a bispecific minibody.

In another aspect, the invention includes a method of treating a disease or condition in a subject comprising administering a population of modified T cells capable of expressing and secreting a minibody to a subject in need thereof. The modified T cells express a nucleic acid encoding a minibody comprising a secretion signal, a variable heavy chain fragment, a variable light chain fragment and a constant chain fragment, and the modified T cells secrete the minibody.

The modified T cells can be administered to an animal, preferably a mammal, even more preferably a human, to treat a tumor, cancer or a condition related to cancer, such as various cancers including but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. In one aspect, the invention includes treating a condition, such as cancer, in a subject, comprising administering to the subject a therapeutically effective amount of a pharmaceutical composition comprising a population of modified T cells capable of expressing a minibody.

In another embodiment, the T cells capable of expressing a minibody described herein may be used for the manufacture of a medicament for the treatment of an immune response in a subject in need thereof.

Cells of the invention can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogenic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

Pharmaceutical Compositions

Pharmaceutical compositions of the present invention may comprise a modified T cell population capable of expressing a minibody as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the modified T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer modified T cells to a subject and then subsequently redraw blood (or have an apheresis performed), isolate T cells therefrom and further modify the T cells according to the present invention, and reinfuse the patient with these modified T cells. This process can be carried out multiple times every few weeks. In certain embodiments, T cells can be obtained from blood draws of from 10 ml to 400 ml. In certain embodiments, T cells are obtained from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, T cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Flow Cytometry Analysis. Tumor cells were cultured in the absence or presence of IFN-γ (R&D systems, Minneapolis, MN) at 20 ng/ml for 24 hrs before the cells were harvested for staining with PDL1-PE (BioLegend). Live cells were gated on the live cell population by forward scatter/side scatter (FSC/SSC) and then PDL-1 positivity by PE expression. K562 cells and K562 PDL1/CD19 cells were stained with PDL1-PE (BioLegend, San Diego, CA) and CD19-PacBlue (Life Technologies, Carlsbad, CA). Live cells were gated on the live cell population by forward scatter/side scatter (FSC/SSC) and then PDL1 and CD19 positivity by PE and PacBlue expression. For the in-direct detection of antibody fragments and detection of CAR cells, cells were stained with biotin anti-human IgG1 (Jackson ImmunoReasearch, West Grove, PA) and then a strep-avidin secondary antibody (BD, Franklin Lakes, NJ).

Intracellular cytokine analysis. CAR-transduced or untransduced T cells were cocultured with target cells (tumors, cell lines, or human primary cells) in a 1:1 ratio at $2\times10^6$/ml in 96-well round bottom tissue culture plates at 37° C., 5% $CO_2$ for 6 hours in RPMI 1640 plus 10% FBS in the presence of Golgi inhibitors, monensin and brefeldin A. Cells were washed, stained with live/dead viability stain, followed by surface staining for CD3, then fixed and permeabilized, and intra-cellularly stained for IFN-γ, TNF-α, and IL-2. Cells were analyzed on a LSRII (BD) and gated on live, single-cell lymphocytes and CD3-positive lymphocytes.

CFSE Proliferation. T cells were electroporated with mRNA and after 24 hrs were harvested and labeled with 5 mM carboxyfluorescein diacetate succinimidyl ester (CF SE) (Life Technologies), then plated in a 96-well plate at 1:1 ratio of T cells to tumor cells (K562 PDL1/CD19), and incubated for analysis by flow cytometry at day 2, day 4, day 8. All cells were harvested and stained with CD3 to identify T cells and then gated CFSE-positive to determine proliferation of T cells. Samples were acquired on LSR II, and data were analyzed with FlowJo v8.8.7 (TreeStar, Ashland, OR).

Antibody Generation. Sequences were synthesized via Gene Art (Life Technologies, Carlsbad, CA) and then cloned into pTRPE lentivial vectors, pGEM.64A-based vector, using xbal & salI restriction sites. Strep-tagII (WSHPQFEK) was added to the c-terminus of the antibody fragments by PCR.

Isolation, Electroporation, and Expansion of Primary Human T Lymphocytes. Isolated T cells were obtained from leukapheresis products from healthy donors under an institutional review board-approved protocol. T cells were stimulated with Dynabeads Human T-Activator CD3/CD28 (Life Technologies, Carlsbad, CA) at a bead to cell ratio of 3:1 (first stimulation). T cells were cultured in RPMI 1640 medium supplemented with 10% fetal calf serum, hepes buffer (20 mM), and penicillin and streptomycin (1%). The end of the first stimulation was determined on the basis of a decrease of log-phase growth and a reduction of mean lymphocytic volume to 300 to 330 fl as measured on a Coulter Multisizer (Beckman Coulter, Sharon Hill, PA), typically about 10 days after stimulation, at which point cells were frozen down for use at a later time.

For preparation of in-vitro-transcribed (IVT) RNA, the CAR-encoding gene constructs were subcloned into the pGEM.64A-based vector. mRNA was prepared using T7 MSCRIPT™ Standard mRNA Production System (Cell Script, Madison, WI). Using the BTX CM380 (Harvard Apparatus BTX, Cambridge, MA) electroporation machine, the IVT RNA was introduced into the T cells at a ratio of 1 μg RNA per $10^6$ cells. Cells were allowed to rest for 24 hrs before use in functional assays.

Mouse models. All mouse experiments were conducted according to Institutional Animal Care and Use Committee (IACUC)-approved protocols. For orthotopic models, $1\times10^4$ D270-luc+ cells were implanted intracranially into 6- to 8-week-old female NSG mice, with 10 mice per group. The stereotactic surgical implants with tumor cells were implanted 1 mm right and 1 mm anterior to the bregma with a 3 mm depth into the brain. Before surgery and for 3 days after surgery, mice were treated with an analgesic and monitored for adverse symptoms in accordance with the IACUC. Three days post-surgery, mice were injected with $5\times10^6$ CAR T positive cells in 100 μl of PBS intravenously via the tail vein. Bioluminescent measurements were used as a surrogate for tumor volume.

In subcutaneous models, NSG mice were injected with $5.0\times10^5$ U87-vIII/luc+ tumors subcutaneously in 100 μl of PBS on day 0. Tumor progression was evaluated by luminescence emission on a Xenogen IVIS Spectrum after intraperitoneal D-luciferin injection according to the manufacturer's directions (GoldBio, St. Louis, MO). Additionally, tumor size was measured by calipers in three dimensions, L×W×H, for the duration of the experiment. Mice were treated with $3.0\times10^6$ CAR positive T cells or a matched number of untransduced T cells intravenously via tail vein in 100 μl of PBS 7 days post subcutaneous tumor injections. Survival was followed over time until predetermined IACUC-approved endpoint was reached (n=10 mice per group).

Cell lines and culture. The human glioma cell lines U87 and U87-EGFRvIII and the human D270 glioblastoma xenograft were kindly provided by Dr. Darell Bigner of Duke University, Durham NC. These cell lines were lentivirally transduced to express the click beetle green luciferase and green fluorescent protein (GFP) under control of the EF-1a promoter. At 48 hours after transduction, cells were sorted on an Influx cell sorter (BD Biosciences) on the basis of GFP expression and cells evaluated as 100% GFP-positive were subsequently expanded. These cells were cultured in MEM (Richter's modification), no phenol red with 10% fetal bovine serum (FBS), hepes buffer (20 mM), GlutaMax (100×), sodium pyruvate (1 mM) and penicillin and streptomycin (1%).

PD1 Minibody. The PD1 minibody was designed based on the variable region of the heavy and light of PD1-17 as disclosed in U.S. Pat. No. 7,488,802. The other elements were based on human IgG1 and the CH3 domain from the protein, P01857, in the UniProt database. PD1-PDL1 bispecific was designed based on the scFv for PD1 as described herein for the PD1 minibody and the PDL1 scFv was based on PDL1 in International Patent No. WO2007005874 A2. Both proteins contain a secretion sequence based on the T84.66 light chain leader sequence.

The results of the experiments are now described.

FIG. 1 is a panel of graphs showing that PDL1 expression was upregulated in tumor cell lines in response to IFNg. Various cell lines were stained for PDL1 expression using anti-PDL1-PE both at normal culture conditions and then at 24 hours post-treatment with 20 ng/ml of IFNg. Tumor cells can upregulate PDL1 upon treatment with INFg. This is important to note because when endogenous or synthetic T cells (CAR T cells) are activated to attack tumors, the tumors respond by upregulating PDL1 to inhibit T cell function and lead to immune evasion.

Figure 2:
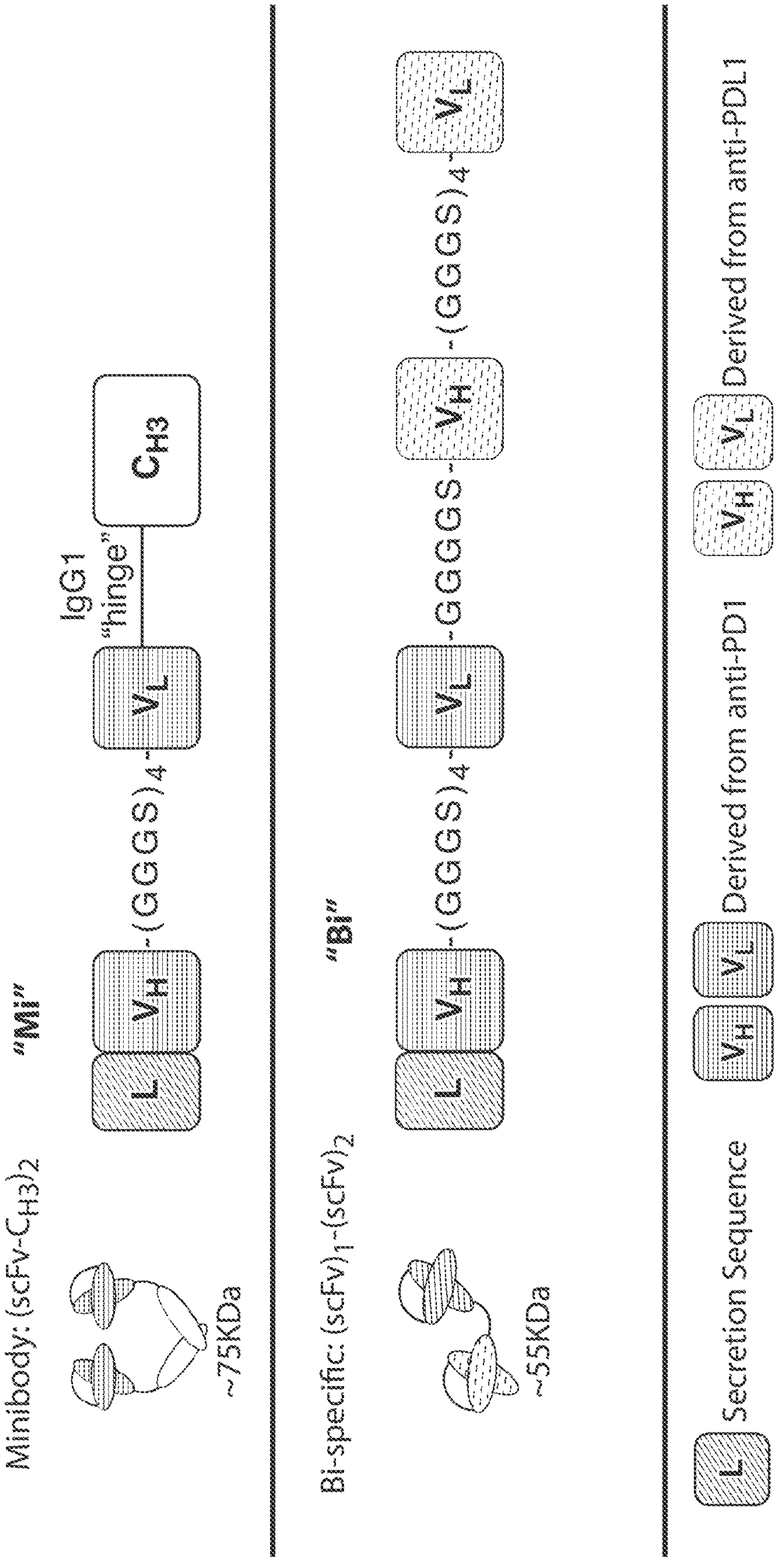
FIG. 2 is a schematic representation of the design of PD1 minibody and PD1-PDL1 bispecific minibody/antibody fragments for T cell secretion. The PD1 minibody was designed based on the variable region of the heavy and light chain of PD1-17 as disclosed in U.S. Pat. No. 7,488,802. The transmembrane domain was from human IgG1 and the intracellular domain was from the CH3 domain from the protein, P01857, in the UniProt database. PD1-PDL1 bispecific minibody was designed based on the scFv for PD1 as described herein for the PD1 minibody and the PDL1 scFv was based on PDL1 as disclosed in International Patent No. WO2007005874 A2. Both proteins contain a secretion sequence based on the T84.66 light chain leader sequence.

FIG. 2 shows a schematic representation of the design of PD1 minibody and PD1-PDL1 bispecific minibody fragments for T cell secretion.

FIG. 3 is an image showing the PD1 minibody amino acid sequence (SEQ ID NO:1). The secretion signal comprises an amino acid sequence corresponding to SEQ ID NO:2. The linker comprises an amino acid sequence corresponding to SEQ ID NO:3. The hinge comprises an amino acid sequence corresponding to SEQ ID NO:4. The constant chain fragment from IgG comprises an amino acid sequence SEQ ID NO:5. The variable heavy chain fragment comprises an amino acid sequence SEQ ID NO:6. The variable light chain fragment comprises an amino acid sequence (SEQ ID NO:7).

FIG. 4 is an image showing the PD1-PDL1 bispecific minibody amino acid sequence (SEQ ID NO:8).

Figure 5:
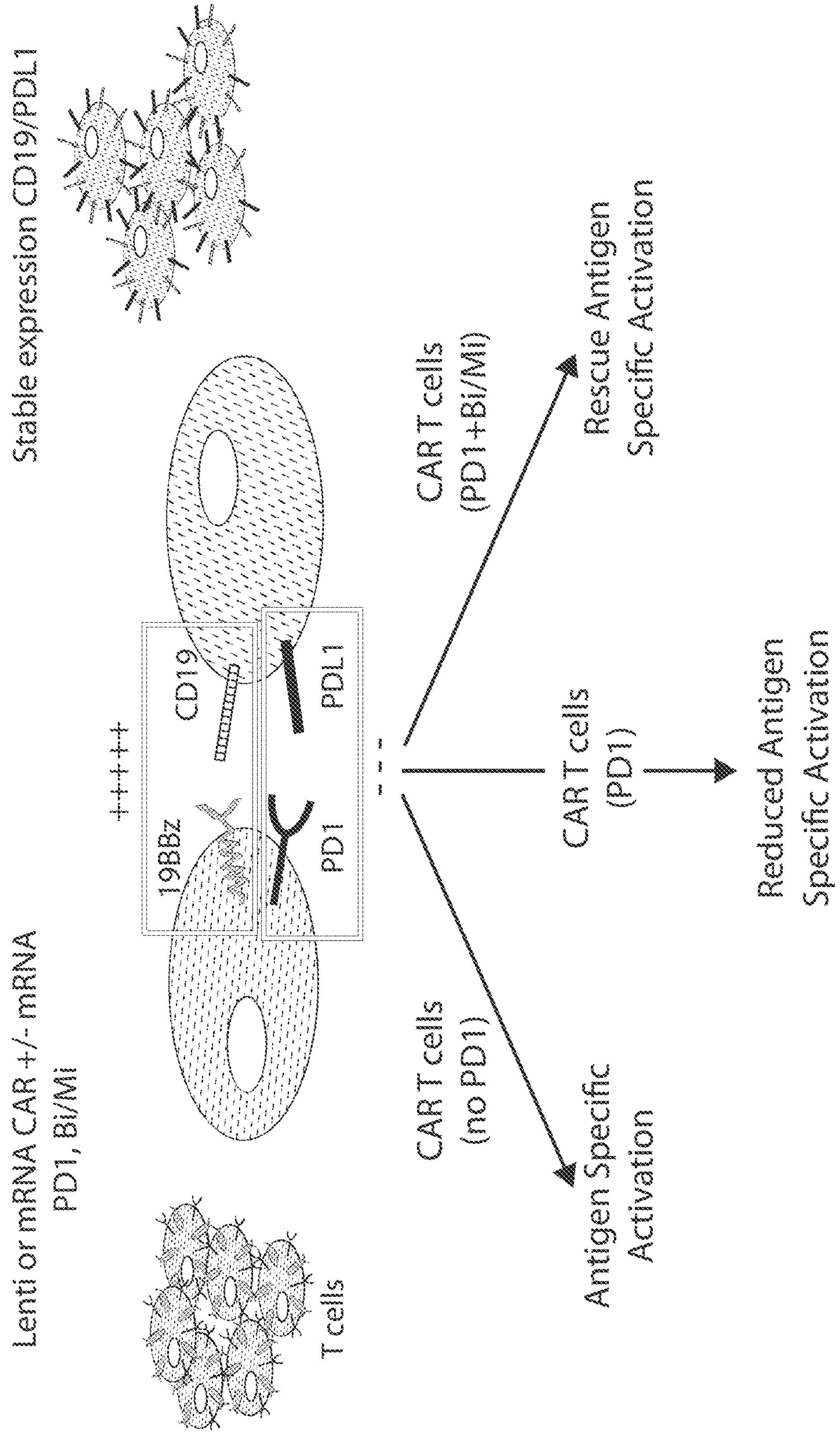
FIG. 5 is a schematic illustration of a system used to test PD1 minibody or PD1-PDL1 bispecific minibody. T cells expressing CD19 specific CARs in the presence or absence of PD1 minibody or PD1-PDL1 bispecific minibody are mixed with K562 cells expressing CD19 (antigen) and PDL1 (negative signal for T cells). The CAR T cells are shown to have three possible outcomes. CAR T cells with no PD1 expression exhibit antigen specific activation after interaction with the K562 cells. CAR T cells with PD1 expression exhibit reduced antigen specific activation after interaction with the K562 cells. CAR T cells with PD1 expression and PD1 minibody or PD1-PDL1 bispecific minibody expression exhibit rescued antigen specific activation after interaction with the K562 cells.

FIG. 5 is a schematic illustration of a system used to test PD1 minibody or PD1-PDL1 bispecific minibody. T cells expressing CD19 specific CARs in the presence or absence of PD1 minibody or PD1-PDL1 bispecific minibody are mixed with K562 cells expressing CD19 (antigen) and PDL1 (negative signal for T cells). The CAR T cells are shown to have three possible outcomes. CAR T cells with no PD1 expression have antigen specific activation after interaction with the K562 cells. CAR T cells with PD1 expression have reduced antigen specific activation after interaction with the K562 cells. CAR T cells with PD1 expression and PD1 minibody or PD1-PDL1 bispecific minibody expression have rescued antigen specific activation after interaction with the K562 cells.

Figure 6:
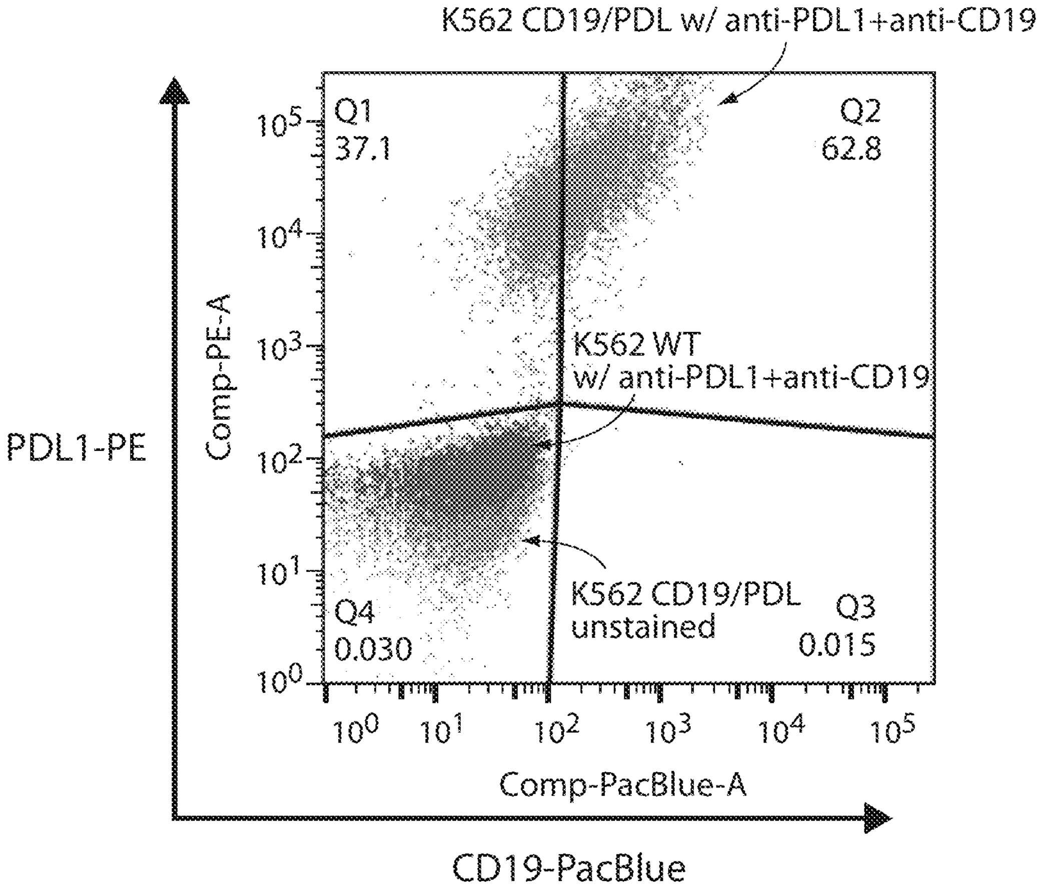
FIG. 6 is a graph showing K562 target cells expressing CD19 and PDL1. K562 WT or K562 CD19/PDL1 cells were stained with anti-CD19 PacBlue and anti-PDL1 PE to show that the K562 target cells expressed CD19 and PDL1.

FIG. 6 is a graph showing K562 target cells expressing CD19 and PDL1. K562 WT or K562 CD19/PDL1 cells were stained with anti-CD19 PacBlue and anti-PDL1 PE to show that the K562 target cells expressed CD19 and PDL1.

Figure 7:
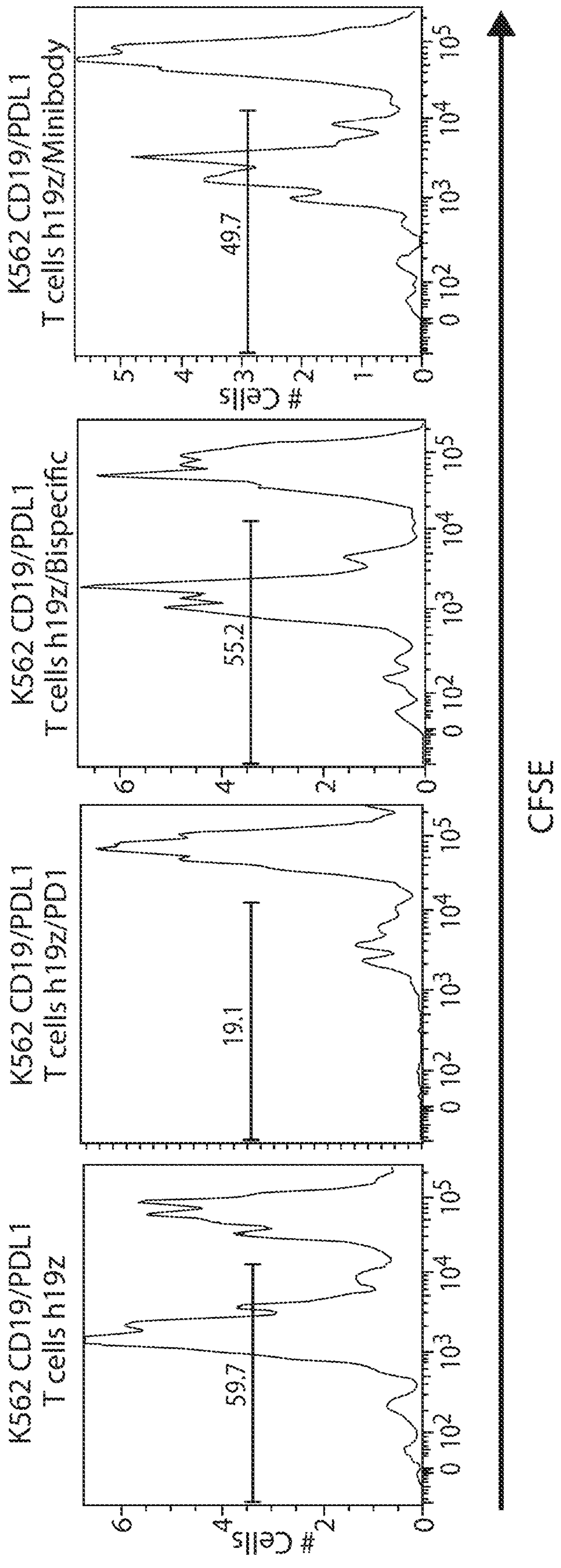
FIG. 7 is a panel of graphs showing the results of testing CAR T cells expressing PD1 minibody or PD1-PDL1 bispecific minibody in a CFSE proliferation assay after culturing with K562 cells. T cells were electroporated with mRNA: CD19z CAR, CD19z CAR+PD1, CD19z CAR+PD1+PD1-PDL1 bispecific minibody, CAR+PD1+PD1 minibody and then labeled with CFSE. The CFSE labeled T cells were cultured 1:1 with target K562 CD19/PDL1 cells. These cultures were then assayed using flow cytometry for proliferation by CFSE dilution. Data shown is from day 8.

FIG. 7 is a panel of graphs showing the results of testing CAR T cells expressing PD1 minibody or PD1-PDL1 bispecific minibody in a CFSE proliferation assay after culturing with K562 cells. T cells were electroporated with mRNA: CD19z CAR, CD19z CAR+PD1, CD19z CAR+PD1+PD1 minibody, and then labeled with CFSE. The CFSE labeled T cells were cultured 1:1 with target K562 CD19/PDL1 cells. These cultures were then assayed for proliferation by CFSE dilution. Data shown is from day 8. These data show that the secreted PD1 minibody or PD1-PDL1 bispecific minibody can rescue proliferation of CART cells that were inhibited by the T cells expressing PD1.

Figure 8:
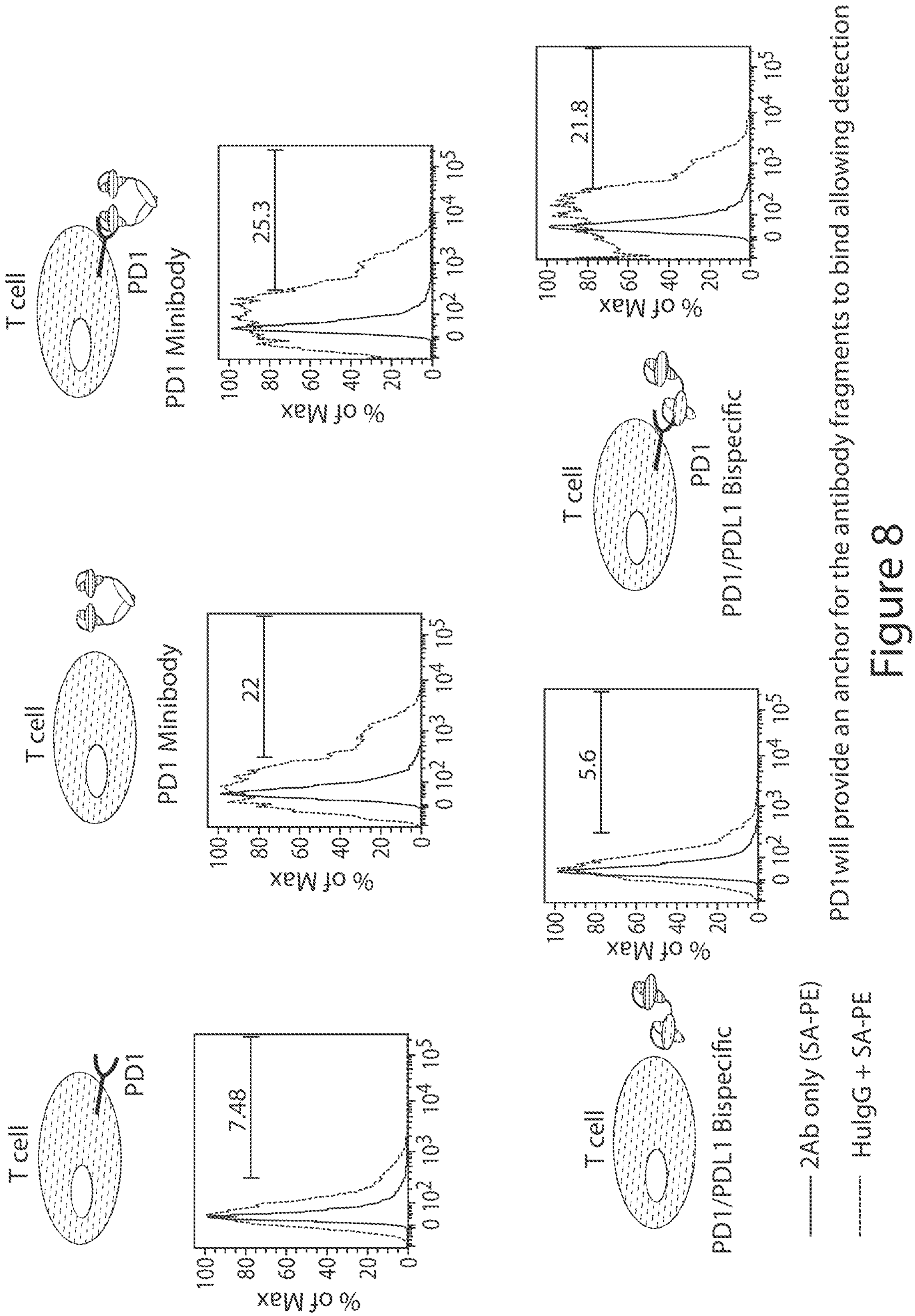
FIG. 8 is a panel of images and graphs showing detection of PD1 minibody or PD1-PDL1 bispecific minibody bound on T cells. T cells were electroporated with mRNA (PD1, PD1 and PD1 minibody, and PD1 and PD1-PDL1 bispecific minibody) as specified. The T cells were stained with biotinylated goat anti-human IgG1 and then streptavidin-PE. Biotin anti-human IgG1 specifically detected PD1 minibody or PD1-PDL1 bispecific minibody secreted into the supernatant when the cells expressed PD1. PD1 expressed on the T cell acted as an anchor for the secreted antibodies to bind that would otherwise not interact with the T cell.

FIG. 8 is a panel of images and graphs showing detection of PD1 minibody or PD1-PDL1 bispecific minibody on T cells. T cells were electroporated with mRNA (PD1, PD1 and PD1 minibody, and PD1 and PD1-PDL1 bispecific minibody) as specified. The T cells were stained with biotin anti-human IgG1 and then streptavidin PE. Biotin anti-human IgG1 specifically detected PD1 minibody or PD1-PDL1 bispecific minibody when the cells expressed PD1. PD1 expressed on the T cell acted as an anchor for the secreted antibodies to bind that would otherwise not interact with the T cell. This data shows that the PD1 minibody and PD1-PDL1 bispecific minibodies were secreted by the T cells and capable of binding PD1 expressing T cells, after staining with anti-human IgG1 and detection by flow cytometry.

Figure 9:
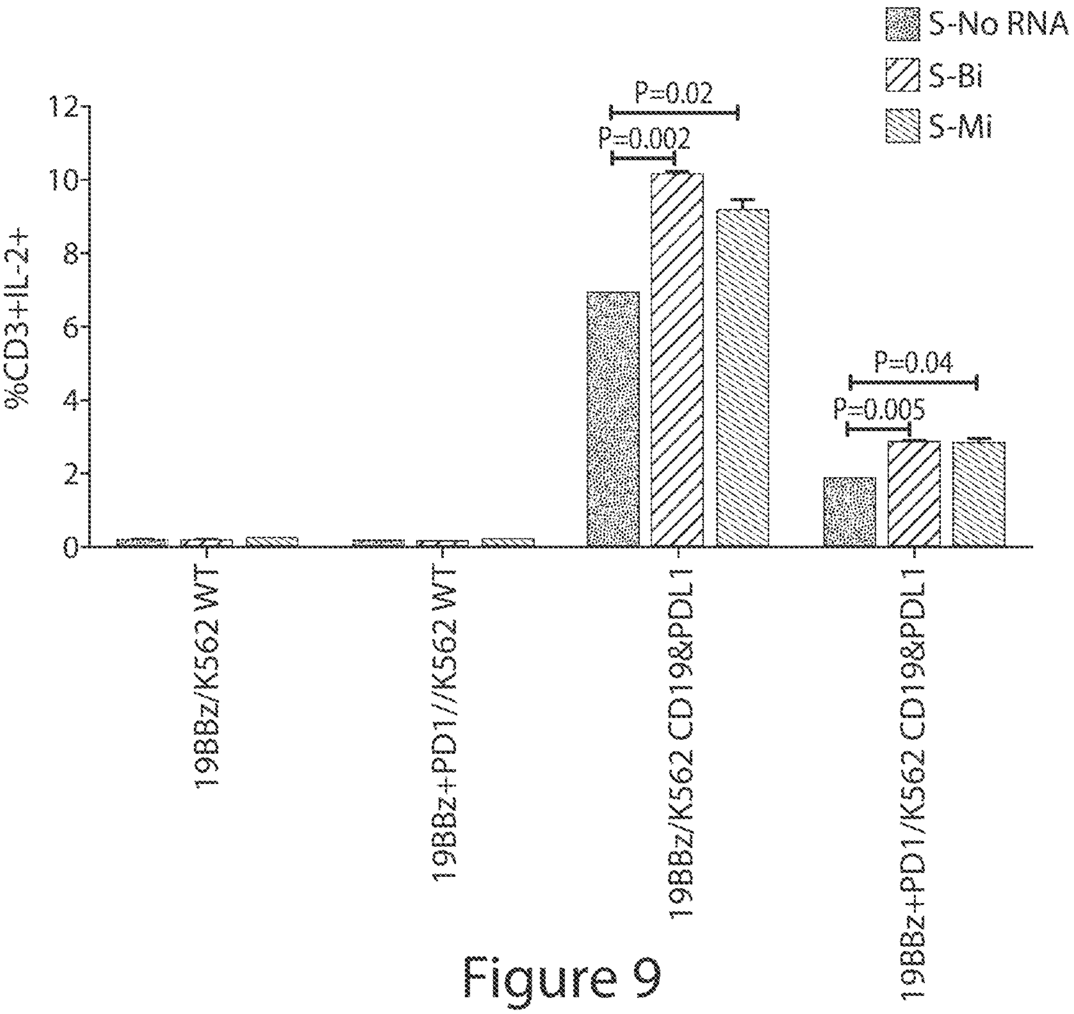
FIG. 9 is a graph showing that PD1 minibody or PD1-PDL1 bispecific minibody secreted by T cells rescued PD1/PDL1 specific inhibition of IL-2 production by CD19 CAR (CART19) T cells. PD1 minibody is abbreviated as Mi and PD1-PDL1 bispecific minibody is abbreviated as Bi. Intracellular cytokine analysis was performed on CAR-transduced or untransduced T cells cocultured with target cells and T cells secreting PD1 minibody or PD1-PDL1 bispecific minibody in 1:1:1 (CAR/untransduced T cells, secreting T cells (no RNA, Bi, Mi), and tumor target cells) for 3 cell culture bottom tissue culture plates at 37° C., 5% CO2 for 16 hours in RPMI 1640 plus 10% FBS in the presence of golgi inhibitors monensin and brefeldin A. Cells were washed, stained with live/dead viability stain, followed by surface staining for CD3 and CD8, then fixed and permeabilized, and intracellularly stained for IFN-g, TNF-a, and IL-2. Cells were analyzed by six-color flow cytometry (Becton Dickinson Fortessa or LSR II) and gated on live, CD3 positive, single-cell lymphocytes. Only IL-2 data is shown but similar results were obtained for TNFa and IFNg.

FIG. 9 is a graph showing that PD1 minibody or PD1-PDL1 bispecific minibody rescued PD1/PDL1 specific inhibition of CART cells. PD1 minibody abbreviated as Mi and PD1-PDL1 bispecific minibody abbreviated as Bi. Cells were analyzed by six-color flow cytometry (Becton Dickinson Fortessa or LSR II) and gated on live, single-cell CD3 positive lymphocytes. Only IL-2 data shown but similar results were obtained for TNFa and IFNg. These data show that T cells expressed and secreted PD1 minibody and PD1-PDL1 bispecific minibodies. Also, antigen specific activation of PD1 expressing CART cells was detected after the T cells encountered their cognate antigen.

Figure 10:
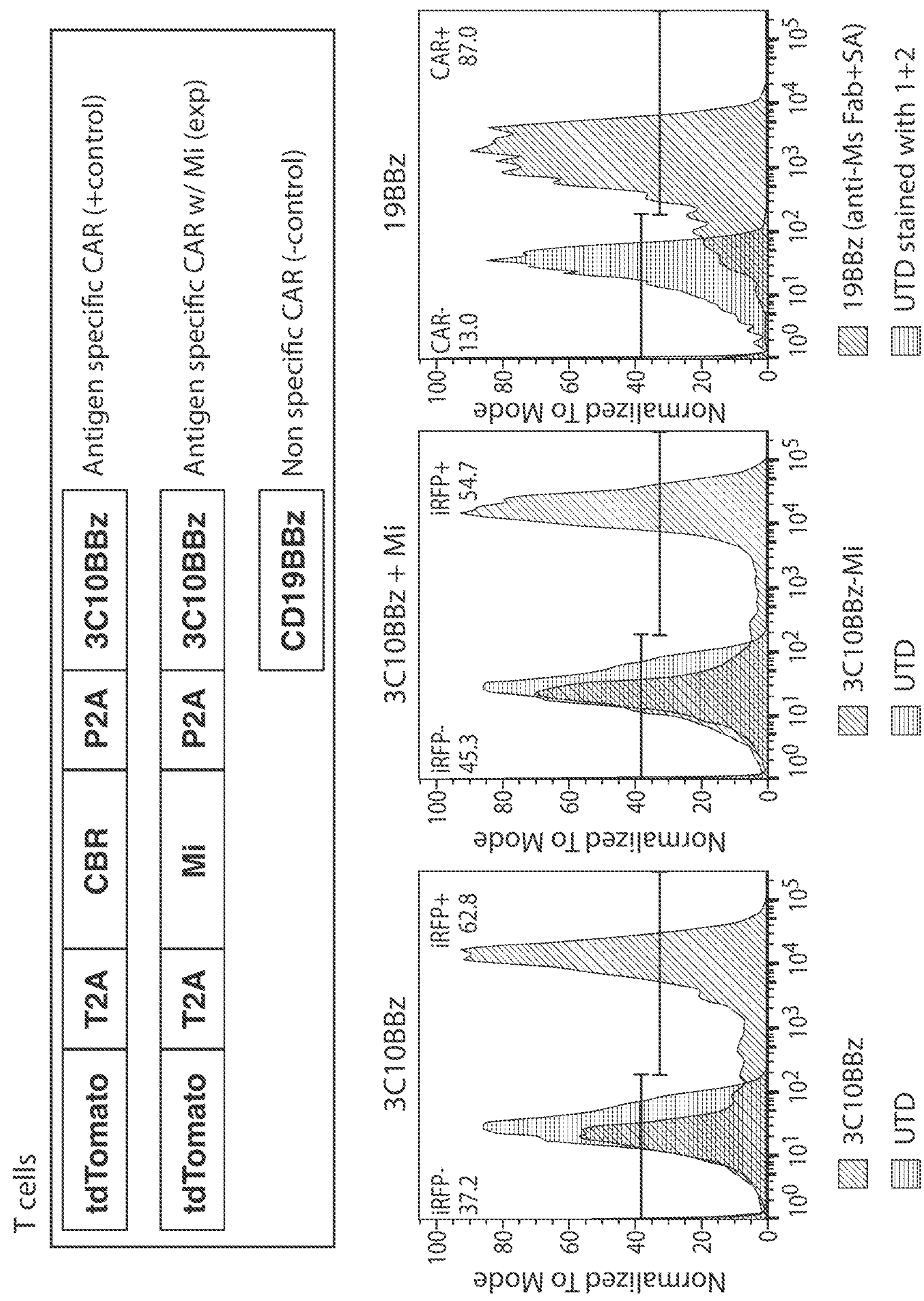
FIG. 10 is a panel of images showing the constructs that were expressed in human T cells and protein expression of the constructs. Shown in the figures are the CAR plasmids expressed in human T cells. tdTomato was used as a surrogate for CAR expression in the EGFRvIII-specific CAR 3C10BBz expressing cells. The CD19-specific CAR 19BBz cells were stained with primary biotin anti-mouse F(ab)' and streptavidin-PE bound secondary.

FIG. 10 is a panel of images showing the constructs expressed in human T cells and protein expression. Shown in the figures are the CAR plasmids expressed in human T cells. tdTomato was used as a surrogate for CAR expression in 3C10BBz expressing cells. The 19BBz cells were stained with primary biotin anti-mouse Fab and streptavidin secondary antibody.

Figure 11:
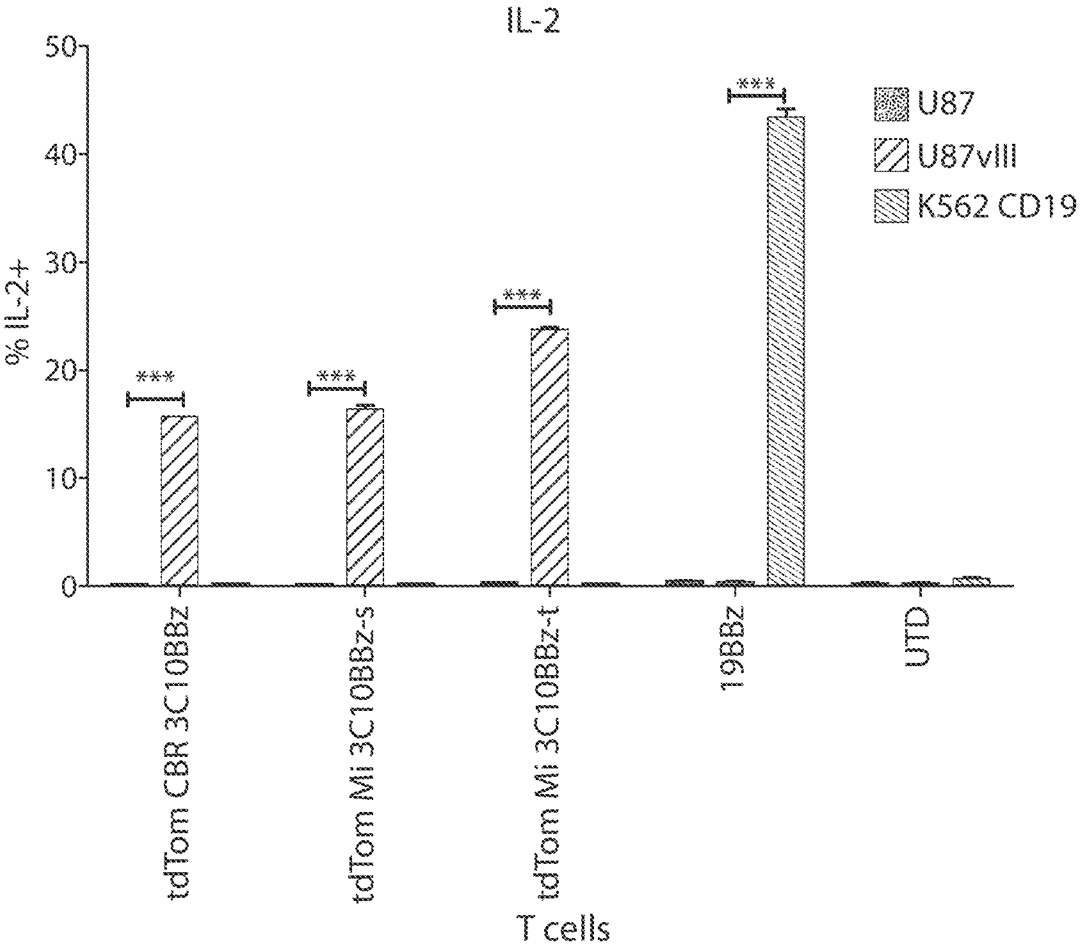
FIG. 11 is a graph showing in vitro testing of bulk populations of different batches of transduced T cells. T cell function is demonstrated in an intracellular cytokine staining (ICS) assay. The data shows that all CAR T cells were functional against their cognate tumor targets, by ICS. Intracellular cytokine analysis of CAR-transduced (3C10BBz only, 3C10BBz+Mi, 19BBz) or untransduced (UTD) T cells cocultured with target cells (U87, U87vIII antigen+, K562 CD19 antigen+) in a 1:1 ratio at 2×10^6/mL in 96-well round bottom tissue culture plates at 37° C., 5% CO2 for 6 hours in RPMI 1640 plus 10% FBS, the last 6 hours in the presence of golgi inhibitors, monensin and brefeldin A. Cells were washed, stained with live/dead viability stain then fixed and permeabilized, and intracellularly stained for IFN-g, TNF-a, and IL-2. Cells were analyzed using six-color flow cytometry (Becton Dickinson Fortessa or LSR II) and gated on live, CD3+ single-cell lymphocytes. Only IL-2 data shown but the results are similar for TNFa and IFNg.

FIG. 11 is a graph showing in vitro testing of different bulk lots of CAR transduced T cell function in an intracellular cytokine staining (ICS) assay. The data shows that the CAR T cells were functional by ICS. Cells were analyzed by six-color flow cytometry (Becton Dickinson Fortessa or LSR II) and gated on live, single-cell lymphocytes. Only IL-2 data shown but the results are similar for TNFa and IFNg. These data show that the CAR T cells used for in vivo experiments are functional only in the presence of cognate antigen.

Figure 12:
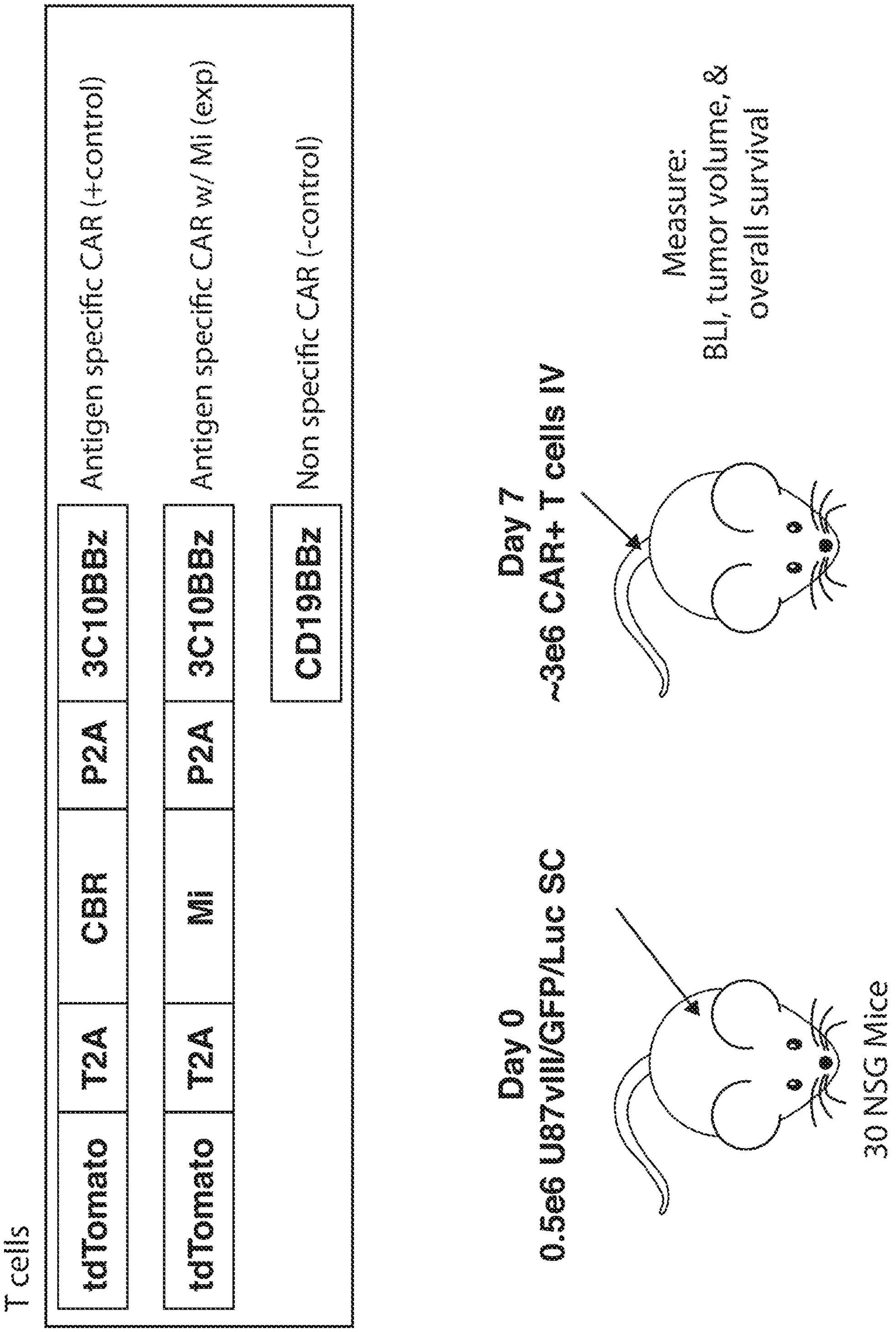
FIG. 12 is a panel of images showing the constructs and in vivo assay used to test CAR T cells expressing PD1 minibodies. NSG mice were injected with 5.0×10^5 U87-vIII/Luc+ tumors subcutaneously in 100 μL of PBS on day 0. Tumor progression was evaluated by luminescence emission on a Xenogen IVIS Spectrum after intraperitoneal D-luciferin injection according to the manufacturer's directions (GoldBio). Additionally, tumor size was measured by calipers in three dimensions, L×w×H, for the duration of the experiment. Seven days after tumor injection, CAR positive T cell numbers were normalized and mice were injected with $6\times10^6$ total T cells (~50% CAR+) via the tail vein in 100 µL of PBS. Survival was followed over time until a predetermined protocol-approved endpoint was reached (n=10 mice per group).

FIG. 12 is a panel of images showing the constructs and in vivo assay used to test CAR T cells expressing minibodies.

Figure 13:
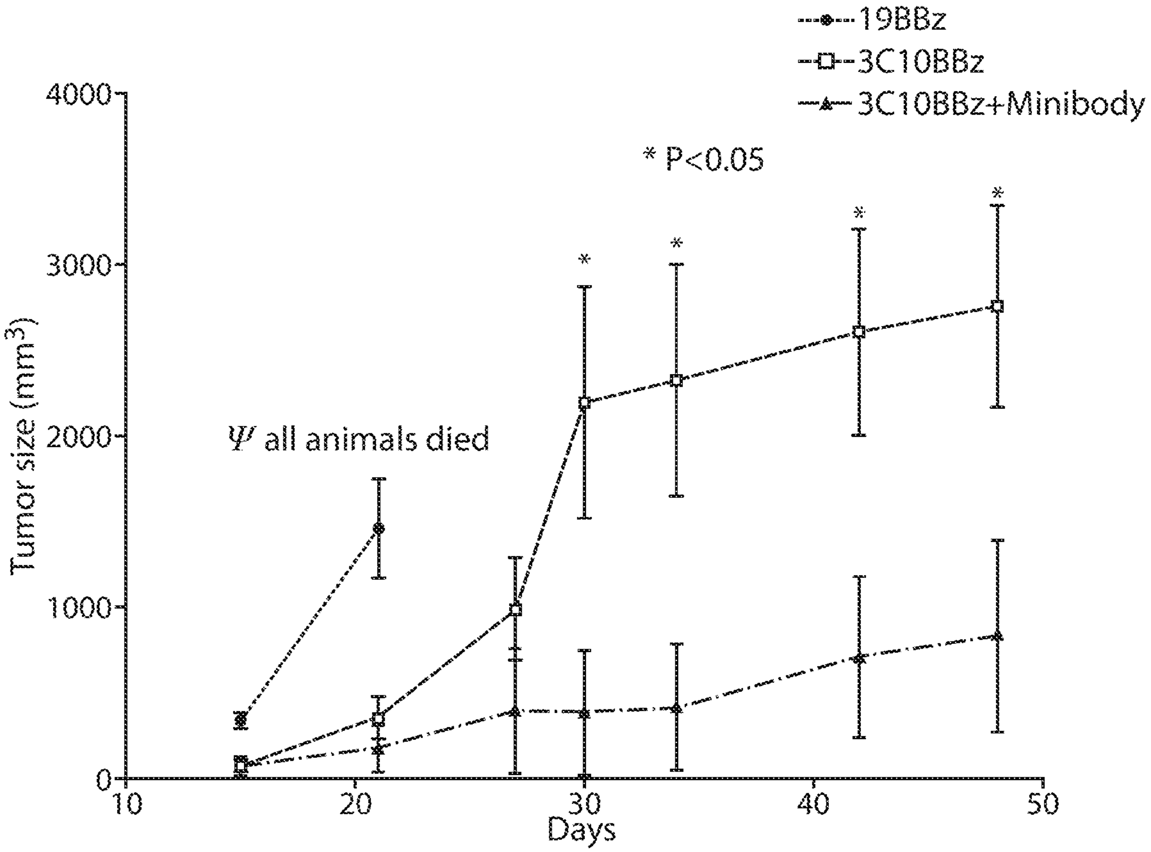
FIG. 13 is a graph showing mean tumor volumes in immunodeficient NSG mice injected with CAR T cells expressing minibodies. NSG mice were injected with 5.0×10^5 U87vIII/Luc+ tumors subcutaneously in 100 µL of PBS on day 0. Seven days later, mice were injected with $6\times10^6$ total T cells (~50% CAR+) via the tail vein in 100 µL of PBS. Mean tumor volumes for each treatment group are shown. Mice injected with 3C10 CART cells only had tumors that grew significantly larger than the tumors in the mice injected with 3C10 CAR T cells+PD1 minibody. n=10 mice per group.

FIG. 13 is a graph showing mean tumor volumes in tumor-bearing NSG mice injected with CAR T cells expressing or not expressing PD1 minibodies. Mice injected with non-specific CD19 CAR T cells had fast-growing tumors. Mice injected with 3C10 (EGFRvIII) CAR T cells showed delayed tumor growth compared with CD19 CAR treated mice. Mice injected with 3C10 PD1 minibody secreting T cells showed statistically improved tumor treatment over 3C10 CAR alone.

Figure 14:
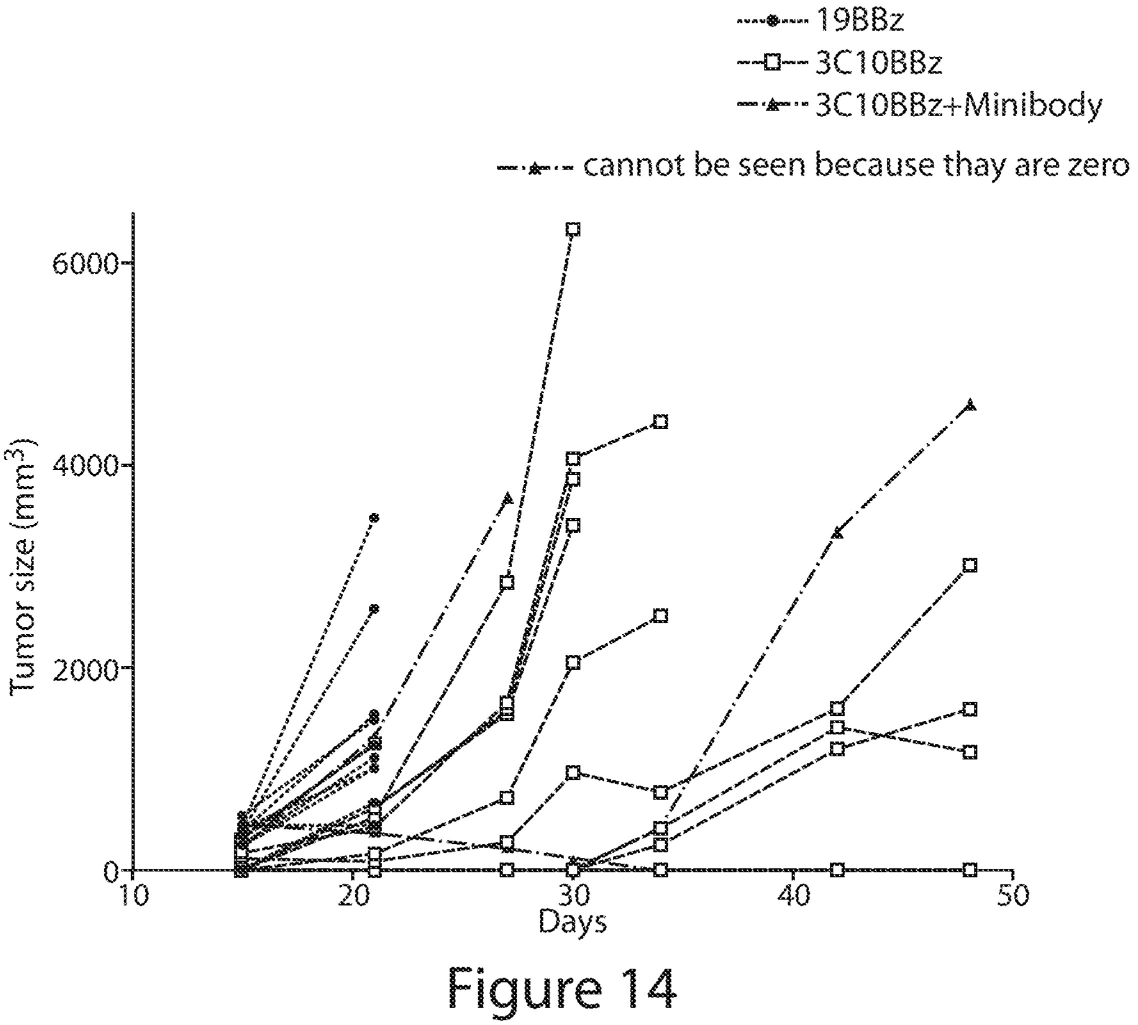
FIG. 14 is a graph showing tumor volumes in individual NSG mice injected with CAR T cells expressing minibodies. NSG mice were injected with $5.0\times10^5$ U87-vIII/Luc+ tumors subcutaneously in 100 ml of PBS on day 0. Seven days later, mice were injected with $6\times10^6$ total T cells (~50% CAR+) via the tail vein in 100 µL of PBS. Tumor volumes for each mouse are shown. 10/10 mice injected with CART19 T cells showed rapid tumor growth; 2/10 mice injected with 3C10 CAR T cells were cured of tumor, with 7/8 remaining mice showing slowed tumor progression compared with CART19 treated mice; 8/10 mice injected with PD1 minibody secreting 3C10 CARs were cured, with 1/2 remaining showing reduced tumor progression. Note that 3C10BBz+PD1 minibody lines are not visible because they are zero. n=10 mice per group.

FIG. 14 is a graph showing tumor volumes in individual NSG mice injected with CAR T cells expressing minibodies. 10/10 mice injected with CART19 T cells showed rapid tumor growth; 2/10 mice injected with 3C10 CAR T cells were cured of tumor, with 7/8 remaining mice showing slowed tumor progression compared with CART19 treated mice; 8/10 mice injected with PD1 minibody secreting 3C10 CARs were cured, with 1/2 remaining showing reduced tumor progression. Note that 3C10BBz+PD1 minibody lines are not visible because they are zero. Mice injected with 3C10 PD1 minibody secreting T cells showed statistically improved tumor treatment over 3C10 CAR alone.

Figure 15:
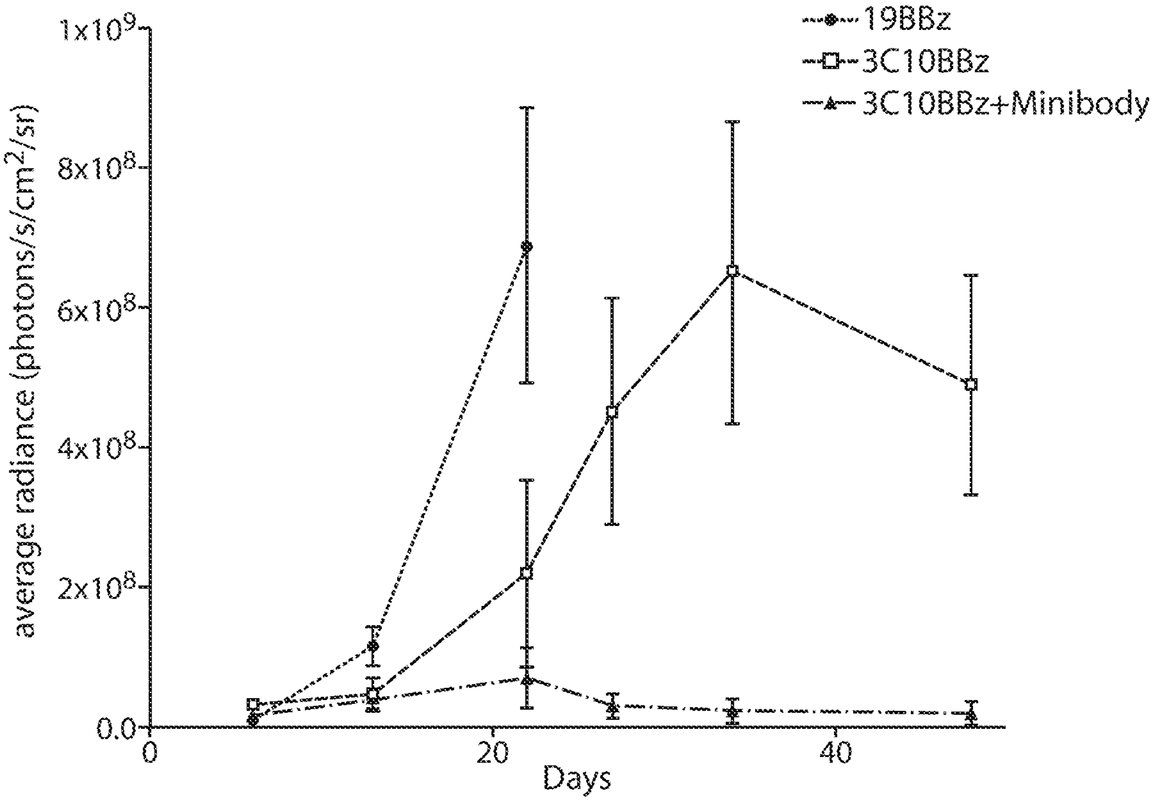
FIG. 15 is a graph showing bioluminescent imaging (BLI) of mean tumor emissions in NSG mice injected with CAR T cells expressing PD1 minibodies. NSG mice were injected with $5.0\times10^5$ U87-vIII/Luc+ tumors subcutaneously in 100 µL of PBS on day 0. Seven days later, mice were injected with $6\times10^6$ total CAR T cells (~50% CAR+) via the tail vein in 100 µL of PBS. Tumor luminescence for each treatment group are shown. Mice injected with 19BBz CAR T cells or 3C10 CAR T cells developed tumors that grew significantly larger than the tumors in mice injected with 3C10 CAR T cells+PD1 minibody. n=10 mice per group.

FIG. 15 is a graph showing bioluminescent imaging (BLI) of mean tumor emissions in NSG mice injected with CAR T cells expressing minibodies. Mice injected with 19BBz CAR T cells or 3C10 CART cells developed tumors that emitted higher BLI than the tumors in mice injected with 3C10 CART cells+PD1 minibody.

Figure 16:
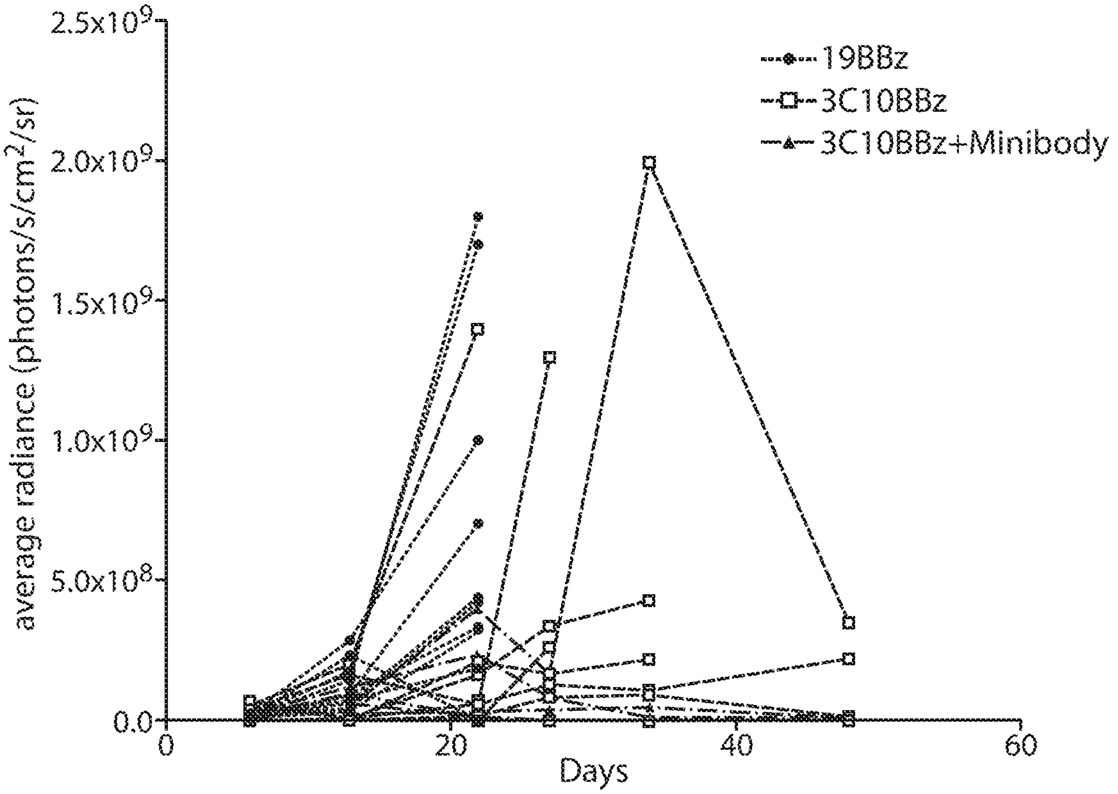
FIG. 16 is a graph showing BLI of tumor in individual NSG mice injected with CAR T cells expressing minibodies. NSG mice were injected with $5.0\times10^5$ U87-vIII/Luc+ tumors subcutaneously in 100 µL of PBS on day 0. Seven days later, mice were injected with $6\times10^6$ total CAR T cells (~50% CAR+) via the tail vein in 100 µL of PBS. Tumor luminescence readings for each mouse are shown. Mice injected with 19BBz CAR T cells or 3C10 CAR T cells developed tumors that grew significantly larger than mice injected with 3C10 CAR T cells+PD1 minibody. Note that lines that represent mice injected with 3C10BBz T cells+PD1 minibody lines are not visible because they have values substantially equal to background levels. n=10 mice per group.

FIG. 16 is a graph showing mean BLI of tumors in individual NSG mice injected with CAR T cells expressing minibodies. Mice injected with 19BBz CAR T cells or 3C10 CAR T cells developed tumors that grew significantly larger than mice injected with 3C10 CAR T cells+PD1 minibody. Note that lines that represent mice injected with 3C10BBz T cells+PD1 minibody lines are not visible because they have values substantially equal to background.

Figure 17:
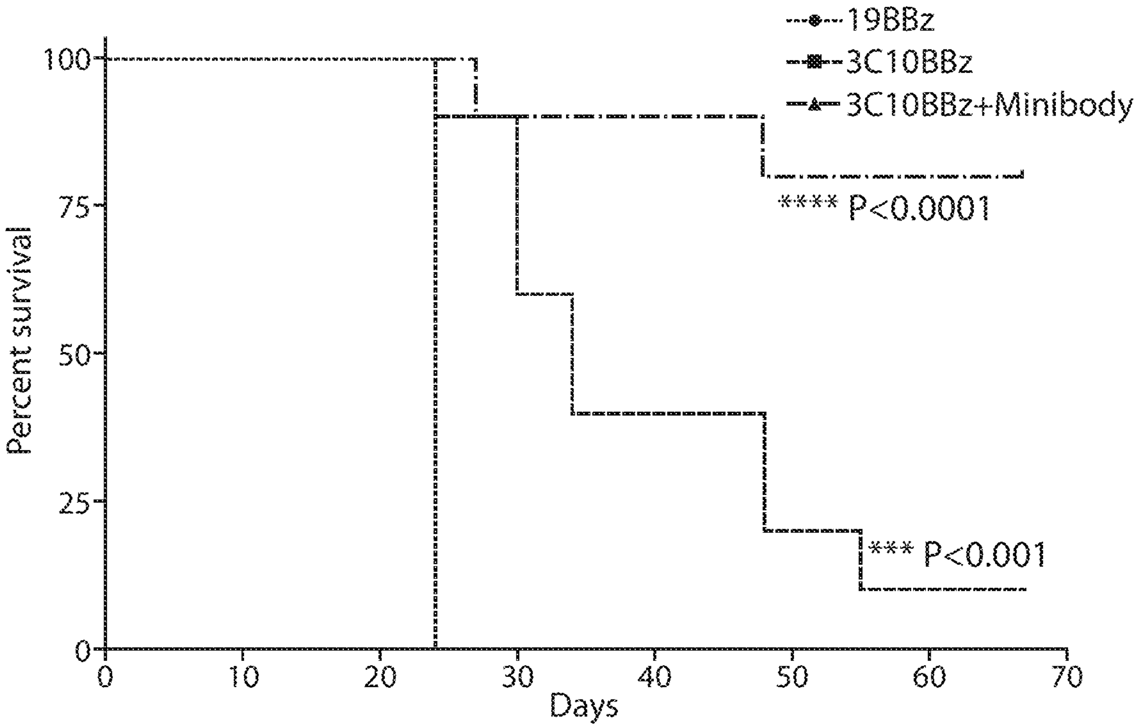
FIG. 17 is a graph showing overall survival of mice injected with tumors and treated with CAR T cells with or without PD1 minibody. Mice injected with 19BBz CAR T cells or 3C10 CAR T cells developed tumors and mice with tumor specific 3C10BBz CAR T cells lived significantly longer than mice treated with non-specific CD19BBz CAR T cells. (3C10BBz only vs 19BBz P<0.001 & 3C10BBz+PD1 minibody vs 19BBz P<0.0001). Also, the mice that received 3C10BBz T cells with PD1 minibody lived significantly longer than 3C10BBz CAR T cells only treated mice. (P=0.0024). One of ten 3C10BBz T cells treated mice lived beyond 70 days while eight of 10 3C10BBz T cells+minibody mice lived beyond 70 days.

FIG. 17 is a graph showing overall survival of mice injected with CAR T cells with or without PD1 minibody. Mice injected with tumor specific 3C10BBz CART cells lived significantly longer than mice treated with non-specific CD19BBz CAR T cells. Mice that received 3C10BBz T cells with PD1 minibody lived significantly longer than 3C10BBz CAR T cell treated mice. (P=0.0024). All CD19 CAR treated mice died by 25 days. Median survival of 3C10 CAR treated mice was 33 days, while median survival of 3C10 plus PD1 minibody mice was not reached. 1/10 3C10BBz T cell treated mice lived beyond 70 days while 8/10 3C10BBz T cells+minibody mice lived beyond 70 days (duration of study). (3C10BBz only vs 19BBz $P<0.001$ & 3C10BBz+PD1 minibody vs 19BBz $P<0.0001$).

Figure 18:
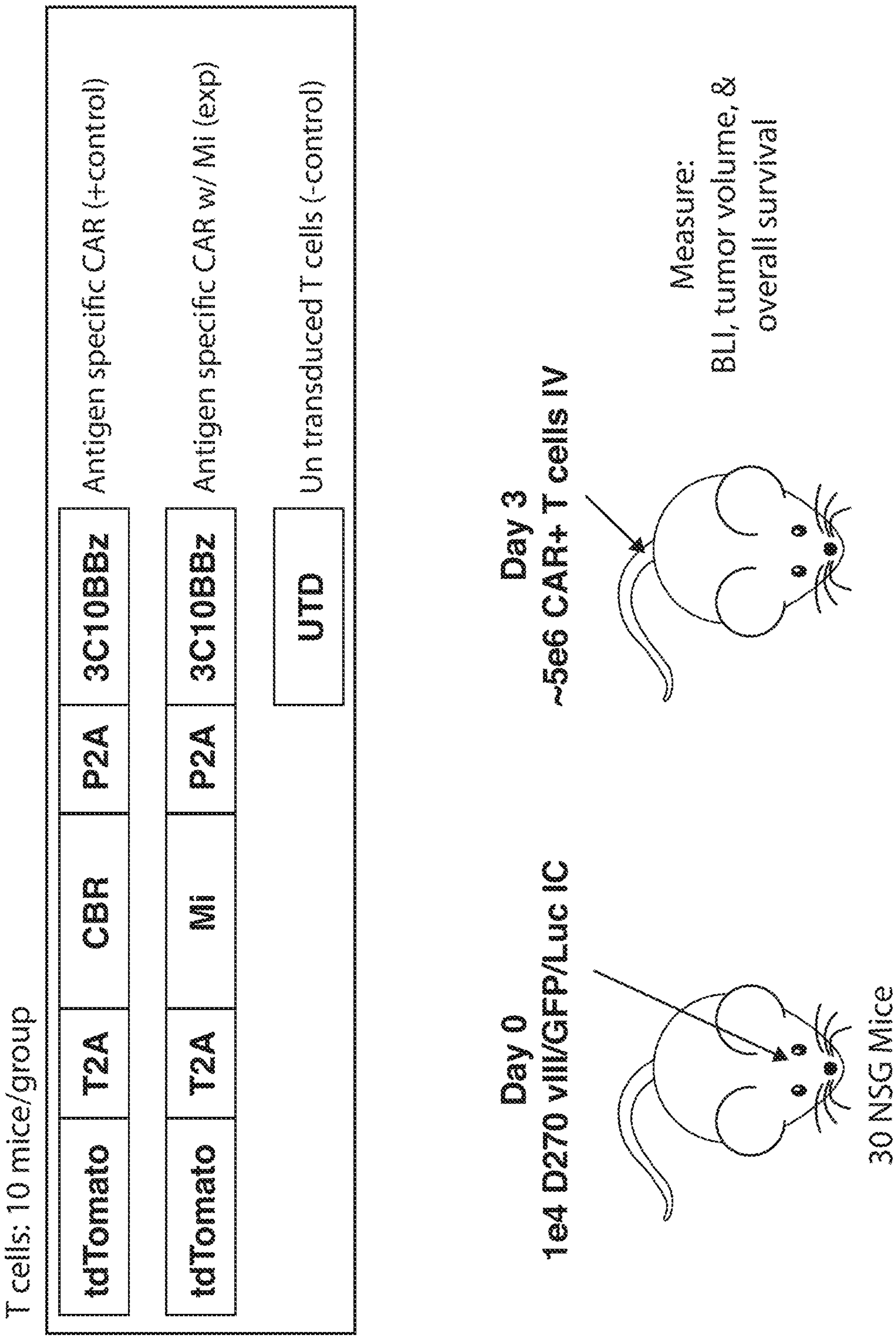
FIG. 18 is a panel of images showing the constructs and in vivo assay used to test minibodies in the D270IC model. Shown is the in vivo assay to intracranially implant D270 GBM cells into NSG mice. For orthotopic models, $1\times10^4$ D270 luc+ cells were implanted intracranially into 6- to 8-week-old female NSG mice, with 10 mice per group. The surgical implants were injected using a stereotactic surgical frame with tumor cells implanted 2 mm right of the bregma and 3 mm depth into the brain. Before surgery and for 3 days after surgery, mice were treated with an analgesic and monitored for adverse symptoms in accordance with the approved protocol. Mice were injected with CAR T cells in 100 µL of PBS intravenously via the tail vein 3 days after tumor injections. Bioluminescent measurements were used to establish tumor growth.

FIG. 18 is a panel of images showing the constructs and in vivo assay used to test minibodies in the D270IC model.

Figure 19:
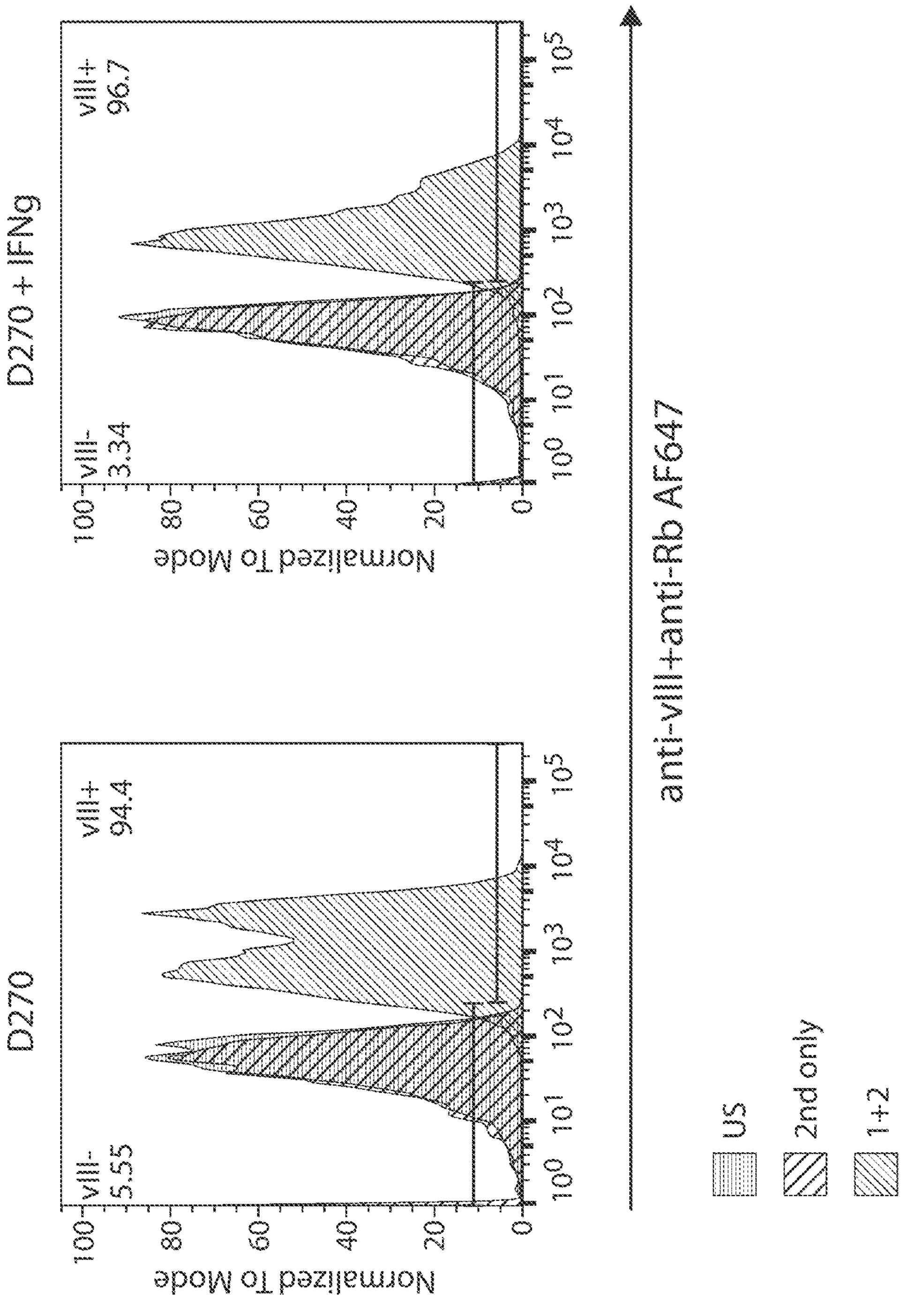
FIG. 19 is a panel of graphs showing expression of EGFRvIII in D270 GBM cells. D270 human GBM were cultured without or with 20 ng/ml rhIFNg for 24 hours and then stained with anti-EGFRvIII antibody (3C10scFv with an rabbit IgG) and labeled anti-rabbit secondary antibody. Green=unstained, blue=secondary antibody alone, red=primary and secondary antibody.

FIG. 19 is a panel of graphs showing expression of EGFRvIII in D270 cells. D270 human GBM xenograft cells were cultured without or with 20 ng/ml IFNg for 24 hours and then stained with anti-EGFRvIII antibody (3C10scFv with a rabbit IgG) and anti-rabbit secondary. D270 shows endogenous expression of EGFRvIII that was not changed significantly upon exposure to IFNg.

Figure 20:
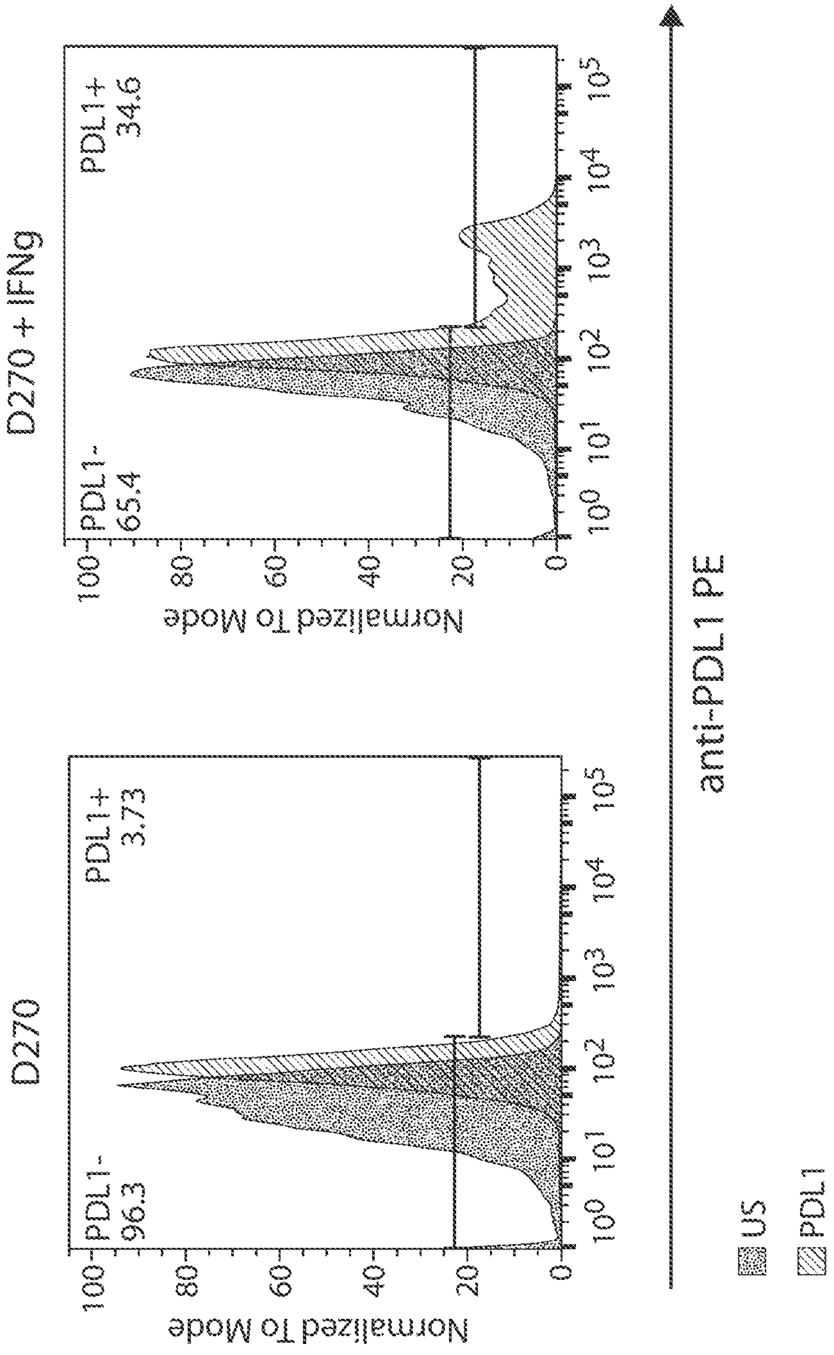
FIG. 20 is a panel of graphs showing expression of PDL1 in D270 cells. D270 human GBM cells were cultured without or with 20 ng/ml IFNg for 24 hours and stained with anti-PDL1mAb-PE. Grey=unstained, red=anti-PDL1-PE. D270 upregulated PDL1 expression after IFNg exposure.

FIG. 20 is a panel of graphs showing expression of PDL1 in D270 cells. D270 human GBM xenograft cells were cultured without or with 20 ng/ml IFNg for 24 hours and stained with anti-PDL1 PE. At baseline, D270 has minor expression of PDL1, which was upregulated after exposure to IFNg.

Figure 21:
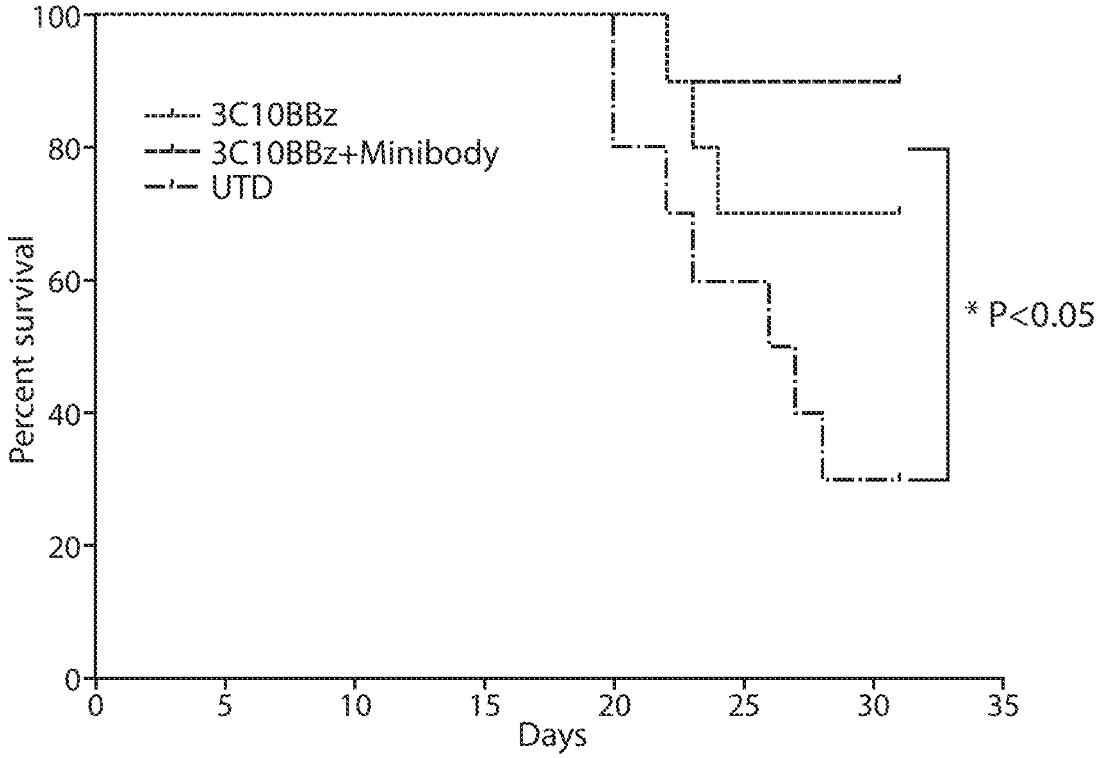
FIG. 21 is a graph showing overall survival of D270IC mice treated with CAR T cells expressing minibodies. Overall mouse survival was significantly increased with treatment of either 3C10BBz CART cells only or 3C10BBz CAR T cells with PD1 minibody compared to untransduced (UTD) cells.

FIG. 21 is a graph showing overall survival of NSG mice orthotopically implanted with D270 GBM, then treated with intravenous delivery of CAR T cells that do or do not express PD1 minibodies. Mice treated with 3C10 CARs showed improved survival compared with mice receiving non-specific T cells (70% versus 30% survival at 30 days), and mice receiving 3C10 CARs secreting PD1 minibody showed further increased survival, with 90% of animals alive at 30 days.

Figure 22:
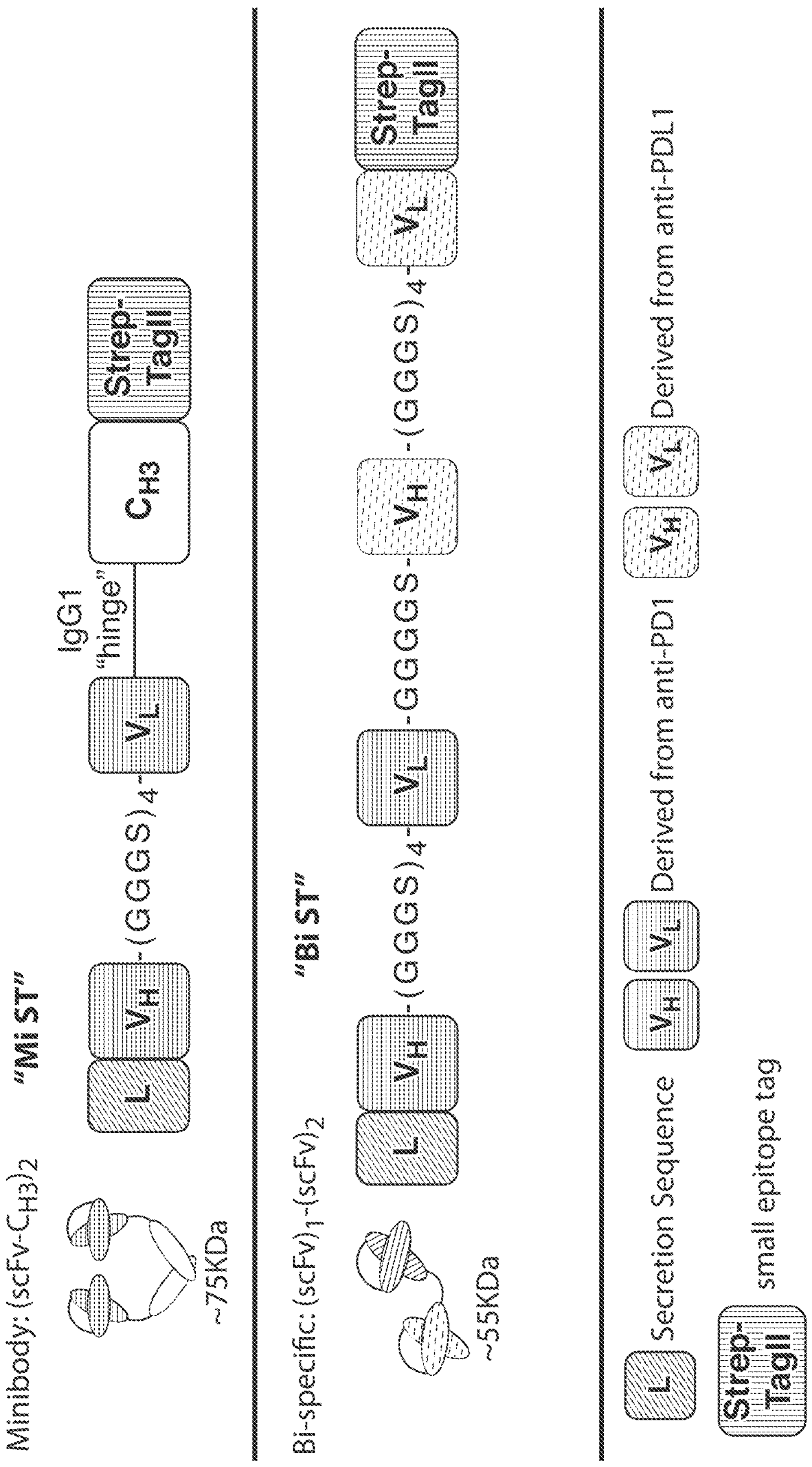
FIG. 22 is an illustration of epitope tagged minibody and bispecific minibody for use in blocking human PD1/PDL1. A strep-tagII was added to the c-terminus of both the PD1 minibody and PD1/PDL1 bispecific minibody.

FIG. 22 is an illustration of epitope tagged minibody and bispecific minibody for use in blocking human PD1/PDL1. A strep-tagII was added to the c-terminus of both the PD1 minibody and PD1/PDL1 bispecific minibody. The strep-tagII has an amino acid sequence of SEQ ID NO:9.

Figure 23:
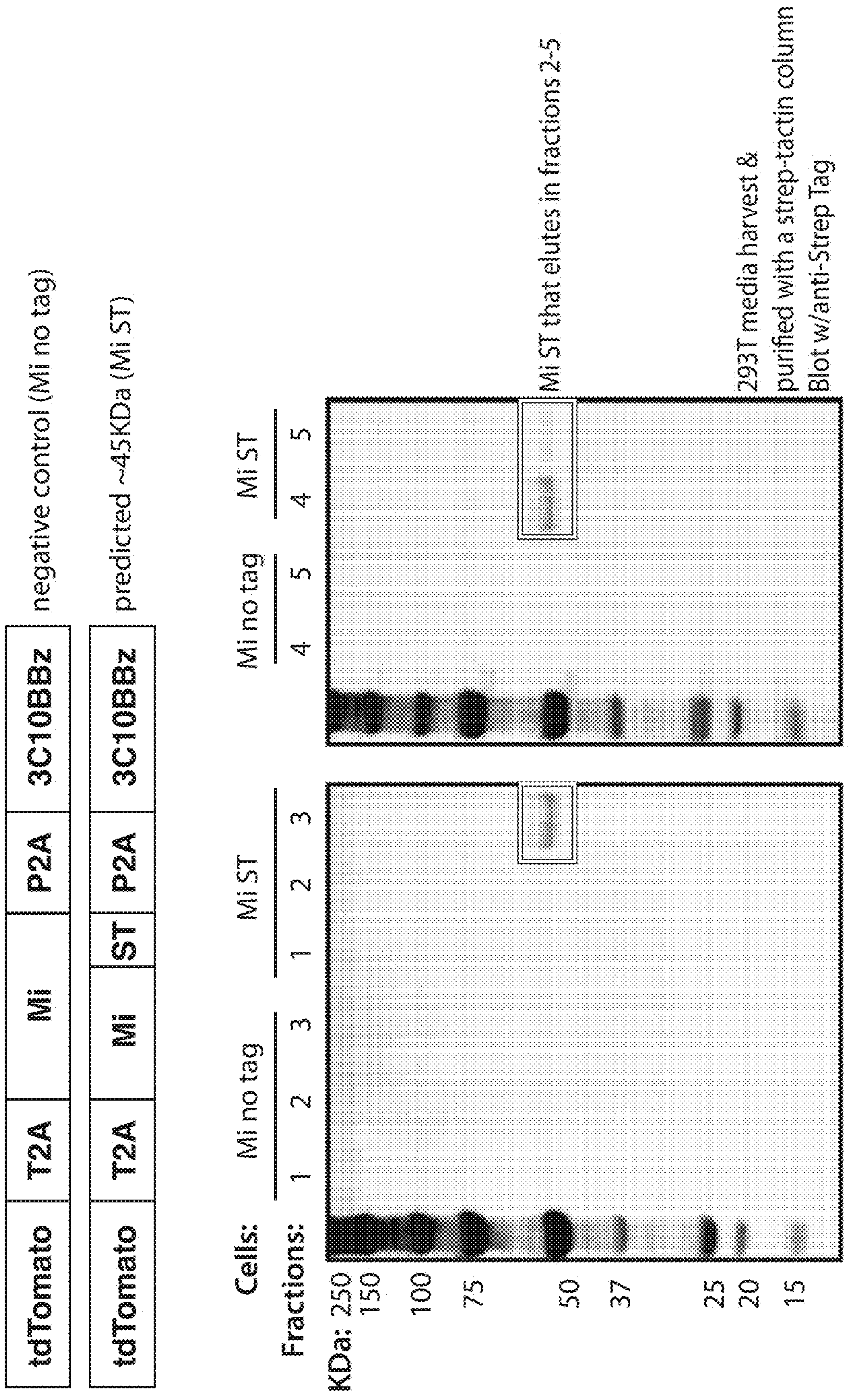
FIG. 23 is a panel of images showing the strep-tagII constructs and detection of the strep-tagII in the media of PD1 mi ST transduced 293T cells. The strep-tagged PD1 minibody was detected in the media of 293T cells. Shown is a western blot of the media from 293T cells that stably expressed the constructs shown. The proteins were purified with a step-tactin column to enrich for the tagged proteins. The columns were eluted in 5 fractions and shown is the strep-tagII tagged PD1 minibody detected in fractions 3-5. Only PD1 minibody data is shown but the results are similar for PD1-PDL1 bispecific antibody.

FIG. 23 is a panel of images showing the strep-tagII constructs and detection of the strep-tagII in the media of 293T cells. The strep-tagged PD1 minibody was detected in the media of 293T cells. Shown is a western blot of the media from 293T cells that stably expressed the constructs shown. The proteins were purified with a step-tactin column to enrich for the tagged proteins. The columns were eluted in 5 fractions and shown is the strep-tagII tagged PD1 minibody detected in fractions 3-5. These data show that the strep-tagII PD1 minibody is secreted from cells and can be purified and detected in the supernatant of cultured cells.

The specific minibodies demonstrated here include a minibody targeted to bind to and block PD1 signaling on immune effector cells (including T lymphocytes), and a bispecific minibody with one portion targeting and blocking PD1 on effector T cells and another portion targeting and blocking PDL1 on target (e.g., cancer or immune-suppressive) cells. These minibodies are encoded into DNA or RNA and delivered into lymphocytes to genetically engineer them to produce and secrete these minibodies in vivo, effectively providing a long-term continued supply of minibody at the site of disease, and reducing systemic toxicity caused by high doses of exogenously supplied drugs.

Other Embodiments

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING

```
Sequence total quantity: 957
SEQ ID NO: 1            moltype = AA  length = 405
FEATURE                 Location/Qualifiers
REGION                  1..405
                        note = source = /note="Description of Artificial Sequence:
                         Synthetic polypeptide"
source                  1..405
                        mol_type = protein
                        organism = synthetic construct
SEQUENCE: 1
METDTLLLWV LLLWVPGSTG QVQLQESGPG VVKPSGTLSL TCAISGGSIG SGGSIRSTRW  60
WSWVRQSPGK GLEWIGEIYH SGSTNYNPSL KSRVTISLDK SRNHFSLRLN SVTAADTAVY  120
YCARQDYGDS GDWYFDLWGK GTMVTVSSGG GSGGGSGGGS GGGSNFMLTQ PHSVSESPGK  180
TVTISCTRSS GSIASNSVQW YQQRPGSSPT TVIYEDNQRP SGVPDRFSGS IDSSSNSASL  240
TVSGLKTEDE ADYYCQSSDS SAVVFGSGTK LTVLEPKSCD KTHTCPPCGG GSSGGGSGGQ  300
PREPQVYTLP PSRDELTKNQ VSLTCLVKGF YPSDIAVEWE SNGQPENNYK TTPPVLDSDG  360
SFFLYSKLTV DKSRWQQGNV FSCSVMHEAL HNHYTQKSLS LSPGK                   405

SEQ ID NO: 2            moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 2
METDTLLLWV LLLWVPGSTG                                               20

SEQ ID NO: 3            moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 3
GGGSGGGSGG GSGGGSN                                                  17

SEQ ID NO: 4            moltype = AA  length = 24
FEATURE                 Location/Qualifiers
REGION                  1..24
                        note = source = /note="Description of Artificial Sequence:
                         Synthetic peptide"
source                  1..24
                        mol_type = protein
                        organism = synthetic construct
SEQUENCE: 4
EPKSCDKTHT CPPCGGGSSG GGSG                                          24

SEQ ID NO: 5            moltype = AA  length = 107
```

-continued

```
FEATURE                Location/Qualifiers
REGION                 1..107
                       note = source = /note="Description of Artificial Sequence:
                        Synthetic polypeptide"
source                 1..107
                       mol_type = protein
                       organism = synthetic construct
SEQUENCE: 5
GQPREPQVYT LPPSRDELTK NQVSLTCLVK GFYPSDIAVE WESNGQPENN YKTTPPVLDS  60
DGSFFLYSKL TVDKSRWQQG NVFSCSVMHE ALHNHYTQKS LSLSPGK               107

SEQ ID NO: 6           moltype = AA  length = 128
FEATURE                Location/Qualifiers
REGION                 1..128
                       note = source = /note="Description of Artificial Sequence:
                        Synthetic polypeptide"
source                 1..128
                       mol_type = protein
                       organism = synthetic construct
SEQUENCE: 6
QVQLQESGPG VVKPSGTLSL TCAISGGSIG SGGSIRSTRW WSWVRQSPGK GLEWIGEIYH  60
SGSTNYNPSL KSRVTISLDK SRNHFSLRLN SVTAADTAVY YCARQDYGDS GDWYFDLWGK  120
GTMVTVSS                                                          128

SEQ ID NO: 7           moltype = AA  length = 110
FEATURE                Location/Qualifiers
REGION                 1..110
                       note = source = /note="Description of Artificial Sequence:
                        Synthetic polypeptide"
source                 1..110
                       mol_type = protein
                       organism = synthetic construct
SEQUENCE: 7
NFMLTQPHSV SESPGKTVTI SCTRSSGSIA SNSVQWYQQR PGSSPTTVIY EDNQRPSGVP  60
DRFSGSIDSS SNSASLTVSG LKTEDEADYY CQSSDSSAVV FGSGTKLTVL            110

SEQ ID NO: 8           moltype = AA  length = 535
FEATURE                Location/Qualifiers
REGION                 1..535
                       note = source = /note="Description of Artificial Sequence:
                        Synthetic polypeptide"
source                 1..535
                       mol_type = protein
                       organism = synthetic construct
SEQUENCE: 8
METDTLLLWV LLLWVPGSTG QVQLQESGPG VVKPSGTLSL TCAISGGSIG SGGSIRSTRW  60
WSWVRQSPGK GLEWIGEIYH SGSTNYNPSL KSRVTISLDK SRNHFSLRLN SVTAADTAVY  120
YCARQDYGDS GDWYFDLWGK GTMVTVSSGG GSGGGSGGGS GGGSNFMLTQ PHSVSESPGK  180
TVTISCTRSS GSIASNSVQW YQQRPGSSPT TVIYEDNQRP SGVPDRFSGS IDSSSNSASL  240
TVSGLKTEDE ADYYCQSSDS SAVVFGSGTK LTVLGGGSGG GSGGGSGGGS QVQLVQSGAE  300
VKKPGSSVKV SCKTSGDTFS TYAISWVRQA PGQGLEWMGG IIPIFGKAHY AQKFQGRVTI  360
TADESTSTAY MELSSLRSED TAVYFCARKF HFVSGSPFGM DVWGQGTTVT VSSGGGSGGG  420
SGGGSGGGSE IVLTQSPATL SLSPGERATL SCRASQSVSS YLAWYQQKPG QAPRLLIYDA  480
SNRATGIPAR FSGSGSGTDF TLTISSLEPE DFAVYYCQQR SNWPTFGQGT KVEIK       535

SEQ ID NO: 9           moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 9
WSHPQFEK                                                          8

SEQ ID NO: 10          moltype = DNA  length = 1215
FEATURE                Location/Qualifiers
misc_feature           1..1215
                       note = source = /note="Description of Artificial Sequence:
                        Synthetic polynucleotide"
source                 1..1215
                       mol_type = other DNA
                       organism = synthetic construct
SEQUENCE: 10
atggaaaccg acaccctgct gctgtgggtg ctgctgctgt gggtgccagg ctctacagga  60
caggtgcagc tgcaggaatc tggccctggc gtcgtgaagc ctagcggcac actgagcctg  120
acctgtgcca tcagcggcgg ctctattggc tccggcggca gcatcagatc caccagatgg  180
tggtcttggg tgcgccagtc tcctggcaag ggcctggaat ggatcggcga gatctaccac  240
```

```
agcggctcca ccaactacaa ccccagcctg aagtccagag tgaccatcag cctggacaag  300
agccggaacc acttcagcct gagactgaac agcgtgacag ccgccgacac cgccgtgtac  360
tactgcgcca gacaggacta cggcgacagc ggcgactggt acttcgacct gtggggcaag  420
ggcacaatgg tcaccgtgtc tagcggcgga ggaagcggag gcggatctgg gggaggaagt  480
ggcggaggca gcaacttcat gctgacccag cctcacagcg tgtccgagag ccctggcaag  540
accgtgacca tctcctgcac cagaagctcc ggctctatcg ccagcaacag cgtgcagtgg  600
tatcagcaga ggcccggcag cagccctacc accgtgatct acgaggacaa ccagaggccc  660
agcggcgtgc ccgatagatt ctctggcagc atcgacagca gctccaacag cgccagcctg  720
accgtgtccg gcctgaaaac agaggacgag gccgactact actgccagag cagcgatagc  780
agcgccgtgg tgtttggcag cggcaccaag ctgaccgtgc tggaacccaa gagctgcgac  840
aagacccaca cctgtccccc ttgtggcggc ggatcttctg gcggaggatc tggcggacag  900
cccagagaac cccaggtgta cacactgccc cccagcagag atgagctgac caagaaccag  960
gtgtccctga cctgcctcgt gaagggcttc taccccctccg atatcgccgt ggaatgggag  1020
agcaatggcc agcccgagaa caactacaag accactcccc ctgtgctgga cagcgacggc  1080
tcattcttcc tgtacagcaa gctgacagtg gacaagtccc ggtggcagca gggcaacgtg  1140
ttcagctgca gcgtgatgca cgaggccctg cacaaccact acacccagaa gtccctgtcc  1200
ctgagccccg gcaaa                                                   1215
```

```
SEQ ID NO: 11          moltype = DNA  length = 1604
FEATURE                Location/Qualifiers
misc_feature           1..1604
                       note = source = /note="Description of Artificial Sequence:
                        Synthetic polynucleotide"
source                 1..1604
                       mol_type = other DNA
                       organism = synthetic construct
SEQUENCE: 11
atggaaaccg acaccctgct gctgtgggtg ctgctgctgt gggtgccagg ctctacagga  60
caggtgcagc tgcaggaatc tggccctggc gtcgtgaagc ctagcggcac actgagcctg  120
acctgtgcca tcagcggcgg ctctattggc tccggcggca gcatcagatc caccagatgg  180
tggtcttggg tgcgccagtc tcctggcaag ggcctggaat ggatcggcga gatctaccac  240
agcggctcca ccaactacaa ccccagcctg aagtccagag tgaccatcag cctggacaag  300
agccggaacc acttcagcct gagactgaac agcgtgacag ccgccgacac cgccgtgtac  360
tactgcgcca gacaggacta cggcgacagc ggcgactggt acttcgacct gtggggcaag  420
ggcacaatgg tcaccgtgtc tagcggcgga gaagcggagg cggatctggg ggaggaagtg  480
gcggaggcag caacttcatg ctgacccagc ctcacagcgt gtccgagagc cctggcaaga  540
ccgtgaccat ctcctgcacc agaagctccg gctctatcgc cagcaacagc gtgcagtggt  600
atcagcagag gcccggcagc agccctacca ccgtgatcta cgaggacaac cagaggccca  660
gcggcgtgcc cgatagattc tctggcagca tcgacagcag ctccaacagc gccagcctga  720
ccgtgtccgg cctgaaaaca gaggacgagg ccgactacta ctgccagagc agcgatagca  780
gcgccgtggt gtttggcagc ggcaccaagc tgacagtgct gggaggcggc tcaggcggag  840
gatctggcgg cggatccggc ggaggctctc aggtgcagct ggtgcagtct ggcgccgaag  900
tgaagaaacc cggcagctcc gtgaaggtgt cctgcaagac aagcggcgac accttctcca  960
cctacgccat cagttgggtg cggcaggcac ctggacaggg actggaatgg atgggaggca  1020
tcatccccat cttcggcaag gcccactacg cccagaaatt ccagggccgc gtgacaatca  1080
ccgccgacga gagcacaagc accgcctaca tggaactgag cagcctgcgg agcgaggata  1140
ccgctgtgta cttctgtgcc cggaagttcc actttgtgtc cggcagcccc ttcggcatgg  1200
atgtgtgggg acagggcacc acagtgactg tgtcctccgg gggaggcagc ggagggggaa  1260
gtggcggcgg aagtgggggga ggatctgaga tcgtgctgac acagagcccc gccaccctgt  1320
cactgtctcc aggcgaaaga gccaccctga gctgcagagc cagccagtct gtgtccagct  1380
acctggcctg gtatcagcag aaacccggcc aggcccccag actgctgatc tatgacgcca  1440
gcaatcgggc caccggcatc cctgccagat ttccggaag cggctccggc accgacttca  1500
ccctgacaat cagcagcctg gaacccgagg acttcgccgt gtattattgc cagcagcgga  1560
gcaactggcc cacctttggc cagggcacta aggtggaaat caag                  1604
```

```
SEQ ID NO: 12          moltype = AA  length = 24
FEATURE                Location/Qualifiers
REGION                 1..24
                       note = source = /note="Description of Artificial Sequence:
                        Synthetic peptide"
source                 1..24
                       mol_type = protein
                       organism = synthetic construct
SEQUENCE: 12
IYIWAPLAGT CGVLLLSLVI TLYC                                         24
```

```
SEQ ID NO: 13          moltype = DNA  length = 72
FEATURE                Location/Qualifiers
misc_feature           1..72
                       note = source = /note="Description of Artificial Sequence:
                        Synthetic oligonucleotide"
source                 1..72
                       mol_type = other DNA
                       organism = synthetic construct
SEQUENCE: 13
atctacatct gggcgccctt ggccgggact tgtggggtcc ttctcctgtc actggttatc  60
accctttact gc                                                      72
```

```
SEQ ID NO: 14          moltype = AA  length = 42
```

-continued

```
FEATURE                 Location/Qualifiers
REGION                  1..42
                        note = source = /note="Description of Artificial Sequence:
                         Synthetic polypeptide"
source                  1..42
                        mol_type = protein
                        organism = synthetic construct
SEQUENCE: 14
KRGRKKLLYI FKQPFMRPVQ TTQEEDGCSC RFPEEEEGGC EL                    42

SEQ ID NO: 15           moltype = DNA  length = 126
FEATURE                 Location/Qualifiers
misc_feature            1..126
                        note = source = /note="Description of Artificial Sequence:
                         Synthetic polynucleotide"
source                  1..126
                        mol_type = other DNA
                        organism = synthetic construct
SEQUENCE: 15
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 16           moltype = AA  length = 48
FEATURE                 Location/Qualifiers
REGION                  1..48
                        note = source = /note="Description of Artificial Sequence:
                         Synthetic polypeptide"
source                  1..48
                        mol_type = protein
                        organism = synthetic construct
SEQUENCE: 16
QRRKYRSNKG ESPVEPAEPC RYSCPREEEG STIPIQEDYR KPEPACSP              48

SEQ ID NO: 17           moltype = DNA  length = 123
FEATURE                 Location/Qualifiers
misc_feature            1..123
                        note = source = /note="Description of Artificial Sequence:
                         Synthetic polynucleotide"
source                  1..123
                        mol_type = other DNA
                        organism = synthetic construct
SEQUENCE: 17
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123

SEQ ID NO: 18           moltype = AA  length = 112
FEATURE                 Location/Qualifiers
REGION                  1..112
                        note = source = /note="Description of Artificial Sequence:
                         Synthetic polypeptide"
source                  1..112
                        mol_type = protein
                        organism = synthetic construct
SEQUENCE: 18
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 19           moltype = DNA  length = 336
FEATURE                 Location/Qualifiers
misc_feature            1..336
                        note = source = /note="Description of Artificial Sequence:
                         Synthetic polynucleotide"
source                  1..336
                        mol_type = other DNA
                        organism = synthetic construct
SEQUENCE: 19
agagtgaagt tcagcaggag cgcagacgcc cccgcgtaca agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 20           moltype = AA  length = 112
FEATURE                 Location/Qualifiers
REGION                  1..112
                        note = source = /note="Description of Artificial Sequence:
```

-continued

```
                         Synthetic polypeptide"
source                  1..112
                        mol_type = protein
                        organism = synthetic construct
SEQUENCE: 20
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 21           moltype = DNA  length = 336
FEATURE                 Location/Qualifiers
misc_feature            1..336
                        note = source = /note="Description of Artificial Sequence:
                         Synthetic polynucleotide"
source                  1..336
                        mol_type = other DNA
                        organism = synthetic construct
SEQUENCE: 21
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 22           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 22
GGGGS                                                              5

SEQ ID NO: 23           moltype = DNA  length = 30
FEATURE                 Location/Qualifiers
misc_feature            1..30
                        note = source = /note="Description of Artificial Sequence:
                         Synthetic oligonucleotide"
source                  1..30
                        mol_type = other DNA
                        organism = synthetic construct
SEQUENCE: 23
ggtggcggag gttctggagg tggaggttcc                                   30

SEQ ID NO: 24           moltype = AA  length = 150
FEATURE                 Location/Qualifiers
REGION                  1..150
                        note = source = /note="Description of Artificial Sequence:
                         Synthetic polypeptide"
source                  1..150
                        mol_type = protein
                        organism = synthetic construct
SEQUENCE: 24
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV                                   150

SEQ ID NO: 25           moltype = DNA  length = 450
FEATURE                 Location/Qualifiers
misc_feature            1..450
                        note = source = /note="Description of Artificial Sequence:
                         Synthetic polynucleotide"
source                  1..450
                        mol_type = other DNA
                        organism = synthetic construct
SEQUENCE: 25
cccggatggt ttctggactc tccggatcgc ccgtggaatc ccccaacctt ctcaccggca  60
ctcttggttg tgactgaggg cgataatgcg accttcacgt gctcgttctc caacacctcc  120
gaatcattcg tgctgaactg gtaccgcatg agcccgtcaa accagaccga caagctcgcc  180
gcgtttccgg aagatcggtc gcaaccggga caggattgtc ggttccgcgt gactcaactg  240
ccgaatggca gagacttcca catgagcgtg gtccgcgcta ggcgaaacga ctccgggacc  300
tacctgtgcg gagccatctc gctggcgcct aaggcccaaa tcaaagagag cttgagggcc  360
gaactgagag tgaccgagcg cagagctgag gtgccaactg cacatccatc cccatcgcct  420
cggcctgcgg ggcagtttca gaccctggtc                                   450

SEQ ID NO: 26           moltype = AA  length = 394
FEATURE                 Location/Qualifiers
```

-continued

```
REGION                  1..394
                        note = source = /note="Description of Artificial Sequence:
                         Synthetic polypeptide"
source                  1..394
                        mol_type = protein
                        organism = synthetic construct
SEQUENCE: 26
MALPVTALLL PLALLLHAAR PPGWFLDSPD RPWNPPTFSP ALLVVTEGDN ATFTCSFSNT  60
SESFVLNWYR MSPSNQTDKL AAFPEDRSQP GQDCRFRVTQ LPNGRDFHMS VVRARRNDSG  120
TYLCGAISLA PKAQIKESLR AELRVTERRA EVPTAHPSPS PRPAGQFQTL VTTTPAPRPP  180
TPAPTIASQP LSLRPEACRP AAGGAVHTRG LDFACDIYIW APLAGTCGVL LLSLVITLYC  240
KRGRKKLLYI FKQPFMRPVQ TTQEEDGCSC RFPEEEEGGC ELRVKFSRSA DAPAYKQGQN  300
QLYNELNLGR REEYDVLDKR RGRDPEMGGK PRRKNPQEGL YNELQKDKMA EAYSEIGMKG  360
ERRRGKGHDG LYQGLSTATK DTYDALHMQA LPPR                            394

SEQ ID NO: 27           moltype = DNA  length = 1182
FEATURE                 Location/Qualifiers
misc_feature            1..1182
                        note = source = /note="Description of Artificial Sequence:
                         Synthetic polynucleotide"
source                  1..1182
                        mol_type = other DNA
                        organism = synthetic construct
SEQUENCE: 27
atggccctcc ctgtcactgc cctgcttctc cccctcgcac tcctgctcca cgccgctaga  60
ccacccggat ggtttctgga ctctccggat cgcccgtgga atcccccaac cttctcaccg  120
gcactcttgg ttgtgactga gggcgataat gcgaccttca cgtgctcgtt ctccaacacc  180
tccgaatcat tcgtgctgaa ctggtaccgc atgagcccgt caaaccagac cgacaagctc  240
gccgcgtttc cggaagatcg gtcgcaaccg ggacaggatt gtcggttccg cgtgactcaa  300
ctgccgaatg gcagagactt ccacatgagc gtggtccgcg ctaggcgaaa cgactccggg  360
acctacctgt gcggagccat ctcgctggcg cctaaggccc aaatcaaaga gagcttgagg  420
gccgaactga gagtgaccga gcgcagagct gaggtgccaa ctgcacatcc atccccatcg  480
cctcggcctg cggggcagtt tcagaccctg gtcacgacca ctccggcgcc gcgcccaccg  540
actccggccc caactatcgc gagccagccc ctgtcgctga ggccggaagc atgccgccct  600
gccgccggag gtgctgtgca tacccgggga ttggacttcg catgcgacat ctacatttgg  660
gctcctctcg ccggaacttg tggcgtgctc cttctgtccc tggtcatcac cctgtactgc  720
aagcggggtc ggaaaaagct tctgtacatt ttcaagcagc ccttcatgag gcccgtgcaa  780
accacccagg aggaggacgg ttgctcctgc cggttccccg aagaggaaga aggaggttgc  840
gagctgcgcg tgaagttctc ccggagcgcc gacgcccccg cctataagca gggccagaac  900
cagctgtaca acgaactgaa cctgggacgg cgggaagagt acgatgtgct ggacaagcgg  960
cgcggccggg accccgaaat gggcgggaag cctagaagaa agaaccctca ggaaggcctg  1020
tataacgagc tgcagaagga caagatggcc gaggcctact ccgaaattgg gatgaaggga  1080
gagcggcgga ggggaaaggg gcacgacggc ctgtaccaag gactgtccac cgccaccaag  1140
gacacatacg atgccctgca catgcaggcc cttccccctc gc                    1182

SEQ ID NO: 28           moltype = AA  length = 40
FEATURE                 Location/Qualifiers
REGION                  1..40
                        note = MISC_FEATURE - /note="This sequence may encompass
                         1-10 'Gly Gly Gly Ser' repeating units"
REGION                  1..40
                        note = source = /note="Description of Artificial Sequence:
                         Synthetic polypeptide"
source                  1..40
                        mol_type = protein
                        organism = synthetic construct
SEQUENCE: 28
GGGSGGGSGG GSGGGSGGGS GGGSGGGSGG GSGGGSGGGS                      40

SEQ ID NO: 29           moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 29
GGGGSGGGGS GGGGSGGGGS                                            20

SEQ ID NO: 30           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 30
```

```
GGGGSGGGGS GGGGS                                                15

SEQ ID NO: 31          moltype = AA  length = 4
FEATURE                Location/Qualifiers
REGION                 1..4
                       note = source = /note="Description of Artificial Sequence:
                        Synthetic peptide"
source                 1..4
                       mol_type = protein
                       organism = synthetic construct
SEQUENCE: 31
GGGS                                                            4

SEQ ID NO: 32          moltype = DNA  length = 2000
FEATURE                Location/Qualifiers
misc_feature           1..2000
                       note = source = /note="Description of Artificial Sequence:
                        Synthetic polynucleotide"
source                 1..2000
                       mol_type = other DNA
                       organism = synthetic construct
SEQUENCE: 32
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa                                              2000

SEQ ID NO: 33          moltype = DNA  length = 150
FEATURE                Location/Qualifiers
misc_feature           1..150
                       note = source = /note="Description of Artificial Sequence:
                        Synthetic polynucleotide"
source                 1..150
                       mol_type = other DNA
                       organism = synthetic construct
SEQUENCE: 33
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa                                   150

SEQ ID NO: 34          moltype = DNA  length = 5000
FEATURE                Location/Qualifiers
misc_feature           1..5000
                       note = source = /note="Description of Artificial Sequence:
                        Synthetic polynucleotide"
source                 1..5000
                       mol_type = other DNA
                       organism = synthetic construct
SEQUENCE: 34
```

-continued aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740

-continued aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

SEQ ID NO: 35 moltype = DNA length = 100
FEATURE Location/Qualifiers
misc_feature 1..100
note = source = /note="Description of Artificial Sequence: Synthetic polynucleotide"
source 1..100
mol_type = other DNA
organism = synthetic construct
SEQUENCE: 35
tttttttttt tttttttttt tttttttttt tttttttttt tttttttttt tttttttttt 60
tttttttttt tttttttttt tttttttttt tttttttttt 100

SEQ ID NO: 36 moltype = DNA length = 5000
FEATURE Location/Qualifiers
misc_feature 1..5000
note = source = /note="Description of Artificial Sequence: Synthetic polynucleotide"
source 1..5000
mol_type = other DNA
organism = synthetic construct
SEQUENCE: 36
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380
tttttttttt tttttttttt tttttttttt tttttttttt tttttttttt tttttttttt 1440
tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100
tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820
tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

SEQ ID NO: 37 moltype = DNA length = 5000
FEATURE Location/Qualifiers
misc_feature 1..5000
note = source = /note="Description of Artificial Sequence: Synthetic polynucleotide"
source 1..5000
mol_type = other DNA
organism = synthetic construct
SEQUENCE: 37
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220

-continued

```
aaaaaaaaaa aaaaaaaaaa aaaaaaaaaa aaaaaaaaaa aaaaaaaaaa aaaaaaaaaa  2280
aaaaaaaaaa aaaaaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaaaaaaaa aaaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa aaaaaaaaaa aaaaaaaaaa aaaaaaaaaa aaaaaaaaaa  2580
aaaaaaaaaa aaaaaaaaaa aaaaaaaaaa aaaaaaaaaa aaaaaaaaaa aaaaaaaaaa  2640
aaaaaaaaaa aaaaaaaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaaa aaaaaaaaaa aaaaaaaaaa aaaaaaaaaa aaaaaaaaaa aaaaaaaaaa  2820
aaaaaaaaaa aaaaaaaaaa aaaaaaaaaa aaaaaaaaaa aaaaaaaaaa aaaaaaaaaa  2880
aaaaaaaaaa aaaaaaaaaa aaaaaaaaaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000
aaaaaaaaaa aaaaaaaaaa aaaaaaaaaa aaaaaaaaaa aaaaaaaaaa aaaaaaaaaa  3060
aaaaaaaaaa aaaaaaaaaa aaaaaaaaaa aaaaaaaaaa aaaaaaaaaa aaaaaaaaaa  3120
aaaaaaaaaa aaaaaaaaaa aaaaaaaaaa aaaaaaaaaa aaaaaaaaaa aaaaaaaaaa  3180
aaaaaaaaaa aaaaaaaaaa aaaaaaaaaa aaaaaaaaaa aaaaaaaaaa aaaaaaaaaa  3240
aaaaaaaaaa aaaaaaaaaa aaaaaaaaaa aaaaaaaaaa aaaaaaaaaa aaaaaaaaaa  3300
aaaaaaaaaa aaaaaaaaaa aaaaaaaaaa aaaaaaaaaa aaaaaaaaaa aaaaaaaaaa  3360
aaaaaaaaaa aaaaaaaaaa aaaaaaaaaa aaaaaaaaaa aaaaaaaaaa aaaaaaaaaa  3420
aaaaaaaaaa aaaaaaaaaa aaaaaaaaaa aaaaaaaaaa aaaaaaaaaa aaaaaaaaaa  3480
aaaaaaaaaa aaaaaaaaaa aaaaaaaaaa aaaaaaaaaa aaaaaaaaaa aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaaaa  3660
aaaaaaaaaa aaaaaaaaaa aaaaaaaaaa aaaaaaaaaa aaaaaaaaaa aaaaaaaaaa  3720
aaaaaaaaaa aaaaaaaaaa aaaaaaaaaa aaaaaaaaaa aaaaaaaaaa aaaaaaaaaa  3780
aaaaaaaaaa aaaaaaaaaa aaaaaaaaaa aaaaaaaaaa aaaaaaaaaa aaaaaaaaaa  3840
aaaaaaaaaa aaaaaaaaaa aaaaaaaaaa aaaaaaaaaa aaaaaaaaaa aaaaaaaaaa  3900
aaaaaaaaaa aaaaaaaaaa aaaaaaaaaa aaaaaaaaaa aaaaaaaaaa aaaaaaaaaa  3960
aaaaaaaaaa aaaaaaaaaa aaaaaaaaaa aaaaaaaaaa aaaaaaaaaa aaaaaaaaaa  4020
aaaaaaaaaa aaaaaaaaaa aaaaaaaaaa aaaaaaaaaa aaaaaaaaaa aaaaaaaaaa  4080
aaaaaaaaaa aaaaaaaaaa aaaaaaaaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaaaa aaaaaaaaaa aaaaaaaaaa  4260
aaaaaaaaaa aaaaaaaaaa aaaaaaaaaa aaaaaaaaaa aaaaaaaaaa aaaaaaaaaa  4320
aaaaaaaaaa aaaaaaaaaa aaaaaaaaaa aaaaaaaaaa aaaaaaaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaaaa aaaaaaaaaa aaaaaaaaaa  4620
aaaaaaaaaa aaaaaaaaaa aaaaaaaaaa aaaaaaaaaa aaaaaaaaaa aaaaaaaaaa  4680
aaaaaaaaaa aaaaaaaaaa aaaaaaaaaa aaaaaaaaaa aaaaaaaaaa aaaaaaaaaa  4740
aaaaaaaaaa aaaaaaaaaa aaaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaaaaa aaaaaaaaaa aaaaaaaaaa aaaaaaaaaa  4920
aaaaaaaaaa aaaaaaaaaa aaaaaaaaaa aaaaaaaaaa aaaaaaaaaa aaaaaaaaaa  4980
aaaaaaaaaa aaaaaaaaaa                                              5000

SEQ ID NO: 38          moltype = DNA  length = 400
FEATURE                Location/Qualifiers
misc_feature           1..400
                       note = source = /note="Description of Artificial Sequence:
                        Synthetic polynucleotide"
source                 1..400
                       mol_type = other DNA
                       organism = synthetic construct
SEQUENCE: 38
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa                        400

SEQ ID NO: 39          moltype = AA  length = 373
FEATURE                Location/Qualifiers
REGION                 1..373
                       note = source = /note="Description of Artificial Sequence:
                        Synthetic polypeptide"
source                 1..373
                       mol_type = protein
                       organism = synthetic construct
SEQUENCE: 39
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV TTTPAPRPPT PAPTIASQPL SLRPEACRPA  180
AGGAVHTRGL DFACDIYIWA PLAGTCGVLL LSLVITLYCK RGRKKLLYIF KQPFMRPVQT  240
TQEEDGCSCR FPEEEEGGCE LRVKFSRSAD APAYKQGQNQ LYNELNLGRR EEYDVLDKRR  300
```

```
GRDPEMGGKP RRKNPQEGLY NELQKDKMAE AYSEIGMKGE RRRGKGHDGL YQGLSTATKD  360
TYDALHMQAL PPR                                                     373

SEQ ID NO: 40           moltype = DNA  length = 2000
FEATURE                 Location/Qualifiers
misc_feature            1..2000
                        note = /note="This sequence may encompass 50-2000
                         nucleotides"
misc_feature            1..2000
                        note = source = /note="Description of Artificial Sequence:
                         Synthetic polynucleotide"
misc_feature            1..2000
                        note = source = /note="See specification as filed for
                         detailed description of substitutions and preferred
                         embodiments"
source                  1..2000
                        mol_type = other DNA
                        organism = synthetic construct
SEQUENCE: 40
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa                                              2000

SEQ ID NO: 41           moltype = AA  length = 244
FEATURE                 Location/Qualifiers
REGION                  1..244
                        note = source = /note="Description of Artificial Sequence:
                         Synthetic polypeptide"
source                  1..244
                        mol_type = protein
                        organism = synthetic construct
SEQUENCE: 41
QVQLLESGAE LVRPGSSVKI SCKASGYAFS SYWMNWVKQR PGQGLEWIGQ IYPGDGDTNY  60
NGKFKGQATL TADKSSSTAY MQLSGLTSED SAVYSCARKT ISSVVDFYFD YWGQGTTVTG  120
GGSGGGSGGG SGGGSELVLT QSPKFMSTSV GDRVSVTCKA SQNVGTNVAW YQQKPGQSPK  180
PLIYSATYRN SGVPDRFTGS GSGTDFTLTI TNVQSKDLAD YFCQYNRYPY TSFFFTKLEI  240
KRRS                                                               244

SEQ ID NO: 42           moltype = AA  length = 464
FEATURE                 Location/Qualifiers
REGION                  1..464
                        note = source = /note="Description of Artificial Sequence:
                         Synthetic polypeptide"
source                  1..464
                        mol_type = protein
                        organism = synthetic construct
SEQUENCE: 42
QVQLLESGAE LVRPGSSVKI SCKASGYAFS SYWMNWVKQR PGQGLEWIGQ IYPGDGDTNY  60
```

-continued

```
NGKFKGQATL TADKSSSTAY MQLSGLTSED SAVYSCARKT ISSVVDFYFD YWGQGTTVTG  120
GGSGGGSGGG SGGGSELVLT QSPKFMSTSV GDRVSVTCKA SQNVGTNVAW YQQKPGQSPK  180
PLIYSATYRN SGVPDRFTGS GSGTDFTLTI TNVQSKDLAD YFCQYNRYPY TSFFFTKLEI  240
KRRSKIEVMY PPPYLDNEKS NGTIIHVKGK HLCPSPLFPG PSKPFWVLVV VGGVLACYSL  300
LVTVAFIIFW VRSKRSRLLH SDYMNMTPRR PGPTRKHYQP YAPPRDFAAY RSRVKFSRSA  360
DAPAYQQGQN QLYNELNLGR REEYDVLDKR RGRDPEMGGK PRRKNPQEGL YNELQKDKMA  420
EAYSEIGMKG ERRRGKGHDG LYQGLSTATK DTYDALHMQA LPPR                  464

SEQ ID NO: 43          moltype = AA  length = 246
FEATURE                Location/Qualifiers
REGION                 1..246
                       note = source = /note="Description of Artificial Sequence:
                        Synthetic polypeptide"
source                 1..246
                       mol_type = protein
                       organism = synthetic construct
SEQUENCE: 43
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSE                                                            246

SEQ ID NO: 44          moltype = AA  length = 439
FEATURE                Location/Qualifiers
REGION                 1..439
                       note = source = /note="Description of Artificial Sequence:
                        Synthetic polypeptide"
source                 1..439
                       mol_type = protein
                       organism = synthetic construct
SEQUENCE: 44
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSESKYG PPCPPCPMFW VLVVVGGVLA CYSLLVTVAF IIFWVKRGRK KLLYIFKQPF  300
MRPVQTTQEE DGCSCRFEEE EGGCELRVKF SRSADAPAYQ QGQNQLYNEL NLGRREEYDV  360
LDKRRGRDPE MGGKPRRKNP QEGLYNELQK DKMAEAYSEI GMKGERRRGK GHDGLYQGLS  420
TATKDTYDAL HMQALPPRL                                              439

SEQ ID NO: 45          moltype = AA  length = 819
FEATURE                Location/Qualifiers
REGION                 1..819
                       note = source = /note="Description of Artificial Sequence:
                        Synthetic polypeptide"
source                 1..819
                       mol_type = protein
                       organism = synthetic construct
SEQUENCE: 45
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSESKYG PPCPPCPMFW VLVVVGGVLA CYSLLVTVAF IIFWVKRGRK KLLYIFKQPF  300
MRPVQTTQEE DGCSCRFEEE EGGCELRVKF SRSADAPAYQ QGQNQLYNEL NLGRREEYDV  360
LDKRRGRDPE MGGKPRRKNP QEGLYNELQK DKMAEAYSEI GMKGERRRGK GHDGLYQGLS  420
TATKDTYDAL HMQALPPRLE GGGEGRGSLL TCGDVEENPG PRMLLLVTSL LLCELPHPAF  480
LLIPRKVCNG IGIGEFKDSL SINATNIKHF KNCTSISGDL HILPVAFRGD SFTHTPPLDP  540
QELDILKTVK EITGFLLIQA WPENRTDLHA FENLEIIRGR TKQHGQFSLA VVSLNITSLG  600
LRSLKEISDG DVIISGNKNL CYANTINWKK LFGTSGQKTK IISNRGENSC KATGQVCHAL  660
CSPEGCWGPE PRDCVSCRNV SRGRECVDKC NLLEGEPREF VENSECIQCH PECLPQAMNI  720
TCTGRGPDNC IQCAHYIDGP HCVKTCPAGV MGENNTLVWK YADAGHVCHL CHPNCTYGCT  780
GPGLEGCPTN GPKIPSIATG MVGALLLLLV VALGIGLFM                        819

SEQ ID NO: 46          moltype = AA  length = 245
FEATURE                Location/Qualifiers
REGION                 1..245
                       note = source = /note="Description of Artificial Sequence:
                        Synthetic polypeptide"
source                 1..245
                       mol_type = protein
                       organism = synthetic construct
SEQUENCE: 46
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                             245
```

-continued

```
SEQ ID NO: 47          moltype = AA  length = 467
FEATURE                Location/Qualifiers
REGION                 1..467
                       note = source = /note="Description of Artificial Sequence:
                        Synthetic polypeptide"
source                 1..467
                       mol_type = protein
                       organism = synthetic construct
SEQUENCE: 47
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAAIE VMYPPPYLDN EKSNGTIIHV KGKHLCPSPL FPGPSKPFWV LVVVGGVLAC  300
YSLLVTVAFI IFWVRSKRSR LLHSDYMNMT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR               467

SEQ ID NO: 48          moltype = AA  length = 119
FEATURE                Location/Qualifiers
REGION                 1..119
                       note = source = /note="Description of Artificial Sequence:
                        Synthetic polypeptide"
source                 1..119
                       mol_type = protein
                       organism = synthetic construct
SEQUENCE: 48
QVQLLESGAE LVRPGSSVKI SCKASGYAFS SYWMNWVKQR PGQGLEWIGQ IYPGDGDTNY  60
NGKFKGQATL TADKSSSTAY MQLSGLTSED SAVYSCARKT ISSVVDFYFD YWGQGTTVT   119

SEQ ID NO: 49          moltype = AA  length = 111
FEATURE                Location/Qualifiers
REGION                 1..111
                       note = source = /note="Description of Artificial Sequence:
                        Synthetic polypeptide"
source                 1..111
                       mol_type = protein
                       organism = synthetic construct
SEQUENCE: 49
ELVLTQSPKF MSTSVGDRVS VTCKASQNVG TNVAWYQQKP GQSPKPLIYS ATYRNSGVPD  60
RFTGSGSGTD FTLTITNVQS KDLADYFYFC QYNRYPYTSG GGTKLEIKRR S           111

SEQ ID NO: 50          moltype = DNA  length = 100
FEATURE                Location/Qualifiers
misc_feature           1..100
                       note = source = /note="Description of Artificial Sequence:
                        Synthetic polynucleotide"
source                 1..100
                       mol_type = other DNA
                       organism = synthetic construct
SEQUENCE: 50
tttttttttt tttttttttt tttttttttt tttttttttt tttttttttt tttttttttt  60
tttttttttt tttttttttt tttttttttt tttttttttt                        100

SEQ ID NO: 51          moltype = DNA  length = 5000
FEATURE                Location/Qualifiers
misc_feature           1..5000
                       note = /note="This sequence may encompass 50-5000
                        nucleotides"
misc_feature           1..5000
                       note = source = /note="Description of Artificial Sequence:
                        Synthetic polynucleotide"
misc_feature           1..5000
                       note = source = /note="See specification as filed for
                        detailed description of substitutions and preferred
                        embodiments"
source                 1..5000
                       mol_type = other DNA
                       organism = synthetic construct
SEQUENCE: 51
tttttttttt tttttttttt tttttttttt tttttttttt tttttttttt tttttttttt  60
tttttttttt tttttttttt tttttttttt tttttttttt tttttttttt tttttttttt  120
tttttttttt tttttttttt tttttttttt tttttttttt tttttttttt tttttttttt  180
tttttttttt tttttttttt tttttttttt tttttttttt tttttttttt tttttttttt  240
tttttttttt tttttttttt tttttttttt tttttttttt tttttttttt tttttttttt  300
tttttttttt tttttttttt tttttttttt tttttttttt tttttttttt tttttttttt  360
tttttttttt tttttttttt tttttttttt tttttttttt tttttttttt tttttttttt  420
tttttttttt tttttttttt tttttttttt tttttttttt tttttttttt tttttttttt  480
```

-continued

```
tttttttttt tttttttttt tttttttttt tttttttttt tttttttttt tttttttttt  540
tttttttttt tttttttttt tttttttttt tttttttttt tttttttttt tttttttttt  600
tttttttttt tttttttttt tttttttttt tttttttttt tttttttttt tttttttttt  660
tttttttttt tttttttttt tttttttttt tttttttttt tttttttttt tttttttttt  720
tttttttttt tttttttttt tttttttttt tttttttttt tttttttttt tttttttttt  780
tttttttttt tttttttttt tttttttttt tttttttttt tttttttttt tttttttttt  840
tttttttttt tttttttttt tttttttttt tttttttttt tttttttttt tttttttttt  900
tttttttttt tttttttttt tttttttttt tttttttttt tttttttttt tttttttttt  960
tttttttttt tttttttttt tttttttttt tttttttttt tttttttttt tttttttttt  1020
tttttttttt tttttttttt tttttttttt tttttttttt tttttttttt tttttttttt  1080
tttttttttt tttttttttt tttttttttt tttttttttt tttttttttt tttttttttt  1140
tttttttttt tttttttttt tttttttttt tttttttttt tttttttttt tttttttttt  1200
tttttttttt tttttttttt tttttttttt tttttttttt tttttttttt tttttttttt  1260
tttttttttt tttttttttt tttttttttt tttttttttt tttttttttt tttttttttt  1320
tttttttttt tttttttttt tttttttttt tttttttttt tttttttttt tttttttttt  1380
tttttttttt tttttttttt tttttttttt tttttttttt tttttttttt tttttttttt  1440
tttttttttt tttttttttt tttttttttt tttttttttt tttttttttt tttttttttt  1500
tttttttttt tttttttttt tttttttttt tttttttttt tttttttttt tttttttttt  1560
tttttttttt tttttttttt tttttttttt tttttttttt tttttttttt tttttttttt  1620
tttttttttt tttttttttt tttttttttt tttttttttt tttttttttt tttttttttt  1680
tttttttttt tttttttttt tttttttttt tttttttttt tttttttttt tttttttttt  1740
tttttttttt tttttttttt tttttttttt tttttttttt tttttttttt tttttttttt  1800
tttttttttt tttttttttt tttttttttt tttttttttt tttttttttt tttttttttt  1860
tttttttttt tttttttttt tttttttttt tttttttttt tttttttttt tttttttttt  1920
tttttttttt tttttttttt tttttttttt tttttttttt tttttttttt tttttttttt  1980
tttttttttt tttttttttt tttttttttt tttttttttt tttttttttt tttttttttt  2040
tttttttttt tttttttttt tttttttttt tttttttttt tttttttttt tttttttttt  2100
tttttttttt tttttttttt tttttttttt tttttttttt tttttttttt tttttttttt  2160
tttttttttt tttttttttt tttttttttt tttttttttt tttttttttt tttttttttt  2220
tttttttttt tttttttttt tttttttttt tttttttttt tttttttttt tttttttttt  2280
tttttttttt tttttttttt tttttttttt tttttttttt tttttttttt tttttttttt  2340
tttttttttt tttttttttt tttttttttt tttttttttt tttttttttt tttttttttt  2400
tttttttttt tttttttttt tttttttttt tttttttttt tttttttttt tttttttttt  2460
tttttttttt tttttttttt tttttttttt tttttttttt tttttttttt tttttttttt  2520
tttttttttt tttttttttt tttttttttt tttttttttt tttttttttt tttttttttt  2580
tttttttttt tttttttttt tttttttttt tttttttttt tttttttttt tttttttttt  2640
tttttttttt tttttttttt tttttttttt tttttttttt tttttttttt tttttttttt  2700
tttttttttt tttttttttt tttttttttt tttttttttt tttttttttt tttttttttt  2760
tttttttttt tttttttttt tttttttttt tttttttttt tttttttttt tttttttttt  2820
tttttttttt tttttttttt tttttttttt tttttttttt tttttttttt tttttttttt  2880
tttttttttt tttttttttt tttttttttt tttttttttt tttttttttt tttttttttt  2940
tttttttttt tttttttttt tttttttttt tttttttttt tttttttttt tttttttttt  3000
tttttttttt tttttttttt tttttttttt tttttttttt tttttttttt tttttttttt  3060
tttttttttt tttttttttt tttttttttt tttttttttt tttttttttt tttttttttt  3120
tttttttttt tttttttttt tttttttttt tttttttttt tttttttttt tttttttttt  3180
tttttttttt tttttttttt tttttttttt tttttttttt tttttttttt tttttttttt  3240
tttttttttt tttttttttt tttttttttt tttttttttt tttttttttt tttttttttt  3300
tttttttttt tttttttttt tttttttttt tttttttttt tttttttttt tttttttttt  3360
tttttttttt tttttttttt tttttttttt tttttttttt tttttttttt tttttttttt  3420
tttttttttt tttttttttt tttttttttt tttttttttt tttttttttt tttttttttt  3480
tttttttttt tttttttttt tttttttttt tttttttttt tttttttttt tttttttttt  3540
tttttttttt tttttttttt tttttttttt tttttttttt tttttttttt tttttttttt  3600
tttttttttt tttttttttt tttttttttt tttttttttt tttttttttt tttttttttt  3660
tttttttttt tttttttttt tttttttttt tttttttttt tttttttttt tttttttttt  3720
tttttttttt tttttttttt tttttttttt tttttttttt tttttttttt tttttttttt  3780
tttttttttt tttttttttt tttttttttt tttttttttt tttttttttt tttttttttt  3840
tttttttttt tttttttttt tttttttttt tttttttttt tttttttttt tttttttttt  3900
tttttttttt tttttttttt tttttttttt tttttttttt tttttttttt tttttttttt  3960
tttttttttt tttttttttt tttttttttt tttttttttt tttttttttt tttttttttt  4020
tttttttttt tttttttttt tttttttttt tttttttttt tttttttttt tttttttttt  4080
tttttttttt tttttttttt tttttttttt tttttttttt tttttttttt tttttttttt  4140
tttttttttt tttttttttt tttttttttt tttttttttt tttttttttt tttttttttt  4200
tttttttttt tttttttttt tttttttttt tttttttttt tttttttttt tttttttttt  4260
tttttttttt tttttttttt tttttttttt tttttttttt tttttttttt tttttttttt  4320
tttttttttt tttttttttt tttttttttt tttttttttt tttttttttt tttttttttt  4380
tttttttttt tttttttttt tttttttttt tttttttttt tttttttttt tttttttttt  4440
tttttttttt tttttttttt tttttttttt tttttttttt tttttttttt tttttttttt  4500
tttttttttt tttttttttt tttttttttt tttttttttt tttttttttt tttttttttt  4560
tttttttttt tttttttttt tttttttttt tttttttttt tttttttttt tttttttttt  4620
tttttttttt tttttttttt tttttttttt tttttttttt tttttttttt tttttttttt  4680
tttttttttt tttttttttt tttttttttt tttttttttt tttttttttt tttttttttt  4740
tttttttttt tttttttttt tttttttttt tttttttttt tttttttttt tttttttttt  4800
tttttttttt tttttttttt tttttttttt tttttttttt tttttttttt tttttttttt  4860
tttttttttt tttttttttt tttttttttt tttttttttt tttttttttt tttttttttt  4920
tttttttttt tttttttttt tttttttttt tttttttttt tttttttttt tttttttttt  4980
tttttttttt tttttttttt                                              5000

SEQ ID NO: 52          moltype = DNA  length = 5000
FEATURE                Location/Qualifiers
```

-continued

```
misc_feature          1..5000
                      note = /note="This sequence may encompass 100-5000
                       nucleotides"
misc_feature          1..5000
                      note = source = /note="Description of Artificial Sequence:
                       Synthetic polynucleotide"
misc_feature          1..5000
                      note = source = /note="See specification as filed for
                       detailed description of substitutions and preferred
                       embodiments"
source                1..5000
                      mol_type = other DNA
                      organism = synthetic construct
SEQUENCE: 52
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaaaaa aaaaaaaaaa aaaaaaaaaa aaaaaaaaaa aaaaaaaaaa aaaaaaaaaa  2220
aaaaaaaaaa aaaaaaaaaa aaaaaaaaaa aaaaaaaaaa aaaaaaaaaa aaaaaaaaaa  2280
aaaaaaaaaa aaaaaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaaaaaaaa aaaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa aaaaaaaaaa aaaaaaaaaa aaaaaaaaaa aaaaaaaaaa  2580
aaaaaaaaaa aaaaaaaaaa aaaaaaaaaa aaaaaaaaaa aaaaaaaaaa aaaaaaaaaa  2640
aaaaaaaaaa aaaaaaaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaaa aaaaaaaaaa aaaaaaaaaa aaaaaaaaaa aaaaaaaaaa aaaaaaaaaa  2820
aaaaaaaaaa aaaaaaaaaa aaaaaaaaaa aaaaaaaaaa aaaaaaaaaa aaaaaaaaaa  2880
aaaaaaaaaa aaaaaaaaaa aaaaaaaaaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000
aaaaaaaaaa aaaaaaaaaa aaaaaaaaaa aaaaaaaaaa aaaaaaaaaa aaaaaaaaaa  3060
aaaaaaaaaa aaaaaaaaaa aaaaaaaaaa aaaaaaaaaa aaaaaaaaaa aaaaaaaaaa  3120
aaaaaaaaaa aaaaaaaaaa aaaaaaaaaa aaaaaaaaaa aaaaaaaaaa aaaaaaaaaa  3180
aaaaaaaaaa aaaaaaaaaa aaaaaaaaaa aaaaaaaaaa aaaaaaaaaa aaaaaaaaaa  3240
aaaaaaaaaa aaaaaaaaaa aaaaaaaaaa aaaaaaaaaa aaaaaaaaaa aaaaaaaaaa  3300
aaaaaaaaaa aaaaaaaaaa aaaaaaaaaa aaaaaaaaaa aaaaaaaaaa aaaaaaaaaa  3360
aaaaaaaaaa aaaaaaaaaa aaaaaaaaaa aaaaaaaaaa aaaaaaaaaa aaaaaaaaaa  3420
aaaaaaaaaa aaaaaaaaaa aaaaaaaaaa aaaaaaaaaa aaaaaaaaaa aaaaaaaaaa  3480
aaaaaaaaaa aaaaaaaaaa aaaaaaaaaa aaaaaaaaaa aaaaaaaaaa aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaaaa  3660
aaaaaaaaaa aaaaaaaaaa aaaaaaaaaa aaaaaaaaaa aaaaaaaaaa aaaaaaaaaa  3720
aaaaaaaaaa aaaaaaaaaa aaaaaaaaaa aaaaaaaaaa aaaaaaaaaa aaaaaaaaaa  3780
aaaaaaaaaa aaaaaaaaaa aaaaaaaaaa aaaaaaaaaa aaaaaaaaaa aaaaaaaaaa  3840
aaaaaaaaaa aaaaaaaaaa aaaaaaaaaa aaaaaaaaaa aaaaaaaaaa aaaaaaaaaa  3900
```

```
aaaaaaaaaa aaaaaaaaaa aaaaaaaaaa aaaaaaaaaa aaaaaaaaaa aaaaaaaaaa  3960
aaaaaaaaaa aaaaaaaaaa aaaaaaaaaa aaaaaaaaaa aaaaaaaaaa aaaaaaaaaa  4020
aaaaaaaaaa aaaaaaaaaa aaaaaaaaaa aaaaaaaaaa aaaaaaaaaa aaaaaaaaaa  4080
aaaaaaaaaa aaaaaaaaaa aaaaaaaaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaaaa aaaaaaaaaa aaaaaaaaaa  4260
aaaaaaaaaa aaaaaaaaaa aaaaaaaaaa aaaaaaaaaa aaaaaaaaaa aaaaaaaaaa  4320
aaaaaaaaaa aaaaaaaaaa aaaaaaaaaa aaaaaaaaaa aaaaaaaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaaaa aaaaaaaaaa aaaaaaaaaa  4620
aaaaaaaaaa aaaaaaaaaa aaaaaaaaaa aaaaaaaaaa aaaaaaaaaa aaaaaaaaaa  4680
aaaaaaaaaa aaaaaaaaaa aaaaaaaaaa aaaaaaaaaa aaaaaaaaaa aaaaaaaaaa  4740
aaaaaaaaaa aaaaaaaaaa aaaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaaaaa aaaaaaaaaa aaaaaaaaaa aaaaaaaaaa  4920
aaaaaaaaaa aaaaaaaaaa aaaaaaaaaa aaaaaaaaaa aaaaaaaaaa aaaaaaaaaa  4980
aaaaaaaaaa aaaaaaaaaa                                              5000

SEQ ID NO: 53          moltype = DNA  length = 400
FEATURE                Location/Qualifiers
misc_feature           1..400
                       note = /note="This sequence may encompass 100-400
                        nucleotides"
misc_feature           1..400
                       note = source = /note="Description of Artificial Sequence:
                        Synthetic polynucleotide"
misc_feature           1..400
                       note = source = /note="See specification as filed for
                        detailed description of substitutions and preferred
                        embodiments"
source                 1..400
                       mol_type = other DNA
                       organism = synthetic construct
SEQUENCE: 53
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa                        400

SEQ ID NO: 54          moltype = DNA  length = 70
FEATURE                Location/Qualifiers
misc_feature           1..70
                       note = /note="This sequence may encompass 50-70 nucleotides"
misc_feature           1..70
                       note = source = /note="Description of Artificial Sequence:
                        Synthetic oligonucleotide"
misc_feature           1..70
                       note = source = /note="See specification as filed for
                        detailed description of substitutions and preferred
                        embodiments"
source                 1..70
                       mol_type = other DNA
                       organism = synthetic construct
SEQUENCE: 54
aaaaaaaaaa aaaaaaaaaa aaaaaaaaaa aaaaaaaaaa aaaaaaaaaa aaaaaaaaaa  60
aaaaaaaaaa                                                         70

SEQ ID NO: 55          moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 55
GGGSGGGSGG GSGGGS                                                  16

SEQ ID NO: 56          moltype =   length =
SEQUENCE: 56
000

SEQ ID NO: 57          moltype =   length =
SEQUENCE: 57
```

000

SEQ ID NO: 58 moltype = length =
SEQUENCE: 58
000

SEQ ID NO: 59 moltype = length =
SEQUENCE: 59
000

SEQ ID NO: 60 moltype = length =
SEQUENCE: 60
000

SEQ ID NO: 61 moltype = length =
SEQUENCE: 61
000

SEQ ID NO: 62 moltype = length =
SEQUENCE: 62
000

SEQ ID NO: 63 moltype = length =
SEQUENCE: 63
000

SEQ ID NO: 64 moltype = length =
SEQUENCE: 64
000

SEQ ID NO: 65 moltype = length =
SEQUENCE: 65
000

SEQ ID NO: 66 moltype = length =
SEQUENCE: 66
000

SEQ ID NO: 67 moltype = length =
SEQUENCE: 67
000

SEQ ID NO: 68 moltype = length =
SEQUENCE: 68
000

SEQ ID NO: 69 moltype = length =
SEQUENCE: 69
000

SEQ ID NO: 70 moltype = length =
SEQUENCE: 70
000

SEQ ID NO: 71 moltype = length =
SEQUENCE: 71
000

SEQ ID NO: 72 moltype = length =
SEQUENCE: 72
000

SEQ ID NO: 73 moltype = length =
SEQUENCE: 73
000

SEQ ID NO: 74 moltype = length =
SEQUENCE: 74
000

SEQ ID NO: 75 moltype = length =
SEQUENCE: 75
000

SEQ ID NO: 76 moltype = length =
SEQUENCE: 76
000

SEQ ID NO: 77 moltype = length =

```
SEQUENCE: 77
000

SEQ ID NO: 78          moltype = AA  length = 30
FEATURE                Location/Qualifiers
REGION                 1..30
                       note = MISC_FEATURE - /note="This sequence may encompass
                        1-6 'Gly Gly Gly Gly Ser' repeating units"
REGION                 1..30
                       note = source = /note="Description of Artificial Sequence:
                        Synthetic polypeptide"
source                 1..30
                       mol_type = protein
                       organism = synthetic construct
SEQUENCE: 78
GGGGSGGGGS GGGGSGGGGS GGGGSGGGGS                                   30

SEQ ID NO: 79          moltype =   length =
SEQUENCE: 79
000

SEQ ID NO: 80          moltype =   length =
SEQUENCE: 80
000

SEQ ID NO: 81          moltype =   length =
SEQUENCE: 81
000

SEQ ID NO: 82          moltype =   length =
SEQUENCE: 82
000

SEQ ID NO: 83          moltype =   length =
SEQUENCE: 83
000

SEQ ID NO: 84          moltype =   length =
SEQUENCE: 84
000

SEQ ID NO: 85          moltype =   length =
SEQUENCE: 85
000

SEQ ID NO: 86          moltype =   length =
SEQUENCE: 86
000

SEQ ID NO: 87          moltype =   length =
SEQUENCE: 87
000

SEQ ID NO: 88          moltype =   length =
SEQUENCE: 88
000

SEQ ID NO: 89          moltype =   length =
SEQUENCE: 89
000

SEQ ID NO: 90          moltype =   length =
SEQUENCE: 90
000

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
```

000

SEQ ID NO: 95 moltype = length =
SEQUENCE: 95
000

SEQ ID NO: 96 moltype = length =
SEQUENCE: 96
000

SEQ ID NO: 97 moltype = length =
SEQUENCE: 97
000

SEQ ID NO: 98 moltype = length =
SEQUENCE: 98
000

SEQ ID NO: 99 moltype = length =
SEQUENCE: 99
000

SEQ ID NO: 100 moltype = length =
SEQUENCE: 100
000

SEQ ID NO: 101 moltype = length =
SEQUENCE: 101
000

SEQ ID NO: 102 moltype = length =
SEQUENCE: 102
000

SEQ ID NO: 103 moltype = length =
SEQUENCE: 103
000

SEQ ID NO: 104 moltype = length =
SEQUENCE: 104
000

SEQ ID NO: 105 moltype = length =
SEQUENCE: 105
000

SEQ ID NO: 106 moltype = length =
SEQUENCE: 106
000

SEQ ID NO: 107 moltype = length =
SEQUENCE: 107
000

SEQ ID NO: 108 moltype = length =
SEQUENCE: 108
000

SEQ ID NO: 109 moltype = length =
SEQUENCE: 109
000

SEQ ID NO: 110 moltype = length =
SEQUENCE: 110
000

SEQ ID NO: 111 moltype = length =
SEQUENCE: 111
000

SEQ ID NO: 112 moltype = length =
SEQUENCE: 112
000

SEQ ID NO: 113 moltype = length =
SEQUENCE: 113
000

SEQ ID NO: 114 moltype = length =

SEQUENCE: 114
000

SEQ ID NO: 115 moltype = length =
SEQUENCE: 115
000

SEQ ID NO: 116 moltype = length =
SEQUENCE: 116
000

SEQ ID NO: 117 moltype = length =
SEQUENCE: 117
000

SEQ ID NO: 118 moltype = length =
SEQUENCE: 118
000

SEQ ID NO: 119 moltype = length =
SEQUENCE: 119
000

SEQ ID NO: 120 moltype = length =
SEQUENCE: 120
000

SEQ ID NO: 121 moltype = length =
SEQUENCE: 121
000

SEQ ID NO: 122 moltype = length =
SEQUENCE: 122
000

SEQ ID NO: 123 moltype = length =
SEQUENCE: 123
000

SEQ ID NO: 124 moltype = length =
SEQUENCE: 124
000

SEQ ID NO: 125 moltype = length =
SEQUENCE: 125
000

SEQ ID NO: 126 moltype = length =
SEQUENCE: 126
000

SEQ ID NO: 127 moltype = length =
SEQUENCE: 127
000

SEQ ID NO: 128 moltype = length =
SEQUENCE: 128
000

SEQ ID NO: 129 moltype = length =
SEQUENCE: 129
000

SEQ ID NO: 130 moltype = length =
SEQUENCE: 130
000

SEQ ID NO: 131 moltype = length =
SEQUENCE: 131
000

SEQ ID NO: 132 moltype = length =
SEQUENCE: 132
000

SEQ ID NO: 133 moltype = length =
SEQUENCE: 133
000

-continued

SEQ ID NO: 134 moltype = length =
SEQUENCE: 134
000

SEQ ID NO: 135 moltype = length =
SEQUENCE: 135
000

SEQ ID NO: 136 moltype = length =
SEQUENCE: 136
000

SEQ ID NO: 137 moltype = length =
SEQUENCE: 137
000

SEQ ID NO: 138 moltype = length =
SEQUENCE: 138
000

SEQ ID NO: 139 moltype = length =
SEQUENCE: 139
000

SEQ ID NO: 140 moltype = length =
SEQUENCE: 140
000

SEQ ID NO: 141 moltype = length =
SEQUENCE: 141
000

SEQ ID NO: 142 moltype = length =
SEQUENCE: 142
000

SEQ ID NO: 143 moltype = length =
SEQUENCE: 143
000

SEQ ID NO: 144 moltype = length =
SEQUENCE: 144
000

SEQ ID NO: 145 moltype = length =
SEQUENCE: 145
000

SEQ ID NO: 146 moltype = length =
SEQUENCE: 146
000

SEQ ID NO: 147 moltype = length =
SEQUENCE: 147
000

SEQ ID NO: 148 moltype = length =
SEQUENCE: 148
000

SEQ ID NO: 149 moltype = length =
SEQUENCE: 149
000

SEQ ID NO: 150 moltype = length =
SEQUENCE: 150
000

SEQ ID NO: 151 moltype = length =
SEQUENCE: 151
000

SEQ ID NO: 152 moltype = length =
SEQUENCE: 152
000

SEQ ID NO: 153 moltype = length =
SEQUENCE: 153
000

SEQ ID NO: 154 moltype = length =
SEQUENCE: 154
000

SEQ ID NO: 155 moltype = length =
SEQUENCE: 155
000

SEQ ID NO: 156 moltype = length =
SEQUENCE: 156
000

SEQ ID NO: 157 moltype = length =
SEQUENCE: 157
000

SEQ ID NO: 158 moltype = length =
SEQUENCE: 158
000

SEQ ID NO: 159 moltype = length =
SEQUENCE: 159
000

SEQ ID NO: 160 moltype = length =
SEQUENCE: 160
000

SEQ ID NO: 161 moltype = length =
SEQUENCE: 161
000

SEQ ID NO: 162 moltype = length =
SEQUENCE: 162
000

SEQ ID NO: 163 moltype = length =
SEQUENCE: 163
000

SEQ ID NO: 164 moltype = length =
SEQUENCE: 164
000

SEQ ID NO: 165 moltype = length =
SEQUENCE: 165
000

SEQ ID NO: 166 moltype = length =
SEQUENCE: 166
000

SEQ ID NO: 167 moltype = length =
SEQUENCE: 167
000

SEQ ID NO: 168 moltype = length =
SEQUENCE: 168
000

SEQ ID NO: 169 moltype = length =
SEQUENCE: 169
000

SEQ ID NO: 170 moltype = length =
SEQUENCE: 170
000

SEQ ID NO: 171 moltype = length =
SEQUENCE: 171
000

SEQ ID NO: 172 moltype = length =
SEQUENCE: 172
000

SEQ ID NO: 173 moltype = length =
SEQUENCE: 173

-continued

000

SEQ ID NO: 174 moltype = length =
SEQUENCE: 174
000

SEQ ID NO: 175 moltype = length =
SEQUENCE: 175
000

SEQ ID NO: 176 moltype = length =
SEQUENCE: 176
000

SEQ ID NO: 177 moltype = length =
SEQUENCE: 177
000

SEQ ID NO: 178 moltype = length =
SEQUENCE: 178
000

SEQ ID NO: 179 moltype = length =
SEQUENCE: 179
000

SEQ ID NO: 180 moltype = length =
SEQUENCE: 180
000

SEQ ID NO: 181 moltype = length =
SEQUENCE: 181
000

SEQ ID NO: 182 moltype = length =
SEQUENCE: 182
000

SEQ ID NO: 183 moltype = length =
SEQUENCE: 183
000

SEQ ID NO: 184 moltype = length =
SEQUENCE: 184
000

SEQ ID NO: 185 moltype = length =
SEQUENCE: 185
000

SEQ ID NO: 186 moltype = length =
SEQUENCE: 186
000

SEQ ID NO: 187 moltype = length =
SEQUENCE: 187
000

SEQ ID NO: 188 moltype = length =
SEQUENCE: 188
000

SEQ ID NO: 189 moltype = length =
SEQUENCE: 189
000

SEQ ID NO: 190 moltype = length =
SEQUENCE: 190
000

SEQ ID NO: 191 moltype = length =
SEQUENCE: 191
000

SEQ ID NO: 192 moltype = length =
SEQUENCE: 192
000

SEQ ID NO: 193 moltype = length =

SEQUENCE: 193
000

SEQ ID NO: 194 moltype = length =
SEQUENCE: 194
000

SEQ ID NO: 195 moltype = length =
SEQUENCE: 195
000

SEQ ID NO: 196 moltype = length =
SEQUENCE: 196
000

SEQ ID NO: 197 moltype = length =
SEQUENCE: 197
000

SEQ ID NO: 198 moltype = length =
SEQUENCE: 198
000

SEQ ID NO: 199 moltype = length =
SEQUENCE: 199
000

SEQ ID NO: 200 moltype = length =
SEQUENCE: 200
000

SEQ ID NO: 201 moltype = length =
SEQUENCE: 201
000

SEQ ID NO: 202 moltype = length =
SEQUENCE: 202
000

SEQ ID NO: 203 moltype = length =
SEQUENCE: 203
000

SEQ ID NO: 204 moltype = length =
SEQUENCE: 204
000

SEQ ID NO: 205 moltype = length =
SEQUENCE: 205
000

SEQ ID NO: 206 moltype = length =
SEQUENCE: 206
000

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

-continued

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226
000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =
SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252

000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =

SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

SEQ ID NO: 307 moltype = length =
SEQUENCE: 307
000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =
SEQUENCE: 327
000

SEQ ID NO: 328 moltype = length =
SEQUENCE: 328
000

SEQ ID NO: 329 moltype = length =
SEQUENCE: 329
000

SEQ ID NO: 330 moltype = length =
SEQUENCE: 330
000

SEQ ID NO: 331 moltype = length =
SEQUENCE: 331

000

SEQ ID NO: 332 moltype = length =
SEQUENCE: 332
000

SEQ ID NO: 333 moltype = length =
SEQUENCE: 333
000

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345
000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =

SEQUENCE: 351
000

SEQ ID NO: 352 moltype = length =
SEQUENCE: 352
000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

-continued

SEQ ID NO: 371 moltype = length =
SEQUENCE: 371
000

SEQ ID NO: 372 moltype = length =
SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

SEQ ID NO: 396 moltype = length =
SEQUENCE: 396
000

SEQ ID NO: 397 moltype = length =
SEQUENCE: 397
000

SEQ ID NO: 398 moltype = length =
SEQUENCE: 398
000

SEQ ID NO: 399 moltype = length =
SEQUENCE: 399
000

SEQ ID NO: 400 moltype = DNA length = 1184
FEATURE Location/Qualifiers
misc_feature 1..1184
note = source = /note="Description of Artificial Sequence: Synthetic polynucleotide"
source 1..1184
mol_type = other DNA
organism = synthetic construct
SEQUENCE: 400
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacctggctg cagtacgtga ttcttgatcc cgagcttcgg gttggaagtg 360
ggtgggagag ttcgaggcct tgcgcttaag gagccccttc gcctcgtgct tgagttgagg 420
cctggcctgg gcgctggggc cgccgcgtgc gaatctggtg gcaccttcgc gcctgtctcg 480
ctgctttcga taagtctcta gccatttaaa atttttgatg acctgctgcg acgctttttt 540
tctggcaaga tagtcttgta aatgcgggcc aagatctgca cactggtatt tcggtttttg 600
gggccgcggg cggcgacggg gcccgtgcgt cccagcgcac atgttcggcg aggcggggcc 660
tgcgagcgcg gccaccgaga atcggacggg ggtagtctca agctggccgg cctgctctgg 720
tgcctggcct cgcgccgccg tgtatcgccc cgccctgggc ggcaaggctg gcccggtcgg 780
caccagttgc gtgagcggaa agatggccgc ttcccggccc tgctgcaggg agctcaaaat 840
ggaggacgcg gcgctcggga gagcgggcgg gtgagtcacc cacacaaagg aaaagggcct 900
ttccgtcctc agccgtcgct tcatgtgact ccacggagta ccgggcgccg tccaggcacc 960
tcgattagtt ctcgagcttt tggagtacgt cgtctttagg ttggggggag gggttttatg 1020
cgatggagtt tccccacact gagtgggtgg agactgaagt taggccagct tggcacttga 1080
tgtaattctc cttggaattt gccctttttg agtttggatc ttggttcatt ctcaagcctc 1140
agacagtggt tcaaagtttt tttcttccat ttcaggtgtc gtga 1184

SEQ ID NO: 401 moltype = AA length = 21
FEATURE Location/Qualifiers
REGION 1..21
note = source = /note="Description of Artificial Sequence: Synthetic peptide"
source 1..21
mol_type = protein
organism = synthetic construct
SEQUENCE: 401
MALPVTALLL PLALLLHAAR P 21

SEQ ID NO: 402 moltype = DNA length = 63

-continued

```
FEATURE                Location/Qualifiers
misc_feature           1..63
                       note = source = /note="Description of Artificial Sequence:
                        Synthetic oligonucleotide"
source                 1..63
                       mol_type = other DNA
                       organism = synthetic construct
SEQUENCE: 402
atggccctgc ctgtgacagc cctgctgctg cctctggctc tgctgctgca tgccgctaga  60
ccc                                                                 63

SEQ ID NO: 403         moltype = AA  length = 45
FEATURE                Location/Qualifiers
REGION                 1..45
                       note = source = /note="Description of Artificial Sequence:
                        Synthetic polypeptide"
source                 1..45
                       mol_type = protein
                       organism = synthetic construct
SEQUENCE: 403
TTTPAPRPPT PAPTIASQPL SLRPEACRPA AGGAVHTRGL DFACD                   45

SEQ ID NO: 404         moltype = DNA  length = 135
FEATURE                Location/Qualifiers
misc_feature           1..135
                       note = source = /note="Description of Artificial Sequence:
                        Synthetic polynucleotide"
source                 1..135
                       mol_type = other DNA
                       organism = synthetic construct
SEQUENCE: 404
accacgacgc cagcgccgcg accaccaaca ccggcgccca ccatcgcgtc gcagcccctg  60
tccctgcgcc cagaggcgtg ccggccagcg gcgggggggcg cagtgcacac gagggggctg  120
gacttcgcct gtgat                                                    135

SEQ ID NO: 405         moltype = AA  length = 230
FEATURE                Location/Qualifiers
REGION                 1..230
                       note = source = /note="Description of Artificial Sequence:
                        Synthetic polypeptide"
source                 1..230
                       mol_type = protein
                       organism = synthetic construct
SEQUENCE: 405
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKM              230

SEQ ID NO: 406         moltype = DNA  length = 690
FEATURE                Location/Qualifiers
misc_feature           1..690
                       note = source = /note="Description of Artificial Sequence:
                        Synthetic polynucleotide"
source                 1..690
                       mol_type = other DNA
                       organism = synthetic construct
SEQUENCE: 406
gagagcaagt acggccctcc ctgccccccct tgccctgccc ccgagttcct gggcggaccc  60
agcgtgttcc tgttcccccc caagcccaag gacaccctga tgatcagccg gacccccgag  120
gtgacctgtg tggtggtgga cgtgtcccag gaggaccccg aggtccagtt caactggtac  180
gtggacggcg tggaggtgca caacgccaag accaagcccc gggaggagca gttcaatagc  240
acctaccggg tggtgtccgt gctgaccgtg ctgcaccagg actggctgaa cggcaaggaa  300
tacaagtgta aggtgtccaa caagggcctg cccagcagca tcgagaaaac catcagcaag  360
gccaagggcc agcctcggga gccccaggtg tacaccctgc cccctagcca agaggagatg  420
accaagaacc aggtgtccct gacctgcctg gtgaagggct tctaccccag cgacatcgcc  480
gtggagtggg agagcaacgg ccagcccgag aacaactaca agaccacccc ccctgtgctg  540
gacagcgacg gcagcttctt cctgtacagc cggctgaccg tggacaagag ccggtggcag  600
gagggcaacg tctttagctg ctccgtgatg cacgaggccc tgcacaacca ctacacccag  660
aagagcctga gcctgtccct gggcaagatg                                    690

SEQ ID NO: 407         moltype = AA  length = 282
FEATURE                Location/Qualifiers
REGION                 1..282
                       note = source = /note="Description of Artificial Sequence:
                        Synthetic polypeptide"
source                 1..282
                       mol_type = protein
                       organism = synthetic construct
```

```
SEQUENCE: 407
RWPESPKAQA SSVPTAQPQA EGSLAKATTA PATTRNTGRG GEEKKKEKEK EEQEERETKT  60
PECPSHTQPL GVYLLTPAVQ DLWLRDKATF TCFVVGSDLK DAHLTWEVAG KVPTGGVEEG  120
LLERHSNGSQ SQHSRLTLPR SLWNAGTSVT CTLNHPSLPP QRLMALREPA AQAPVKLSLN  180
LLASSDPPEA ASWLLCEVSG FSPPNILLMW LEDQREVNTS GFAPARPPPQ PGSTTFWAWS  240
VLRVPAPPSP QPATYTCVVS HEDSRTLLNA SRSLEVSYVT DH                    282

SEQ ID NO: 408         moltype = DNA  length = 847
FEATURE                Location/Qualifiers
misc_feature           1..847
                       note = source = /note="Description of Artificial Sequence:
                        Synthetic polynucleotide"
source                 1..847
                       mol_type = other DNA
                       organism = synthetic construct
SEQUENCE: 408
aggtggcccg aaagtcccaa ggcccaggca tctagtgttc ctactgcaca gccccaggca  60
gaaggcagcc tagccaaagc tactactgca cctgccacta cgcgcaatac tggccgtggc  120
ggggaggaga agaaaaagga gaaagagaaa gaagaacagg aagagaggga gaccaagacc  180
cctgaatgtc catcccatac ccagccgctg ggcgtctatc tcttgactcc cgcagtacag  240
gacttgtggc ttagagataa ggccaccttt acatgtttcg tcgtgggctc tgacctgaag  300
gatgcccatt tgacttggga ggttgccgga aaggtaccca caggggggt tgaggaaggg  360
ttgctggagc gccattccaa tggctctcag agccagcact caagactcac ccttccgaga  420
tccctgtgga acgccgggac ctctgtcaca tgtactctaa atcatcctag cctgcccca  480
cagcgtctga tggcccttag agagccagcc gcccaggcac cagttaagct tagcctgaat  540
ctgctcgcca gtagtgatcc cccagaggcc gccagctggc tcttatgcga agtgtccggc  600
tttagcccgc ccaacatctt gctcatgtgg ctggaggacc agcgagaagt gaacaccagc  660
ggcttcgctc cagcccggcc cccaccccag ccgggttcta ccacattctg ggcctggagt  720
gtcttaaggg tcccagcacc acctagcccc cagccagcca catacacctg tgttgtgtcc  780
catgaagata gcaggaccct gctaaatgct tctaggagtc tggaggtttc ctacgtgact  840
gaccatt                                                            847

SEQ ID NO: 409         moltype =   length =
SEQUENCE: 409
000

SEQ ID NO: 410         moltype =   length =
SEQUENCE: 410
000

SEQ ID NO: 411         moltype =   length =
SEQUENCE: 411
000

SEQ ID NO: 412         moltype =   length =
SEQUENCE: 412
000

SEQ ID NO: 413         moltype =   length =
SEQUENCE: 413
000

SEQ ID NO: 414         moltype =   length =
SEQUENCE: 414
000

SEQ ID NO: 415         moltype =   length =
SEQUENCE: 415
000

SEQ ID NO: 416         moltype =   length =
SEQUENCE: 416
000

SEQ ID NO: 417         moltype =   length =
SEQUENCE: 417
000

SEQ ID NO: 418         moltype =   length =
SEQUENCE: 418
000

SEQ ID NO: 419         moltype =   length =
SEQUENCE: 419
000

SEQ ID NO: 420         moltype =   length =
SEQUENCE: 420
000
```

SEQ ID NO: 421 moltype = length =
SEQUENCE: 421
000

SEQ ID NO: 422 moltype = length =
SEQUENCE: 422
000

SEQ ID NO: 423 moltype = length =
SEQUENCE: 423
000

SEQ ID NO: 424 moltype = length =
SEQUENCE: 424
000

SEQ ID NO: 425 moltype = length =
SEQUENCE: 425
000

SEQ ID NO: 426 moltype = length =
SEQUENCE: 426
000

SEQ ID NO: 427 moltype = length =
SEQUENCE: 427
000

SEQ ID NO: 428 moltype = length =
SEQUENCE: 428
000

SEQ ID NO: 429 moltype = length =
SEQUENCE: 429
000

SEQ ID NO: 430 moltype = length =
SEQUENCE: 430
000

SEQ ID NO: 431 moltype = length =
SEQUENCE: 431
000

SEQ ID NO: 432 moltype = length =
SEQUENCE: 432
000

SEQ ID NO: 433 moltype = length =
SEQUENCE: 433
000

SEQ ID NO: 434 moltype = length =
SEQUENCE: 434
000

SEQ ID NO: 435 moltype = length =
SEQUENCE: 435
000

SEQ ID NO: 436 moltype = length =
SEQUENCE: 436
000

SEQ ID NO: 437 moltype = length =
SEQUENCE: 437
000

SEQ ID NO: 438 moltype = length =
SEQUENCE: 438
000

SEQ ID NO: 439 moltype = length =
SEQUENCE: 439
000

SEQ ID NO: 440 moltype = length =
SEQUENCE: 440

000

SEQ ID NO: 441 moltype = length =
SEQUENCE: 441
000

SEQ ID NO: 442 moltype = length =
SEQUENCE: 442
000

SEQ ID NO: 443 moltype = length =
SEQUENCE: 443
000

SEQ ID NO: 444 moltype = length =
SEQUENCE: 444
000

SEQ ID NO: 445 moltype = length =
SEQUENCE: 445
000

SEQ ID NO: 446 moltype = length =
SEQUENCE: 446
000

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = length =
SEQUENCE: 450
000

SEQ ID NO: 451 moltype = length =
SEQUENCE: 451
000

SEQ ID NO: 452 moltype = length =
SEQUENCE: 452
000

SEQ ID NO: 453 moltype = length =
SEQUENCE: 453
000

SEQ ID NO: 454 moltype = length =
SEQUENCE: 454
000

SEQ ID NO: 455 moltype = length =
SEQUENCE: 455
000

SEQ ID NO: 456 moltype = length =
SEQUENCE: 456
000

SEQ ID NO: 457 moltype = length =
SEQUENCE: 457
000

SEQ ID NO: 458 moltype = length =
SEQUENCE: 458
000

SEQ ID NO: 459 moltype = length =
SEQUENCE: 459
000

SEQ ID NO: 460 moltype = length =

SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =
SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

-continued

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

```
SEQ ID NO: 500         moltype =   length =
SEQUENCE: 500
000

SEQ ID NO: 501         moltype =   length =
SEQUENCE: 501
000

SEQ ID NO: 502         moltype =   length =
SEQUENCE: 502
000

SEQ ID NO: 503         moltype =   length =
SEQUENCE: 503
000

SEQ ID NO: 504         moltype =   length =
SEQUENCE: 504
000

SEQ ID NO: 505         moltype = AA  length = 41
FEATURE                Location/Qualifiers
REGION                 1..41
                       note = source = /note="Description of Artificial Sequence:
                        Synthetic polypeptide"
source                 1..41
                       mol_type = protein
                       organism = synthetic construct
SEQUENCE: 505
RSKRSRLLHS DYMNMTPRRP GPTRKHYQPY APPRDFAAYR S                      41

SEQ ID NO: 506         moltype =   length =
SEQUENCE: 506
000

SEQ ID NO: 507         moltype =   length =
SEQUENCE: 507
000

SEQ ID NO: 508         moltype =   length =
SEQUENCE: 508
000

SEQ ID NO: 509         moltype =   length =
SEQUENCE: 509
000

SEQ ID NO: 510         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 510
GGGGSGGGGS                                                         10

SEQ ID NO: 511         moltype = DNA  length = 30
FEATURE                Location/Qualifiers
misc_feature           1..30
                       note = source = /note="Description of Artificial Sequence:
                        Synthetic oligonucleotide"
source                 1..30
                       mol_type = other DNA
                       organism = synthetic construct
SEQUENCE: 511
ggtggcggag gttctggagg tggaggttcc                                   30

SEQ ID NO: 512         moltype = AA  length = 230
FEATURE                Location/Qualifiers
REGION                 1..230
                       note = source = /note="Description of Artificial Sequence:
                        Synthetic polypeptide"
source                 1..230
                       mol_type = protein
                       organism = synthetic construct
SEQUENCE: 512
```

```
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKM             230

SEQ ID NO: 513         moltype = DNA  length = 690
FEATURE                Location/Qualifiers
misc_feature           1..690
                       note = source = /note="Description of Artificial Sequence:
                        Synthetic polynucleotide"
source                 1..690
                       mol_type = other DNA
                       organism = synthetic construct
SEQUENCE: 513
gagagcaagt acggccctcc ctgccccccct tgccctgccc ccgagttcct gggcggaccc  60
agcgtgttcc tgttccccccc caagcccaag gacaccctga tgatcagccg gacccccgag  120
gtgacctgtg tggtggtgga cgtgtcccag gaggaccccg aggtccagtt caactggtac  180
gtggacggcg tggaggtgca caacgccaag accaagcccc gggaggagca gttcaatagc  240
acctaccggg tggtgtccgt gctgaccgtg ctgcaccagg actggctgaa cggcaaggaa  300
tacaagtgta aggtgtccaa caagggcctg cccagcagca tcgagaaaac catcagcaag  360
gccaagggcc agcctcggga gccccaggtg tacaccctgc cccctagcca agaggagatg  420
accaagaacc aggtgtccct gacctgcctg gtgaagggct tctaccccag cgacatcgcc  480
gtggagtggg agagcaacgg ccagcccgag aacaactaca agaccacccc ccctgtgctg  540
gacagcgacg gcagcttctt cctgtacagc cggctgaccg tggacaagag ccggtggcag  600
gagggcaacg tctttagctg ctccgtgatg cacgaggccc tgcacaacca ctacacccag  660
aagagcctga gcctgtccct gggcaagatg                                   690

SEQ ID NO: 514         moltype = AA  length = 282
FEATURE                Location/Qualifiers
REGION                 1..282
                       note = source = /note="Description of Artificial Sequence:
                        Synthetic polypeptide"
source                 1..282
                       mol_type = protein
                       organism = synthetic construct
SEQUENCE: 514
RWPESPKAQA SSVPTAQPQA EGSLAKATTA PATTRNTGRG GEEKKKEKEK EEQEERETKT  60
PECPSHTQPL GVYLLTPAVQ DLWLRDKATF TCFVVGSDLK DAHLTWEVAG KVPTGGVEEG  120
LLERHSNGSQ SQHSRLTLPR SLWNAGTSVT CTLNHPSLPP QRLMALREPA AQAPVKLSLN  180
LLASSDPPEA ASWLLCEVSG FSPPNILLMW LEDQREVNTS GFAPARPPPQ PGSTTFWAWS  240
VLRVPAPPSP QPATYTCVVS HEDSRTLLNA SRSLEVSYVT DH                     282

SEQ ID NO: 515         moltype = DNA  length = 847
FEATURE                Location/Qualifiers
misc_feature           1..847
                       note = source = /note="Description of Artificial Sequence:
                        Synthetic polynucleotide"
source                 1..847
                       mol_type = other DNA
                       organism = synthetic construct
SEQUENCE: 515
aggtggcccg aaagtcccaa ggcccaggca tctagtgttc ctactgcaca gccccaggca  60
gaaggcagcc tagccaaagc tactactgca cctgccacta cgcgcaatac tggccgtggc  120
ggggaggaga agaaaaagga gaaagagaaa gaagaacagg aagagaggga gaccaagacc  180
cctgaatgtc catcccatac ccagccgctg ggcgtctatc tcttgactcc cgcagtacag  240
gacttgtggc ttagagataa ggccaccttt acatgtttcg tcgtgggctc tgacctgaag  300
gatgcccatt tgacttggga ggttgccgga aaggtaccca caggggggggt tgaggaaggg  360
ttgctggagc gccattccaa tggctctcag agccagcact caagactcac ccttccgaga  420
tccctgtgga acgccgggac ctctgtcaca tgtactctaa atcatcctag cctgccccca  480
cagcgtctga tggcccttag agagccagcc gcccaggcac cagttaagct tagcctgaat  540
ctgctcgcca gtagtgatcc cccagaggcc gccagctggc tcttatgcga agtgtccggc  600
tttagcccgc ccaacatctt gctcatgtgg ctggaggacc agcgagaagt gaacaccagc  660
ggcttcgctc cagcccggcc cccaccccag ccgggttcta ccacattctg ggcctggagt  720
gtcttaaggg tcccagcacc acctagcccc cagccagcca catacacctg tgttgtgtcc  780
catgaagata gcaggaccct gctaaatgct tctaggagtc tggaggtttc ctacgtgact  840
gaccatt                                                            847

SEQ ID NO: 516         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 516
GGGGSGGGGS                                                         10

SEQ ID NO: 517         moltype = DNA  length = 30
```

```
FEATURE                 Location/Qualifiers
misc_feature            1..30
                        note = source = /note="Description of Artificial Sequence:
                         Synthetic oligonucleotide"
source                  1..30
                        mol_type = other DNA
                        organism = synthetic construct
SEQUENCE: 517
ggtggcggag gttctggagg tggaggttcc                                   30

SEQ ID NO: 518          moltype = DNA  length = 63
FEATURE                 Location/Qualifiers
misc_feature            1..63
                        note = source = /note="Description of Artificial Sequence:
                         Synthetic oligonucleotide"
source                  1..63
                        mol_type = other DNA
                        organism = synthetic construct
SEQUENCE: 518
atggccctcc ctgtcaccgc cctgctgctt ccgctggctc ttctgctcca cgccgctcgg  60
ccc                                                                63

SEQ ID NO: 519          moltype = DNA  length = 63
FEATURE                 Location/Qualifiers
misc_feature            1..63
                        note = source = /note="Description of Artificial Sequence:
                         Synthetic oligonucleotide"
source                  1..63
                        mol_type = other DNA
                        organism = synthetic construct
SEQUENCE: 519
atggccttac cagtgaccgc cttgctcctg ccgctggcct tgctgctcca cgccgccagg  60
ccg                                                                63

SEQ ID NO: 520          moltype = DNA  length = 72
FEATURE                 Location/Qualifiers
misc_feature            1..72
                        note = source = /note="Description of Artificial Sequence:
                         Synthetic oligonucleotide"
source                  1..72
                        mol_type = other DNA
                        organism = synthetic construct
SEQUENCE: 520
atctacattt gggcccctct ggctggtact tgcggggtcc tgctgctttc actcgtgatc  60
actctttact gt                                                      72

SEQ ID NO: 521          moltype = DNA  length = 126
FEATURE                 Location/Qualifiers
misc_feature            1..126
                        note = source = /note="Description of Artificial Sequence:
                         Synthetic polynucleotide"
source                  1..126
                        mol_type = other DNA
                        organism = synthetic construct
SEQUENCE: 521
aagcgcggtc ggaagaagct gctgtacatc tttaagcaac ccttcatgag gcctgtgcag  60
actactcaag aggaggacgg ctgttcatgc cggttcccag aggaggagga aggcggctgc  120
gaactg                                                             126

SEQ ID NO: 522          moltype = DNA  length = 336
FEATURE                 Location/Qualifiers
misc_feature            1..336
                        note = source = /note="Description of Artificial Sequence:
                         Synthetic polynucleotide"
source                  1..336
                        mol_type = other DNA
                        organism = synthetic construct
SEQUENCE: 522
cgcgtgaaat tcagccgcag cgcagatgct ccagcctaca agcaggggca gaaccagctc  60
tacaacgaac tcaatcttgg tcggagagag gagtacgacg tgctggacaa gcggagagga  120
cgggacccag aaatgggcgg gaagccgcgc agaaagaatc cccaagaggg cctgtacaac  180
gagctccaaa aggataagat ggcagaagcc tatagcgaga ttggtatgaa aggggaacgc  240
agaagaggca aaggccacga cggactgtac cagggactca gcaccgccac caaggacacc  300
tatgacgctc ttcacatgca ggccctgccg cctcgg                            336

SEQ ID NO: 523          moltype =   length =
SEQUENCE: 523
000
```

-continued

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563

000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

SEQ ID NO: 571 moltype = length =
SEQUENCE: 571
000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =

```
SEQUENCE: 583
000

SEQ ID NO: 584          moltype =   length =
SEQUENCE: 584
000

SEQ ID NO: 585          moltype =   length =
SEQUENCE: 585
000

SEQ ID NO: 586          moltype =   length =
SEQUENCE: 586
000

SEQ ID NO: 587          moltype =   length =
SEQUENCE: 587
000

SEQ ID NO: 588          moltype =   length =
SEQUENCE: 588
000

SEQ ID NO: 589          moltype =   length =
SEQUENCE: 589
000

SEQ ID NO: 590          moltype =   length =
SEQUENCE: 590
000

SEQ ID NO: 591          moltype =   length =
SEQUENCE: 591
000

SEQ ID NO: 592          moltype =   length =
SEQUENCE: 592
000

SEQ ID NO: 593          moltype =   length =
SEQUENCE: 593
000

SEQ ID NO: 594          moltype =   length =
SEQUENCE: 594
000

SEQ ID NO: 595          moltype =   length =
SEQUENCE: 595
000

SEQ ID NO: 596          moltype =   length =
SEQUENCE: 596
000

SEQ ID NO: 597          moltype =   length =
SEQUENCE: 597
000

SEQ ID NO: 598          moltype =   length =
SEQUENCE: 598
000

SEQ ID NO: 599          moltype =   length =
SEQUENCE: 599
000

SEQ ID NO: 600          moltype = DNA  length = 123
FEATURE                 Location/Qualifiers
misc_feature            1..123
                        note = source = /note="Description of Artificial Sequence:
                         Synthetic polynucleotide"
source                  1..123
                        mol_type = other DNA
                        organism = synthetic construct
SEQUENCE: 600
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123
```

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609
000

SEQ ID NO: 610 moltype = length =
SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =
SEQUENCE: 616
000

SEQ ID NO: 617 moltype = length =
SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620

000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =

SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

-continued

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

-continued

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688
000

SEQ ID NO: 689 moltype = length =
SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =
SEQUENCE: 695
000

SEQ ID NO: 696 moltype = length =
SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699

000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =
SEQUENCE: 708
000

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

SEQ ID NO: 715 moltype = length =
SEQUENCE: 715
000

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =

SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755
000

SEQ ID NO: 756 moltype = length =
SEQUENCE: 756
000

SEQ ID NO: 757 moltype = length =
SEQUENCE: 757
000

SEQ ID NO: 758 moltype = length =
SEQUENCE: 758
000

SEQ ID NO: 759 moltype = length =
SEQUENCE: 759
000

SEQ ID NO: 760 moltype = length =
SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767
000

SEQ ID NO: 768 moltype = length =
SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =
SEQUENCE: 775
000

SEQ ID NO: 776 moltype = length =
SEQUENCE: 776
000

SEQ ID NO: 777 moltype = length =
SEQUENCE: 777
000

SEQ ID NO: 778 moltype = length =
SEQUENCE: 778

000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =
SEQUENCE: 787
000

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

SEQ ID NO: 797 moltype = length =
SEQUENCE: 797
000

SEQ ID NO: 798 moltype = length =

SEQUENCE: 798
000

SEQ ID NO: 799 moltype = length =
SEQUENCE: 799
000

SEQ ID NO: 800 moltype = length =
SEQUENCE: 800
000

SEQ ID NO: 801 moltype = length =
SEQUENCE: 801
000

SEQ ID NO: 802 moltype = length =
SEQUENCE: 802
000

SEQ ID NO: 803 moltype = length =
SEQUENCE: 803
000

SEQ ID NO: 804 moltype = length =
SEQUENCE: 804
000

SEQ ID NO: 805 moltype = length =
SEQUENCE: 805
000

SEQ ID NO: 806 moltype = length =
SEQUENCE: 806
000

SEQ ID NO: 807 moltype = length =
SEQUENCE: 807
000

SEQ ID NO: 808 moltype = length =
SEQUENCE: 808
000

SEQ ID NO: 809 moltype = length =
SEQUENCE: 809
000

SEQ ID NO: 810 moltype = length =
SEQUENCE: 810
000

SEQ ID NO: 811 moltype = length =
SEQUENCE: 811
000

SEQ ID NO: 812 moltype = length =
SEQUENCE: 812
000

SEQ ID NO: 813 moltype = length =
SEQUENCE: 813
000

SEQ ID NO: 814 moltype = length =
SEQUENCE: 814
000

SEQ ID NO: 815 moltype = length =
SEQUENCE: 815
000

SEQ ID NO: 816 moltype = length =
SEQUENCE: 816
000

SEQ ID NO: 817 moltype = length =
SEQUENCE: 817
000

-continued

SEQ ID NO: 818 moltype = length =
SEQUENCE: 818
000

SEQ ID NO: 819 moltype = length =
SEQUENCE: 819
000

SEQ ID NO: 820 moltype = length =
SEQUENCE: 820
000

SEQ ID NO: 821 moltype = length =
SEQUENCE: 821
000

SEQ ID NO: 822 moltype = length =
SEQUENCE: 822
000

SEQ ID NO: 823 moltype = length =
SEQUENCE: 823
000

SEQ ID NO: 824 moltype = length =
SEQUENCE: 824
000

SEQ ID NO: 825 moltype = length =
SEQUENCE: 825
000

SEQ ID NO: 826 moltype = length =
SEQUENCE: 826
000

SEQ ID NO: 827 moltype = length =
SEQUENCE: 827
000

SEQ ID NO: 828 moltype = length =
SEQUENCE: 828
000

SEQ ID NO: 829 moltype = length =
SEQUENCE: 829
000

SEQ ID NO: 830 moltype = length =
SEQUENCE: 830
000

SEQ ID NO: 831 moltype = length =
SEQUENCE: 831
000

SEQ ID NO: 832 moltype = length =
SEQUENCE: 832
000

SEQ ID NO: 833 moltype = length =
SEQUENCE: 833
000

SEQ ID NO: 834 moltype = length =
SEQUENCE: 834
000

SEQ ID NO: 835 moltype = length =
SEQUENCE: 835
000

SEQ ID NO: 836 moltype = length =
SEQUENCE: 836
000

SEQ ID NO: 837 moltype = length =
SEQUENCE: 837
000

SEQ ID NO: 838 moltype = length =
SEQUENCE: 838
000

SEQ ID NO: 839 moltype = length =
SEQUENCE: 839
000

SEQ ID NO: 840 moltype = length =
SEQUENCE: 840
000

SEQ ID NO: 841 moltype = length =
SEQUENCE: 841
000

SEQ ID NO: 842 moltype = length =
SEQUENCE: 842
000

SEQ ID NO: 843 moltype = length =
SEQUENCE: 843
000

SEQ ID NO: 844 moltype = length =
SEQUENCE: 844
000

SEQ ID NO: 845 moltype = length =
SEQUENCE: 845
000

SEQ ID NO: 846 moltype = length =
SEQUENCE: 846
000

SEQ ID NO: 847 moltype = length =
SEQUENCE: 847
000

SEQ ID NO: 848 moltype = length =
SEQUENCE: 848
000

SEQ ID NO: 849 moltype = length =
SEQUENCE: 849
000

SEQ ID NO: 850 moltype = length =
SEQUENCE: 850
000

SEQ ID NO: 851 moltype = length =
SEQUENCE: 851
000

SEQ ID NO: 852 moltype = length =
SEQUENCE: 852
000

SEQ ID NO: 853 moltype = length =
SEQUENCE: 853
000

SEQ ID NO: 854 moltype = length =
SEQUENCE: 854
000

SEQ ID NO: 855 moltype = length =
SEQUENCE: 855
000

SEQ ID NO: 856 moltype = length =
SEQUENCE: 856
000

SEQ ID NO: 857 moltype = length =
SEQUENCE: 857

000

SEQ ID NO: 858 moltype = length =
SEQUENCE: 858
000

SEQ ID NO: 859 moltype = length =
SEQUENCE: 859
000

SEQ ID NO: 860 moltype = length =
SEQUENCE: 860
000

SEQ ID NO: 861 moltype = length =
SEQUENCE: 861
000

SEQ ID NO: 862 moltype = length =
SEQUENCE: 862
000

SEQ ID NO: 863 moltype = length =
SEQUENCE: 863
000

SEQ ID NO: 864 moltype = length =
SEQUENCE: 864
000

SEQ ID NO: 865 moltype = length =
SEQUENCE: 865
000

SEQ ID NO: 866 moltype = length =
SEQUENCE: 866
000

SEQ ID NO: 867 moltype = length =
SEQUENCE: 867
000

SEQ ID NO: 868 moltype = length =
SEQUENCE: 868
000

SEQ ID NO: 869 moltype = length =
SEQUENCE: 869
000

SEQ ID NO: 870 moltype = length =
SEQUENCE: 870
000

SEQ ID NO: 871 moltype = length =
SEQUENCE: 871
000

SEQ ID NO: 872 moltype = length =
SEQUENCE: 872
000

SEQ ID NO: 873 moltype = length =
SEQUENCE: 873
000

SEQ ID NO: 874 moltype = length =
SEQUENCE: 874
000

SEQ ID NO: 875 moltype = length =
SEQUENCE: 875
000

SEQ ID NO: 876 moltype = length =
SEQUENCE: 876
000

SEQ ID NO: 877 moltype = length =

```
SEQUENCE: 877
000

SEQ ID NO: 878          moltype =   length =
SEQUENCE: 878
000

SEQ ID NO: 879          moltype =   length =
SEQUENCE: 879
000

SEQ ID NO: 880          moltype =   length =
SEQUENCE: 880
000

SEQ ID NO: 881          moltype =   length =
SEQUENCE: 881
000

SEQ ID NO: 882          moltype =   length =
SEQUENCE: 882
000

SEQ ID NO: 883          moltype =   length =
SEQUENCE: 883
000

SEQ ID NO: 884          moltype =   length =
SEQUENCE: 884
000

SEQ ID NO: 885          moltype =   length =
SEQUENCE: 885
000

SEQ ID NO: 886          moltype =   length =
SEQUENCE: 886
000

SEQ ID NO: 887          moltype =   length =
SEQUENCE: 887
000

SEQ ID NO: 888          moltype =   length =
SEQUENCE: 888
000

SEQ ID NO: 889          moltype =   length =
SEQUENCE: 889
000

SEQ ID NO: 890          moltype =   length =
SEQUENCE: 890
000

SEQ ID NO: 891          moltype = AA  length = 486
FEATURE                 Location/Qualifiers
REGION                  1..486
                        note = source = /note="Description of Artificial Sequence:
                         Synthetic polypeptide"
source                  1..486
                        mol_type = protein
                        organism = synthetic construct
SEQUENCE: 891
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                           486

SEQ ID NO: 892          moltype = AA  length = 465
FEATURE                 Location/Qualifiers
REGION                  1..465
                        note = source = /note="Description of Artificial Sequence:
                         Synthetic polypeptide"
```

```
source                1..465
                      mol_type = protein
                      organism = synthetic construct
SEQUENCE: 892
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSEVKLQESG PGLVAPSQSL SVTCTVSGVS LPDYGVSWIR QPPRKGLEWL GVIWGSETTY  180
YNSALKSRLT IIKDNSKSQV FLKMNSLQTD DTAIYYCAKH YYYGGSYAMD YWGQGTSVTV  240
SSTTTPAPRP PTPAPTIASQ PLSLRPEACR PAAGGAVHTR GLDFACDIYI WAPLAGTCGV  300
LLLSLVITLY CKRGRKKLLY IFKQPFMRPV QTTQEEDGCS CRFPEEEEGG CELRVKFSRS  360
ADAPAYKQGQ NQLYNELNLG RREEYDVLDK RRGRDPEMGG KPRRKNPQEG LYNELQKDKM  420
AEAYSEIGMK GERRRGKGHD GLYQGLSTAT KDTYDALHMQ ALPPR                 465

SEQ ID NO: 893        moltype = AA  length = 242
FEATURE               Location/Qualifiers
REGION                1..242
                      note = source = /note="Description of Artificial Sequence:
                       Synthetic polypeptide"
source                1..242
                      mol_type = protein
                      organism = synthetic construct
SEQUENCE: 893
EIVMTQSPAT LSLSPGERAT LSCRASQDIS KYLNWYQQKP GQAPRLLIYH TSRLHSGIPA  60
RFSGSGSGTD YTLTISSLQP EDFAVYFCQQ GNTLPYTFGQ GTKLEIKGGG GSGGGGSGGG  120
GSQVQLQESG PGLVKPSETL SLTCTVSGVS LPDYGVSWIR QPPGKGLEWI GVIWGSETTY  180
YSSSLKSRVT ISKDNSKNQV SLKLSSVTAA DTAVYYCAKH YYYGGSYAMD YWGQGTLVTV  240
SS                                                                242

SEQ ID NO: 894        moltype = DNA  length = 813
FEATURE               Location/Qualifiers
misc_feature          1..813
                      note = source = /note="Description of Artificial Sequence:
                       Synthetic polynucleotide"
source                1..813
                      mol_type = other DNA
                      organism = synthetic construct
SEQUENCE: 894
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcc aggtccaact ccaagaaagc ggaccgggtc ttgtgaagcc atcagaaact  480
ctttcactga cttgtactgt gagcggagtg tctctccccg attacggggt gtcttggatc  540
agacagccac cggggaaggg tctggaatgg attggagtga tttggggctc tgagactact  600
tactactctt catccctcaa gtcacgcgtc accatctcaa aggacaactc taagaatcag  660
gtgtcactga aactgtcatc tgtgaccgca gccgacaccg ccgtgtacta ttgcgctaag  720
cattactatt atggcgggag ctacgcaatg gattactggg gacagggtac tctggtcacc  780
gtgtccagcc accaccatca tcaccatcac cat                              813

SEQ ID NO: 895        moltype = AA  length = 271
FEATURE               Location/Qualifiers
REGION                1..271
                      note = source = /note="Description of Artificial Sequence:
                       Synthetic polypeptide"
source                1..271
                      mol_type = protein
                      organism = synthetic construct
SEQUENCE: 895
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSQVQLQES GPGLVKPSET LSLTCTVSGV SLPDYGVSWI  180
RQPPGKGLEW IGVIWGSETT YYSSSLKSRV TISKDNSKNQ VSLKLSSVTA ADTAVYYCAK  240
HYYYGGSYAM DYWGQGTLVT VSSHHHHHHH H                                271

SEQ ID NO: 896        moltype = DNA  length = 1458
FEATURE               Location/Qualifiers
misc_feature          1..1458
                      note = source = /note="Description of Artificial Sequence:
                       Synthetic polynucleotide"
source                1..1458
                      mol_type = other DNA
                      organism = synthetic construct
SEQUENCE: 896
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
```

```
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcc aggtccaact ccaagaaagc ggaccgggtc ttgtgaagcc atcagaaact  480
ctttcactga cttgtactgt gagcggagtg tctctccccg attacggggt gtcttggatc  540
agacagccac cggggaaggg tctggaatgg attggagtga tttggggctc tgagactact  600
tactactctt catccctcaa gtcacgcgtc accatctcaa aggacaactc taagaatcag  660
gtgtcactga aactgtcatc tgtgaccgca gccgacaccg ccgtgtacta ttgcgctaag  720
cattactatt atggcgggag ctacgcaatg gattactggg gacagggtac tctggtcacc  780
gtgtccagca ccactacccc agcaccgagg ccacccaccc cggctcctac catcgcctcc  840
cagcctctgt ccctgcgtcc ggaggcatgt agacccgcag ctggtggggc cgtgcatacc  900
cggggtcttg acttcgcctg cgatatctac atttgggccc ctctggctgg tacttgcggg  960
gtcctgctgc tttcactcgt gatcactctt tactgtaagc gcggtcggaa gaagctgctg  1020
tacatcttta agcaaccctt catgaggcct gtgcagacta ctcaagagga ggacggctgt  1080
tcatgccggt tcccagagga ggaggaaggc ggctgcgaac tgcgcgtgaa attcagccgc  1140
agcgcagatg ctccagccta caagcagggg cagaaccagc tctacaacga actcaatctt  1200
ggtcggagag aggagtacga cgtgctggac aagcggagag gacgggaccc agaaatgggc  1260
gggaagccgc gcagaaagaa tccccaagag ggcctgtaca acgagctcca aaaggataag  1320
atggcagaag cctatagcga gattggtatg aaaggggaac gcagaagagg caaaggccac  1380
gacggactgt accagggact cagcaccgcc accaaggaca cctatgacgc tcttcacatg  1440
caggccctgc cgcctcgg                                               1458

SEQ ID NO: 897         moltype = AA  length = 486
FEATURE                Location/Qualifiers
REGION                 1..486
                       note = source = /note="Description of Artificial Sequence:
                        Synthetic polypeptide"
source                 1..486
                       mol_type = protein
                       organism = synthetic construct
SEQUENCE: 897
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSQVQLQES GPGLVKPSET LSLTCTVSGV SLPDYGVSWI  180
RQPPGKGLEW IGVIWGSETT YYSSSLKSRV TISKDNSKNQ VSLKLSSVTA ADTAVYYCAK  240
HYYYGGSYAM DYWGQGTLVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 898         moltype = AA  length = 242
FEATURE                Location/Qualifiers
REGION                 1..242
                       note = source = /note="Description of Artificial Sequence:
                        Synthetic polypeptide"
source                 1..242
                       mol_type = protein
                       organism = synthetic construct
SEQUENCE: 898
EIVMTQSPAT LSLSPGERAT LSCRASQDIS KYLNWYQQKP GQAPRLLIYH TSRLHSGIPA  60
RFSGSGSGTD YTLTISSLQP EDFAVYFCQQ GNTLPYTFGQ GTKLEIKGGG GSGGGGSGGG  120
GSQVQLQESG PGLVKPSETL SLTCTVSGVS LPDYGVSWIR QPPGKGLEWI GVIWGSETTY  180
YQSSLKSRVT ISKDNSKNQV SLKLSSVTAA DTAVYYCAKH YYYGGSYAMD YWGQGTLVTV  240
SS                                                                242

SEQ ID NO: 899         moltype = DNA  length = 813
FEATURE                Location/Qualifiers
misc_feature           1..813
                       note = source = /note="Description of Artificial Sequence:
                        Synthetic polynucleotide"
source                 1..813
                       mol_type = other DNA
                       organism = synthetic construct
SEQUENCE: 899
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcc aggtccaact ccaagaaagc ggaccgggtc ttgtgaagcc atcagaaact  480
ctttcactga cttgtactgt gagcggagtg tctctccccg attacggggt gtcttggatc  540
agacagccac cggggaaggg tctggaatgg attggagtga tttggggctc tgagactact  600
tactaccaat catccctcaa gtcacgcgtc accatctcaa aggacaactc taagaatcag  660
gtgtcactga aactgtcatc tgtgaccgca gccgacaccg ccgtgtacta ttgcgctaag  720
cattactatt atggcgggag ctacgcaatg gattactggg gacagggtac tctggtcacc  780
```

```
gtgtccagcc accaccatca tcaccatcac cat                           813

SEQ ID NO: 900          moltype = AA  length = 271
FEATURE                 Location/Qualifiers
REGION                  1..271
                        note = source = /note="Description of Artificial Sequence:
                         Synthetic polypeptide"
source                  1..271
                        mol_type = protein
                        organism = synthetic construct
SEQUENCE: 900
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSQVQLQES GPGLVKPSET LSLTCTVSGV SLPDYGVSWI  180
RQPPGKGLEW IGVIWGSETT YYQSSLKSRV TISKDNSKNQ VSLKLSSVTA ADTAVYYCAK  240
HYYYGGSYAM DYWGQGTLVT VSSHHHHHHH H                             271

SEQ ID NO: 901          moltype = DNA  length = 1458
FEATURE                 Location/Qualifiers
misc_feature            1..1458
                        note = source = /note="Description of Artificial Sequence:
                         Synthetic polynucleotide"
source                  1..1458
                        mol_type = other DNA
                        organism = synthetic construct
SEQUENCE: 901
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcc aggtccaact ccaagaaagc ggaccgggtc ttgtgaagcc atcagaaact  480
ctttcactga cttgtactgt gagcggagtg tctctccccg attacggggt gtcttggatc  540
agacagccac cggggaaggg tctggaatgg attggagtga tttggggctc tgagactact  600
tactaccaat catccctcaa gtcacgcgtc accatctcaa aggacaactc taagaatcag  660
gtgtcactga aactgtcatc tgtgaccgca gccgacaccg ccgtgtacta ttgcgctaag  720
cattactatt atggcgggag ctacgcaatg gattactggg gacagggtac tctggtcacc  780
gtgtccagca ccactacccc agcaccgagg ccacccaccc cggctcctac catcgcctcc  840
cagcctctgt ccctgcgtcc ggaggcatgt agacccgcag ctggtggggc cgtgcatacc  900
cggggtcttg acttcgcctg cgatatctac atttgggccc ctctggctgg tacttgcggg  960
gtcctgctgc tttcactcgt gatcactctt tactgtaagc gcggtcggaa gaagctgctg  1020
tacatcttta agcaaccctt catgaggcct gtgcagacta ctcaagagga ggacggctgt  1080
tcatgccggt tcccagagga ggaggaaggc ggctgcgaac tgcgcgtgaa attcagccgc  1140
agcgcagatg ctccagccta caagcagggg cagaaccagc tctacaacga actcaatctt  1200
ggtcggagag aggagtacga cgtgctggac aagcggagag gacgggaccc agaaatgggc  1260
gggaagccgc gcagaaagaa tccccaagag ggcctgtaca acgagctcca aaaggataag  1320
atggcagaag cctatagcga gattggtatg aaaggggaac gcagaagagg caaaggccac  1380
gacggactgt accagggact cagcaccgcc accaaggaca cctatgacgc tcttcacatg  1440
caggccctgc cgcctcgg                                            1458

SEQ ID NO: 902          moltype = AA  length = 486
FEATURE                 Location/Qualifiers
REGION                  1..486
                        note = source = /note="Description of Artificial Sequence:
                         Synthetic polypeptide"
source                  1..486
                        mol_type = protein
                        organism = synthetic construct
SEQUENCE: 902
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSQVQLQES GPGLVKPSET LSLTCTVSGV SLPDYGVSWI  180
RQPPGKGLEW IGVIWGSETT YYQSSLKSRV TISKDNSKNQ VSLKLSSVTA ADTAVYYCAK  240
HYYYGGSYAM DYWGQGTLVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                         486

SEQ ID NO: 903          moltype = AA  length = 242
FEATURE                 Location/Qualifiers
REGION                  1..242
                        note = source = /note="Description of Artificial Sequence:
                         Synthetic polypeptide"
source                  1..242
                        mol_type = protein
                        organism = synthetic construct
```

```
SEQUENCE: 903
QVQLQESGPG LVKPSETLSL TCTVSGVSLP DYGVSWIRQP PGKGLEWIGV IWGSETTYYS  60
SSLKSRVTIS KDNSKNQVSL KLSSVTAADT AVYYCAKHYY YGGSYAMDYW GQGTLVTVSS  120
GGGGSGGGGS GGGGSEIVMT QSPATLSLSP GERATLSCRA SQDISKYLNW YQQKPGQAPR  180
LLIYHTSRLH SGIPARFSGS GSGTDYTLTI SSLQPEDFAV YFCQQGNTLP YTFGQGTKLE  240
IK                                                               242

SEQ ID NO: 904          moltype = DNA  length = 813
FEATURE                 Location/Qualifiers
misc_feature            1..813
                        note = source = /note="Description of Artificial Sequence:
                         Synthetic polynucleotide"
source                  1..813
                        mol_type = other DNA
                        organism = synthetic construct
SEQUENCE: 904
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
tcatcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccga aatcgtgatg  480
acccagagcc ctgcaaccct gtccctttct cccggggaac gggctaccct ttcttgtcgg  540
gcatcacaag atatctcaaa atacctcaat tggtatcaac agaagccggg acaggcccct  600
aggcttctta tctaccacac ctctcgcctg catagcggga ttcccgcacg ctttagcggg  660
tctggaagcg ggaccgacta cactctgacc atctcatctc tccagcccga ggacttcgcc  720
gtctacttct gccagcaggg taacaccctg ccgtacacct tcggccaggg caccaagctt  780
gagatcaaac atcaccacca tcatcaccat cac                             813

SEQ ID NO: 905          moltype = AA  length = 271
FEATURE                 Location/Qualifiers
REGION                  1..271
                        note = source = /note="Description of Artificial Sequence:
                         Synthetic polypeptide"
source                  1..271
                        mol_type = protein
                        organism = synthetic construct
SEQUENCE: 905
MALPVTALLL PLALLLHAAR PQVQLQESGP GLVKPSETLS LTCTVSGVSL PDYGVSWIRQ  60
PPGKGLEWIG VIWGSETTYY SSSLKSRVTI SKDNSKNQVS LKLSSVTAAD TAVYYCAKHY  120
YYGGSYAMDY WGQGTLVTVS SGGGGSGGGG SGGGGSEIVM TQSPATLSLS PGERATLSCR  180
ASQDISKYLN WYQQKPGQAP RLLIYHTSRL HSGIPARFSG SGSGTDYTLT ISSLQPEDFA  240
VYFCQQGNTL PYTFGQGTKL EIKHHHHHHH H                               271

SEQ ID NO: 906          moltype = DNA  length = 1458
FEATURE                 Location/Qualifiers
misc_feature            1..1458
                        note = source = /note="Description of Artificial Sequence:
                         Synthetic polynucleotide"
source                  1..1458
                        mol_type = other DNA
                        organism = synthetic construct
SEQUENCE: 906
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
tcatcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccga aatcgtgatg  480
acccagagcc ctgcaaccct gtccctttct cccggggaac gggctaccct ttcttgtcgg  540
gcatcacaag atatctcaaa atacctcaat tggtatcaac agaagccggg acaggcccct  600
aggcttctta tctaccacac ctctcgcctg catagcggga ttcccgcacg ctttagcggg  660
tctggaagcg ggaccgacta cactctgacc atctcatctc tccagcccga ggacttcgcc  720
gtctacttct gccagcaggg taacaccctg ccgtacacct tcggccaggg caccaagctt  780
gagatcaaaa ccactactcc cgctccaagg ccacccaccc ctgccccgac catcgcctct  840
cagccgcttt ccctgcgtcc ggaggcatgt agacccgcag ctggtggggc cgtgcatacc  900
cggggtcttg acttcgcctg cgatatctac atttgggccc ctctggctgg tacttgcggg  960
gtcctgctgc tttcactcgt gatcactctt tactgtaagc gcggtcggaa gaagctgctg  1020
tacatcttta agcaaccctt catgaggcct gtgcagacta ctcaagagga ggacggctgt  1080
tcatgccggt tcccagagga ggaggaaggc ggctgcgaac tgcgcgtgaa attcagccgc  1140
agcgcagatg ctccagccta caagcagggg cagaaccagc tctacaacga actcaatctt  1200
ggtcggagag aggagtacga cgtgctggac aagcggagag gacgggaccc agaaatgggc  1260
gggaagccgc gcagaaagaa tccccaagag ggcctgtaca acgagctcca aaaggataag  1320
atggcagaag cctatagcga gattggtatg aaaggggaac gcagaagagg caaaggccac  1380
gacggactgt accagggact cagcaccgcc accaaggaca cctatgacgc tcttcacatg  1440
```

```
caggccctgc cgcctcgg                                               1458

SEQ ID NO: 907          moltype = AA  length = 486
FEATURE                 Location/Qualifiers
REGION                  1..486
                        note = source = /note="Description of Artificial Sequence:
                         Synthetic polypeptide"
source                  1..486
                        mol_type = protein
                        organism = synthetic construct
SEQUENCE: 907
MALPVTALLL PLALLLHAAR PQVQLQESGP GLVKPSETLS LTCTVSGVSL PDYGVSWIRQ  60
PPGKGLEWIG VIWGSETTYY SSSLKSRVTI SKDNSKNQVS LKLSSVTAAD TAVYYCAKHY  120
YYGGSYAMDY WGQGTLVTVS SGGGGSGGGG SGGGGSEIVM TQSPATLSLS PGERATLSCR  180
ASQDISKYLN WYQQKPGQAP RLLIYHTSRL HSGIPARFSG SGSGTDYTLT ISSLQPEDFA  240
VYFCQQGNTL PYTFGQGTKL EIKTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 908          moltype = AA  length = 242
FEATURE                 Location/Qualifiers
REGION                  1..242
                        note = source = /note="Description of Artificial Sequence:
                         Synthetic polypeptide"
source                  1..242
                        mol_type = protein
                        organism = synthetic construct
SEQUENCE: 908
QVQLQESGPG LVKPSETLSL TCTVSGVSLP DYGVSWIRQP PGKGLEWIGV IWGSETTYYQ  60
SSLKSRVTIS KDNSKNQVSL KLSSVTAADT AVYYCAKHYY YGGSYAMDYW GQGTLVTVSS  120
GGGGSGGGGS GGGGSEIVMT QSPATLSLSP GERATLSCRA SQDISKYLNW YQQKPGQAPR  180
LLIYHTSRLH SGIPARFSGS GSGTDYTLTI SSLQPEDFAV YFCQQGNTLP YTFGQGTKLE  240
IK                                                                242

SEQ ID NO: 909          moltype = DNA  length = 813
FEATURE                 Location/Qualifiers
misc_feature            1..813
                        note = source = /note="Description of Artificial Sequence:
                         Synthetic polynucleotide"
source                  1..813
                        mol_type = other DNA
                        organism = synthetic construct
SEQUENCE: 909
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
caatcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccga aatcgtgatg  480
acccagagcc ctgcaaccct gtccctttct cccggggaac gggctaccct ttcttgtcgg  540
gcatcacaag atatctcaaa atacctcaat tggtatcaac agaagccggg acaggcccct  600
aggcttctta tctaccacac ctctcgcctg catagcggga ttcccgcacg ctttagcggg  660
tctggaagcg ggaccgacta cactctgacc atctcatctc tccagcccga ggacttcgcc  720
gtctacttct gccagcaggg taacaccctg ccgtacacct tcggccaggg caccaagctt  780
gagatcaaac atcaccacca tcatcaccat cac                              813

SEQ ID NO: 910          moltype = AA  length = 271
FEATURE                 Location/Qualifiers
REGION                  1..271
                        note = source = /note="Description of Artificial Sequence:
                         Synthetic polypeptide"
source                  1..271
                        mol_type = protein
                        organism = synthetic construct
SEQUENCE: 910
MALPVTALLL PLALLLHAAR PQVQLQESGP GLVKPSETLS LTCTVSGVSL PDYGVSWIRQ  60
PPGKGLEWIG VIWGSETTYY QSSLKSRVTI SKDNSKNQVS LKLSSVTAAD TAVYYCAKHY  120
YYGGSYAMDY WGQGTLVTVS SGGGGSGGGG SGGGGSEIVM TQSPATLSLS PGERATLSCR  180
ASQDISKYLN WYQQKPGQAP RLLIYHTSRL HSGIPARFSG SGSGTDYTLT ISSLQPEDFA  240
VYFCQQGNTL PYTFGQGTKL EIKHHHHHHH H                                271

SEQ ID NO: 911          moltype = DNA  length = 1458
FEATURE                 Location/Qualifiers
misc_feature            1..1458
                        note = source = /note="Description of Artificial Sequence:
```

```
                         Synthetic polynucleotide"
source                  1..1458
                        mol_type = other DNA
                        organism = synthetic construct
SEQUENCE: 911
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
caatcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccga aatcgtgatg  480
acccagagcc ctgcaaccct gtccctttct cccggggaac gggctaccct ttcttgtcgg  540
gcatcacaag atatctcaaa atacctcaat tggtatcaac agaagccggg acaggcccct  600
aggcttctta tctaccacac ctctcgcctg catagcggga ttcccgcacg ctttagcggg  660
tctggaagcg ggaccgacta cactctgacc atctcatctc tccagcccga ggacttcgcc  720
gtctacttct gccagcaggg taacaccctg ccgtacacct tcggccaggg caccaagctt  780
gagatcaaaa ccactactcc cgctccaagg ccacccaccc ctgccccgac catcgcctct  840
cagccgcttt ccctgcgtcc ggaggcatgt agacccgcag ctggtggggc cgtgcatacc  900
cggggtcttg acttcgcctg cgatatctac atttgggccc ctctggctgg tacttgcggg  960
gtcctgctgc tttcactcgt gatcactctt tactgtaagc gcggtcggaa gaagctgctg  1020
tacatcttta agcaaccctt catgaggcct gtgcagacta ctcaagagga ggacggctgt  1080
tcatgccggt tcccagagga ggaggaaggc ggctgcgaac tgcgcgtgaa attcagccgc  1140
agcgcagatg ctccagccta caagcagggg cagaaccagc tctacaacga actcaatctt  1200
ggtcggagag aggagtacga cgtgctggac aagcggagag gacgggaccc agaaatgggc  1260
gggaagccgc gcagaaagaa tccccaagag ggcctgtaca acgagctcca aaaggataag  1320
atggcagaag cctatagcga gattggtatg aaaggggaac gcagaagagg caaaggccac  1380
gacggactgt accagggact cagcaccgcc accaaggaca cctatgacgc tcttcacatg  1440
caggccctgc cgcctcgg                                               1458

SEQ ID NO: 912          moltype = AA  length = 486
FEATURE                 Location/Qualifiers
REGION                  1..486
                        note = source = /note="Description of Artificial Sequence:
                         Synthetic polypeptide"
source                  1..486
                        mol_type = protein
                        organism = synthetic construct
SEQUENCE: 912
MALPVTALLL PLALLLHAAR PQVQLQESGP GLVKPSETLS LTCTVSGVSL PDYGVSWIRQ  60
PPGKGLEWIG VIWGSETTYY QSSLKSRVTI SKDNSKNQVS LKLSSVTAAD TAVYYCAKHY  120
YYGGSYAMDY WGQGTLVTVS SGGGGSGGGG SGGGGSEIVM TQSPATLSLS PGERATLSCR  180
ASQDISKYLN WYQQKPGQAP RLLIYHTSRL HSGIPARFSG SGSGTDYTLT ISSLQPEDFA  240
VYFCQQGNTL PYTFGQGTKL EIKTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 913          moltype = AA  length = 247
FEATURE                 Location/Qualifiers
REGION                  1..247
                        note = source = /note="Description of Artificial Sequence:
                         Synthetic polypeptide"
source                  1..247
                        mol_type = protein
                        organism = synthetic construct
SEQUENCE: 913
EIVMTQSPAT LSLSPGERAT LSCRASQDIS KYLNWYQQKP GQAPRLLIYH TSRLHSGIPA  60
RFSGSGSGTD YTLTISSLQP EDFAVYFCQQ GNTLPYTFGQ GTKLEIKGGG GSGGGGSGGG  120
GSGGGGSQVQ LQESGPGLVK PSETLSLTCT VSGVSLPDYG VSWIRQPPGK GLEWIGVIWG  180
SETTYYSSSL KSRVTISKDN SKNQVSLKLS SVTAADTAVY YCAKHYYYGG SYAMDYWGQG  240
TLVTVSS                                                           247

SEQ ID NO: 914          moltype = DNA  length = 828
FEATURE                 Location/Qualifiers
misc_feature            1..828
                        note = source = /note="Description of Artificial Sequence:
                         Synthetic polynucleotide"
source                  1..828
                        mol_type = other DNA
                        organism = synthetic construct
SEQUENCE: 914
atggccctcc cagtgaccgc tctgctgctg cctctcgcac ttcttctcca tgccgctcgg  60
cctgagatcg tcatgaccca aagccccgct accctgtccc tgtcacccgg cgagagggca  120
accctttcat gcagggccag ccaggacatt tctaagtacc tcaactggta tcagcagaag  180
ccagggcagg ctcctcgcct gctgatctac cacaccagcc gcctccacag cggtatcccc  240
gccagatttt ccgggagcgg gtctggaacc gactacaccc tcaccatctc ttctctgcag  300
```

```
cccgaggatt tcgccgtcta tttctgccag caggggaata ctctgccgta caccttcggt  360
caaggtacca agctggaaat caagggaggc ggaggatcag gcggtggcgg aagcggagga  420
ggtggctccg gaggaggagg ttcccaagtg cagcttcaag aatcaggacc cggacttgtg  480
aagccatcag aaaccctctc cctgacttgt accgtgtccg gtgtgagcct ccccgactac  540
ggagtctctt ggattcgcca gcctccgggg aagggtcttg aatggattgg ggtgatttgg  600
ggatcagaga ctacttacta ctcttcatca cttaagtcac gggtcaccat cagcaaagat  660
aatagcaaga accaagtgtc acttaagctg tcatctgtga ccgccgctga caccgccgtg  720
tactattgtg ccaaacatta ctattacgga gggtcttatg ctatggacta ctggggacag  780
gggaccctgg tgactgtctc tagccatcac catcaccacc atcatcac             828
```

```
SEQ ID NO: 915         moltype = AA  length = 276
FEATURE                Location/Qualifiers
REGION                 1..276
                       note = source = /note="Description of Artificial Sequence:
                        Synthetic polypeptide"
source                 1..276
                       mol_type = protein
                       organism = synthetic construct
SEQUENCE: 915
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYSSS LKSRVTISKD NSKNQVSLKL SSVTAADTAV  240
YYCAKHYYYG GSYAMDYWGQ GTLVTVSSHH HHHHHH                           276
```

```
SEQ ID NO: 916         moltype = DNA  length = 1473
FEATURE                Location/Qualifiers
misc_feature           1..1473
                       note = source = /note="Description of Artificial Sequence:
                        Synthetic polynucleotide"
source                 1..1473
                       mol_type = other DNA
                       organism = synthetic construct
SEQUENCE: 916
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcg gcggaggcgg gagccaggtc caactccaag aaagcggacc gggtcttgtg  480
aagccatcag aaactctttc actgacttgt actgtgagcg gagtgtctct ccccgattac  540
ggggtgtctt ggatcagaca gccaccgggg aagggtctgg aatggattgg agtgatttgg  600
ggctctgaga ctacttacta ctcttcatcc ctcaagtcac gcgtcaccat ctcaaaggac  660
aactctaaga atcaggtgtc actgaaactg tcatctgtga ccgcagccga caccgccgtg  720
tactattgcg ctaagcatta ctattatggc gggagctacg caatggatta ctggggacag  780
ggtactctgg tcaccgtgtc cagcaccact accccagcac cgaggccacc caccccggct  840
cctaccatcg cctcccagcc tctgtccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                             1473
```

```
SEQ ID NO: 917         moltype = AA  length = 491
FEATURE                Location/Qualifiers
REGION                 1..491
                       note = source = /note="Description of Artificial Sequence:
                        Synthetic polypeptide"
source                 1..491
                       mol_type = protein
                       organism = synthetic construct
SEQUENCE: 917
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYSSS LKSRVTISKD NSKNQVSLKL SSVTAADTAV  240
YYCAKHYYYG GSYAMDYWGQ GTLVTVSSTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491
```

```
SEQ ID NO: 918          moltype = AA  length = 247
FEATURE                 Location/Qualifiers
REGION                  1..247
                        note = source = /note="Description of Artificial Sequence:
                         Synthetic polypeptide"
source                  1..247
                        mol_type = protein
                        organism = synthetic construct
SEQUENCE: 918
EIVMTQSPAT LSLSPGERAT LSCRASQDIS KYLNWYQQKP GQAPRLLIYH TSRLHSGIPA  60
RFSGSGSGTD YTLTISSLQP EDFAVYFCQQ GNTLPYTFGQ GTKLEIKGGG GSGGGGSGGG  120
GSGGGGSQVQ LQESGPGLVK PSETLSLTCT VSGVSLPDYG VSWIRQPPGK GLEWIGVIWG  180
SETTYYQSSL KSRVTISKDN SKNQVSLKLS SVTAADTAVY YCAKHYYYGG SYAMDYWGQG  240
TLVTVSS                                                           247

SEQ ID NO: 919          moltype = DNA  length = 828
FEATURE                 Location/Qualifiers
misc_feature            1..828
                        note = source = /note="Description of Artificial Sequence:
                         Synthetic polynucleotide"
source                  1..828
                        mol_type = other DNA
                        organism = synthetic construct
SEQUENCE: 919
atggccctcc cagtgaccgc tctgctgctg cctctcgcac ttcttctcca tgccgctcgg  60
cctgagatcg tcatgaccca aagccccgct accctgtccc tgtcacccgg cgagagggca  120
accctttcat gcagggccag ccaggacatt tctaagtacc tcaactggta tcagcagaag  180
ccagggcagg ctcctcgcct gctgatctac cacaccagcc gcctccacag cggtatcccc  240
gccagatttt ccgggagcgg gtctggaacc gactacaccc tcaccatctc ttctctgcag  300
cccgaggatt tcgccgtcta tttctgccag caggggaata ctctgccgta caccttcggt  360
caaggtacca agctggaaat caagggaggc ggaggatcag gcggtggcgg aagcggagga  420
ggtggctccg gaggaggagg ttcccaagtg cagcttcaag aatcaggacc cggacttgtg  480
aagccatcag aaaccctctc cctgacttgt accgtgtccg gtgtgagcct ccccgactac  540
ggagtctctt ggattcgcca gcctccgggg aagggtcttg aatggattgg ggtgatttgg  600
ggatcagaga ctacttacta ccagtcatca cttaagtcac gggtcaccat cagcaaagat  660
aatagcaaga accaagtgtc acttaagctg tcatctgtga ccgccgctga caccgccgtg  720
tactattgtg ccaaacatta ctattacgga gggtcttatg ctatggacta ctggggacag  780
gggaccctgg tgactgtctc tagccatcac catcaccacc atcatcac              828

SEQ ID NO: 920          moltype = AA  length = 276
FEATURE                 Location/Qualifiers
REGION                  1..276
                        note = source = /note="Description of Artificial Sequence:
                         Synthetic polypeptide"
source                  1..276
                        mol_type = protein
                        organism = synthetic construct
SEQUENCE: 920
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYQSS LKSRVTISKD NSKNQVSLKL SSVTAADTAV  240
YYCAKHYYYG GSYAMDYWGQ GTLVTVSSHH HHHHHH                            276

SEQ ID NO: 921          moltype = DNA  length = 1473
FEATURE                 Location/Qualifiers
misc_feature            1..1473
                        note = source = /note="Description of Artificial Sequence:
                         Synthetic polynucleotide"
source                  1..1473
                        mol_type = other DNA
                        organism = synthetic construct
SEQUENCE: 921
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcg gaggcggagg gagccaggtc caactccaag aaagcggacc gggtcttgtg  480
aagccatcag aaactctttc actgacttgt actgtgagcg gagtgtctct ccccgattac  540
ggggtgtctt ggatcagaca gccaccgggg aagggtctgg aatggattgg agtgatttgg  600
ggctctgaga ctacttacta ccaatcatcc ctcaagtcac gcgtcaccat ctcaaaggac  660
aactctaaga atcaggtgtc actgaaactg tcatctgtga ccgcagccga caccgccgtg  720
tactattgcg ctaagcatta ctattatggc gggagctacg caatggatta ctggggacag  780
ggtactctgg tcaccgtgtc cagcaccact accccagcac cgaggccacc caccccggct  840
cctaccatcg cctcccagcc tctgtccctg cgtccggagg catgtagacc cgcagctggt  900
ggggccgtgc atacccgggg tcttgacttc gcctgcgata tctacatttg ggcccctctg  960
```

```
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                               1473

SEQ ID NO: 922         moltype = AA  length = 491
FEATURE                Location/Qualifiers
REGION                 1..491
                       note = source = /note="Description of Artificial Sequence:
                        Synthetic polypeptide"
source                 1..491
                       mol_type = protein
                       organism = synthetic construct
SEQUENCE: 922
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYQSS LKSRVTISKD NSKNQVSLKL SSVTAADTAV  240
YYCAKHYYYG GSYAMDYWGQ GTLVTVSSTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 923         moltype = AA  length = 247
FEATURE                Location/Qualifiers
REGION                 1..247
                       note = source = /note="Description of Artificial Sequence:
                        Synthetic polypeptide"
source                 1..247
                       mol_type = protein
                       organism = synthetic construct
SEQUENCE: 923
QVQLQESGPG LVKPSETLSL TCTVSGVSLP DYGVSWIRQP PGKGLEWIGV IWGSETTYYS  60
SSLKSRVTIS KDNSKNQVSL KLSSVTAADT AVYYCAKHYY YGGSYAMDYW GQGTLVTVSS  120
GGGGSGGGGS GGGGSGGGGS EIVMTQSPAT LSLSPGERAT LSCRASQDIS KYLNWYQQKP  180
GQAPRLLIYH TSRLHSGIPA RFSGSGSGTD YTLTISSLQP EDFAVYFCQQ GNTLPYTFGQ  240
GTKLEIK                                                            247

SEQ ID NO: 924         moltype = DNA  length = 828
FEATURE                Location/Qualifiers
misc_feature           1..828
                       note = source = /note="Description of Artificial Sequence:
                        Synthetic polynucleotide"
source                 1..828
                       mol_type = other DNA
                       organism = synthetic construct
SEQUENCE: 924
atggcactgc ctgtcactgc cctcctgctg cctctggccc tccttctgca tgccgccagg  60
ccccaagtcc agctgcaaga gtcaggaccc ggactggtga agccgtctga gactctctca  120
ctgacttgta ccgtcagcgg cgtgtccctc cccgactacg gagtgtcatg gatccgccaa  180
cctcccggga aagggcttga atggattggt gtcatctggg gttctgaaac cacctactac  240
tcatcttccc tgaagtccag ggtgaccatc agcaaggata attccaagaa ccaggtcagc  300
cttaagctgt catctgtgac cgctgctgac accgccgtgt attactgcgc caagcactac  360
tattacggag gaagctacgc tatggactat tggggacagg gcactctcgt gactgtgagc  420
agcggcggtg gagggtctgg aggtggagga tccggtggtg gtgggtcagg cggaggaggg  480
agcgagattg tgatgactca gtcaccagcc accctttctc tttcacccgg cgagagagca  540
accctgagct gtagagccag ccaggacatt tctaagtacc tcaactggta tcagcaaaaa  600
ccggggcagg cccctcgcct cctgatctac catacctcac gccttcactc tggtatcccc  660
gctcggttta gcggatcagg atctggtacc gactacactc tgaccatttc cagcctgcag  720
ccagaagatt tcgcagtgta tttctgccag cagggcaata cccttcctta caccttcggt  780
cagggaacca agctcgaaat caagcaccat caccatcatc accaccat               828

SEQ ID NO: 925         moltype = AA  length = 276
FEATURE                Location/Qualifiers
REGION                 1..276
                       note = source = /note="Description of Artificial Sequence:
                        Synthetic polypeptide"
source                 1..276
                       mol_type = protein
                       organism = synthetic construct
SEQUENCE: 925
MALPVTALLL PLALLLHAAR PQVQLQESGP GLVKPSETLS LTCTVSGVSL PDYGVSWIRQ  60
PPGKGLEWIG VIWGSETTYY SSSLKSRVTI SKDNSKNQVS LKLSSVTAAD TAVYYCAKHY  120
```

```
YYGGSYAMDY WGQGTLVTVS SGGGGSGGGG SGGGGSGGGG SEIVMTQSPA TLSLSPGERA  180
TLSCRASQDI SKYLNWYQQK PGQAPRLLIY HTSRLHSGIP ARFSGSGSGT DYTLTISSLQ  240
PEDFAVYFCQ QGNTLPYTFG QGTKLEIKHH HHHHHH                            276

SEQ ID NO: 926         moltype = DNA  length = 1473
FEATURE                Location/Qualifiers
misc_feature           1..1473
                       note = source = /note="Description of Artificial Sequence:
                        Synthetic polynucleotide"
source                 1..1473
                       mol_type = other DNA
                       organism = synthetic construct
SEQUENCE: 926
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
tcatcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccgg aggtggcgga  480
agcgaaatcg tgatgaccca gagccctgca accctgtccc tttctcccgg ggaacgggct  540
acccttctt gtcgggcatc acaagatatc tcaaaatacc tcaattggta tcaacagaag  600
ccgggacagg cccctaggct tcttatctac cacacctctc gcctgcatag cgggattccc  660
gcacgcttta gcgggtctgg aagcgggacc gactacactc tgaccatctc atctctccag  720
cccgaggact tcgccgtcta cttctgccag cagggtaaca ccctgccgta caccttcggc  780
cagggcacca agcttgagat caaaaccact actcccgctc caaggccacc cacccctgcc  840
ccgaccatcg cctctcagcc gctttccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                              1473

SEQ ID NO: 927         moltype = AA  length = 491
FEATURE                Location/Qualifiers
REGION                 1..491
                       note = source = /note="Description of Artificial Sequence:
                        Synthetic polypeptide"
source                 1..491
                       mol_type = protein
                       organism = synthetic construct
SEQUENCE: 927
MALPVTALLL PLALLLHAAR PQVQLQESGP GLVKPSETLS LTCTVSGVSL PDYGVSWIRQ  60
PPGKGLEWIG VIWGSETTYY SSSLKSRVTI SKDNSKNQVS LKLSSVTAAD TAVYYCAKHY  120
YYGGSYAMDY WGQGTLVTVS SGGGGSGGGG SGGGGSGGGG SEIVMTQSPA TLSLSPGERA  180
TLSCRASQDI SKYLNWYQQK PGQAPRLLIY HTSRLHSGIP ARFSGSGSGT DYTLTISSLQ  240
PEDFAVYFCQ QGNTLPYTFG QGTKLEIKTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 928         moltype = AA  length = 247
FEATURE                Location/Qualifiers
REGION                 1..247
                       note = source = /note="Description of Artificial Sequence:
                        Synthetic polypeptide"
source                 1..247
                       mol_type = protein
                       organism = synthetic construct
SEQUENCE: 928
QVQLQESGPG LVKPSETLSL TCTVSGVSLP DYGVSWIRQP PGKGLEWIGV IWGSETTYYQ  60
SSLKSRVTIS KDNSKNQVSL KLSSVTAADT AVYYCAKHYY YGGSYAMDYW GQGTLVTVSS  120
GGGGSGGGGS GGGGSGGGGS EIVMTQSPAT LSLSPGERAT LSCRASQDIS KYLNWYQQKP  180
GQAPRLLIYH TSRLHSGIPA RFSGSGSGTD YTLTISSLQP EDFAVYFCQQ GNTLPYTFGQ  240
GTKLEIK                                                           247

SEQ ID NO: 929         moltype = DNA  length = 828
FEATURE                Location/Qualifiers
misc_feature           1..828
                       note = source = /note="Description of Artificial Sequence:
                        Synthetic polynucleotide"
source                 1..828
```

```
                         mol_type = other DNA
                         organism = synthetic construct
SEQUENCE: 929
atggcactgc ctgtcactgc cctcctgctg cctctggccc tccttctgca tgccgccagg  60
ccccaagtcc agctgcaaga gtcaggaccc ggactggtga agccgtctga gactctctca  120
ctgacttgta ccgtcagcgg cgtgtccctc cccgactacg gagtgtcatg gatccgccaa  180
cctcccggga aagggcttga atggattggt gtcatctggg gttctgaaac cacctactac  240
cagtcttccc tgaagtccag ggtgaccatc agcaaggata attccaagaa ccaggtcagc  300
cttaagctgt catctgtgac cgctgctgac accgccgtgt attactgcgc caagcactac  360
tattacggag gaagctacgc tatggactat tggggacagg gcactctcgt gactgtgagc  420
agcggcggtg gagggtctgg aggtggagga tccggtggtg gtgggtcagg cggaggaggg  480
agcgagattg tgatgactca gtcaccagcc accctttctc tttcacccgg cgagagagca  540
accctgagct gtagagccag ccaggacatt tctaagtacc tcaactggta tcagcaaaaa  600
ccggggcagg cccctcgcct cctgatctac catacctcac gccttcactc tggtatcccc  660
gctcggttta gcggatcagg atctggtacc gactacactc tgaccatttc cagcctgcag  720
ccagaagatt tcgcagtgta tttctgccag cagggcaata cccttcctta caccttcggt  780
cagggaacca agctcgaaat caagcaccat caccatcatc atcaccac              828

SEQ ID NO: 930           moltype = AA  length = 276
FEATURE                  Location/Qualifiers
REGION                   1..276
                         note = source = /note="Description of Artificial Sequence:
                          Synthetic polypeptide"
source                   1..276
                         mol_type = protein
                         organism = synthetic construct
SEQUENCE: 930
MALPVTALLL PLALLLHAAR PQVQLQESGP GLVKPSETLS LTCTVSGVSL PDYGVSWIRQ  60
PPGKGLEWIG VIWGSETTYY QSSLKSRVTI SKDNSKNQVS LKLSSVTAAD TAVYYCAKHY  120
YYGGSYAMDY WGQGTLVTVS SGGGGSGGGG SGGGGSGGGG SEIVMTQSPA TLSLSPGERA  180
TLSCRASQDI SKYLNWYQQK PGQAPRLLIY HTSRLHSGIP ARFSGSGSGT DYTLTISSLQ  240
PEDFAVYFCQ QGNTLPYTFG QGTKLEIKHH HHHHHH                            276

SEQ ID NO: 931           moltype = DNA  length = 1473
FEATURE                  Location/Qualifiers
misc_feature             1..1473
                         note = source = /note="Description of Artificial Sequence:
                          Synthetic polynucleotide"
source                   1..1473
                         mol_type = other DNA
                         organism = synthetic construct
SEQUENCE: 931
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
caatcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccgg aggcggtggg  480
tcagaaatcg tgatgaccca gagccctgca accctgtccc tttctcccgg ggaacgggct  540
accctttctt gtcgggcatc acaagatatc tcaaaatacc tcaattggta tcaacagaag  600
ccgggacagg cccctaggct tcttatctac cacacctctc gcctgcatag cgggattccc  660
gcacgcttta gcgggtctgg aagcgggacc gactacactc tgaccatctc atctctccag  720
cccgaggact tcgccgtcta cttctgccag cagggtaaca ccctgccgta caccttcggc  780
cagggcacca agcttgagat caaaaccact actcccgctc caaggccacc cacccctgcc  840
ccgaccatcg cctctcagcc gctttccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                              1473

SEQ ID NO: 932           moltype = AA  length = 491
FEATURE                  Location/Qualifiers
REGION                   1..491
                         note = source = /note="Description of Artificial Sequence:
                          Synthetic polypeptide"
source                   1..491
                         mol_type = protein
                         organism = synthetic construct
SEQUENCE: 932
MALPVTALLL PLALLLHAAR PQVQLQESGP GLVKPSETLS LTCTVSGVSL PDYGVSWIRQ  60
PPGKGLEWIG VIWGSETTYY QSSLKSRVTI SKDNSKNQVS LKLSSVTAAD TAVYYCAKHY  120
```

-continued

```
YYGGSYAMDY WGQGTLVTVS SGGGGSGGGG SGGGGSGGGG SEIVMTQSPA TLSLSPGERA  180
TLSCRASQDI SKYLNWYQQK PGQAPRLLIY HTSRLHSGIP ARFSGSGSGT DYTLTISSLQ  240
PEDFAVYFCQ QGNTLPYTFG QGTKLEIKTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 933          moltype = AA  length = 247
FEATURE                 Location/Qualifiers
REGION                  1..247
                        note = source = /note="Description of Artificial Sequence:
                         Synthetic polypeptide"
source                  1..247
                        mol_type = protein
                        organism = synthetic construct
SEQUENCE: 933
EIVMTQSPAT LSLSPGERAT LSCRASQDIS KYLNWYQQKP GQAPRLLIYH TSRLHSGIPA  60
RFSGSGSGTD YTLTISSLQP EDFAVYFCQQ GNTLPYTFGQ GTKLEIKGGG GSGGGGSGGG  120
GSGGGGSQVQ LQESGPGLVK PSETLSLTCT VSGVSLPDYG VSWIRQPPGK GLEWIGVIWG  180
SETTYYNSSL KSRVTISKDN SKNQVSLKLS SVTAADTAVY YCAKHYYYGG SYAMDYWGQG  240
TLVTVSS                                                            247

SEQ ID NO: 934          moltype = DNA  length = 828
FEATURE                 Location/Qualifiers
misc_feature            1..828
                        note = source = /note="Description of Artificial Sequence:
                         Synthetic polynucleotide"
source                  1..828
                        mol_type = other DNA
                        organism = synthetic construct
SEQUENCE: 934
atggccctcc cagtgaccgc tctgctgctg cctctcgcac ttcttctcca tgccgctcgg  60
cctgagatcg tcatgaccca aagccccgct accctgtccc tgtcacccgg cgagagggca  120
accctttcat gcagggccag ccaggacatt tctaagtacc tcaactggta tcagcagaag  180
ccagggcagg ctcctcgcct gctgatctac cacaccagcc gcctccacag cggtatcccc  240
gccagatttt ccgggagcgg gtctggaacc gactacaccc tcaccatctc ttctctgcag  300
cccgaggatt tcgccgtcta tttctgccag caggggaata ctctgccgta caccttcggt  360
caaggtacca agctggaaat caagggaggc ggaggatcag gcggtggcgg aagcggagga  420
ggtggctccg gaggaggagg ttcccaagtg cagcttcaag aatcaggacc cggacttgtg  480
aagccatcag aaaccctctc cctgacttgt accgtgtccg gtgtgagcct ccccgactac  540
ggagtctctt ggattcgcca gcctccgggg aagggtcttg aatggattgg ggtgatttgg  600
ggatcagaga ctacttacta caattcatca cttaagtcac gggtcaccat cagcaaagat  660
aatagcaaga accaagtgtc acttaagctg tcatctgtga ccgccgctga caccgccgtg  720
tactattgtg ccaaacatta ctattacgga gggtcttatg ctatggacta ctggggacag  780
gggaccctgg tgactgtctc tagccatcac catcaccacc atcatcac            828

SEQ ID NO: 935          moltype = AA  length = 276
FEATURE                 Location/Qualifiers
REGION                  1..276
                        note = source = /note="Description of Artificial Sequence:
                         Synthetic polypeptide"
source                  1..276
                        mol_type = protein
                        organism = synthetic construct
SEQUENCE: 935
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYNSS LKSRVTISKD NSKNQVSLKL SSVTAADTAV  240
YYCAKHYYYG GSYAMDYWGQ GTLVTVSSHH HHHHHH                            276

SEQ ID NO: 936          moltype = DNA  length = 1473
FEATURE                 Location/Qualifiers
misc_feature            1..1473
                        note = source = /note="Description of Artificial Sequence:
                         Synthetic polynucleotide"
source                  1..1473
                        mol_type = other DNA
                        organism = synthetic construct
SEQUENCE: 936
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcg gaggcggtgg gagccaggtc caactccaag aaagcggacc gggtcttgtg  480
```

```
aagccatcag aaactctttc actgacttgt actgtgagcg gagtgtctct ccccgattac  540
ggggtgtctt ggatcagaca gccaccgggg aagggtctgg aatggattgg agtgatttgg  600
ggctctgaga ctacttacta caactcatcc ctcaagtcac gcgtcaccat ctcaaaggac  660
aactctaaga atcaggtgtc actgaaactg tcatctgtga ccgcagccga caccgccgtg  720
tactattgcg ctaagcatta ctattatggc gggagctacg caatggatta ctggggacag  780
ggtactctgg tcaccgtgtc cagcaccact accccagcac cgaggccacc caccccggct  840
cctaccatcg cctcccagcc tctgtccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                             1473

SEQ ID NO: 937         moltype = AA  length = 491
FEATURE                Location/Qualifiers
REGION                 1..491
                       note = source = /note="Description of Artificial Sequence:
                        Synthetic polypeptide"
source                 1..491
                       mol_type = protein
                       organism = synthetic construct
SEQUENCE: 937
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYNSS LKSRVTISKD NSKNQVSLKL SSVTAADTAV  240
YYCAKHYYYG GSYAMDYWGQ GTLVTVSSTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                     491

SEQ ID NO: 938         moltype = AA  length = 247
FEATURE                Location/Qualifiers
REGION                 1..247
                       note = source = /note="Description of Artificial Sequence:
                        Synthetic polypeptide"
source                 1..247
                       mol_type = protein
                       organism = synthetic construct
SEQUENCE: 938
QVQLQESGPG LVKPSETLSL TCTVSGVSLP DYGVSWIRQP PGKGLEWIGV IWGSETTYYN  60
SSLKSRVTIS KDNSKNQVSL KLSSVTAADT AVYYCAKHYY YGGSYAMDYW GQGTLVTVSS  120
GGGGSGGGGS GGGGSGGGGS EIVMTQSPAT LSLSPGERAT LSCRASQDIS KYLNWYQQKP  180
GQAPRLLIYH TSRLHSGIPA RFSGSGSGTD YTLTISSLQP EDFAVYFCQQ GNTLPYTFGQ  240
GTKLEIK                                                          247

SEQ ID NO: 939         moltype = DNA  length = 828
FEATURE                Location/Qualifiers
misc_feature           1..828
                       note = source = /note="Description of Artificial Sequence:
                        Synthetic polynucleotide"
source                 1..828
                       mol_type = other DNA
                       organism = synthetic construct
SEQUENCE: 939
atggcactgc ctgtcactgc cctcctgctg cctctggccc tccttctgca tgccgccagg  60
ccccaagtcc agctgcaaga gtcaggaccc ggactggtga agccgtctga gactctctca  120
ctgacttgta ccgtcagcgg cgtgtccctc cccgactacg gagtgtcatg gatccgccaa  180
cctcccggga aagggcttga atggattggt gtcatctggg gttctgaaac cacctactac  240
aactcttccc tgaagtccag ggtgaccatc agcaaggata attccaagaa ccaggtcagc  300
cttaagctgt catctgtgac cgctgctgac accgccgtgt attactgcgc caagcactac  360
tattacggag gaagctacgc tatggactat tggggacagg gcactctcgt gactgtgagc  420
agcggcggtg gagggtctgg aggtggagga tccggtggtg gtgggtcagg cggaggaggg  480
agcgagattg tgatgactca gtcaccagcc accctttctc tttcacccgg cgagagagca  540
accctgagct gtagagccag ccaggacatt tctaagtacc tcaactggta tcagcaaaaa  600
ccggggcagg cccctcgcct cctgatctac catacctcac gccttcactc tggtatcccc  660
gctcggttta gcggatcagg atctggtacc gactacactc tgaccatttc cagcctgcag  720
ccagaagatt tcgcagtgta tttctgccag cagggcaata cccttcctta caccttcggt  780
cagggaacca agctcgaaat caagcaccat caccatcatc accaccat              828

SEQ ID NO: 940         moltype = AA  length = 276
FEATURE                Location/Qualifiers
REGION                 1..276
```

```
                        note = source = /note="Description of Artificial Sequence:
                         Synthetic polypeptide"
source                  1..276
                        mol_type = protein
                        organism = synthetic construct
SEQUENCE: 940
MALPVTALLL PLALLLHAAR PQVQLQESGP GLVKPSETLS LTCTVSGVSL PDYGVSWIRQ  60
PPGKGLEWIG VIWGSETTYY NSSLKSRVTI SKDNSKNQVS LKLSSVTAAD TAVYYCAKHY  120
YYGGSYAMDY WGQGTLVTVS SGGGGSGGGG SGGGGSGGGG SEIVMTQSPA TLSLSPGERA  180
TLSCRASQDI SKYLNWYQQK PGQAPRLLIY HTSRLHSGIP ARFSGSGSGT DYTLTISSLQ  240
PEDFAVYFCQ QGNTLPYTFG QGTKLEIKHH HHHHHH                          276

SEQ ID NO: 941          moltype = DNA  length = 1473
FEATURE                 Location/Qualifiers
misc_feature            1..1473
                        note = source = /note="Description of Artificial Sequence:
                         Synthetic polynucleotide"
source                  1..1473
                        mol_type = other DNA
                        organism = synthetic construct
SEQUENCE: 941
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcg gaggcggtgg gagccaggtc caactccaag aaagcggacc gggtcttgtg  480
aagccatcag aaactctttc actgacttgt actgtgagcg gagtgtctct ccccgattac  540
ggggtgtctt ggatcagaca gccaccgggg aagggtctgg aatggattgg agtgatttgg  600
ggctctgaga ctacttacta caactcatcc ctcaagtcac gcgtcaccat ctcaaaggac  660
aactctaaga atcaggtgtc actgaaactg tcatctgtga ccgcagccga caccgccgtg  720
tactattgcg ctaagcatta ctattatggc gggagctacg caatggatta ctggggacag  780
ggtactctgg tcaccgtgtc cagcaccact accccagcac cgaggccacc caccccggct  840
cctaccatcg cctcccagcc tctgtccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                              1473

SEQ ID NO: 942          moltype = AA  length = 491
FEATURE                 Location/Qualifiers
REGION                  1..491
                        note = source = /note="Description of Artificial Sequence:
                         Synthetic polypeptide"
source                  1..491
                        mol_type = protein
                        organism = synthetic construct
SEQUENCE: 942
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSGGGGSQV QLQESGPGLV KPSETLSLTC TVSGVSLPDY  180
GVSWIRQPPG KGLEWIGVIW GSETTYYNSS LKSRVTISKD NSKNQVSLKL SSVTAADTAV  240
YYCAKHYYYG GSYAMDYWGQ GTLVTVSSTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 943          moltype = AA  length = 242
FEATURE                 Location/Qualifiers
REGION                  1..242
                        note = source = /note="Description of Artificial Sequence:
                         Synthetic polypeptide"
source                  1..242
                        mol_type = protein
                        organism = synthetic construct
SEQUENCE: 943
EIVMTQSPAT LSLSPGERAT LSCRASQDIS KYLNWYQQKP GQAPRLLIYH TSRLHSGIPA  60
RFSGSGSGTD YTLTISSLQP EDFAVYFCQQ GNTLPYTFGQ GTKLEIKGGG GSGGGGSGGG  120
GSQVQLQESG PGLVKPSETL SLTCTVSGVS LPDYGVSWIR QPPGKGLEWI GVIWGSETTY  180
YNSSLKSRVT ISKDNSKNQV SLKLSSVTAA DTAVYYCAKH YYYGGSYAMD YWGQGTLVTV  240
```

```
SS                                                                242

SEQ ID NO: 944          moltype = DNA  length = 813
FEATURE                 Location/Qualifiers
misc_feature            1..813
                        note = source = /note="Description of Artificial Sequence:
                         Synthetic polynucleotide"
source                  1..813
                        mol_type = other DNA
                        organism = synthetic construct
SEQUENCE: 944
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcc aggtccaact ccaagaaagc ggaccgggtc ttgtgaagcc atcagaaact  480
ctttcactga cttgtactgt gagcggagtg tctctccccg attacggggt gtcttggatc  540
agacagccac cggggaaggg tctggaatgg attggagtga tttggggctc tgagactact  600
tactacaatt catccctcaa gtcacgcgtc accatctcaa aggacaactc taagaatcag  660
gtgtcactga aactgtcatc tgtgaccgca gccgacaccg ccgtgtacta ttgcgctaag  720
cattactatt atggcgggag ctacgcaatg gattactggg gacagggtac tctggtcacc  780
gtgtccagcc accaccatca tcaccatcac cat                              813

SEQ ID NO: 945          moltype = AA  length = 271
FEATURE                 Location/Qualifiers
REGION                  1..271
                        note = source = /note="Description of Artificial Sequence:
                         Synthetic polypeptide"
source                  1..271
                        mol_type = protein
                        organism = synthetic construct
SEQUENCE: 945
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSQVQLQES GPGLVKPSET LSLTCTVSGV SLPDYGVSWI  180
RQPPGKGLEW IGVIWGSETT YYNSSLKSRV TISKDNSKNQ VSLKLSSVTA ADTAVYYCAK  240
HYYYGGSYAM DYWGQGTLVT VSSHHHHHHH H                                271

SEQ ID NO: 946          moltype = DNA  length = 1473
FEATURE                 Location/Qualifiers
misc_feature            1..1473
                        note = source = /note="Description of Artificial Sequence:
                         Synthetic polynucleotide"
source                  1..1473
                        mol_type = other DNA
                        organism = synthetic construct
SEQUENCE: 946
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
aactcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccgg aggtggcgga  480
agcgaaatcg tgatgaccca gagccctgca accctgtccc tttctcccgg ggaacgggct  540
accctttctt gtcgggcatc acaagatatc tcaaaatacc tcaattggta tcaacagaag  600
ccgggacagg cccctaggct tcttatctac cacacctctc gcctgcatag cgggattccc  660
gcacgcttta gcgggtctgg aagcgggacc gactacactc tgaccatctc atctctccag  720
cccgaggact tcgccgtcta cttctgccag cagggtaaca ccctgccgta caccttcggc  780
cagggcacca agcttgagat caaaaccact actcccgctc caaggccacc cacccctgcc  840
ccgaccatcg cctctcagcc gctttccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                              1473

SEQ ID NO: 947          moltype = AA  length = 491
FEATURE                 Location/Qualifiers
REGION                  1..491
```

```
                        note = source = /note="Description of Artificial Sequence:
                         Synthetic polypeptide"
source                  1..491
                        mol_type = protein
                        organism = synthetic construct
SEQUENCE: 947
MALPVTALLL PLALLLHAAR PQVQLQESGP GLVKPSETLS LTCTVSGVSL PDYGVSWIRQ  60
PPGKGLEWIG VIWGSETTYY NSSLKSRVTI SKDNSKNQVS LKLSSVTAAD TAVYYCAKHY  120
YYGGSYAMDY WGQGTLVTVS SGGGGSGGGG SGGGGSGGGG SEIVMTQSPA TLSLSPGERA  180
TLSCRASQDI SKYLNWYQQK PGQAPRLLIY HTSRLHSGIP ARFSGSGSGT DYTLTISSLQ  240
PEDFAVYFCQ QGNTLPYTFG QGTKLEIKTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 948          moltype = AA  length = 242
FEATURE                 Location/Qualifiers
REGION                  1..242
                        note = source = /note="Description of Artificial Sequence:
                         Synthetic polypeptide"
source                  1..242
                        mol_type = protein
                        organism = synthetic construct
SEQUENCE: 948
QVQLQESGPG LVKPSETLSL TCTVSGVSLP DYGVSWIRQP PGKGLEWIGV IWGSETTYYN  60
SSLKSRVTIS KDNSKNQVSL KLSSVTAADT AVYYCAKHYY YGGSYAMDYW GQGTLVTVSS  120
GGGGSGGGGS GGGGSEIVMT QSPATLSLSP GERATLSCRA SQDISKYLNW YQQKPGQAPR  180
LLIYHTSRLH SGIPARFSGS GSGTDYTLTI SSLQPEDFAV YFCQQGNTLP YTFGQGTKLE  240
IK                                                                 242

SEQ ID NO: 949          moltype = DNA  length = 813
FEATURE                 Location/Qualifiers
misc_feature            1..813
                        note = source = /note="Description of Artificial Sequence:
                         Synthetic polynucleotide"
source                  1..813
                        mol_type = other DNA
                        organism = synthetic construct
SEQUENCE: 949
atggctctgc ccgtgaccgc actcctcctg ccactggctc tgctgcttca cgccgctcgc  60
ccacaagtcc agcttcaaga atcagggcct ggtctggtga agccatctga gactctgtcc  120
ctcacttgca ccgtgagcgg agtgtccctc ccagactacg gagtgagctg gattagacag  180
cctcccggaa agggactgga gtggatcgga gtgatttggg gtagcgaaac cacttactat  240
aactcttccc tgaagtcacg ggtcaccatt tcaaaggata actcaaagaa tcaagtgagc  300
ctcaagctct catcagtcac cgccgctgac accgccgtgt attactgtgc caagcattac  360
tactatggag ggtcctacgc catggactac tggggccagg gaactctggt cactgtgtca  420
tctggtggag gaggtagcgg aggaggcggg agcggtggag gtggctccga aatcgtgatg  480
acccagagcc ctgcaaccct gtccctttct cccggggaac gggctaccct ttcttgtcgg  540
gcatcacaag atatctcaaa atacctcaat tggtatcaac agaagccggg acaggcccct  600
aggcttctta tctaccacac ctctcgcctg catagcggga ttcccgcacg ctttagcggg  660
tctggaagcg ggaccgacta cactctgacc atctcatctc tccagcccga ggacttcgcc  720
gtctacttct gccagcaggg taacaccctg ccgtacacct tcggccaggg caccaagctt  780
gagatcaaac atcaccacca tcatcaccat cac                               813

SEQ ID NO: 950          moltype = AA  length = 271
FEATURE                 Location/Qualifiers
REGION                  1..271
                        note = source = /note="Description of Artificial Sequence:
                         Synthetic polypeptide"
source                  1..271
                        mol_type = protein
                        organism = synthetic construct
SEQUENCE: 950
MALPVTALLL PLALLLHAAR PQVQLQESGP GLVKPSETLS LTCTVSGVSL PDYGVSWIRQ  60
PPGKGLEWIG VIWGSETTYY NSSLKSRVTI SKDNSKNQVS LKLSSVTAAD TAVYYCAKHY  120
YYGGSYAMDY WGQGTLVTVS SGGGGSGGGG SGGGGSEIVM TQSPATLSLS PGERATLSCR  180
ASQDISKYLN WYQQKPGQAP RLLIYHTSRL HSGIPARFSG SGSGTDYTLT ISSLQPEDFA  240
VYFCQQGNTL PYTFGQGTKL EIKHHHHHHH H                                 271

SEQ ID NO: 951          moltype = DNA  length = 1458
FEATURE                 Location/Qualifiers
misc_feature            1..1458
                        note = source = /note="Description of Artificial Sequence:
                         Synthetic polynucleotide"
source                  1..1458
                        mol_type = other DNA
                        organism = synthetic construct
SEQUENCE: 951
```

```
atggccctcc ctgtcaccgc cctgctgctt ccgctggctc ttctgctcca cgccgctcgg  60
cccgaaattg tgatgaccca gtcacccgcc actcttagcc tttcacccgg tgagcgcgca  120
accctgtctt gcagagcctc ccaagacatc tcaaaatacc ttaattggta tcaacagaag  180
cccggacagg ctcctcgcct tctgatctac cacaccagcc ggctccattc tggaatccct  240
gccaggttca gcggtagcgg atctgggacc gactacaccc tcactatcag ctcactgcag  300
ccagaggact tcgctgtcta tttctgtcag caagggaaca ccctgcccta cacctttgga  360
cagggcacca agctcgagat taaaggtgga ggtggcagcg gaggaggtgg gtccggcggt  420
ggaggaagcc aggtccaact ccaagaaagc ggaccgggtc ttgtgaagcc atcagaaact  480
ctttcactga cttgtactgt gagcggagtg tctctccccg attacggggt gtcttggatc  540
agacagccac cggggaaggg tctggaatgg attggagtga tttggggctc tgagactact  600
tactacaact catccctcaa gtcacgcgtc accatctcaa aggacaactc taagaatcag  660
gtgtcactga aactgtcatc tgtgaccgca gccgacaccg ccgtgtacta ttgcgctaag  720
cattactatt atggcgggag ctacgcaatg gattactggg gacagggtac tctggtcacc  780
gtgtccagca ccactacccc agcaccgagg ccacccaccc cggctcctac catcgcctcc  840
cagcctctgt ccctgcgtcc ggaggcatgt agacccgcag ctggtggggc cgtgcatacc  900
cggggtcttg acttcgcctg cgatatctac atttgggccc ctctggctgg tacttgcggg  960
gtcctgctgc tttcactcgt gatcactctt tactgtaagc gcggtcggaa gaagctgctg  1020
tacatcttta agcaaccctt catgaggcct gtgcagacta ctcaagagga ggacggctgt  1080
tcatgccggt tcccagagga ggaggaaggc ggctgcgaac tgcgcgtgaa attcagccgc  1140
agcgcagatg ctccagccta caagcagggg cagaaccagc tctacaacga actcaatctt  1200
ggtcggagag aggagtacga cgtgctggac aagcggagag gacgggaccc agaaatgggc  1260
gggaagccgc gcagaaagaa tccccaagag ggcctgtaca acgagctcca aaaggataag  1320
atggcagaag cctatagcga gattggtatg aaaggggaac gcagaagagg caaaggccac  1380
gacggactgt accagggact cagcaccgcc accaaggaca cctatgacgc tcttcacatg  1440
caggccctgc cgcctcgg                                                1458

SEQ ID NO: 952         moltype = AA  length = 486
FEATURE                Location/Qualifiers
REGION                 1..486
                       note = source = /note="Description of Artificial Sequence:
                        Synthetic polypeptide"
source                 1..486
                       mol_type = protein
                       organism = synthetic construct
SEQUENCE: 952
MALPVTALLL PLALLLHAAR PEIVMTQSPA TLSLSPGERA TLSCRASQDI SKYLNWYQQK  60
PGQAPRLLIY HTSRLHSGIP ARFSGSGSGT DYTLTISSLQ PEDFAVYFCQ QGNTLPYTFG  120
QGTKLEIKGG GGSGGGGSGG GGSQVQLQES GPGLVKPSET LSLTCTVSGV SLPDYGVSWI  180
RQPPGKGLEW IGVIWGSETT YYNSSLKSRV TISKDNSKNQ VSLKLSSVTA ADTAVYYCAK  240
HYYYGGSYAM DYWGQGTLVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                             486

SEQ ID NO: 953         moltype = DNA  length = 813
FEATURE                Location/Qualifiers
misc_feature           1..813
                       note = source = /note="Description of Artificial Sequence:
                        Synthetic polynucleotide"
source                 1..813
                       mol_type = other DNA
                       organism = synthetic construct
SEQUENCE: 953
atggccctgc ccgtcaccgc tctgctgctg ccccttgctc tgcttcttca tgcagcaagg  60
ccggacatcc agatgaccca aaccacctca tccctctctg cctctcttgg agacagggtg  120
accatttctt gtcgcgccag ccaggacatc agcaagtatc tgaactggta tcagcagaag  180
ccggacggaa ccgtgaagct cctgatctac catacctctc gcctgcatag cggcgtgccc  240
tcacgcttct ctggaagcgg atcaggaacc gattattctc tcactatttc aaatcttgag  300
caggaagata ttgccaccta tttctgccag cagggtaata ccctgcccta caccttcgga  360
ggagggacca agctcgaaat caccggtgga ggaggcagcg gcggtggagg gtctggtgga  420
ggtggttctg aggtgaagct gcaagaatca ggccctggac ttgtggcccc ttcacagtcc  480
ctgagcgtga cttgcaccgt gtccggagtc tccctgcccg actacggagt gtcatggatc  540
agacaacctc cacggaaagg actggaatgg ctcggtgtca tctggggtag cgaaactact  600
tactacaatt cagccctcaa aagcaggctg actattatca aggacaacag caagtcccaa  660
gtctttctta agatgaactc actccagact gacgacaccg caatctacta ttgtgctaag  720
cactactact acggaggatc ctacgctatg gattactggg gacaaggtac ttccgtcact  780
gtctcttcac accatcatca ccatcaccat cac                               813

SEQ ID NO: 954         moltype = AA  length = 271
FEATURE                Location/Qualifiers
REGION                 1..271
                       note = source = /note="Description of Artificial Sequence:
                        Synthetic polypeptide"
source                 1..271
                       mol_type = protein
                       organism = synthetic construct
SEQUENCE: 954
MALPVTALLL PLALLLHAAR PDIQMTQTTS SLSASLGDRV TISCRASQDI SKYLNWYQQK  60
```

-continued

PDGTVKLLIY HTSRLHSGVP SRFSGSGSGT DYSLTISNLE QEDIATYFCQ QGNTLPYTFG 120
GGTKLEITGG GGSGGGGSGG GGSEVKLQES GPGLVAPSQS LSVTCTVSGV SLPDYGVSWI 180
RQPPRKGLEW LGVIWGSETT YYNSALKSRL TIIKDNSKSQ VFLKMNSLQT DDTAIYYCAK 240
HYYYGGSYAM DYWGQGTSVT VSSHHHHHHH H 271

SEQ ID NO: 955 moltype = DNA length = 1458
FEATURE Location/Qualifiers
misc_feature 1..1458
note = source = /note="Description of Artificial Sequence:
Synthetic polynucleotide"
source 1..1458
mol_type = other DNA
organism = synthetic construct
SEQUENCE: 955
atggccttac cagtgaccgc cttgctcctg ccgctggcct tgctgctcca cgccgccagg 60
ccggacatcc agatgacaca gactacatcc tccctgtctg cctctctggg agacagagtc 120
accatcagtt gcagggcaag tcaggacatt agtaaatatt taaattggta tcagcagaaa 180
ccagatggaa ctgttaaact cctgatctac catacatcaa gattacactc aggagtccca 240
tcaaggttca gtggcagtgg gtctggaaca gattattctc tcaccattag caacctggag 300
caagaagata ttgccactta cttttgccaa cagggtaata cgcttccgta cacgttcgga 360
ggggggacca agctggagat cacaggtggc ggtggctcgg gcggtggtgg gtcgggtggc 420
ggcggatctg aggtgaaact gcaggagtca ggacctggcc tggtggcgcc ctcacagagc 480
ctgtccgtca catgcactgt ctcaggggtc tcattacccg actatggtgt aagctggatt 540
cgccagcctc cacgaaaggg tctggagtgg ctgggagtaa tatggggtag tgaaaccaca 600
tactataatt cagctctcaa atccagactg accatcatca aggacaactc caagagccaa 660
gttttcttaa aaatgaacag tctgcaaact gatgacacag ccatttacta ctgtgccaaa 720
cattattact acggtggtag ctatgctatg gactactggg gccaaggaac ctcagtcacc 780
gtctcctcaa ccacgacgcc agcgccgcga ccaccaacac cggcgcccac catcgcgtcg 840
cagcccctgt ccctgcgccc agaggcgtgc cggccagcgg cggggggcgc agtgcacacg 900
agggggctgg acttcgcctg tgatatctac atctgggcgc ccttggccgg gacttgtggg 960
gtccttctcc tgtcactggt tatcaccctt tactgcaaac ggggcagaaa gaaactcctg 1020
tatatattca aacaaccatt tatgagacca gtacaaacta ctcaagagga agatggctgt 1080
agctgccgat ttccagaaga agaagaagga ggatgtgaac tgagagtgaa gttcagcagg 1140
agcgcagacg cccccgcgta caagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgc 1458

SEQ ID NO: 956 moltype = AA length = 486
FEATURE Location/Qualifiers
REGION 1..486
note = source = /note="Description of Artificial Sequence:
Synthetic polypeptide"
source 1..486
mol_type = protein
organism = synthetic construct
SEQUENCE: 956
MALPVTALLL PLALLLHAAR PDIQMTQTTS SLSASLGDRV TISCRASQDI SKYLNWYQQK 60
PDGTVKLLIY HTSRLHSGVP SRFSGSGSGT DYSLTISNLE QEDIATYFCQ QGNTLPYTFG 120
GGTKLEITGG GGSGGGGSGG GGSEVKLQES GPGLVAPSQS LSVTCTVSGV SLPDYGVSWI 180
RQPPRKGLEW LGVIWGSETT YYNSALKSRL TIIKDNSKSQ VFLKMNSLQT DDTAIYYCAK 240
HYYYGGSYAM DYWGQGTSVT VSSTTTPAPR PPTPAPTIAS QPLSLRPEAC RPAAGGAVHT 300
RGLDFACDIY IWAPLAGTCG VLLLSLVITL YCKRGRKKLL YIFKQPFMRP VQTTQEEDGC 360
SCRFPEEEEG GCELRVKFSR SADAPAYKQG QNQLYNELNL GRREEYDVLD KRRGRDPEMG 420
GKPRRKNPQE GLYNELQKDK MAEAYSEIGM KGERRRGKGH DGLYQGLSTA TKDTYDALHM 480
QALPPR 486

SEQ ID NO: 957 moltype = AA length = 242
FEATURE Location/Qualifiers
REGION 1..242
note = source = /note="Description of Artificial Sequence:
Synthetic polypeptide"
source 1..242
mol_type = protein
organism = synthetic construct
SEQUENCE: 957
DIQMTQTTSS LSASLGDRVT ISCRASQDIS KYLNWYQQKP DGTVKLLIYH TSRLHSGVPS 60
RFSGSGSGTD YSLTISNLEQ EDIATYFCQQ GNTLPYTFGG GTKLEITGGG GSGGGGSGGG 120
GSEVKLQESG PGLVAPSQSL SVTCTVSGVS LPDYGVSWIR QPPRKGLEWL GVIWGSETTY 180
YNSALKSRLT IIKDNSKSQV FLKMNSLQTD DTAIYYCAKH YYYGGSYAMD YWGQGTSVTV 240
SS 242

What is claimed is:

1. A method of treating a disease or condition in a subject comprising administering a population of modified T cells to a subject in need thereof, wherein:

(i) the modified T cells express a nucleic acid encoding a minibody, wherein the minibody comprises a single chain antibody comprising a secretion signal, a variable heavy chain fragment, a variable light chain fragment and a constant chain fragment, and a minibody hinge domain between the variable light chain fragment and the constant chain fragment and the modified T cells secrete the minibody, wherein the minibody binds to an immune checkpoint molecule; and (ii) the modified T cells express a nucleic acid encoding a chimeric antigen receptor (CAR).

2. The method of claim 1, wherein the CAR comprises an antigen binding domain, a transmembrane domain, and an intracellular signaling domain.

3. The method of claim 2, wherein the intracellular domain comprises a primary signaling domain, a costimulatory domain, or both of a primary signaling domain and a costimulatory domain.

4. The method of claim 3, wherein the primary signaling domain comprises a functional signaling domain of one or more proteins selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12.

5. The method of claim 3, wherein the costimulatory domain comprises a functional domain of one or more proteins selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

6. The method of claim 2, wherein the antigen binding domain binds a tumor antigen.

7. The method of claim 6, wherein the tumor antigen is selected from the group consisting of CD19; CD123; CD22; CD30; CD171; CS-1 (CD2 subset 1, CRACC, SLAMF7, CD319, 19A24); CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac (2-8) aNeu5Ac (2-3) bDGalp (1-4) bDGlcp (1-1) Cer); TNF receptor family member B cell maturation (BCMA); Tn antigen (Tn Ag or GalNAcα-Ser/Thr); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac (2-3) bDGalp (1-4) bDGlcp (1-1) Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ETS fusion gene TMPRSS2-ERG; N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

8. The method of claim 2, wherein the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

9. The method of claim 2, wherein the antigen binding domain is connected to the transmembrane domain by a CAR hinge region.

10. The method of claim 2, wherein the nucleic acid encoding the CAR further encodes a leader sequence.

11. The method of claim 1, wherein the immune checkpoint molecule is selected from the group consisting of Programmed Death 1 (PD-1), PD-1, PD-L1, PD-L2, Cytotoxic T-Lymphocyte Antigen 4 (CTLA-4), TIM-3, CEACAM-1, CEACAM-3, CEACAM-5, LAG-3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GAL9, and adenosine.

12. The method of claim 1, wherein the nucleic acid encoding the minibody is disposed on the same nucleic acid molecule as the nucleic acid encoding the CAR.

13. The method of claim 1, wherein the nucleic acid encoding the minibody is disposed on a first nucleic acid molecule and the nucleic acid encoding the CAR is disposed on a second different nucleic acid molecule.

14. The method of claim 1, wherein the minibody is a bispecific minibody, wherein the bispecific minibody binds to two immune checkpoint molecules selected from the group consisting of Programmed Death 1 (PD-1), PD-L1, PD-L2, Cytotoxic T-Lymphocyte Antigen 4 (CTLA-4), TIM-3, CEACAM-1, CEACAM-3, CEACAM-5, LAG-3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GAL9, and adenosine.

15. The method of claim 6, wherein the tumor antigen is a solid tumor antigen.

16. The method of claim 6, wherein the tumor antigen is mesothelin.

17. The method of claim 6, wherein the tumor antigen is expressed in a solid tumor that also expresses the immune checkpoint molecule.

18. The method of claim 6, wherein the tumor antigen is PD-L1.

19. The method of claim 2, wherein the antigen binding domain comprises an antibody, an antibody fragment, an scFv, a Fv, a Fab, a (Fab')2, a single domain antibody (SDAB), a VH or VL domain, or a camelid VHH domain.

20. The method of claim 1, wherein the immune checkpoint molecule is PD-1.

21. The method of claim 1, wherein the minibody is a bispecific minibody, wherein the bispecific minibody binds to PD-1 and PD-L1.

22. The method of claim 1, wherein the disease or condition is a cancer.

23. The method of claim 22, wherein the cancer is a breast cancer, a prostate cancer, an ovarian cancer, a cervical cancer, a skin cancer, a pancreatic cancer, a colorectal cancer, a renal cancer, a liver cancer, a brain cancer, a lymphoma, a leukemia, a lung cancer, or a thyroid cancer.

24. The method of claim 1, wherein the disease or condition is an autoimmune disease.

* * * * *